(12) United States Patent
Kuramochi et al.

(10) Patent No.: US 8,399,464 B2
(45) Date of Patent: Mar. 19, 2013

(54) HSP90 INHIBITOR

(75) Inventors: Hiroshi Kuramochi, Tokyo (JP); Setsuko Niitsuma, Tokyo (JP); Masaharu Nakamura, Tokyo (JP); Yoshitaka Sato, Tokyo (JP); Seiichi Saito, Tokyo (JP); Arihiro Tomura, Tokyo (JP); Yuh-ichiro Ichikawa, Tokyo (JP); Yousuke Kasuga, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 868 days.

(21) Appl. No.: 11/885,575

(22) PCT Filed: Mar. 8, 2006

(86) PCT No.: PCT/JP2006/304496
§ 371 (c)(1),
(2), (4) Date: Sep. 4, 2007

(87) PCT Pub. No.: WO2006/095783
PCT Pub. Date: Sep. 14, 2006

(65) Prior Publication Data
US 2008/0269218 A1 Oct. 30, 2008

(30) Foreign Application Priority Data

Mar. 9, 2005 (JP) ................................. 2005-065027
Jun. 23, 2005 (JP) ................................. 2005-183259

(51) Int. Cl.
*A61K 31/535* (2006.01)
(52) U.S. Cl. ...................... 514/236.2; 514/384; 514/326; 548/263.2; 544/132; 546/210
(58) Field of Classification Search .................. 548/188, 548/174, 165, 161; 514/236.2
See application file for complete search history.

(56) References Cited

U.S. PATENT DOCUMENTS

| 5,489,598 | A * | 2/1996 | Connor et al. ............... 514/384 |
| 7,662,813 | B2 | 2/2010 | Ying et al. |
| 8,053,456 | B2 | 11/2011 | Sun et al. |
| 2006/0167070 | A1 * | 7/2006 | Ying et al. ..................... 514/383 |
| 2007/0155809 | A1 | 7/2007 | Ying et al. |
| 2008/0176840 | A1 | 7/2008 | Sun et al. |
| 2008/0182857 | A1 | 7/2008 | Eggenweiler et al. |

FOREIGN PATENT DOCUMENTS

| CN | 101072759 A1 | 11/2007 |
| CN | 101119978 A1 | 9/2009 |
| WO | 02/36075 | 5/2002 |
| WO | 03/055860 | 7/2003 |
| WO | 2004/050087 | 6/2004 |
| WO | 2004/056782 | 7/2004 |
| WO | 2004/072051 | 8/2004 |
| WO | 2004/096212 | 11/2004 |
| WO | 2005/000300 | 1/2005 |
| WO | 2005/000778 | 1/2005 |
| WO | 2005/041879 | 5/2005 |

OTHER PUBLICATIONS

Patani et al "Bioisosterism: A rational Approach in Drug Design", Chem. Rev. 1996, vol. 96, No. 8, pp. 3147-3176.*
Mockus et al, "The chemical abstracts service chemical registry system VII. Tautomerism and alternating bonds", J. Chem. Comput. Sci. 1980, vol. 20, pp. 18-22.*
Wolff, Manfred E., Ed. Burger's Medicinal Chemistry and Drug Discovery—Fifth Edition, New York: John Wiley & Sons,1995, vol. 1, pp. 974-977.*
International Search Report date Apr. 25, 2006.
Trends in Molecular Medicine vol. 8 No. 4 (Suppt.) 2002; p. S55-61; Len Neckers; "Hsp90 inhibitors as novel cancer chemotherapeutic agents".
Proc. Natl. Acad. Sci, vol. 91, pp. 8324-8328, Aug. 1994 Cell Biology; Luke Whitesell et al.; Inhibition of heat shock protein HSP90-pp60$^{v-src}$ heteroprotein complex formation by benzoquinone ansamycins: Essential role for stress proteins in oncogenic transformation.
Cell, vol. 89 (2), 239-250, Apr. 18, 1997; Charles E. Stebbins et al.; "Crystal Structure of an Hsp90-Geldanamycin Complex: Targeting of a Protein Chaperone by an Antitumor Agent".
Current Cancer Drug Targets, vol. 3, No. 5, Oct. 2003; pp. 385-390; Udai Banerji et al.; "The Clinical Applications of Heat Shock Protein Inhibitors in Cancer-Present and Future".
Chemistry & Biology 8 (2001) pp. 289-299; Gabriela Chiosis et al.; "A small molecule designed to bind to the adenine nucleotide pocket of Hsp90 causes Her2 degradation and the growth arrest and differentiation of breast cancer cells".
Chemistry & Biology, vol. 11, pp. 787-797, Jun. 2004; Maria Vilenchik et al.; "Targeting Wide-Range Oncogenic Transformation via PU24FC1, a Specific Inhibitor of Tumor Hsp90".

(Continued)

*Primary Examiner* — Brandon Fetterolf
*Assistant Examiner* — Jean Cornet
(74) *Attorney, Agent, or Firm* — Nields, Lemack & Frame, LLC

(57) ABSTRACT

Disclosed is a triazole derivative(s) represented by the general formula (1) below or a pharmacologically acceptable salt(s) thereof. Also disclosed are a prodrug(s) of such a triazole derivative(s) and an HSP90 inhibitor(s) containing any one of them as an active constituent. (1) (In the formula, X represents a halogen atom, an optionally substituted alkyl group, an optionally substituted alkynyl group or the like; Y represents a mercapto group, a hydroxyl group, an optionally substituted sulfonyl group, an optionally substituted amino group or the like; and R represents an optionally substituted aryl or alkyl group or the like.)

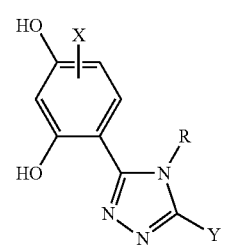

(1)

14 Claims, 4 Drawing Sheets

OTHER PUBLICATIONS

Bioorganic & Medicinal Chemistry Letters 14 (2004) p. 325-328; Brian Dymock et al.; "Adenine derived inhibitors of the molecular chaperone HSP90-SAR Explained through multiple X-ray structures".

Database Caplus Chemical Abstracts Service, Columbus, Ohio, 1989—XP002524995 Database accession No. 1989:8130—Abstract, N.G. Gawande et al.; "Synthesis of some thiosemicarbazides and related compounds". Acta Ciencia Indica, Chemistry, vol. 13, No. 2, 1987, pp. 109-111.

European communication dated May 7, 2009.

Chinese Office Action dated Nov. 13, 2009.

* cited by examiner

HSP90 INHIBITOR

TECHNICAL FIELD

The present invention relates to a novel triazole derivative and an HSP90 inhibitor containing the triazole derivative as an active ingredient. The triazole derivative of the present invention inhibits the function of HSP90 by binding to its ATP binding site, blocks the binding of HSP90 and its client protein and finally suppresses cellular growth.

BACKGROUND ART

Molecular chaperones are a general term for proteins that form a complex temporally with client proteins to promote the formation of the conformation of the client proteins. These proteins, the activity of which is to help folding and association of protein and to prevent aggregation, are broadly defined as molecular chaperones and classified into several families according to their molecular weights (HSP90, HSP70, HSP60, HSP40, small HSPs and the like). In particular, HSP90 has been known to interact with many molecules which are involved in the intracellular signal transduction, and it is becoming clear that HSP90 is deeply involved in cell cycle regulation, and carcinogenesis, growth and survival signal of cells.

HSP90 is a molecular chaperone present in cells in abundance (occupies 1-2% of total soluble protein), distributed in the cytoplasm evenly and exists mainly as dimers. The activity of HSP90 alone in protein folding is low, and HSP90 functions cooperatively with other molecular chaperones having a folding activity (hereinafter called co-chaperones) such as HSP70 and p23. HSP90 is often needed for its function of client proteins that form a complex, and the action mechanism is based on the biochemical characteristic that HSP90 specifically recognizes a protein under the condition of unstable folding and binds to it. HSP90 performs ATP dependent folding (re-folding) of a denatured protein or a protein that is not folded. Especially, it is needed for constructing the structure of various key proteins (steroid receptors, Raf serine kinases, tyrosine kinases) which are involved in cancer related signal transduction. According to the recent findings, the control function of many key signal molecules is lost in human tumors, and these require HSP90 to maintain the function (non-patent document 1).

Geldanamycin (hereinafter called GM) is an ansamycin natural product, which was initially discovered in microorganisms as a tyrosine kinase inhibitor, but its direct inhibitory effect on a tyrosine kinase was low, and later it was found that this drug acted on HSP90 specifically. Radicicol (hereinafter called RD) is a macrolide natural product which, as a different structure from GM, also acts on HSP90 and inhibits its function. It has been known that GM and RD induce degradation of various key proteins (steroid receptor, Raf, Her2 and the like) which are involved in signal transduction related to cancer and cause growth inhibition of various cancer cells in vitro. HSP90 contains at the N-terminal an ATP/ADP binding site which plays an important role in controlling the chaperone function. This site is specific for and well preserved in the HSP90 family, and does not exist in other molecular chaperones. It has been elucidated by crystallographic analysis that GM and RD directly bind to this ATP/ADP binding site as antagonists (non-patent documents 2 and 3). It is also known that these antagonists inhibit the association with a co-chaperone such as p23 by binding to the ATP/ADP binding site. As the result, the composition of the chaperone complex which contains client proteins and HSP90 is changed, and eventually the client proteins are released from the complex and degraded mainly in the ubiquitin-proteasome pathway. Thus, the antiproliferative action on cancer cells by HSP90 antagonists will be caused by a depression of the client protein of HSP90 and the blocking of signal transduction pathway by the depression.

The HSP90 antagonist acts selectively on client proteins folded into HSP90, and does not affect the function and the amount of expression of other proteins at all. Studies have shown that in the process of carcinogenesis, a plurality of gene abnormalities are accumulated, and in many tumor cells, mutated proteins require more of the chaperone activity than normal proteins. HSP90 is overexpressed in various cancers. From the analyses of pharmacokinetics of a GM derivative, 17-AAG, in animal models, more of the 17-AAG is accumulated in cancer in comparison to the normal cells. From these reports, it is expected that the HSP90 antagonist acts on cancer cells specifically, not on normal cells. Also, since cancer cells under a kind of stressful condition such as abnormal protein expression, low oxygen and nutritional starvation are dependent on HSP90 at a higher degree, it would appear that the sensitivity of cancer cells against the HSP90 antagonist is higher.

Among the HSP90 antagonists, 17-AAG is subjected to ongoing Phase I/II clinical trials, and investigations on RD derivatives are also being conducted (non-patent document 4), but any one of these has problems for use as a pharmaceutical product in physical properties such as molecular weight, stability, and water solubility. A water soluble and low molecular weight HSP90 inhibitor is sought as a useful pharmaceutical product. An adenine derivative, PU3 and its derivatives have been reported to be a low molecular weight HSP90 inhibitor (Patent Document 1, non-patent document 5, non-patent document 6 and non-patent document 7). Also, a 1,3-dihydroxybenzene derivative, to which a 5-member ring is bound, has been reported to be a HSP90 inhibitor (patent document 2, patent document 3, patent document 4, patent document 5, patent document 6, and patent document 7), but the antiproliferative activity against cancer cells in vitro is weak (patent document 2). Further, the patent document 8 describes benzene derivatives, to which a 5-member ring is bound, as an antagonist of HSP90, but data of the HSP90 inhibitory activity of a derivative in which the 5-member ring has a triazole skeleton is not disclosed. On the other hand, the fact that the triazole derivatives of the present invention have HSP90 inhibitory activity is not known in literature.

Patent Document 1: International Publication No. 02/036075
Patent Document 2: International Publication No. 03/055860
Patent Document 3: International Publication No. 04/050087
Patent Document 4: International Publication No. 04/056782
Patent Document 5: International Publication No. 04/096212
Patent Document 6: International Publication No. 04/072051
Patent Document 7: International Publication No. 05/000300
Patent Document 8: International Publication No. 05/041879
Non-Patent Document 1: Hsp90 inhibitors as novel cancer chemotherapeutic agents. Trends Mol. Med. 2002; 8(4 Suppl.): p. S55-61.
Non-Patent Document 2: Inhibition of heat shock protein HSP90-pp 60v-src heteroprotein complex formation by benzoquinone ansamycins: essential role for stress proteins in oncogenic transformation. Proc Natl Acad Sci U.S.A. 1994; 91(18): p 8324-8328.
Non-Patent Document 3: Crystal structure of an Hsp90-geldanamycin complex: targeting of a protein chaperone by an antitumor agent. Cell 1997 Apr. 18; 89(2): p. 239-250.

Non-Patent Document 4: The clinical applications of heat shock protein inhibitors in cancer—present and future. Curr. Cancer Drug Targets. 2003 October; 3(5): p. 385-390.

Non-Patent Document 5: A small molecule designed to bind to the adenine nucleotide pocket of Hsp90 causes Her2 degradation and the growth arrest and differentiation of breast cancer cells. G. Chiosis et al., Chem. Biol. 2001 March; 8(3): p. 289-299.

Non-Patent Document 6: Targeting Wide-Range Oncogenic Transformation via PU24FCl, a specific Inhibitor of Tumor Hsp90. M. Vilenchik et al., Chem. Bio., 11, p. 787-797 (2004).

Non-Patent Document 7: Adenine derived inhibitors of the molecular chaperone HSP90-SAR explained through multiple X-ray structures. D. Dymock et al., Bioorg. Med. Chem. Lett., 14 (02), p. 325-328 (2004).

DISCLOSURE OF THE INVENTION

Problems to be Solved by the Invention

The inhibitors of HSP90, which is involved in cell growth, are expected to be effective against cancer cells selectively as described above, and some of them have been under development, but so far no inhibitor having sufficient stability and efficacy required for pharmaceutical drugs has been obtained, and a HSP90 inhibitor usable as a drug is desired.

To solve the problem described above, the present inventors investigated rigorously and as the result discovered that a triazole derivative represented by the following general formula (1),

[Formula 1]

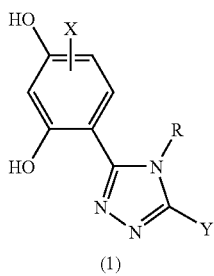

(1)

a prodrug thereof or a pharmaceutically acceptable salt thereof inhibits HSP90 to complete the present invention.

That is, the present invention relates to (1) a triazole derivative represented by the following general formula (1) or a pharmaceutically acceptable salt thereof,

[Formula 2]

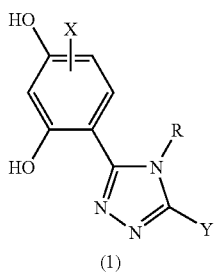

(1)

wherein N represents a nitrogen atom; X represents a mercapto group, hydroxy group, halogen atom, nitro group, cyano group, an optionally substituted alkyl group, an optionally substituted alkenyl group, an optionally substituted alkynyl group, optionally substituted carbocyclic or heterocyclic aryl group, an optionally substituted alkylthio group, an optionally substituted arylthio group, an optionally substituted alkylsulfinyl group, an optionally substituted arylsulfinyl group, an optionally substituted alkylsulfonyl group, an optionally substituted arylsulfonyl group, an optionally substituted sulfamoyl group, an optionally substituted alkoxyl group, an optionally substituted aryloxy group, an optionally substituted acyloxy group, an optionally substituted alkoxycarbonyloxy group, an optionally substituted carbamoyloxy group, an optionally substituted amino group, an optionally substituted acylamino group, an optionally substituted alkoxycarbonylamino group, an optionally substituted ureido group, an optionally substituted sulfonylamino group, an optionally substituted sulfamoylamino group, a formyl group, an optionally substituted acyl group, an optionally substituted carboxyl group, alkoxycarbonyl group, an optionally substituted carbamoyl group, an optionally substituted or an optionally substituted silyl group; Y represents a mercapto group, hydroxy group, halogen atom, cyano group, sulfonyl group, an optionally substituted alkylthio group, an optionally substituted arylthio group, an optionally substituted alkylsulfinyl group, an optionally substituted arylsulfinyl group, an optionally substituted sulfamoyl group, an optionally substituted alkoxyl group, an optionally substituted aryloxy group, an optionally substituted acyloxy group, an optionally substituted alkoxycarbonyloxy group, an optionally substituted carbamoyloxy group, an optionally substituted amino group, an optionally substituted acylamino group, an optionally substituted alkoxycarbonylamino group, an optionally substituted ureido group, an optionally substituted sulfonylamino group, an optionally substituted sulfamoylamino group, a formyl group, an optionally substituted acyl group or an optionally substituted silyl group; R represents an optionally substituted carbocyclic or heterocyclic aryl group, or an optionally substituted alkyl group, an optionally substituted alkenyl group, an optionally substituted alkynyl group or an optionally substituted amino group;

(2) The triazole derivative according to the aforementioned (1), wherein X is located at the 5 position of a 2,4-dihydroxyphenyl group which binds to triazole ring at 1 position in the general formula (1) of the aforementioned (1), or a pharmaceutically acceptable salt thereof;

(3) The triazole derivative according to the aforementioned (1) or (2), wherein X is an optionally substituted alkyl group, an optionally substituted alkenyl group or an optionally substituted alkynyl group, or a halogen atom in the general formula 1 of the aforementioned (1), or a pharmaceutically acceptable salt thereof;

(4) The triazole derivative according to any one of the aforementioned (1) to (3), wherein the compound represented by the general formula (1) of the aforementioned (1) is an acetylene derivative represented by the following general formula (1-1) or a pharmaceutically acceptable salt thereof;

[Formula 3]

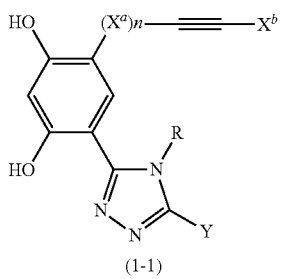

(1-1)

wherein R and Y represent the same meanings as in R and Y of the general formula (1) of the aforementioned (1), $X^a$ represents an optionally substituted methylene group, n represents an integer from 0 to 3, $X^b$ represents a hydrogen atom, an optionally substituted alkyl group, an optionally substituted alkenyl group or an optionally substituted alkynyl group, an optionally substituted carbocyclic or heterocyclic aryl group, halogen atom, sulfamoyl group, formyl group, acyl group, carboxyl group, carbamoyl group or silyl group;

(5) The triazole derivative according to the aforementioned (4) or a pharmaceutically acceptable salt thereof, wherein n is 1 in the general formula (1-1) of the aforementioned (4);

(6) The triazole derivative according to any one of the aforementioned (1) to (5) or a pharmaceutically acceptable salt thereof, wherein Y is any of a mercapto group, hydroxy group, an optionally substituted sulfonyl group or alkylthio group in the general formula (1) of the aforementioned (1) or the general formula (1-1) of the aforementioned (4);

(7) The triazole derivative according to any one of the aforementioned (1) to (6) or a pharmaceutically acceptable salt thereof, wherein Y is an alkylsulfonyl group optionally substituted on the alkyl group thereof, or an arylsulfonyl group optionally substituted on the aryl group thereof in the general formula (1) of the aforementioned (1) or the general formula (1-1) of the aforementioned (4);

(8) The triazole derivative according to any one of the aforementioned (1) to (6) or a pharmaceutically acceptable salt thereof, wherein Y is a mercapto group in the general formula (1) of the aforementioned (1) or the general formula (1-1) of the aforementioned (4);

(9) The triazole derivative according to any one of the aforementioned (1) to (6) or a pharmaceutically acceptable salt thereof, wherein Y is a hydroxy group in the general formula (1) of the aforementioned (1) or the general formula (1-1) of the aforementioned (4);

(10) The triazole derivative according to any one of the aforementioned (1) to (9) or a pharmaceutically acceptable salt thereof, wherein R is an optionally substituted carbocyclic or heterocyclic aryl group in the general formula (1) of the aforementioned (1) or the general formula (1-1) of the aforementioned (4);

(11) The triazole derivative according to any one of the aforementioned (1) to (10) or a pharmaceutically acceptable salt thereof, wherein R is represented by the following general formula (2) in the general formula (1) of the aforementioned (1),

[Formula 4]

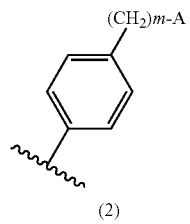

(2)

wherein m is an integer from 0 to 5, A is an optionally substituted cyclic or non-cyclic amino group, an optionally substituted cyclic or non-cyclic acylamino group or an optionally substituted cyclic or non-cyclic sulfonylamino group;

(12) The triazole derivative according to the aforementioned (11) or a pharmaceutically acceptable salt thereof, wherein m is 0 or 1 and A is a cyclic amino group in the general formula (2) of the aforementioned (11);

(13) The triazole derivative according to any one of the aforementioned (1) to (10) or a pharmaceutically acceptable salt thereof, wherein R is represented by the following general formula (2-2) in the general formula (1) of the aforementioned (1) or the general formula (1-1) of the aforementioned (4),

[Formula 5]

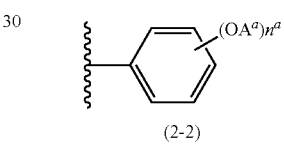

(2-2)

wherein $n^a$ is an integer from 1 to 5, $A^a$ is an optionally substituted alkyl group having carbons from 1 to 6 and when $n^a$ is 2 to 5, the neighboring substituents taken together may form a ring;

(14) The triazole derivative according to any one of the aforementioned (1) to (9) or a pharmaceutically acceptable salt thereof, wherein R is an optionally substituted alkyl group in the general formula (1) of the aforementioned (1) or the general formula (1-1) of the aforementioned (4);

(15) The triazole derivative according to any one of the aforementioned (1) to (12) or a pharmaceutically acceptable salt thereof, wherein the compound represented by the general formula (1) of the aforementioned (1) is represented by the following general formula (4),

[Formula 6]

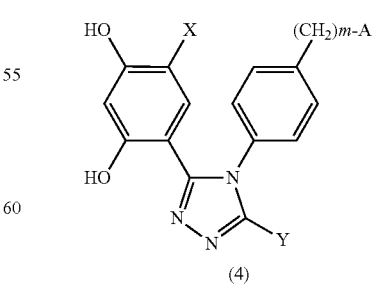

(4)

wherein X represents a chlorine atom, ethyl group, isopropyl group, tert-butyl group, 2,2-dimethylpropyl group, 2-propynyl group or 2-butynyl group; Y represents a mercapto group, an optionally substituted alkylsulfonyl group or hydroxy group; m is 0 or 1; and A represents a cyclic amino group;
(16) The triazole derivative according to any one of the aforementioned (1) to (10) and (15), or a pharmaceutically acceptable salt thereof, wherein the compound represented by the general formula (1) of the aforementioned (1) is represented by the following general formula (1-2),

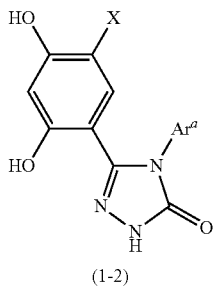

[Formula 7]

(1-2)

wherein X represents a chlorine atom, ethyl group, isopropyl group, tert-butyl group, 2,2-dimethylpropyl group, 2-propynyl group or 2-butynyl group; Ara represents a 4-methoxyphenyl group, 3-methoxyphenyl group, 3,4-dimethoxyphenyl group, 3,4,5-trimethoxyphenyl group or 3,4-methylenedioxyphenyl group;
(17) The triazole derivative according to any one of the aforementioned (1) to (10) and (14), or a pharmaceutically acceptable salt thereof, wherein the compound represented by the general formula (1) of the aforementioned (1) is represented by the following general formula (1-3),

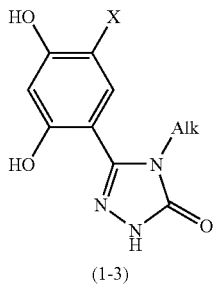

[Formula 8]

(1-3)

wherein X represents a chlorine atom, ethyl group, isopropyl group, tert-butyl group, 2,2-dimethylpropyl group, 2-propynyl group or 2-butynyl group; Alk represents an optionally substituted alkyl group;
(18) The triazole derivative according to the aforementioned (1) or a pharmaceutically acceptable salt thereof, which is selected from the group consisting of:
4-isopropyl-6-{5-mercapto-4-[4-(morpholin-4-yl)-phenyl]-4H-[1,2,4]triazol-3-yl}-benzene-1,3-diol (SH-a01),
4-isopropyl-6-{5-mercapto-4-[4-(morpholin-4-ylmethyl)-phenyl]-4H-[1,2,4]triazol-3-yl}-benzene-1,3-diol (SH-a02),
4-[4-(4-bromo-phenyl)-5-mercapto-4H-[1,2,4]triazol-3-yl]-6-isopropyl-benzene-1,3-diol (SH-a03),
4-{(5-hydroxy-4-[4-(morpholin-4-yl)-phenyl]-4H-[1,2,4]triazol-3-yl}-6-isopropyl-benzene-1,3-diol (OH-a01),
4-{5-hydroxy-4-[4-(morpholin-4-ylmethyl)-phenyl]-4H-[1,2,4]triazol-3-yl}-6-isopropyl-benzene-1,3-diol (OH-a02), 5-[5-(but-2-ynyl)-2,4-dihydroxy-phenyl]-4-[4-(morpholin-4-ylmethyl)-phenyl]-2,4-dihydro-[1,2,4]triazol-3-one (OH-c02),
4-(but-2-ynyl-2-yl)-6-{5-mercapto-4-[4-(morpholin-4-ylmethyl)-phenyl]-4H-[1,2,4]triazol-3-yl}-benzene-1,3-diol (SH-c02),
4-bromo-6-{5-mercapto-4-[4-(morpholin-4-yl)-phenyl]-4H-[1,2,4]triazol-3-yl}-benzene-1,3-diol (SH-d01),
4-isopropyl-6-{5-methanesulfonyl-4-[4-(morpholin-4-ylmethyl)-phenyl]-4H-[1,2,4]triazol-3-yl}-benzene-1,3-diol (SFN-a02),
4-isopropyl-6-[5-methylsulfinyl-4-(4-methoxy-phenyl)-4H-[1,2,4]triazol-3-yl]-benzene-1,3-diol (SFX-a08),
4-isopropyl-6-[5-methanesulfonyl-4-(4-methoxy-phenyl)-4H-[1,2,4]triazol-3-yl]-benzene-1,3-diol (SFN-a08),
5-[2,4-dihydroxy-5-(prop-2-ynyl)-phenyl]-4-[4-(morpholin-4-ylmethyl)-phenyl]-2,4-dihydro-[1,2,4]triazol-3-one (OH-e02),
5-(2,4-dihydroxy-5-isopropyl-phenyl)-4-(4-methoxy-phenyl)-2,4-dihydro-[1,2,4]triazol-3-one (OH-a08),
5-(2,4-dihydroxy-5-isopropyl-phenyl)-4-(3-methoxy-phenyl)-2,4-dihydro-[1,2,4]triazol-3-one (OH-a09),
5-(2,4-dihydroxy-5-isopropyl-phenyl)-4-(3,4-dimethoxy-phenyl)-2,4-dihydro-[1,2,4]triazol-3-one (OH-a10),
4-[benzo[1,3]dioxol-5-yl]-5-(2,4-dihydroxy-5-isopropyl-phenyl)-2,4-dihydro-[1,2,4]triazol-3-one,
5-(2,4-dihydroxy-5-isopropyl-phenyl)-4-(4-hydroxy-phenyl)-2,4-dihydro-[1,2,4]triazol-3-one (OH-a11),
5-(2,4-dihydroxy-5-isopropyl-phenyl)-4-[2-(morpholin-4-yl)-pyrimidin-5-yl]-2,4-dihydro-[1,2,4]triazol-3-one (OH-a17),
5-(2,4-dihydroxy-5-isopropyl-phenyl)-4-[4-(4-methyl-piperazin-1-ylmethyl)-phenyl]-2,4-dihydro-[1,2,4]triazol-3-one (OH-a13),
5-(2,4-dihydroxy-5-isopropyl-phenyl)-4-isopropyl-2,4-dihydro-[1,2,4]triazol-3-one (OH-a21),
4-[5-(3-dimethylamino-propane-1-sulfonyl)-4-(4-methoxy-phenyl)-4H-[1,2,4]triazol-3-yl]-6-isopropyl-benzene-1,3-diol (SFN2-a08),
4-isopropyl-6-[(4-(4-methoxy-phenyl)-5-(3-piperidin-1-yl-propane-1-sulfonyl)-4H-[1,2,4]triazol-3-yl]-benzene-1,3-diol (SFN3-a08), and
N-[5-(2,4-dihydroxy-5-isopropyl-phenyl)-4-(4-methoxy-phenyl)-4H-[1,2,4]triazol-3-yl]-methane sulfonamide (N-1-a08).
(19) A prodrug of the triazole derivative according to any one of the aforementioned (1) to (18) or a pharmaceutically acceptable salt thereof;
(20) A medicine containing as an active ingredient the prodrug of the triazole derivative according to any one of the aforementioned (1) to (18) or a pharmaceutically acceptable salt of the prodrug;
(21) An HSP90 inhibitor containing as an active ingredient the triazole derivative according to any one of the aforementioned (1) to (18), a prodrug thereof or a pharmaceutically acceptable salt thereof; and
(22) An anticancer agent containing as an active ingredient the triazole derivative according to any one of the aforementioned (1) to (18), a prodrug thereof or a pharmaceutically acceptable salt thereof.

EFFECT OF THE INVENTION

The present invention can provide a drug composition containing a compound having a superior HSP90 inhibitory activity or a pharmaceutically acceptable salt thereof as an active ingredient, in particular a therapeutic agent for cancer.

BEST MODE FOR CARRYING OUT THE INVENTION

Following is the detailed description of the present invention.

In the present invention, a halogen atom indicates a fluorine atom, chlorine atom, bromine atom or iodine atom.

In the present invention, an alkyl group means, unless specified otherwise, a linear, branched or cyclic alkyl group having 1-20 carbons, preferably 1-8 carbons. The linear alkyl group includes, for example, a methyl group, ethyl group, propyl group, n-butyl group, n-pentyl group, and n-hexyl group. The branched alkyl group includes, for example, an isopropyl group, tert-butyl group, and 2,2-dimethylpropyl group. The cyclic alkyl group includes, for example, a cyclopropyl group, cyclobutyl group, cyclopentyl group, cyclohexyl group, and adamantyl group.

In the present invention, an alkenyl group means a linear, branched or cyclic alkenyl group having a carbon-carbon double bond at one or more places and having 2-20 carbons, preferably 2-8 carbons. The linear alkenyl group includes, for example: a 1-alkenyl group such as an ethenyl group, 1-propenyl group, and 1-butenyl group; and a 2-alkenyl group such as a 2-butenyl group, and 2-pentenyl group. The branched alkenyl group includes, for example, an isopropenyl group, 3-methyl-1-butenyl group, and geranyl group.

In the present invention, an alkynyl group means an alkynyl group having a carbon-carbon triple bond at one or more places and having 2-20 carbons, preferably 2-8 carbons. Examples include: a 1-alkynyl group such as ethynyl group, 1-propynyl group, and 3,3-dimethyl-1-butynyl group; and a 2-alkynyl group such as a 2-propynyl group, 2-butynyl group, 3-phenyl-2-propynyl group, 4,4-dimethyl-2-pentynyl group, and 3-trimethylsilyl-2-propynyl group.

In the present invention, a carbocyclic aryl group includes, for example, a phenyl group, and naphthyl group. A heterocyclic aryl group includes, for example, a pyridyl group, pyrimidinyl group, quinolyl group, quinazolyl group, naphthyridinyl group, furyl group, pyrrolyl group, indolyl group, imidazolyl group, pyrazolyl group, oxazolyl group, isoxazolyl group, and triazolyl group.

In the present invention, when the description "an optionally substituted" is used, the substituent includes, for example, a hydrogen atom, mercapto group, hydroxy group, halogen atom, nitro group, cyano group, alkyl group, alkenyl group, alkynyl group, carbocyclic or heterocyclic aryl group, alkylthio group, arylthio group, alkylsulfinyl group, arylsulfinyl group, alkylsulfonyl group, arylsulfonyl group, sulfamoyl group, alkoxyl group, aryloxy group, acyloxy group, alkoxycarbonyloxy group, carbamoyloxy group, substituted or non-substituted amino group, acylamino group, alkoxycarbonylamino group, ureido group, sulfonylamino group, sulfamoylamino group, formyl group, acyl group, carboxyl group, alkoxycarbonyl group, carbamoyl group, and silyl group. The position of substitution on an aromatic ring may be ortho, meta or para.

In the present invention, an alkylthio group means the alkylthio group having 1-8 carbons and includes, for example, a methylthio group, isopropylthio group, and benzylthio group. An arylthio group includes, for example, a phenylthio group, naphthylthio group, and pyridylthio group. An alkylsulfinyl group means the alkylsulfinyl group having 1-8 carbons and includes, for example, a methylsulfinyl group, isopropylsulfinyl group, and benzylsulfinyl group. An arylsulfinyl group includes, for example, phenylsulfinyl group, naphthylsulfinyl group, and pyridylsulfinyl group. An optionally substituted sulfonyl group includes, for example, an alkylsulfonyl group, alkenylsulfonyl group, alkynylsulfonyl group, and arylsulfonyl group. An alkylsulfonyl group means the alkylsulfonyl group having 1-8 carbons and includes, for example, a methylsulfonyl group, isopropylsulfonyl group, and benzylsulfonyl group. An arylsulfonyl group includes, for example, a phenylsulfonyl group, naphthylsulfonyl group, and pyridylsulfonyl group. A sulfamoyl group includes, for example, a dimethylsulfamoyl group, and phenylsulfamoyl group.

In the present invention, an alkoxyl group means the alkoxyl group having 1-8 carbons and includes, for example, a methoxyl group, isopropoxyl group, and benzyloxy group. An aryloxy group includes, for example, a phenoxyl group, naphthyloxy group, and pyridyloxy group. An acyloxy group means the acyloxy group having 1-8 carbons and includes, for example, an acetoxyl group, and benzoyloxy group. An alkoxycarbonyloxy group means the alkoxycarbonyloxy group having 1-8 carbons and includes, for example, a methoxycarbonyloxy group, and trifluoromethoxycarbonyl group. A carbamoyloxy group includes, for example, a dimethylcarbamoyloxy group, and phenylcarbamoyloxy group.

In the present invention, an amino group includes, for example, a non-substituted amino group, dimethylamino group, morpholino group, piperidinyl group, 4-methylpiperazine-1-yl group, and phenylamino group. An acylamino group includes, for example, an acetylamino group, and benzoylamino group. An alkoxycarbonylamino group includes, for example, a methoxycarbonylamino group, ethoxycarbonylamino group, and benzyloxycarbonylamino group. An ureido group includes, for example, a trimethylureido group, and 1-methyl-3-phenyl-ureido group. A sulfonylamino group includes, for example, a methanesulfonylamino group, and benzenesulfonylamino group. A sulfamoylamino group includes, for example, a dimethylsulfamoylamino group.

In the present invention, an acyl group includes, for example, an acetyl group, pivaloyl group, benzoyl group, and pyridinecarbonyl group. An alkoxycarbonyl group includes, for example, a methoxycarbonyl group, and benzyloxycarbonyl group. A carbamoyl group includes for example, a dimethylcarbamoyl group, and phenylcarbamoyl group.

In the present invention, a silyl group includes, for example, a trimethylsilyl group, triisopropylsilyl group, and tert-butyl-diphenyl-silyl group.

In the present invention, R represents an optionally substituted carbocyclic or heterocyclic aryl group or an optionally substituted alkyl group, an optionally substituted alkenyl group or an optionally substituted alkynyl group or substituted or non-substituted amino group. An optionally substituted carbocyclic aryl group represented by R includes, for example: a phenyl group; bromophenyl group; aminophenyl group; methylphenyl group; a group represented by the following general formula (2),

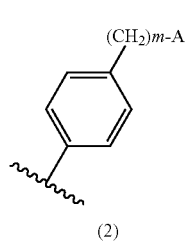

[Formula 9]

(2)

wherein m represents any one of integer 0-5, A represents an optionally substituted cyclic or non-cyclic amino group, an optionally substituted cyclic or non-cyclic acylamino group or an optionally substituted cyclic or non-cyclic sulfonylamino group; and a group represented by the following general formula (2-2),

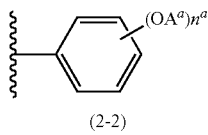

[Formula 10]

(2-2)

wherein $n^a$ represents any one of integer 1-5, $A^a$ represents an alkyl group having 1-6 carbons that may have a substituent and, when $n^a$ is 2-5, the neighboring substituents taken together may form a ring.

In the substituent represented by the general formula (2), m is especially preferable to be 0 or 1. A includes an amino group, acylamino group, and sulfonylamino group. The amino group includes a cyclic amino group, non-cyclic amino group or aromatic amino group. The cyclic amino group includes, for example, a morpholino group, piperidinyl group, piperazinyl group, 4-methylpiperazin-1-yl group, and pyrrolidinyl group. The non-cyclic amino group includes, for example, dimethylamino group, isopropylamino group, cyclohexylamino group, 2-hydroxyethylamino group, and 2-methoxyethylamino group. The aromatic amino group includes, for example, a phenylamino group. The acylamino group includes, for example, an acetylamino group, and benzoylamino group. The sulfonylamino group includes, for example, a methanesulfonylamino group, and benzenesulfonylamino group. Among them, the cyclic amino groups such as the morpholino group, piperidinyl group, piperazinyl group, 4-methylpiperazin-1-yl group, and pyrrolidinyl group are especially preferred.

As a substituent represented by the general formula (2), 4-(morpholin-4-yl)-phenyl group, 4-(morpholin-4-ylmethyl)-phenyl group and 4-(4-methyl-piperazin-1-ylmethyl)-phenyl group are especially preferred.

Among the substituents represented by the general formula (2-2), $n^a$ is preferably 1 and 2. $A^a$ includes a methyl group, ethyl group, and methylene group, and among them, the methyl group is especially preferable. As an alkoxyphenyl group represented by the general formula (2-2), a 4-methoxyphenyl group, 3-methoxyphenyl group, 3,4-dimethoxyphenyl group and 3,4-methylenedioxyphenyl group are preferable and especially the 4-methoxyphenyl group is preferable.

A heterocyclic aryl group represented by R includes, for example, a pyridyl group, pyrimidinyl group, quinolyl group, quinazolyl group, naphthylidinyl group, furyl group, pyrrolyl group, indolyl group, imidazolyl group, pyrazolyl group, oxazolyl group, isoxazolyl group, and triazolyl group, and among them, the pyridyl group and pyrimidinyl group are preferable. A heterocyclic aryl group that has a substituent includes, for example, 2-morpholin-4-yl-pyrimidin-5-yl group.

An alkyl group represented by R includes, for example: a linear alkyl group such as a methyl group, ethyl group, propyl group, and butyl group; a branched alkyl group such as an isopropyl group, 2-methyl propyl group, and tert-butyl group; and a cyclic alkyl group such as a cyclopropyl group, cyclobutyl group, cyclopentyl group, and cyclohexyl group. The alkyl group, represented by R, may have a substituent(s), and the substituent includes, for example: a hydroxy group; a linear alkoxyl group such as a methoxy group, and ethoxy group; a cyclic alkoxyl group such as a tetrahydrofuryl group; an amino group such as a morpholino group; and a cyclic acylamino group such as a 2-oxo-pyrrolidin-1-yl group. Among the alkyl group represented by R, the isopropyl group is especially preferable.

An amino group represented by R includes, for example: a linear amino group such as a dimethylamino group; and a cyclic amino group such as a piperidino group, and morpholino group, and among them, the cyclic amino groups such as the piperidino group are preferable.

In the present invention, as a substituent represented by R, an optionally substituted carbocyclic or heterocyclic aryl group and an optionally substituted alkyl group are preferable. Among them, an optionally substituted carbocyclic aryl group and represented by the general formulas (2) and (2-2), and an optionally substituted alkyl group are preferable, and especially a 4-methoxyphenyl group, 4-(morpholin-4-yl)-phenyl group, 4-(morpholin-4-ylmethyl)-phenyl group, 4-(4-methyl-piperazin-1-ylmethyl)-phenyl group and isopropyl group are preferable.

In the present invention, a substituent represented by Y includes a mercapto group, hydroxy group, halogen atom, cyano group, sulfonyl group, an optionally substituted alkylthio group, an optionally substituted arylthio group, an optionally substituted alkylsulfinyl group, an optionally substituted arylsulfinyl group, an optionally substituted sulfamoyl group, an optionally substituted alkoxyl group, an optionally substituted aryloxy group, an optionally substituted acyloxy group, an optionally substituted alkoxycarbonyloxy group, an optionally substituted carbamoyloxy group, an optionally substituted amino group, an optionally substituted acylamino group, an optionally substituted alkoxycarbonylamino group, an optionally substituted ureido group, an optionally substituted sulfonylamino group, an optionally substituted sulfamoylamino group, a formyl group, an optionally substituted acyl group or an optionally substituted silyl group.

An optionally substituted alkylsulfonyl group represented by Y includes, for example, a 3-dimethylamino-propane-1-sulfonyl group, 3-piperidin-1-yl-propane-1-sulfonyl group, pyridin-3-yl-methanesulfonyl group, dimethylcarbamoylmethyl group, tetrahydro-pyran-2-yl-methanesulfonyl group, and 2-(2-methoxy-ethoxy)-ethanesulfonyl group, and among them, the 3-dimethylamino-propane-1-sulfonyl group and 3-piperidin-1-yl-propane-1-sulfonyl group are preferable.

A sulfonylamino group represented by Y includes, for example, a methanesulfonylamino group, ethanesulfonylamino group, and benzenesulfonylamino group, and among them, the methanesulfonylamino group is preferable.

In the present invention, as a substituent represented by Y, a hydroxy group, mercapto group, an optionally substituted alkylsulfonyl group or sulfonylamino group are preferable, and among them, the hydroxy group is especially preferable.

Among the compounds represented by the general formula (1), the compound represented by the general formula (1-Y'H) where the substituent represented by Y is Y'—H (Y' is S: sulfur atom, O: Oxygen atom, or N: nitrogen atom, H represents hydrogen atom) is often described by the general formula (1'-Y=H). (1-Y'H) and (1'-Y'H) are tautomers and the same compounds.

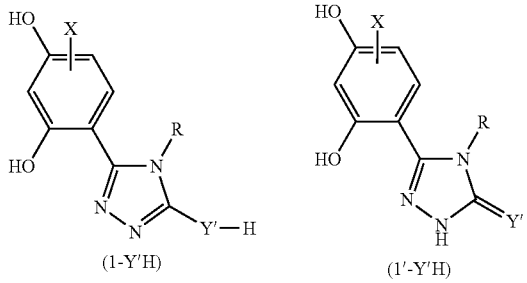

(1-Y'H)    (1'-Y'H)

In the aforementioned general formula (1), X can be: a mercapto group; hydroxy group; halogen atom; nitro group; cyano group; an optionally substituted alkyl group, an optionally substituted alkenyl group or an optionally substituted alkynyl group; an optionally substituted carbocyclic or heterocyclic aryl group; an optionally substituted alkylthio group; an optionally substituted arylthio group, an optionally substituted alkylsulfinyl group, an optionally substituted arylsulfinyl group, an optionally substituted alkylsulfonyl group, an optionally substituted arylsulfonyl group, an optionally substituted sulfamoyl group, an optionally substituted alkoxyl group, an optionally substituted aryloxy group, an optionally substituted acyloxy group, an optionally substituted alkoxycarbonyloxy group, an optionally substituted carbamoyloxy group, an optionally substituted or non-substituted amino group, an optionally substituted acylamino group, an optionally substituted alkoxycarbonylamino group, an optionally substituted ureido group, an optionally substituted sulfonylamino group, an optionally substituted sulfamoylamino group, a formyl group, an optionally substituted acyl group, an optionally substituted carboxyl group, an optionally substituted alkoxycarbonyl group, an optionally substituted carbamoyl group or an optionally substituted silyl group.

An optionally substituted alkyl group represented by X includes, for example, a methyl group, ethyl group, isopropyl group, tert-butyl group, 2,2-dimethylpropyl group, cyclopropyl group, N,N-dimethylaminomethyl group, N,N-dimethylaminoethyl group, morpholinylmethyl group, piperidinylmethyl group, hydroxymethyl group, 1-hydroxyethyl group, 2-hydroxyethyl group, 1-hydroxy-1-methyl-ethyl group, methoxyethyl group, methoxymethyl group, benzyl group, 2-phenylethyl group, and pyridylmethyl group, and the ethyl group, isopropyl group, tert-butyl group and 2,2-dimethylpropyl group are preferable.

An acyl group represented by X includes an acetyl group, propionyl group, pivaloyl group, and benzoyl group, and among them, the acetyl group is preferable.

A carbamoyl group represented by X includes a dimethylcarbamoyl group, 1-piperidinecarbonyl group, and 4-morpholinecarbonyl group, and among them, the dimethylcarbamoyl group is preferable.

An alkenyl group represented by X that may have a substituent includes a 1-alkenyl group, and 2-alkenyl group, and the 1-alkenyl group includes, for example, an ethenyl group, isopropenyl group, 3-hydroxy-1-propenyl group, 2-acetylethenyl group, and 2-phenyl-ethenyl group, and the 2-alkenyl group includes, for example, an allyl group, and 2-butenyl group.

An optionally substituted alkynyl group represented by X includes a 1-alkynyl group and 2-alkynyl group, and the 1-alkynyl group includes, for example, an ethynyl group, 3,3-dimethyl-1-butynyl group, 2-phenyl-ethynyl group, and 2-trimethylsilyl-1-ethynyl group, and the 2-alkynyl group includes, for example, a 2-propynyl group, 2-butynyl group, 3-phenyl-2-propynyl group, 4,4-dimethyl-2-pentynyl group, and 3-trimethylsilyl-2-propynyl group, and the 2-propynyl group and 2-butynyl group are preferable.

An optionally substituted carbocyclic aryl group represented by X includes, for example, a phenyl group, naphthyl group, chlorophenyl group, and methoxyphenyl group.

An optionally substituted heterocyclic aromatic substituent represented by X includes, for example, a pyridyl group, quinolyl group, pyrimidinyl group, and furyl group.

A 2,4-dihydroxyphenyl group may be substituted by one to three Xs at any of the 3, 5, or 6 position, and may be mono-substitution, disubstitution or trisubstitution. For example, a compound in which the 5 position of the 2,4-dihydroxyphenyl group is substituted by X means a 5-monosubstituent represented by the following general formula (3).

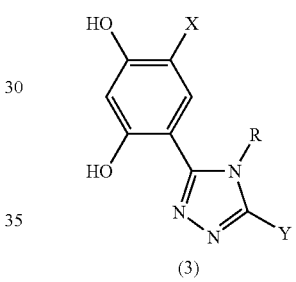

(3)

wherein X, R and Y are the same as X, R and Y as the aforementioned general formula (1).

A compound represented by the general formula (1-1) includes, for example, a compound represented by the following general formula (3-1),

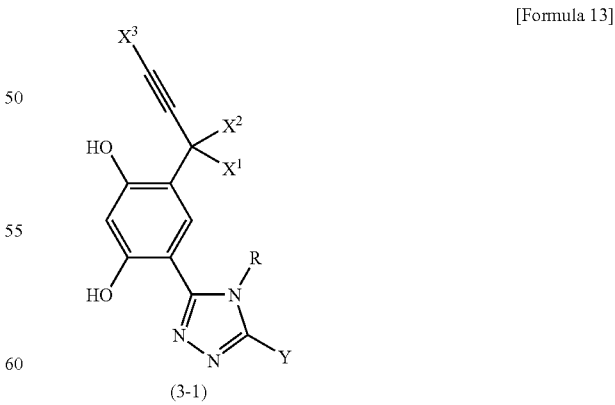

(3-1)

wherein R and Y are the same as R and Y as the general formula (1) described above. $X^1$, $X^2$ and $X^3$ are each independently the same meaning as X of the general formula (1) described above, or the following general formula (3-2),

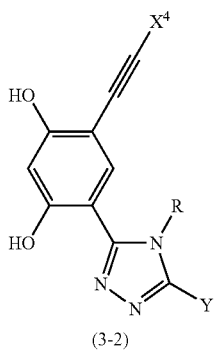

(3-2)

[Formula 14]

wherein R and Y are the same as R and Y as the general formula (1) described above. $X^4$ is the same meaning as X of the general formula (1) described above.

In the general formula (3-1) and (3-2) described above, $X^1$ and $X^2$ may be the same or different and are preferably a hydrogen atom, methyl group or 1-propynyl group. $X^3$ and $X^4$ are preferably a hydrogen atom or methyl group.

As a substituent represented by X of the general formula (1) described above, a chlorine atom, ethyl group, isopropyl group, tert-butyl group, 2,2-dimethylpropyl group, 2-propynyl group or 2-butynyl group is especially preferable.

As a compound represented by the general formula (1), among them, a compound represented by the following general formula (4),

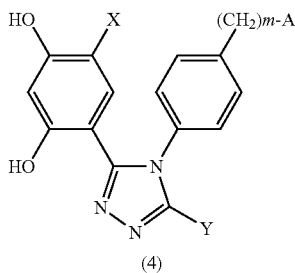

(4)

[Formula 15]

wherein X represents a chlorine atom, ethyl group, isopropyl group, tert-butyl group, 2,2-dimethylpropyl group, 2-propynyl group or 2-butynyl group; Y represents a mercapto group, an optionally substituted alkylsulfonyl group or hydroxy group; m is 0 or 1; and A represents a cyclic amino group, a compound represented by the following general formula (1-2),

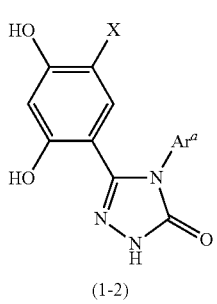

(1-2)

[Formula 16]

wherein X represents a chlorine atom, ethyl group, isopropyl group, tert-butyl group, 2,2-dimethylpropyl group, 2-propynyl group or 2-butynyl group; and Ara represents a 4-methoxyphenyl group, 3-methoxyphenyl group, 3,4-dimethoxyphenyl group, 3,4,5-trimethoxyphenyl group or 3,4-methylenedioxyphenyl group, and a compound represented by the following general formula (1-3),

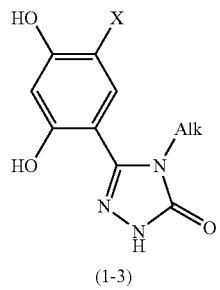

(1-3)

[Formula 17]

wherein X represents a chlorine atom, ethyl group, isopropyl group, tert-butyl group, 2,2-dimethylpropyl group, 2-propynyl group or 2-butynyl group; and Alk represents an optionally substituted alkyl group, are preferable.

Particular examples of the compound represented by the general formula (1) are shown in Table 1 to Table 3-2.

The prodrug of the present invention includes, for example, a compound represented by the following general formula (5),

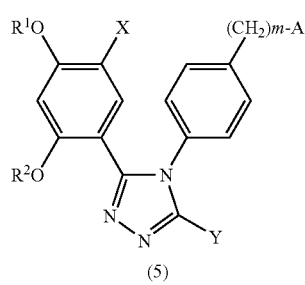

(5)

[Formula 18]

wherein $OR^1$ and $OR^2$ represent a substituent which is converted to a hydroxy group easily due to dissociation of O—$R^1$ bond and O—$R^2$ bond in vivo; and any one of $R^1$ and R may be a hydrogen atom. $R^1$ and $R^2$ include, for example: an acyl group such as an acetyl group, and trifluoroacetyl group; a carbamoyl group such as a dimethylcarbamoyl group; an alkoxycarbonyl group such as a methoxycarbonyl group; a phosphoryl group such as a $(MeO)_2P(=O)—$; and an alkoxymethyl group such as a methoxymethyl group.

The triazole derivative of the present invention may form a salt with an acid or a base, and the present invention includes a HSP90 inhibitor and a cancer therapeutic agent containing a salt of a compound represented by the general formula (1) as an active ingredient. A salt with an acid includes, for example, an inorganic acid salt such as a hydrochloride, hydrobromide, and sulfate and a salt with an organic acid such as a trifluoroacetic acid, methanesulfonic acid, and p-toluenesulfonic acid. A salt with a base includes, for example, a sodium salt. These salts can be produced by a standard method, and particular examples include for example, the following compounds.

4-{5-Hydroxy-4-[4-(morpholin-4-yl}-phenyl]-4H-[1,2,4]triazol-3-yl}-6-isopropyl-benzene-1,3-diol (OH-a01) hydrochloride, 4-{5-hydroxy-4-[4-(morpholin-4-ylmethyl)-phenyl]-4H-[1,2,4]triazol-3-yl}-6-isopropyl-benzene-1,3-diol (OH-a02) hydrochloride, 5-[5 (but-2-ynyl)-2,4-dihydroxy-phenyl]-4-[4-(morpholin-4-ylmethyl)-phenyl]-2,4-dihydro-[1,2,4]triazol-3-one (OH-c02) hydrochloride, 5-[2,4-dihydroxy-5 (prop-2-ynyl)-phenyl]-4-[4-(morpholin-4-ylmethyl)-phenyl]-2,4-dihydro-[1,2,4]triazol-3-one (OH-e02) hydrochloride, 5-(2,4-dihydroxy-5-isopropyl-phenyl)-4-[4-(4-methyl-piperazin-1-ylmethyl)-phenyl]-2,4-dihydro-[1,2,4]triazol-3-one (OH-a13) dihydrochloride, 5-(2,4-dihydroxy-5-isopropyl-phenyl)-4-[2-(morpholin-4-yl)-pyrimidin-5-yl]-2,4-dihydro-[1,2,4]triazol-3-one (OH-a17) hydrochloride, 4-isopropyl-6-{5-methanesulfonyl-4-[4-(morpholin-4-ylmethyl)-phenyl]-4H-[1,2,4]triazol-3-yl}-benzene-1,3-diol (SFN-a02) hydrochloride, 4-[5-(3-dimethylamino-propane-1-sulfonyl)-4-(4-methoxyphenyl)-4H-[1,2,4]triazol-3-yl]-6-isopropyl-benzene-1,3-diol (SFN2-a08) hydrochloride, 4-isopropyl-6-[4-(4-methoxy-phenyl)-5-(3-piperidin-1-yl-propane-1-sulfonyl)-4H-[1,2,4]triazol-3-yl]-benzene-1,3-diol (SFN3-a08) hydrochloride, 4 (but-2-ynyl)-6-{5-mercapto-4-[4-(morpholin-4-ylmethyl)-phenyl]-4H-[1,2,4]triazol-3-yl}-benzene-1,3-diol trifluoroacetate (SH-c02-TF), 4-isopropyl-6-{5-methylsulfanyl-4-[4-(morpholin-4-ylmethyl)-phenyl]-4H-[1,2,4]triazol-3-yl}-benzene-1,3-diol trifluoroacetate (SMe-a02-TF), 4-isopropyl-6-{5-methylsulfinyl-4-[4-(morpholin-4-oxide-4-ylmethyl)-phenyl]-4H-[1,2,4]triazol-3-yl}-benzene-1, 3-diol trifluoroacetate (SFX-a07-TF), and 4-bromo-6-{5-methylsulfanyl-4-[4-(morpholin-4-yl)-phenyl]-4H-[1,2,4]triazol-3-yl}-benzene-1,3-diol trifluoroacetate (SMe-d01-TF).

The compound of the present invention can be produced, for example, in the following way.

Scheme (1)

[Formula 19]

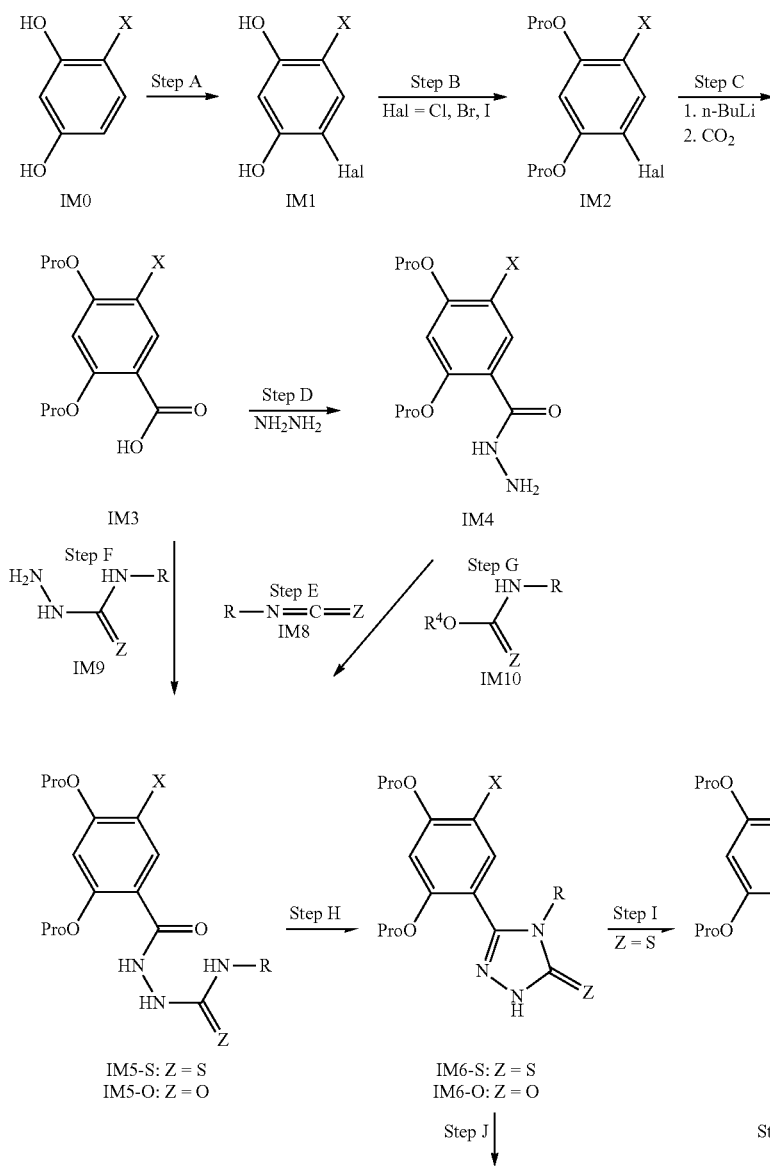

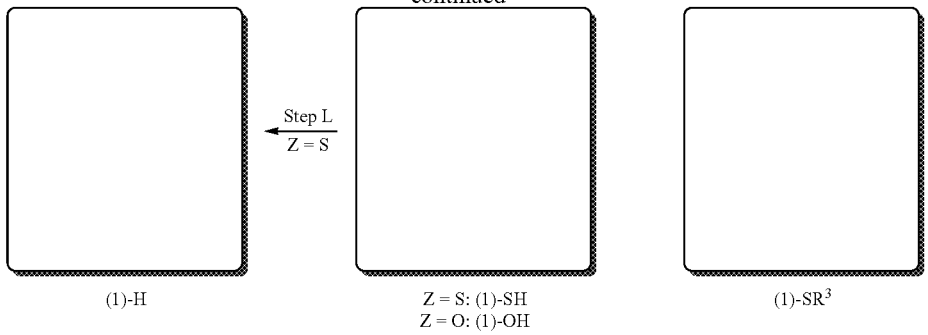

(1)-H     Z = S: (1)-SH     (1)-SR³
             Z = O: (1)-OH

In the scheme (1), X and R have the same meaning as X and R in the general formula (1). Hal represents a halogen atom. Pro represents a protective group of a hydroxy group. Z represents an oxygen atom or sulfur atom. $R^3$ represents an alkyl group. $R^4$ represents an alkyl group or aryl group. Each step will be described below.

Step A: a step for halogenating a resorcinol derivative represented by the general formula (IM0). The halogen atom includes a chlorine atom, bromine atom or iodine atom, and among them, the bromine atom is preferable. In the case where the halogen atom is the bromine atom, a brominating agent includes N-bromosuccinimide, benzyltrimethylammonium tribromide, and bromine, and among them benzyltrimethylammonium tribromide is preferable. In this step, it is preferable to use benzyltrimethylammonium tribromide as a halogenating agent, and the reaction is carried out in a halogenated solvent at a temperature from 0° C. to 50° C.

Step B: a step for protecting the hydroxy group of the resorcinol derivative represented by the general formula (IM1). A protective group, Pro, that may be used in this step includes, for example, an alkoxymethyl group, substituted or non-substituted benzyl group, and silyl group. Among them, the alkoxymethyl group such as a methoxymethyl group, and benzyloxymethyl group are preferable, and the methoxymethyl group is especially preferable. In the case where Pro is the methoxymethyl group, for example, methoxymethylchloride can be used as a methoxymethylating agent, and the reaction can be carried out in a solvent such as a polar non-proton solvent such as dimethylformamide, a halogenated solvent, a nitrile solvent such as acetonitrile or an ether solvent, in the presence of a base such as triethylamine, pyridine, diisopropylethylamine or potassium carbonate, at a temperature from −20° C. to 60° C.

Step C: a step for exchanging the halogen atom in the halogen substituted resorcinol derivative represented by the general formula (IM2) with a metal atom such as lithium, and then converting to a carboxy group. The halogen-lithium exchange reaction is carried out, for example, in an ether solvent such as tetrahydrofuran, and diethylether, using n-butyllithium at a temperature from −100° C. to 0° C., preferably from −60° C. to −30° C. Then dry ice was added to the mixture, and the reaction was performed at a temperature from −80° C. to 50° C. to afford a carboxylic acid (IM3).

Step D: a step for synthesizing an acylhydrazide derivative represented by the general formula (IM4) by reacting a carboxylic acid derivative represented by the general formula (IM3) with hydrazine. The present step can be carried out, for example, using carbonyldiimidazole or the like in tetrahydrofuran solution by adding benzylbromide or the like as necessary to produce 1-acyl-3-benzylimidazolium salt, and then reacting with hydrazine. Alternatively, the reaction with hydrazine can be carried out, using a carbodiimide such as dicyclohexylcarbodiimide or 1-(3-dimethylaminopropyl)-3-ethylcarbodiimide as a condensation agent, and under coexistence of an activating agent such as 1-hydroxybenzotriazole as necessary, in a solvent such as dimethylformamide.

A compound represented by the general formula (IM5-S) and general formula (IM5-O) can be synthesized from an acylhydrazide derivative represented by the general formula (IM4) by Step E or Step G, or from a carboxylic acid derivative represented by the general formula (IM3) by Step F.

Step E: a step for synthesizing a derivative represented by the general formula (IM5-S) or general formula (IM5-O) by reacting an acylhydrazide derivative represented by the general formula (IM4) with an isothiocyanate derivative represented by the general formula (IM8, Z=sulfur atom) or an isocyanate derivative represented by the general formula (IM8, Z=oxygen atom). The present step can be carried out, for example, by reacting an acylhydrazide derivative and isothiocyanate or isocyanate at a temperature from 0° C. to 150° C., preferably from 50° C. to 100° C. in a solvent such as ethanol, tert-butanol, and dimethylformamide.

Step F: a step for synthesizing a derivative represented by the general formula (IM5) by reacting a carboxylic acid derivative represented by the general formula (IM3) and a compound represented by the general formula (IM9). The present step can be carried out, for example, by reacting in a solvent such as dimethylformamide, tetrahydrofuran, and N-methylpyrrolidone, using a condensation agent, for example, dicyclohexylcarbodiimide or 1-(3-dimethylaminopropyl)-3-ethylcarbodiimide, under the coexistence of an activating agent such as 1-hydroxybenzotriazole as necessary, at a temperature from −20° C. to 50° C., preferably from 0° C. to 30° C.

Step G: a step for synthesizing a derivative represented by the general formula (IM5-S) or general formula (IM5-O) by reacting an acylhydrazide derivative represented by the general formula (IM4) with a thiocarbamate derivative or carbamate derivative represented by the general formula (IM10). The present step can be carried out, for example, by reacting an acylhydrazide derivative with a thiocarbamate derivative or a carbamate derivative represented by the general formula (IM10) in a solvent such as ethanol, tert-butanol, and dimethylformamide at a temperature from 0° C. to 150° C., preferably 50° C. to 100° C.

A compound represented by the general formula (IM6-S) or general formula (IM6-O) can be synthesized from a compound represented by the general formula (IM5-S) or general formula (IM5-O) by Step H.

Step H: a step for synthesizing a triazole derivative represented by the general formula (IM6-S) or (IM6-O) by a ring closure reaction of a compound represented by the general formula (IM5-S) or general formula (IM5-O). The present step can be carried out, for example, by reacting in the presence of a base such as sodium hydroxide, and potassium hydroxide in a solvent such as water, and ethanol at a temperature from 20° C. to 150° C., preferably from 70° C. to 120° C.

Step I: a step for synthesizing an alkylsulfanyltriazole derivative represented by the general formula (IM7-SR3) by alkylating a triazolethione derivative represented by the general formula (IM6-S) using an alkylating agent. The alkylating agent includes an alkylhalide such as methyl iodide, and a sulfonic acid alkyl ester or the like. The present step can be carried out, for example, by reacting a triazolethione derivative represented by the general formula (IM6-S) and an alkyl halide such as methyl iodide, in a solvent such as an ether solvent such as tetrahydrofuran, and diethyl ether, a polar solvent such as dimethylformamide, a halogen solvent such as dichloromethane, or a hydrocarbon solvent such as toluene.

Step J and Step K: steps for deprotecting the protective group of the hydroxy group of a compound in which the hydroxy group is protected, represented by the general formulas (IM6-S), (IM6-O) or (IM7-SR3), and for producing a benzene 1,3-diol derivative represented by the general formulas (1) —SH, (1) —OH or (1) —S3. In the case where the protective group of the hydroxy group is a methoxymethyl group, the steps can be carried out under an acidic condition. Any of catalysts, which are known to deprotect a methoxymethyl group and have no effect other than the protective group, may be used as an acid catalyst which includes: an inorganic acid such as hydrochloric acid, and sulfuric acid; a sulfonic acid such as toluenesulfonic acid, methanesulfonic acid, and trifluorosulfonic acid; a carboxylic acid such as acetic acid, and trifluoroacetic acid; and a strong acid-weak base salt such as pyridiniumparatoluenesulfonate. In the case where the protective group is a methoxymethyl group, it is preferable to carry out the reaction, for example, using 0.5-5.0 N hydrochloric acid as an acid catalyst, in a mixed solvent of water and ethanol, methanol, tetrahydrofuran or the like, at a temperature from 10° C. to 40° C., with a reaction time for 3 hours to 3 days.

The isocyanate derivative (IM8:Z=oxygen atom) used in Step E can be synthesized, for example, according to the method described in Angew. Chem. Int. Ed. Engl. 26, 894 (1987).

The isothiocyanate derivative (IM8:Z=sulfur atom) used in Step E can be synthesized, for example, according to the method described in WO9921845.

The derivative (IM9) used in Step F and the carbamate derivative (IM10) used in Step G can be synthesized, for example, according to the method described in Chem. Pharm. Bull. 48 (12) 1935-1946 (2000).

When the triazole derivative of the present invention, a prodrug thereof or a pharmaceutically acceptable salt thereof is used as an anticancer agent, it can be administered safely, orally or parenterally (systemic administration, local administration or the like), in a formulation such as powder, granules, tablets, caplets, capsules, injectables, suppositories, and ointments, singly or mixed with pharmaceutically acceptable additives such as carriers, excipients, disintegrators, binders, lubricants, fluidizers, coating agents, suspending agents, emulsifiers, stabilizers, preservatives, flavoring agents, aroma agents, diluents, and solubilizers. The content of the triazole derivative of the present invention, a prodrug thereof or a pharmaceutically acceptable salt thereof in a formulation may be different depending on the formulation but normally, it is preferable to be 0.1-100 weight %. The dosage may be different depending on the administration route, the age of a patient, the actual symptom to be prevented or treated and the like, but, for example, in the case where the drug is orally administered to an adult, the dosage can be 0.01 mg to 2000 mg as an active ingredient per day, preferably 0.1 mg to 1000 mg, which can be administered once a day or several times a day.

The triazole derivative of the present invention, a prodrug thereof or a pharmaceutically acceptable salt thereof possess a HSP90 inhibitory activity and are useful as the cancer therapeutic agent.

EXAMPLES

Next, the present invention will be described more particularly by the Examples but the present invention is not limited at all by these examples. In addition, the pharmacological test results of the representative compounds of the present invention demonstrating the efficacy of the compound of the present invention are shown in Table 4-1 to 6-4.

The analytical method of LC/MS for the compounds of Examples are as follows:
1)
Instrument: Shimadzu LCMS-QP8000 alpha
Column: Inertsil ODS-III, 2.1 mm i.d.×100 mm,
Mobile phase A: acetonitrile/formic acid (99.9/0.1)
Mobile phase B: water/formic acid (99.9/0.1)

| Gradient: Time (minute) | 0.0 | 5.5 | 5.51 | 10.0 |
|---|---|---|---|---|
| A Concentration | a | 100 | a | a |

Flow rate: 0.3 mL/minute
Method 1) a=20; Method 2) a=5
2)
Instrument: Shimadzu LCMS-2010A
Column: Inertsil ODS-III, 2.1 mm i.d.×100 mm,
Mobile phase A: acetonitrile/formic acid (99.9/0.1)
Mobile phase B: water/formic acid (99.9/0.1)

| Gradient: Time (minute) | 0.0 | 5.5 | 6.5 | 6.51 | 10.0 |
|---|---|---|---|---|---|
| A concentration | a | 90 | 90 | a | a |

Flow rate: 0.3 mL/minute
Method 3) a=20; Method 4) a=5; Method 5) a=40; Method 6) a=0; Method 7) a=60.

Example 1-1

Preparation of 4-isopropyl-6-{5-mercapto-4-[4-(morpholin-4-yl)-phenyl]-4H-[1,2,4]triazol-3-yl}-benzene-1,3-diol (SH-a01) and trifluoroacetate thereof (SH-a01-TF)

Scheme (1-1)

[Formula 20]

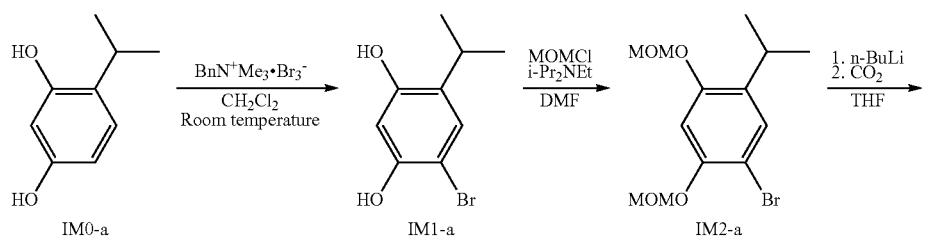

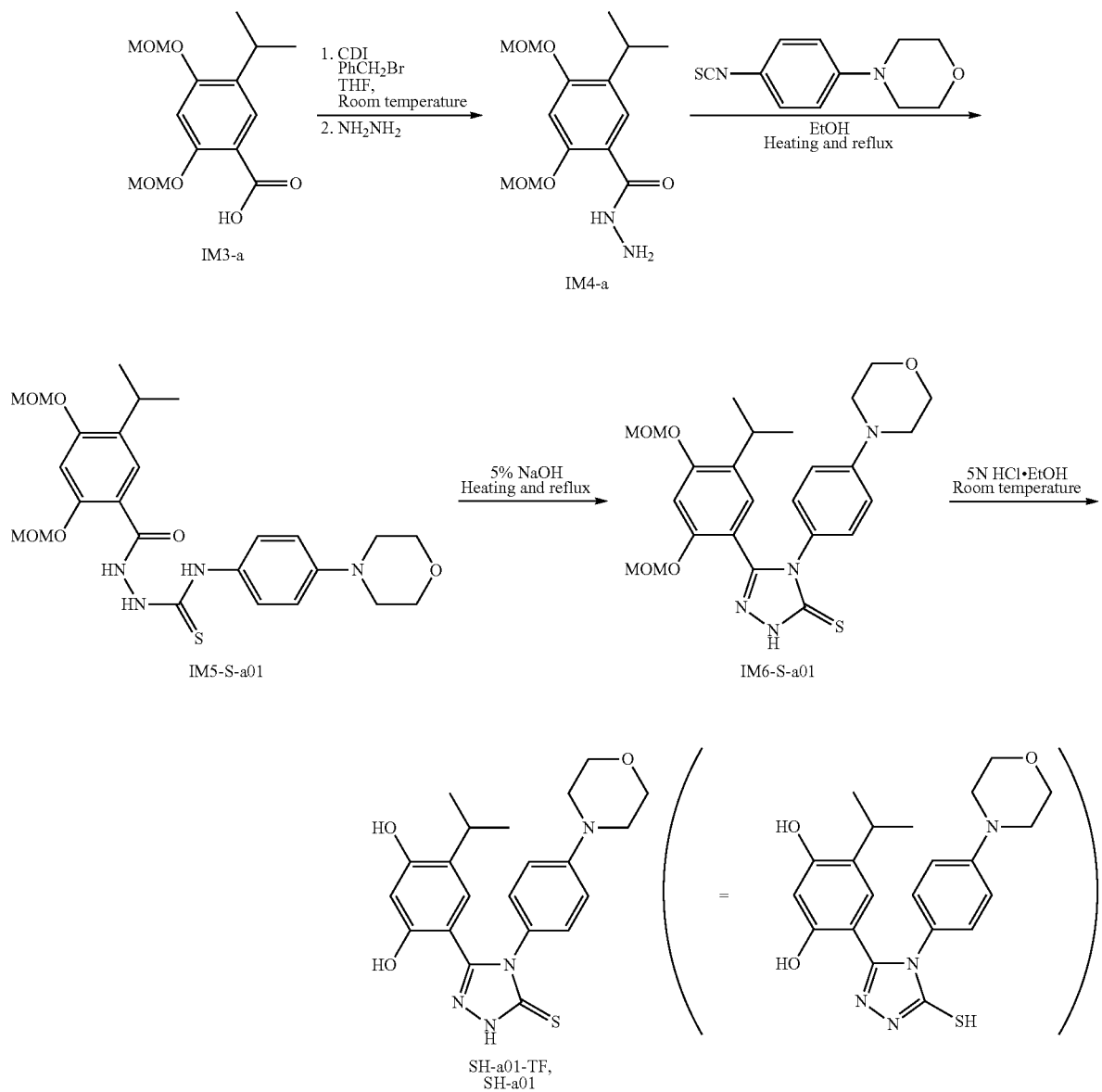

The First Step: Preparation of 4-bromo-6-isopropyl-benzene-1,3-diol (IM1-a)

4-isopropyl-benzene-1,3-diol (IMO-a: 9.13 g, 60 mmol) and benzyltrimethyl ammoniumtribromide (24.6 g, 63 mmol) and methylene chloride 250 mL were placed in a 500 mL three-neck flask and were stirred at room temperature for 4 hours. After the reaction was finished, the reaction mixture was washed twice with saturated ammonium chloride and once with saturated sodium chloride, and then dried over anhydrous sodium sulfate. After filtration and evaporation, the residue was purified by silica gel column chromatography to obtain the title compound (IM1-a: 10.5 g, 76%).

LC/MS (Method 3): m/z (ESI, POS): 229, 231 [M+H]$^+$; retention time: 5.68 minutes.

$^1$H-NMR (200 MHz, CDCl$_3$, TMS) ppm: 7.21 (1H, s), 6.48 (1H, s), 5.33 (1H, s), 4.87 (1H, s), 3.10 (1H, sept, J=6.9 Hz), 1.22 (6H, d, J=6.9 Hz).

The material compound, 4-isopropyl-benzene-1,3-diol (IM0-a) was synthesized by the method according to WO 04/72051 (Patent Document 6).

The Second Step: Preparation of 1-bromo-5-isopropyl-2,4-bis-methoxymethoxy-benzene (IM2-a)

4-bromo-6-isopropyl-benzene-1,3-diol (IM1-a: 10.5 g, 45.5 mmol), dimethyl formamide (50 mL) and ethyldiisopropylamine (39.6 mL, 227 mmol) were placed in a 100 mL eggplant shaped flask, and the solution was cooled to 0° C., mixed with methoxymethylchloride (17.3 mL, 227 mmol) and the mixture was allowed to come to room temperature. After stirring for 12 hours the solution was heated to 50° C. and stirring was continued further for 6.5 hours. After completing the reaction, ethyl acetate was added, and after washing the organic layer 4 times with saturated sodium chloride, the organic layer was dried anhydrous sodium sulfate. After filtration and evaporation, the residue was purified by silica gel column chromatography to obtain the title compound (IM2-a: 12.1 g, 83.1%).

LC/MS (Method 3): m/z (ESI, POS): 318, 320 [M+H]$^+$; retention time: 7.72 minutes.

$^1$H-NMR (200 MHz, CDCl$_3$, TMS) ppm: 7.32 (1H, s), 6.93 (1H, s), 5.21 (2H, s), 5.18 (2H, s), 3.53 (3H, s), 3.49 (3H, s), 3.24 (1H, sept, J=6.8 Hz), 1.19 (6H, d, J=6.8 Hz).

The Third Step: Preparation of
5-isopropyl-2,4-bis-methoxymethoxy-benzoic acid
(IM3-a)

1-bromo-5-isopropyl-2,4-bis-methoxymethoxy-benzene (IM2-a: 12.0 g, 37.8 mmol) and tetrahydrofuran (150 mL) were placed in a 300 mL three-neck flask and cooled to –60° C. To this mixture a hexane solution of N-butyllithium (24 mL, 1.59 M) was added slowly, and after adjusting the temperature of the solution to –40° C. the mixture was stirred for 1 hour. Dry ice powder was added to the reaction mixture and the reaction mixture was allowed to come to room temperature. After completing the reaction, the reaction mixture was mixed with distilled water and extracted with ethyl acetate. The extracted organic layer was dried over anhydrous sodium sulfate. After filtration and evaporation, the solid material obtained was purified by suspending in hexane to obtain the title compound (IM3-a: 6.6 g, 62%).

LC/MS (Method 3): m/z (ESI, POS): 285 [M+H]$^+$; retention time: 5.83 minutes.

$^1$H-NMR (200 MHz, CDCl$_3$, TMS) ppm: 10.6 (1H, brs), 8.03 (1H, s), 7.27 (1H, s), 5.40 (2H, s), 5.27 (2H, s), 3.57 (3H, s), 3.50 (3H, s), 3.26 (1H, sept, J=6.9 Hz), 1.23 (6H, d, J=6.9 Hz).

The Fourth Step: Preparation of
5-isopropyl-2,4-bis-methoxymethoxy-benzoic acid
hydrazide (IM4-a)

5-isopropyl-2,4-bis-methoxymethoxy-benzoic acid (IM3-a: 2.84 g, 10 mmol), N,N'-carbonyldiimidazole (1.62 g, 10 mmol) and tetrahydrofuran 100 mL were placed in a 300 mL eggplant shaped flask and stirred at room temperature for 4 hours. The reaction mixture was mixed with benzylbromide (1.19 mL, 10 mL), stirred at room temperature for further 4 hours and then mixed with hydrazine mono hydrate (0.63 mL, 13 mmol) and stirred at room temperature overnight. After completing the reaction, most of the reaction mixture was removed under reduced pressure, and the residue was mixed with ethyl acetate. The organic layer was washed with saturated sodium hydrogen carbonate and saturated sodium chloride solutions, dried over anhydrous sodium sulfate. After filtration and evaporation, the residue was purified by silica gel column chromatography to obtain the title compound (IM4-a: 2.44 g, 82%).

LC/MS (Method 3): m/z (ESI, POS): 299 [M+H]$^+$; retention time: 4.54 minutes.

$^1$H-NMR (200 MHz, CDCl$_3$, TMS) ppm: 8.85 (1H, brs), 8.05 (1H, s), 6.93 (1H, s), 5.30 (2H, s), 5.24 (2H, s), 3.52 (3H, s), 3.50 (3H, s), 3.26 (1H, sept, J=6.9 Hz), 1.23 (6H, d, J=6.9 Hz).

The Fifth Step: Preparation of 4-[4-(morpholin-4-yl)-phenyl]-1-(5-isopropyl-2,4-bismethoxy methoxy-benzoyl)thiosemicarbazide (IM5-S-a01)

5-isopropyl-2,4-bis-methoxymethoxy-benzoic acid hydrazide (IM4-a: 29.8 mg, 0.1 mmol), 4-(4-isothiocyanate-phenyl)-morpholine (23.4 mg, 0.1 mmol) and ethanol (1 mL) were placed in a test tube and heated under reflux for 2 hours. After completing the reaction the reaction mixture was concentrated under reduced pressure to obtain crude crystals of 4-(4-morpholin-4-yl-phenyl)-1-(5-isopropyl-2,4-bis-methoxymethoxy-benzoyl)thiosemicarbazide (IM5-S-a01). These crude crystals were subjected to the next reaction without purification in particular.

LC/MS (Method 1): m/z (ESI, POS): 519 [M+H]$^+$; retention time: 6.54 minutes.

The Sixth Step: Preparation of 5-(5-isopropyl-2,4-bis-methoxymethoxy-phenyl)-4-[4-(morpholin-4-yl)-phenyl]-2,4-dihydro-[1,2,4]triazol-3-thione (IM6-S-a01)

Crude crystals of 4-[4-(morpholin-4-yl)-phenyl]-1-(5-isopropyl-2,4-bis-methoxymethoxy-benzoyl)thiosemicarbazide (IM5-S-a01) and 5% aqueous sodium hydroxide (1 mL) were placed in a test tube and refluxed for 2 hours. After completing the reaction, the reaction mixture was extracted with methylene chloride, and the organic layer was combined drying over anhydrous sodium sulfate. Filtration and evaporation gave crude crystals of 5-(5-isopropyl-2,4-bis-methoxymethoxy-phenyl)-4-(4-morpholin-4-yl-phenyl)-2,4-dihydro-[1,2,4]triazol-3-thione (IM6-S-a01). These crude crystals were subjected to the next reaction without purification in particular.

LC/MS (Method 1): m/z (ESI, NEG): 499 [M+H]$^-$; retention time: 6.44 minutes.

The Seventh Step: Preparation of 4-isopropyl-6-{5-mercapto-4-[4-(morpholin-4-yl)-phenyl]-4H-[1,2,4]triazol-3-yl}-benzene-1,3-diol (SH-a01) and trifluoroacetate salt thereof (SH-a01-TF)

Crude crystals of 5-(5-isopropyl-2,4-bis-methoxymethoxy-phenyl)-4-[4-(morpholin-4-yl)-phenyl]-2,4-dihydro-[1,2,4]triazol-3-thione (IM6-S-a01) and a mixed solvent of 5.0 N aqueous hydrochloric acid (1 mL) and ethanol (1 mL) were placed in a test tube and stirred at room temperature for 24 hours. After completing the reaction, the reaction mixture was neutralized with 10 N aqueous sodium hydroxide solution and then extracted with ethyl acetate and methylene chloride, and the collected organic layer was dried over anhydrous sodium sulfate. After filtration and evaporation, thus obtained residue was purified by HPLC fractionation to obtain the title compound (SH-a01: 7.6 mg, 17%: 3 steps from IM4-a).

LC/MS (Method 1): m/z (ESI, POS): 413 [M+H]$^+$; retention time: 5.51 minutes.

Also, by using 0.1% trifluoroacetic acid-acetonitrile/water in the purification step by HPLC fractionation, the trifluoroacetate salt was similarly obtained (SH-a01-TF).

Example 1-2

Preparation of 4-isopropyl-6-{5-mercapto-4-[4-(morpholin-4-ylmethyl)-phenyl]-4H-[1,2,4]triazol-3-yl}-benzene-1,3-diol (SH-a02)

Scheme (1-2)

[Formula 21]

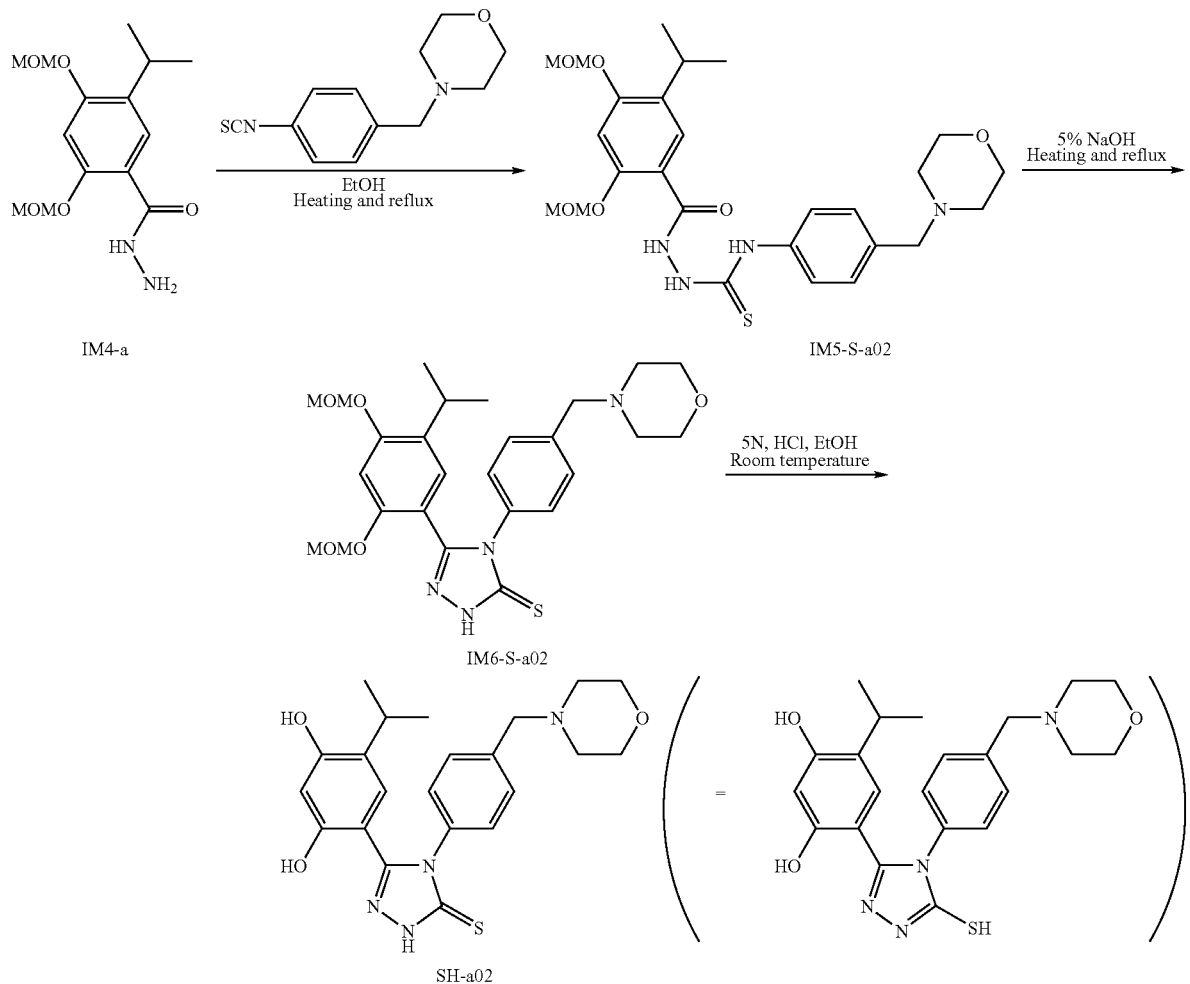

The First Step: Preparation of 4-[4-(morpholin-4-ylmethyl)-phenyl]-1-(5-isopropyl-2,4-bis-methoxymethoxy-benzoyl)thiosemicarbazide (IM5-S-a02)

5-isopropyl-2,4-bis-methoxymethoxy-benzoic acid hydrazide (IM4-a: 1.99 g, 6.67 mmol), 4-(4-isothiocyanate-benzyl)-morpholine (1.72 g, 7.34 mmol) and ethanol (30 mL) were placed in a 100 mL eggplant shaped flask and heated under reflux for 2 hours. After completing the reaction, the reaction mixture was concentrated under reduced pressure to obtain 4-[4-(morpholin-4-ylmethyl)-phenyl]-1-(5-isopropyl-2,4-bismethoxymethoxy-benzoyl)thiosemicarbazide (IM5-S-a02). This crude product was subjected to the next reaction without purification in particular.

LC/MS (Method 3): m/z (ESI, POS): 533 [M+H]$^+$; retention time: 3.72 minutes.

The Second Step: Preparation of 5-(5-isopropyl-2,4-bis-methoxymethoxy-phenyl)-4-[4-(morpholin-4-ylmethyl)-phenyl]-2,4-dihydro-[1,2,4]triazol-3-thione (IM6-S-a02)

Crude crystals of 4-[4-(morpholin-4-ylmethyl)-phenyl]-1-(5-isopropyl-2,4-bismethoxymethoxy-benzoyl)thiosemicarbazide (IM5-S-a02) and 5% aqueous sodium hydroxide (30 mL) were placed in a 100 mL eggplant shaped flask and refluxed for 2 hours. After completing the reaction, the reaction mixture was extracted with methylene chloride, and the organic layer was combined, dried over anhydrous sodium sulfate. After filtration and evaporation, the residue thus obtained was purified by silica gel column chromatography to obtain the title compound (IM6-S-a02: 1.43 g, 41.6%).

LC/MS (Method 3): m/z (ESI, POS): 515 [M+H]$^+$; retention time: 3.42 minutes.

The Third Step: Preparation of 4-isopropyl-6-{5-mercapto-4-[4-(morpholin-4-ylmethyl)-phenyl]-4H-[1,2,4]triazol-3-yl}-benzene-1,3-diol (SH-a02)

Crystals of 5-(5-isopropyl-2,4-bis-methoxymethoxy-phenyl)-4-[4-(morpholin-4-ylmethyl)-phenyl]-2,4-dihydro-[1,2,4]triazol-3-thione (IM6-S-a02) (1.43 g, 2.77 mmol) and a mixed solvent of 5.0 N aqueous hydrochloric acid (15 mL) and ethanol (15 mL) were placed in a 100 mL eggplant shaped flask and stirred at room temperature for 3.5 hours. After completing the reaction, the reaction mixture was neutralized with 5 N aqueous sodium hydroxide and then extracted with ethyl acetate. After drying over anhydrous sodium sulfate the collected organic layer was concentrated under reduced pressure. The residue thus obtained was purified by silica gel column chromatography to obtain the title compound (SH-a02: 647 mg, 54.7%).

LC/MS (Method 4): m/z (ESI, POS): 427 [M+H]$^+$; retention time: 3.83 minutes.

$^1$H-NMR (200 MHz, DMSO-d$_6$, TMS) ppm: 13.9 (1H, s), 9.62 (1H, s), 9.43 (1H, s), 7.32 (2H, d, J=8.1 Hz), 7.18 (2H, d, J=8.1 Hz), 6.80 (1H, s), 6.23 (1H, s), 3.62-3.52 (4H, m), 3.45 (2H, s), 2.94 (1H, sept, J=6.8 Hz), 2.40-2.25 (4H, m), 0.94 (6H, d, J=6.8 Hz)

Example 1-3

Preparation of 4-[4-(4-bromo-phenyl)-5-mercapto-4H-[1,2,4]triazol-3-yl]-6-isopropyl-benzene-1,3-diol (SH-a03)

The title compound (SH-a03) was synthesized in a similar manner as described in Example 1-1.

LC/MS (Method 5): m/z (ESI, POS): 406, 408 [M+H]$^+$; retention time: 4.38 minutes.

$^1$H-NMR (200 MHz, CDCl$_3$, TMS) ppm: 9.25 (1H, s), 7.75 (2H, d, J=8.7 Hz), 7.26 (2H, d, J=8.7 Hz), 6.43 (1H, s), 6.42 (1H, s), 2.91 (1H, sept, J=6.9 Hz), 0.81 (6H, d, J=6.9 Hz).

Example 1-4

Preparation of 4-(but-2-ynyl)-6-{5-mercapto-4-[4-morpholin-4-ylmethyl]-phenyl}-4H-[1,2,4]trioazol-3-yl]-benzene-1,3-diol trifluoroacetate (SH-c02-TF)

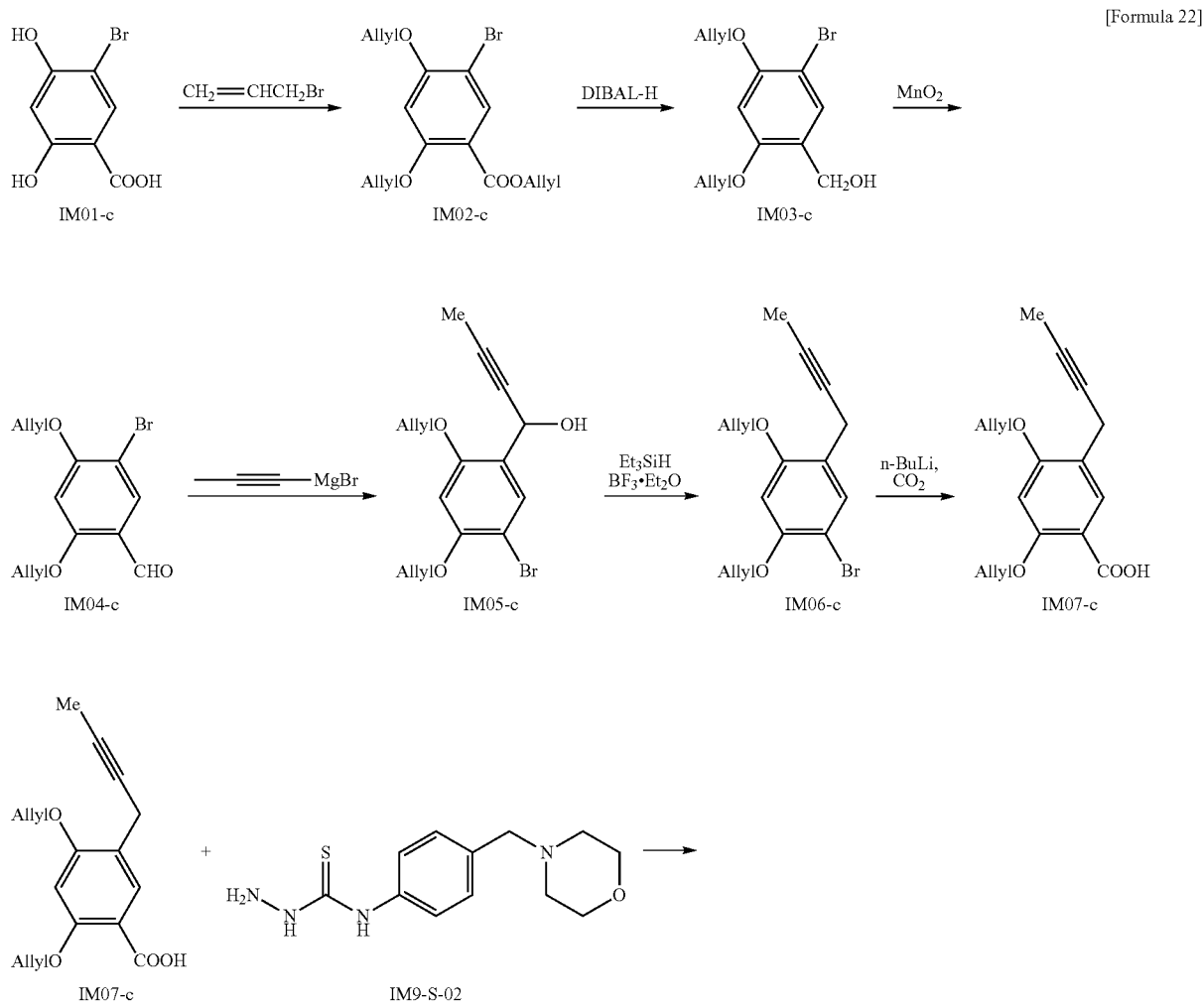

Scheme (1-4) [Formula 22]

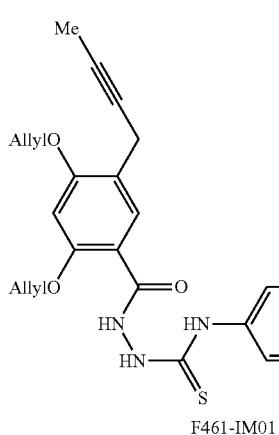
F461-IM01

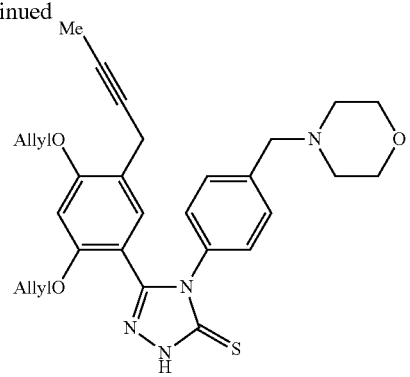
F461-IM02

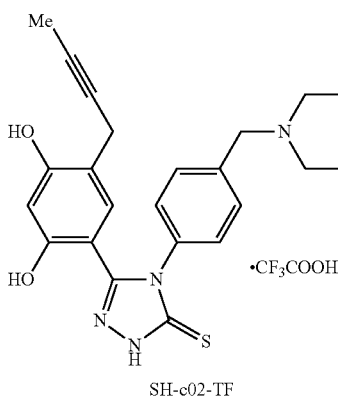
SH-c02-TF

The First Step: Preparation of 2,4-bis-aryloxy-5-bromo-benzoic acid allyl ester (IM02-c)

5-bromo-2,4-dihydroxy-benzoic acid (IM01-c: 6.99 g, 30 mmol), potassium carbonate (16.58 g, 120 mmol) and dimethylformamide (60 mL) were placed in a 500 mL flask under a atmosphere of nitrogen, and while stirring at room temperature, allylbromide (8.6 mL, 100 mmol) was added dropwise. After stirring at room temperature for 3 hours, the reaction mixture was mixed with water (600 mL) and extracted twice with ethyl acetate (600 mL). After washing with saturated sodium chloride solution, the organic layer was dried over anhydrous sodium sulfate. Filtration and evaporation gave the title compound (IM02-c: 10.4 g, 98%).

LC/MS (Method 3): m/z (ESI, POS): 355 [M+2+H]$^+$; retention time: 7.79 minutes.

The Second Step: Preparation of (2,4-bis-allyloxy-5-bromo-phenyl)methanol (IM03-c)

IM02-c (1.41 g, 4 mmol) and dichloromethane (20 mL) were placed in a 300 mL three-neck flask under a atmosphere of nitrogen, cooled to −78° C., and a toluene solution of 1.01M diisobutylaluminum hydride (8.8 mL) was slowly added dropwise so that the inside temperature did not rise to −70° C. or higher. After stirring for 1 hour, methanol (4 mL) and saturated ammonium chloride solution (20 mL) were added, and the mixture was allowed to come to room temperature. The mixture was extracted twice with chloroform (50 mL) (at this time 2M hydrochloric acid was added until the phases were separated). After washing with saturated sodium chloride solution, the organic layer was dried over anhydrous sodium sulfate. After filtration and evaporation, the residue was purified with silica gel column chromatography (hexane-ethyl acetate=2:1) to obtain the title compound (IM03-c: 1.07 g, 90%).

LC/MS (Method 3): m/z (ESI, POS): 299 [M+H]$^+$; retention time: 6.3 minutes.

$^1$H-NMR (400 MHz, CDCl$_3$, TMS) ppm: 7.42 (1H, s), 6.23 (1H, s), 5.97-6.10 (2H, m), 5.30-5.51 (4H, m), 4.61 (2H, s), 4.60-4.55 (4H, m).

The Third Step: Preparation of 2,4-bis-allyloxy-5-bromo-benzaldehyde (IM04-c)

IM03-c (0.55 g, 1.83 mmol), manganese dioxide (5.2 g, 59.8 mmol) and chloroform (50 mL) were placed in a 300 mL flask and stirred at room temperature for 72 hours. After filtering the reaction mixture, the filtrate and wash were collected and concentrated under reduced pressure. The residue was purified by silica gel column chromatography (hexane-ethyl acetate=3:1-2:1) to obtain the title compound (IM04-c: 0.42 g, 78%).

LC/MS (Method 3): m/z (ESI, POS): 299 [M+2+H]$^+$; retention time: 7.2 minutes.

$^1$H-NMR (400 MHz, CDCl$_3$, TMS) ppm: 10.29 (1H, s), 8.02 (1H, s), 6.43 (1H, s), 6.11-6.07 (2H, m), 5.54-5.34 (4H, m), 4.66 (4H, m).

The Fourth Step: Preparation of 1-(2,4-bis-allyloxy-5-bromo-phenyl)-but-2-ynyl-1-ol (IM05-c)

IM04-c (486 mg, 1.6 mmol) and anhydrous tetrahydrofuran (5 mL) were placed in a 30 mL two-neck flask under a nitrogen atmosphere, and a tetrahydrofuran solution of 0.5M 1-propynylmagnesium bromide (8.0 mL, 4.0 mmol) was added dropwise at 0° C. After stirring for 1 hour, the reaction mixture was mixed with saturated ammonium chloride solution (4 mL) and saturated sodium chloride solution (10 mL), and extracted twice with ethyl ether (20 mL). After washing with saturated sodium chloride solution and drying over anhydrous sodium sulfate, filtration and evaporation gave the crude product of the title compound (IM05-c:0.55 g).

LC/MS (Method 3): m/z(ESI, POS):321[M+2+H–H$_2$O]$^+$; retention time: 6.79 minutes.

The Fifth Step: Preparation of 1,5-bis-allyloxy-2-bromo-4-(but-2-ynyl)-benzene (IM06-c)

Crude IM05-c (0.55 g) dissolved in anhydrous acetonitrile (4 mL) was placed in a 50 mL two-neck flask under a nitrogen atmosphere, mixed with triethylsilane (0.28 mL, 1.76 mmol) and boron trifluoride diethyl ether complex (0.223 mL, 1.76 mmol) under ice cold condition and stirred for 1 hour. Potassium carbonate (553 mg, 4 mmol) and water (70 mL) were added to the reaction mixture, which was extracted twice with ethyl acetate (70 mL). The organic layer was washed with saturated sodium chloride solution, dried over anhydrous sodium sulfate. Filtration and evaporation gave the crude title compound (IM06-c: 0.51 g).

LC/MS (Method 3): m/z(ESI, POS):321[M+H]$^+$; retention time: 8.22 minutes.

The Sixth Step: Preparation of 2,4-bis-allyloxy 5-(but-2-ynyl)-benzoic acid (IM07-c)

Crude IM06-c (0.51 g) dissolved in anhydrous tetrahydrofuran (6 mL) was placed in a 50 mL two-neck flask under a nitrogen atmosphere, and after cooling to −78° C., a hexane solution of 1.59M n-butyllithium (1.1 mL, 1.76 mmol) was added dropwise. The reaction mixture was stirred for 1 hour, mixed with dry ice (7 g) and further stirred for 1 hour. The reaction mixture was adjusted to pH 2.5 by mixing with 10% potassium hydrogensulfate and extracted twice with ethyl acetate (40 mL). The organic layer was washed with saturated sodium chloride solution, dried over anhydrous sodium sulfate. After filtration and evaporation, the residue was purified by silica gel column chromatography (hexane-ethylacetate=2:1) to obtain the title compound (IM07-c:0.28 g, yield 62%, 3 steps).

LC/MS (Method 3): m/z(ESI, POS):287[M+H]$^+$; retention time: 6.52 minutes.

$^1$H-NMR (400 MHz, CDCl$_3$, TMS)ppm:10.63 (1H, brs), 8.26 (1H, s), 6.48 (1H, s), 6.14-5.98 (2H, m), 5.54-5.32 (4H, m), 4.76 (2H, m) 4.61 (2H, m), 3.46 (2H, m), 1.85 (3H, t, J=2.6 Hz).

The Seventh Step: Preparation of 4-[4-(morpholin-4-ylmethyl)-phenyl]-1-[5-(but-2-ynyl)-2,4-bis-methoxymethoxy-benzoyl]thiosemicarbazide (F461-IM01)

2,4-bis-allyloxy-5 (but-2-ynyl)-benzoic acid (IM07-c: 286 mg, 1 mmol), 4-[4-(morpholin-4-ylmethyl)-phenyl]thiosemicarbazide (266 mg, 1 mmol), 1-hydroxybenzo triazole monohydrate (135 mg, 1 mmol) and dimethylformamide (3 mL) were placed in a 100 mL eggplant shaped flask. The reaction mixture was cooled to 0° C., and a dimethylformamide solution of 1-ethyl-3-(3-dimethylaminopropyl)carbodiimide (230 mg, 1.2 mmol) (2 mL) was added to the reaction mixture dropwise slowly. After completing the dropwise addition, the reaction mixture was stirred for 4 hours and allowed to come to room temperature. After completing the reaction, the reaction mixture was extracted with ethyl acetate, and the organic layer was washed with saturated sodium chloride solution and concentrated under reduced pressure. The residue was purified by silica gel column chromatography to obtain the title compound (F461-IM01: 307 mg, 57.5%).

LC/MS (Method 3): m/z(ESI, POS):535[M+H]$^+$; retention time: 4.06 minutes.

The Eighth Step: Preparation of 5-[5-(but-2-ynyl)-2,4-bis-methoxymethoxy-phenyl]-4-[4-(morpholin-4-ylmethyl)-phenyl]-2,4-dihydro-[1,2,4]triazol-3-thione (F461-IM02)

4-[4-(morpholin-4-ylmethyl)-phenyl]-1-[5-(but-2-ynyl)-2,4-bismethoxymethoxy-benzoyl]thiosemicarbazide (F461-IM01: 71.3 mg, 0.133 mmol) and 5% aqueous sodium hydroxide (5 mL) were placed in a 30 mL eggplant shaped flask and heated under reflux for 2.5 hours. After completing the reaction, the reaction mixture was extracted with methylene chloride and concentrated under reduced pressure. The crude product (F461-IM02) thus obtained was subjected to the next reaction without purification in particular.

LC/MS (Method 3): m/z(ESI, POS):517[M+H]$^+$; retention time: 3.85 minutes.

The Ninth Step: Preparation of 4-but-2-ynyl-6-{5-mercapto-4-[4-(morpholin-4-ylmethyl)-phenyl]-4H-[1,2,4]triazol-3-yl]-benzene-1,3-diol trifluoroacetate (SH-c02-TF)

Crude 5-[5-(but-2-ynyl)-2,4-bis-methoxymethoxy-phenyl]-4-[4-(morpholin-4-ylmethyl)-phenyl]-2,4-dihydro-[1,2,4]triazol-3-thione (F461-IM02) obtained in the eighth step, potassium carbonate (110 mg, 0.8 mmol) and triphenylphosphinepalladium (7.7 mg, 0.0067 mmol) were placed in a 30 mL eggplant shaped flask and heated under reflux under argon atmosphere for 3.5 hours. After completing the reaction, the reaction mixture was neutralized with 1 N hydrochloric acid and extracted with ethyl acetate. The residue thus obtained was purified by HPLC fractionation to obtain the title compound (SH-c02-TF:10.9 mg, 18.7%:2 steps).

LC/MS (Method 4): m/z(ESI, POS):437[M+H]$^+$; retention time: 3.80 minutes.

$^1$H-NMR (400 MHz, CD$_3$OD, TMS)ppm:7.57 (2H, d, J=8.4 Hz), 7.44 (2H, d, J=8.4 Hz), 7.21 (1H, S), 6.17 (1H, S), 4.38 (2H, S), 4.12-3.96 (2H, br), 3.80-3.60 (2H, br), 3.55-3.35 (2H, br), 3.28-3.20 (2H, m), 3.17-3.15 (2H, br), 1.82 (3H, t, J=2.4 Hz).

Example 1-5

Preparation of 4-bromo-6-{5-mercapto-4-[4-(morpholin-4-yl)-phenyl]-4H-[1,2,4]triazol-3-yl}-benzene-1,3-diol (SH-d01)

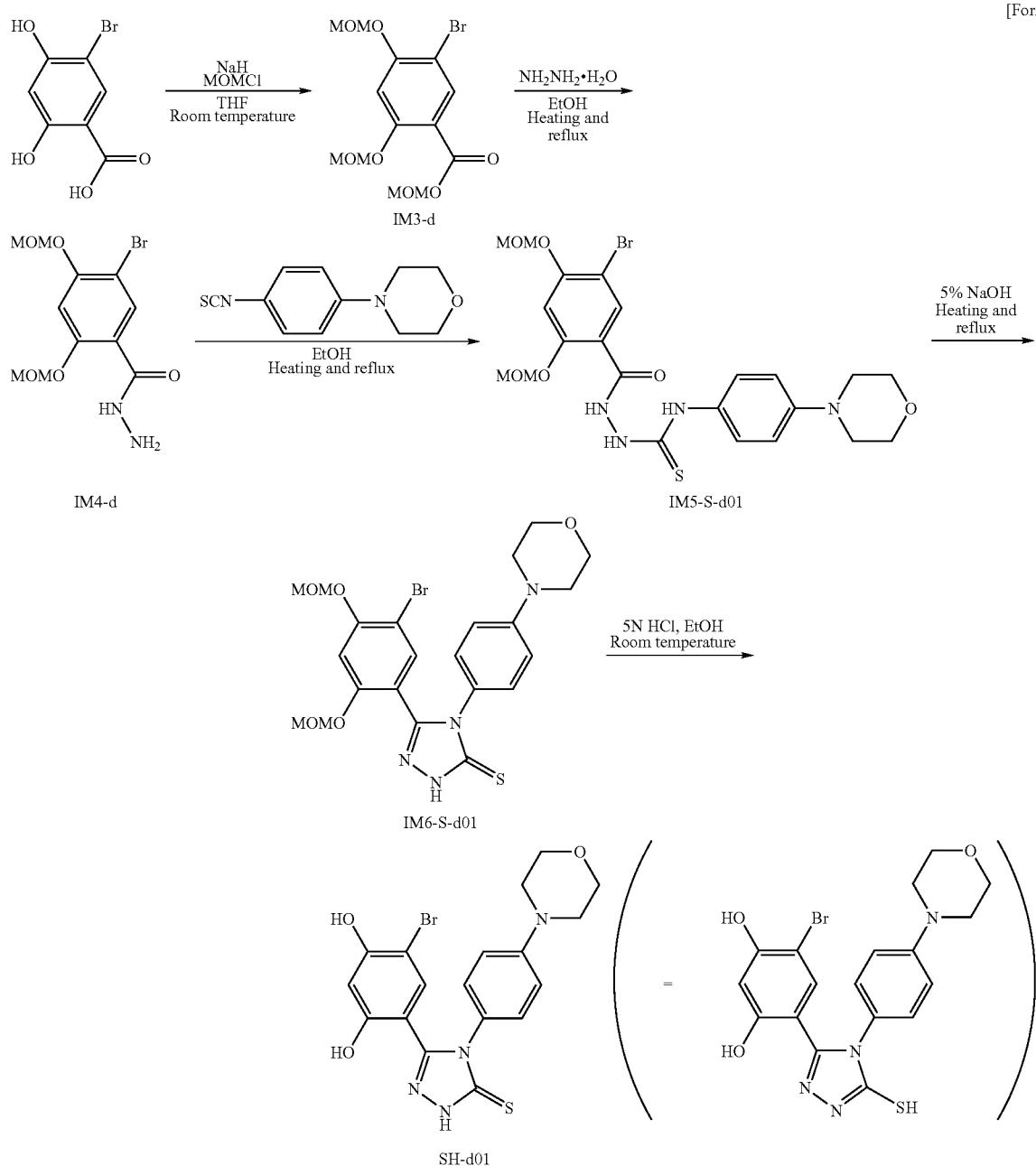

The First Step: Preparation of 5-bromo-2,4-bis-methoxymethoxybenzoic acid methoxymethyl ester (IM3-d)

Sodium hydride (6 g, 150 mmol) and tetrahydrofuran (100 mL) were placed in a 500 mL four-neck flask and cooled to 0° C. A tetrahydrofuran solution (50 mL) of 5-bromo-2,4-dihydroxybenzoic acid monohydrate (12.6 g, 50 mmol) was added to it slowly dropwise, and stirring was continued for 30 minutes while keeping the temperature at 0° C. After that methoxymethylchloride (12.4 mL, 165 mmol) diluted in tetrahydrofuran (30 mL) was added slowly dropwise. After completing the instillation, the reaction mixture was allowed to come to room temperature and stirred for 24 hours. After completing the reaction, saturated aqueous ammonium chloride was added, and the reaction mixture was extracted with ethyl acetate, dried over anhydrous sodium sulfate. After filtration and evaporation, the residue thus obtained was purified by silica gel column chromatography to obtain the title compound (IM3-d:6.95 g, 38%).

LC/MS (Method 3) retention time: 6.29 minutes.

$^1$H-NMR (400 MHz, CDCl$_3$, TMS) ppm: 8.11 (1H, s), 7.03 (1H, s), 5.44 (2H, s), 5.30 (2H, s), 5.26 (2H, s), 3.55 (3H, s), 3.53 (3H, s), 3.52 (3H, s).

The Second Step: Preparation of 5-bromo-2,4-bis-methoxymethoxybenzoic acid hydrazide (IM4-d)

5-bromo-2,4-bis-methoxymethoxybenzoic acid methoxymethylester (IM3-d: 4.36 g, 11.9 mmol), ethanol (15 mL) and hydrazine monohydrate (0.96 mL, 29.8 mmol) were placed in a 100 mL eggplant shaped flask and stirred at 70° C. for 27 hours. After completing the reaction, the reaction mixture was extracted with methylene chloride, and the organic layer was washed with saturated sodium chloride solution and then concentrated under reduced pressure. The solid material thus obtained was suspended in hexane for purification to obtain the title compound (IM4-d: 1.8 g, 46%).

LC/MS (Method 3): m/z (ESI, POS): 336 [M+H]$^+$; retention time: 4.10 minutes.

The Third Step: Preparation of 4-[4-(morpholin-4-yl)-phenyl]-1-(5-bromo-2,4-bis methoxymethoxy-benzoyl)thiosemicarbazide (IM5-S-d01)

5-bromo-2,4-bis-methoxymethoxy-benzoic acid hydrazide (IM4-d: 670 mg, 2 mmol), 4-(4-isothiocyanate-phenyl)-morpholine (441 mg, 2 mmol) and ethanol (10 mL) were placed in a 50 mL eggplant shaped flask and heated under reflux for 2 hours. After completing the reaction, the reaction mixture was concentrated under reduced pressure to obtain crude crystals of 4-[4-(morpholin-4-yl)-phenyl]-1-(5-bromo-2,4-bis methoxymethoxy-benzoyl)thiosemicarbazide (IM5-S-d01). These crude crystals were subjected to the next reaction without purification in particular.

LC/MS (Method 3): m/z (ESI, POS): 555 [M+H]$^+$; retention time: 5.80 minutes.

The Fourth Step: Preparation of 5-(5-bromo-2,4-bis-methoxymethoxy-phenyl)-4-[4-(morpholin-4-yl)-phenyl]-2,4-dihydro-[1,2,4]triazol-3-thione (IM6-S-d01)

The crude crystals of 4-[4-(morpholin-4-yl)-phenyl]-1-(5-bromo-2,4-bis methoxymethoxy-benzoyl)thiosemicarbazide (IM5-S-d01) and 5% aqueous sodium hydroxide (1 mL) were added in a test tube and refluxed for 2 hours. After completing the reaction, the reaction mixture was extracted with methylene chloride, and the combined organic layer was dried over anhydrous sodium sulfate. Filtration and evaporation gave crude crystals of 5-(5-bromo-2,4-bis-methoxymethoxy-phenyl)-4-[4-(morpholin-4-yl)-phenyl]-2,4-dihydro-[1,2,4]triazol-3-thione (IM6-S-d01) (2 steps, 35.6%). These crude crystals were subjected to the next reaction without purification in particular.

LC/MS (Method 3): m/z (ESI, POS): 537 [M+H]$^+$; retention time: 4.3 minutes.

The Fifth Step: Preparation of 4-bromo-6-{5-mercapto-4-[4-(morpholin-4-yl)-phenyl]-4H-[1,2,4]triazol-3-yl}-benzene-1,3-diol (SH-d01)

The crude crystals of 5-(5-bromo-2,4-bis-methoxymethoxy-phenyl)-4-[4-(morpholin-4-yl)-phenyl]-2,4-dihydro-[1,2,4]triazol-3-thione (IM6-S-d01) and a mixed solvent of 5.0 N aqueous hydrochloric acid (1 mL) and ethanol (1 mL) were placed in a test tube and stirred at room temperature for 24 hours. After completing the reaction, the reaction mixture was neutralized with 10 N aqueous sodium hydroxide, and then extracted with ethyl acetate and methylene chloride. The collected organic layer was dried over anhydrous sodium sulfate. After filtration and evaporation, the residue thus obtained was purified by HPLC fractionation to obtain the title compound (SH-d01: 8.6 mg, 34%).

LC/MS (Method 2): m/z (ESI, NEG): 447 [M+H]$^-$; retention time: 4.51 minutes.

Example 1-6

Preparation of 5-(2,4-dihydroxy-5-isopropyl-phenyl)-4-(4-methoxy-phenyl)-2,4-dihydro-[1,2,4]-triazol-3-thione (SH-a08)

Scheme 1-6

[Formula 24]

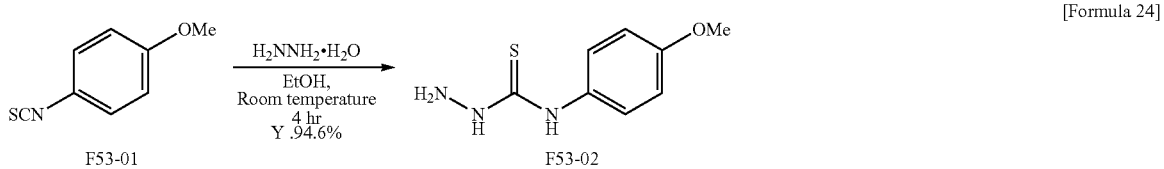

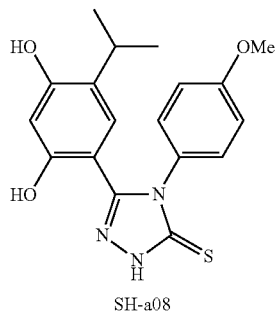

SH-a08

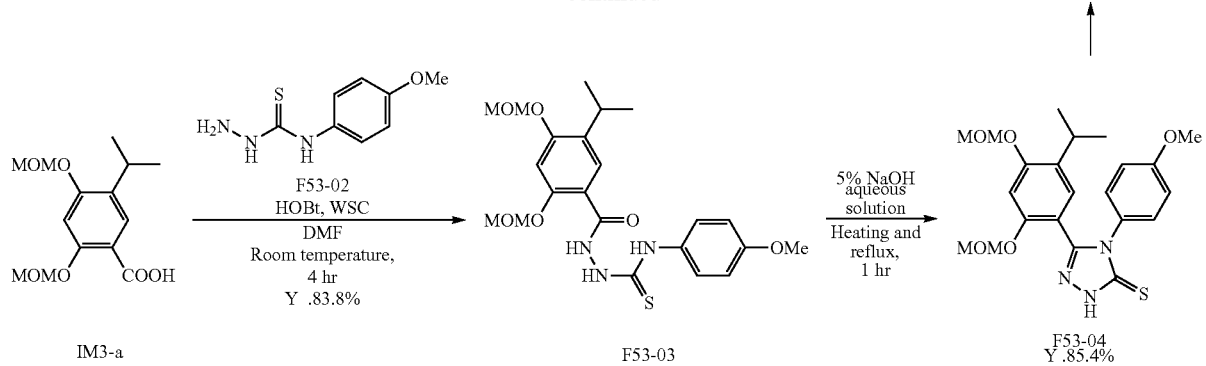

The First Step: Preparation of 4-methoxyphenylthiosemicarbazide (F53-02)

4-methoxyphenylthioisocyanate (10 g, 60.5 mmol) and ethanol (18 mL) were placed in a 100 mL eggplant shaped flask, and then the reaction mixture was cooled to 0° C., to which an ethanol solution (18 mL) of hydrazine monohydrate (2.9 mL, 90.8 mmol) was added dropwise slowly. The reaction mixture was stirred for 4 hours while the temperature was raised to room temperature. After completing the reaction, the deposited solids were filtered under reduced pressure, washed with hexane to obtain the title compound (F53-02: 11.3 g, 94.6%)

LC/MS (Method 1): m/z (ESI, POS): 198 [M+H]$^+$; retention time: 3.59 minutes.

The Second Step: Preparation of 4-methoxyphenyl-1-[5-isopropyl-2,4-bis(methoxymethoxy)-benzoyl]thiosemicarbazide (F53-03)

5-isopropyl-2,4-bis(methoxymethoxy)-benzoic acid (IM3-a: 16.4 g, 54.5 mmol), 4-methoxyphenylthiosemicarbazide (F53-02: 11.3 g, 57.3 mmol), dimethylformamide (150 mL) and 1-hydroxybenzotriazole monohydrate (8.11 g, 60.0 mmol) were placed in a 500 mL eggplant shaped flask. The reaction mixture was cooled to 0° C. and mixed with a suspension of 1-(3-dimethylaminopropyl)-3-ethylcarbodiimide (11.5 g, 60 mmol) in dimethylformamide (100 mL). The mixture was stirred for 4 hours and allowed to come to room temperature. After completing the reaction, saturated sodium chloride solution (500 mL) was added to the reaction mixture, and the mixture was extracted twice with ethyl acetate (500 mL). The organic layer thus obtained was washed 4 times with saturated sodium chloride solution (500 mL) and dried over anhydrous sodium sulfate. After removing sodium sulfate by filtration, the solvent was distilled under reduced pressure, and the solids obtained were suspended in hexane (1000 mL) for purification and collected by filtration. The solids thus obtained were dried under reduced pressure to obtain the title compound (F53-03: 21.9 g, 83.8%).

LC/MS (Method 3): m/z (ESI, POS): 464 [M+H]$^+$; retention time: 6.46 minutes.

The Third Step: Preparation of 5-(5-isopropyl-2,4-bis-methoxymethoxy-phenyl)-4-[4-methoxy-phenyl]-2,4-dihydro-[1,2,4]triazol-3-thione (F53-04)

4-methoxyphenyl-1-[5-isopropyl-2,4-bis(methoxymethoxy)-benzoyl]thiosemicarbazide (F53-03: 24.9 g, 53.7 mmol) and 5% aqueous sodium hydroxide (500 mL) were placed in a 1 L eggplant shaped flask and heated under reflux for 1 hour. After completing the reaction, the reaction mixture was neutralized with saturated aqueous ammonium chloride, and the solids deposited were collected by filtration, washed with distilled water and then dried under reduced pressure. The crude product thus obtained was purified by suspending in ethyl acetate/hexane and concentrating under reduced pressure to obtain the title compound (F53-04: 20.5 g, 85.4%).

LC/MS (Method 3): m/z (ESI, POS): 446 [M+H]$^+$; retention time: 6.33 minutes.

$^1$H-NMR (400 MHz, DMSO-d$_6$, TMS) ppm: 7.19 (1H, s), 7.16 (2H, d, J=9.0 Hz), 6.92 (2H, d, J=9.0 Hz), 6.75 (1H, s), 5.20 (2H, s), 4.94 (2H, s), 3.73 (3H, s), 3.37 (3H, s), 3.21 (3H, s), 3.14 (1H, sept, J=6.8 Hz), 1.07 (6H, d, J=6.8 Hz).

The Fourth Step: Preparation of 5-(2,4-dihydroxy-5-isopropyl-phenyl)-4-(4-methoxy-phenyl)-2,4-dihydro-[1,2,4]-triazole-3-thione (SH-a08)

The title compound (SH-a08, 12 mg, 62.2%) was obtained by using 5-(5-isopropyl-2,4-bis-methoxymethoxy-phenyl)-4-[4-methoxy-phenyl]-2,4-dihydro[1,2,4]triazol-3-thione (F53-04, 24.1 mg, 0.054 mmol), in place of 5-(5-isopropyl-2,4-bis-methoxymethoxy-phenyl)-4-[4-morpholin-4-ylm-ethyl)-phenyl]-2,4-dihydro[1,2,4]triazol-3-one, and treating in the similar manner as in the fourth step in the Example 2-7.

LC/MS (Method 3): m/z (ESI, POS): 358 [M+H]$^+$; retention time: 5.31 minutes.

$^1$H-NMR (400 MHz, CD$_3$OD, TMS) ppm: 7.19 (2H, d, J=9.0 Hz), 6.99 (2H, d, J=9.0 Hz), 6.73 (1H, s), 6.26 (1H, s), 3.82 (3H, s), 3.04 (1H, sept, J=7.0 Hz), 0.94 (6H, d, J=7.0 Hz).

Example 1-7

Preparation of 5-(2,4-dihydroxy-5-isopropyl-phenyl)-4-phenyl-2,4-dihydro-[1,2,4]-triazol-3-one (SH-a15)

The title compound (SH-a15) was obtained by the similar process to that of Example 1-6 in 4 steps using phenylisothiocyanate in place of F53-01 of Example 1-6.

LC/MS (Method 3): m/z (ESI, POS): 328 [M+H]$^+$; retention time: 5.27 minutes.

Example 1-8

Preparation of 5-(2,4-dihydroxy-5-isopropyl-phenyl)-4-pyridin-3-yl-2,4-dihydro-[1,2,4]-triazol-3-one (SH-a16)

The title compound (SH-a16) was obtained by the similar process to that of Example 1-6 in 4 steps using 3-isothiocyanate-pyridine in place of F53-01 of Example 1-6.

LC/MS (Method 3): m/z (ESI, POS): 329 [M+H]$^+$; retention time: 4.29 minutes.

Example 1-9

Preparation of 5-(2,4-dihydroxy-5-isopropyl-phenyl)-4-isopropyl-2,4-dihydro-[1,2,4]-triazol-3-thione (SH-a21)

Scheme 1-9

{Formula 25}

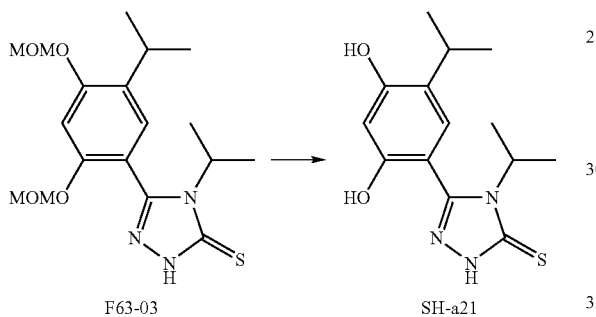

The title compound [SH-a21, 13.8 mg, 47% in 3 steps from IM4-a (the starting material of Example 1-2)] was obtained by a similar process to the fourth step of Example 2-7 using 5-(5-isopropyl-2,4-bis-methoxymethoxy-phenyl)-4-isopropyl-2,4-dihydro-[1,2,4]triazol-3-thion (an intermediate of Example 2-13, F63-03) in place of 5-(5-isopropyl-2,4-bis-methoxymethoxy-phenyl)-4-[4-(morpholin-4-ylmethyl)-phenyl]-2,4-dihydro-[1,2,4]triazol-3-one.

LC/MS (Method 3): m/z (ESI, POS): 294 [M+H]$^+$; retention time: 5.04 minutes.

$^1$H-NMR (400 MHz, CD$_3$OD, TMS) ppm: 6.96 (1H, s), 6.41 (1H, s), 4.63 (1H, sept, J=7.0 Hz), 3.18 (1H, sept, J=6.8 Hz), 1.21 (6H, d, J=7.0 Hz) 1.18 (6H, d, J=6.8 Hz)

Example 1-10

Preparation of 5-(2,4-dihydroxy-5-isopropyl-phenyl)-4-isobutyl-2,4-dihydro-[1,2,4]triazol-3-thione (SH-a22)

The bis(methoxymethyl) protected compound of the title compound (SH-a22) was obtained in 3 steps by a similar process to that of Example 2-13 using isobutylisothiocyanete in place of isopropylisothiocyanate of Example 2-13. This compound was deprotected by a similar operation to that in the fourth step of Example 1-6 to obtain the title compound (SH-a22).

LC/MS (Method 3): m/z (ESI, POS): 308 [M+H]$^+$; retention time: 5.39 minutes.

Example 1-11

Preparation of 5-(2,4-dihydroxy-5-isopropyl-phenyl)-4-cyclohexyl-2,4-dihydro-[1,2,4]triazol-3-thione (SH-a23)

The bis(methoxymethyl) protected compound of the title compound (SH-a23) was obtained in 3 steps by a similar process to that of Example 2-13 using cyclohexylisothiocyanate in place of isopropylisothiocyanate of Example 2-13. This compound was deprotected by a similar operation to that in the fourth step of Example 1-6 to obtain the title compound (SH-a23).

LC/MS (Method 3): m/z (ESI, POS): 334 [M+H]$^+$; retention time: 5.71 minutes.

$^1$H-NMR (400 MHz, CD$_3$OD, TMS) ppm: 6.95 (1H, s), 6.41 (1H, s), 4.30-4.20 (1H, brs), 3.31 (1H, sept, J=7.0 Hz), 2.40-2.20 (2H, brs), 1.85-1.70 (4H, brs), 1.66-1.55 (1H, brs), 1.35-1.20 (2H, m), 1.18 (6H, d, J=7.0 Hz), 1.10-1.00 (1H, m).

Example 1-12

Preparation of 4-{1-benzyl-piperidin-4-yl}-5-(2,4-dihydroxy-5-isopropyl-phenyl)-2,4-dihydro-[1,2,4]triazol-3-one (SH-a25) trifluoroacetate Scheme 1-12

[Formula 26]

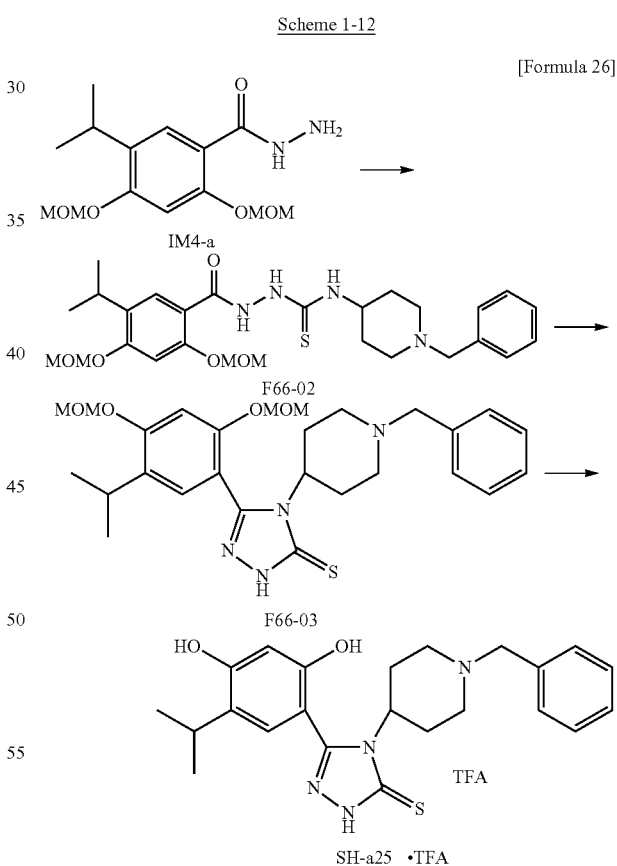

The First Step: Preparation of 4-(1-benzyl-piperidin-4-yl)-1-(5-isopropyl-2,4-bismethoxymethoxy-benzoyl)thiosemicarbazide (F66-02)

Tetrahydrofuran (5 mL), triethylamine (0.086 mL, 1.25 mmol), thiophosgene (0.042 mL, 0.55 mmol) and 4-amino- 1-benzyl-piperidine (0.112 mL, 0.55 mmol) were placed in a 10 mL eggplant shaped flask and stirred at room temperature for 2 hours, and then 5-isopropyl-2,4-bis-methoxymethoxy-benzoic acid hydrazide (IM4-a, 149 mg, 0.5 mmol) was added. The reaction mixture was stirred at room temperature for 24 hours. After completing the reaction, the reaction mixture was concentrated under reduced pressure. The residue obtained was subjected to the next reaction without further purification.

LC/MS (Method 3): m/z (ESI, POS): 531 [M+H]$^+$; retention time: 3.92 minutes.

The Second Step: Preparation of 4-(1-benzyl-piperidin-4-yl)-5-(5-isopropyl-2,4-bis-methoxymethoxy-phenyl)-2,4-dihydro-[1,2,4]triazol-3-one (F66-03)

4-(1-benzyl-piperidin-4-yl)-1-(5-isopropyl-2,4-bis-methoxymethoxy-benzoyl)thiosemicarbazide (the crude product F66-02 of the previous step) and 5% aqueous sodium hydroxide were placed in a 10 mL eggplant shaped flask and heated under reflux for 3 hours. After completing the reaction, the reaction mixture was extracted with methylene chloride, and the extract was dried over anhydrous sodium sulfate. After filtration and evaporation, the residue thus obtained was subjected to the next reaction without further purification.

LC/MS (Method 3): m/z (ESI, POS): 513 [M+H]$^+$; retention time: 3.94 minutes.

The Third Step: Preparation of 4-(1-benzyl-piperidin-4-yl)-5-(2,4-dihydroxy-5-isopropyl-phenyl)-2,4-dihydro-1,2,4-triazol-3-one (SH-a25) trifluoroacetate 4-(1-benzyl-piperidin-4-yl)-5-(5-isopropyl-2,4-bis-methoxymethoxy-phenyl)-2,4-dihydro-[1,2,4]triazol-3-one (the crude product F66-03 of the previous step), ethanol (3 mL) and 5 N hydrochloric acid (3 mL) were placed in a test tube and at room temperature for 24 hours. After completing the reaction, the reaction mixture was extracted with ethyl acetate, and the organic layer was washed 4 times with saturated sodium chloride solution, dried over anhydrous sodium sulfate. After filtration and evaporation, the title compound (SH-a25 trifluoroacetate, 40 mg, 14.9%) was obtained by purifying the residue by HPLC fractionation.

LC/MS (Method 3): m/z (ESI, POS): 425 [M+H]$^+$; retention time: 3.35 minutes.

Example 1-13

Preparation of 5-(2,4-dihydroxy-5-isopropylphenyl)-4-(2-pyridin-3-ylethyl)-2,4-dihydro-[1,2,4]triazol-4-thione (SH-a28)

The bis(methoxymethyl) protected compound of the title compound (SH-a28) was obtained in 4 steps by a similar process to that of Example 2-2(B) using 3-(2-aminoethyl)pyridine in place of 4-molpholin-4-ylmethyl-phenylamine (F45-000) of Example 2-2(B). This compound was deprotected by a similar operation to that in the seventh step of Example 2-13 to obtain the title compound (SH-a28).

LC/MS (Method 6): m/z (ESI, POS): 357 [M+H]$^+$; retention time: 4.32 minutes.

$^1$H-NMR [400 MHz, CDCl$_3$-CD$_3$OD (three drops)] δ 1.18 (d, J=7.0 Hz, 6H), 3.10-3.23 (m, 3H), 4.25 (t, J=7.7 Hz, 2H), 6.39 (s, 1H), 6.95 (s, 1H), 7.23 (dd, J=4.9, 7.9 Hz, 1H), 7.57 (d, J=7.9 Hz, 1H), 8.17 (s, 1H), 8.36 (d, J=4.9 Hz, 1H).

Example 1-14

Preparation of 5-(2,4-dihydroxy-5-isopropylphenyl)-4-(tetrahydrofuran-2-ylmethyl)-2,4-dihydro-[1,2,4]triazol-3-thione (SH-a31)

The bis(methoxymethyl) protected compound of the title compound (SH-a31) was obtained in 4 steps by a similar process to that of Example 2-2(B) using tetrahydrofurfurylamine in place of 4-morpholin-4-ylmethyl-phenylamine (F45-000) of Example 2-2(B). This compound was deprotected by a similar operation to that in the seventh step of Example 2-13 to obtain the title compound (SH-a31).

LC/MS (Method 1): m/z (ESI, POS): 336 [M+H]$^+$; retention time: 5.21 minutes.

$^1$H-NMR [400 MHz, CDCl$_3$-CD$_3$OD (three drops)] δ 1.20 (d, J=7.0 Hz, 6H), 1.52-1.64 (m, 1H), 1.84 (tt, J=7.0, 7.0 Hz, 2H), 1.96-2.06 (m, 1H), 3.21 (sept., J=7.0 Hz, 1H), 3.63 (dt, J=2.6, 7.0 Hz, 2H), 4.00 (dd, J=8.8, 14.0 Hz, 1H), 4.24 (dd, J=4.0, 14.0 Hz, 1H), 4.42-4.52 (m, 1H), 6.38 (s, 1H), 7.32 (s, 1H).

Example 1-15

Preparation of 5-(2,4-dihydroxy-5-isopropyl-phenyl)-4-(2-methoxy-ethyl)-2,4-dihydro-[1,2,4]triazol-3-thione (SH-a32)

The bis(methoxymethyl) protected compound of the title compound (SH-a32) was obtained in 2 steps from IM4-a by sequentially following a similar process to that of Example 2-12 reacting (2-methoxyethyl)thiocarbamic acid O-phenyl ester to IM4-a in place of G06-02 of Example 2-12. This compound was deprotected by a similar operation to that of the seventh step of Example 1-1 to obtain the title compound (SH-a32).

LC/MS (Method 3): m/z (ESI, POS): 310 [M+H]$^+$; retention time: 4.65 minutes.

$^1$H-NMR (400 MHz, CDCl$_3$:CD$_3$OD=3:1, ppm): 7.24 (1H, s), 6.37 (1s), 4.23 (2H, t, J=5.86 Hz), 3.71 (3H, t, J=5.86 Hz), 3.22 (1H, m), 3.20 (3H, s), 1.20 (6H, d, J=6.96 Hz).

Example 1-16

Preparation of 5-(2,4-dihydroxy-5-tert-butyl-phenyl)-4-pyridin-3-yl-2,4-dihydro-[1,2,4]triazol-3-one (SH-f08)

Scheme 1-16

[Formula 27]

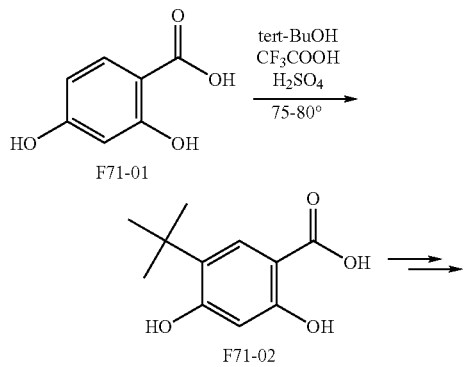

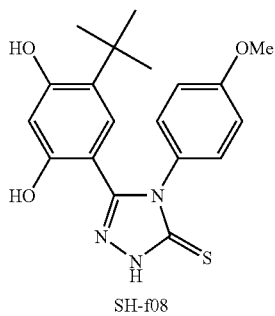

SH-f08

The First Step: Preparation of 5-tert-butyl-2,4-dihydroxy-benzoic acid (F71-02)

To a tert-butanol (14.3 mL, 11.12 g, 150 mmol) suspension of 2,4-dihydroxy-benzoic acid (F71-01: 2312 mg, 15.0 mmol), trifluoroacetic acid (8.0 mL, 11.84 g, 103.8 mmol) and sulfuric acid (0.43 mL, 0.79 g, 8.0 mmol) were added in this order under argon atmosphere while stirring at room temperature. The reacting solution was stirred at room temperature for 10 minutes and then at a bath temperature of 75° C. for 6 hours. Additional trifluoroacetic acid (8.0 mL, 11.84 g, 103.8 mmol) was added, and the reaction mixture was stirred at a bath temperature of 80° C. for further 2.5 hours. After completing the reaction, the reaction mixture was added to ice-water (160 mL) and stirred with the addition of hexane (20 mL). The deposited solids were collected by filtration, washed with water and hexane to obtain the title compound (F71-02: pale pink solid, 2.13 g, 68%).

LC/MS (Method 3): m/z (ESI, POS): 209 [M−H]$^-$; retention time: 5.55 minutes.

$^1$H-NMR (400 MHz, DMSO-D$_6$, TMS) ppm: 1.305 (9H, s, tert-Bu), 6.330 (1H, s, Ar—H), 7.558 (1H, s, Ar—H), 10.430 (1H, s), 11.192 (1H, bs), 12.0-14.0 (b).

Preparation of 5-(2,4-dihydroxy-5-tert-butyl-phenyl)-4-pyridin-3-yl-2,4-dihydro-[1,2,4]triazol-3-one (SH-f08)

The title compound was synthesized in a similar manner to Example 1-6 by using the bis(methoxymethyl) protected compound of 5-tert-butyl-2,4-bis-methoxymethoxy-benzoic acid (F71-02) in place of IM3-a.

LC/MS (Method 3): m/z (ESI, POS): 372 [M+H]$^+$; retention time: 5.78 minutes.

$^1$H-NMR (400 MHz, DMSO-d$_6$, TMS) ppm: 13.8 (1H, s), 9.66 (1H, s), 9.44 (1H, s), 7.15 (2H, d, J=9.0 Hz), 6.93 (2H, d, J=9.0 Hz), 6.87 (1H, s), 6.25 (1H, s), 3.75 (3H, s), 1.18 (9H, s).

Example 2-1A

Production (Method A) of 4-{5-hydroxy-4-[4-(morpholin-4-yl)-phenyl]-4H-[1,2,4]triazol-3-yl}-6-isopropyl-benzene-1,3-diol (OH-a01)

Scheme (2-1A)

[Formula 28]

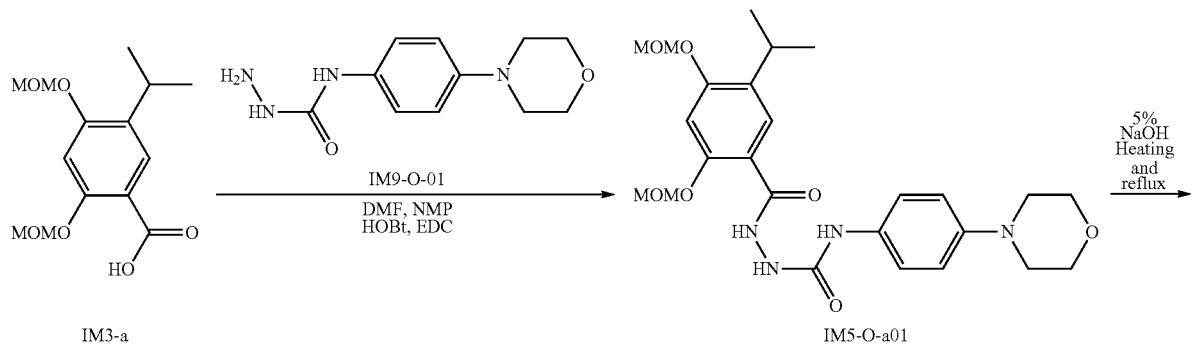

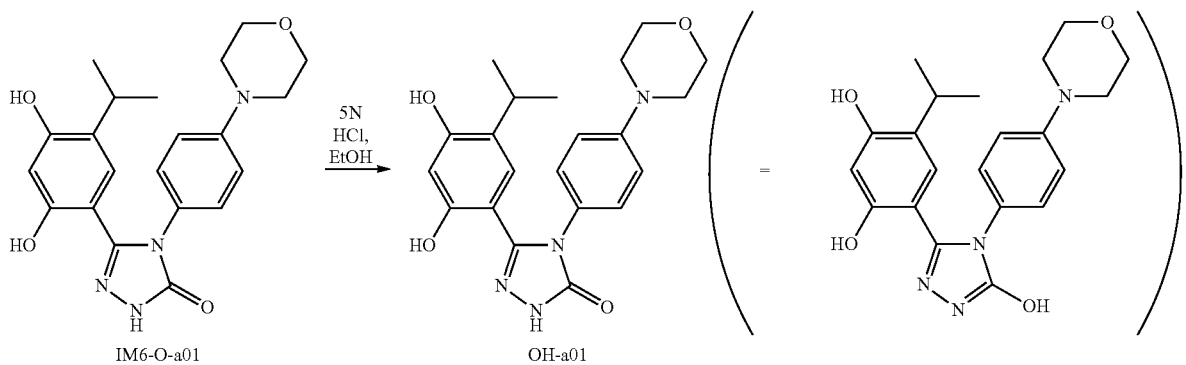

The First Step: Preparation of 4-[4-(morpholin-4-yl)-phenyl]-1-[5-isopropyl-2,4-bis(methoxymethoxy)-benzoyl]semicarbazide (IM5-O-a01)

To a solution of 4-[4-(morpholin-4-yl)-phenyl]semicarbazide (IM9-O-01:70.9 mg, 0.3 mmol) and 5-isopropyl-2,4-bis(methoxymethoxy)-benzoic acid (IM3-a:85.3 mg, 0.3 mmol) in dimethylformamide (4 mL), were added N-methylpyrrolidone (0.2 mL), 1-hydroxybenzotriazole monohydrate (60.8 mg, 0.45 mmol), and 1-(3-dimethylaminopropyl)-3-ethylcarbodiimide (115.0 mg, 0.6 mmol) successively, and the mixture was stirred at room temperature overnight. The reaction mixture was mixed with ethyl acetate (30 mL) and 5% aqueous sodium hydrogencarbonate (20 mL). The aqueous layer was separated, and extracted with ethyl acetate. The combined organic layers thus obtained were dried over anhydrous sodium sulfate. Sodium sulfate was removed by filtration, the solvent was distilled off under reduced pressure, and the residue was purified by silica gel column chromatography (dichloromethane: methanol=30:1-20:1) to obtain the title compound (IM5-O-a01: colorless syrup, 104.9 mg, 70%).

LC/MS (Method 1): m/z (ESI, POS): 503 [M+H]$^+$; retention time: 5.88 minutes.

The Second Step: Preparation of 5-(5-isopropyl-2,4-bis-methoxymethoxy-phenyl)-4-[4-(morpholin-4-yl)-phenyl]-4H-[1,2,4]triazol-3-ol (IM6-O-a01)

4-[4-(morpholin-4-yl)-phenyl]-1-[5-isopropyl-2,4-bis(methoxymethoxy)-benzoyl]semicarbazide (IM5-O-a01: 104.9 mg, 0.209 mmol) was mixed with 5% aqueous sodium hydroxide solution (2 mL) and stirred 105° C. (bath temperature) for 2 hours. Further, potassium hydroxide (100 mg) was added to the reaction mixture and the resulting mixture was stirred at 130° C. (bath temperature) for 3 hours. After cooling to room temperature, the reaction mixture was neutralized with 2 N hydrochloric acid and aqueous sodium hydrogencarbonate, extracted with dichloromethane (50 mL) and dried over anhydrous sodium sulfate. Sodium sulfate was removed by filtration, the solvent was distilled off under reduced pressure, and the residue was purified by silica gel column chromatography (dichloromethane: methanol=20:1) to obtain the title compound (IM6-O-a01: colorless syrup, 16.3 mg, 16%).

LC/MS (Method 1): m/z (ESI, POS): 485 [M+H]$^+$; retention time: 5.89 minutes.

The Third Step: Preparation of 4-{5-hydroxy-4-[4-(morpholin-4-yl)-phenyl]-4H-[1,2,4]triazol-3-yl}-6-isopropyl-benzene-1,3-diol (OH-a01)

An ethanol solution (2 mL) of 1,3-bis(methoxymethoxy)-4-{5-hydroxy-4-[4-(morpholin-4-yl)-phenyl]-4H-[1,2,4]triazol-3-yl}-6-isopropylbenzene (IM6-O-a01: 16.3 mg, 0.034 mmol) was mixed with 5 N hydrochloric acid (1 mL) and reacted at room temperature for 4 hours. The solvent was distilled off under reduced pressure, and the residue was neutralized with 5% sodium hydrogencarbonate and extracted with dichloromethane (30 mL). The extract was dried over anhydrous sodium sulfate. Sodium sulfate was removed by filtration, the solvent was distilled off under reduced pressure, and the residue was purified by silica gel column chromatography (dichloromethane: methanol=30:1-20:1) to obtain the title compound (OH-a01: white solid, 3.0 mg, 22%).

LC/MS (Method 1): m/z (ESI, POS): 397 [M+H]$^+$; retention time: 5.10 minutes.

$^1$H-NMR (200 MHz, CDCl$_3$+CD$_3$OD=2:1, TMS) ppm: 0.79 (6H, d, J=6.8 Hz), 2.19 (1H, sept, J=6.8 Hz), 3.15-3.24 (4H, m), 3.80-3.92 (4H, m), 6.39 (1H, s), 6.54 (1H, s), 7.03 (2H, d, J=9.1 Hz), 7.21 (2H, d, J=9.0 Hz).

Example 2-1B

Production (Method B) of 4-{5-hydroxy-4-[4-(morpholin-4-yl)-phenyl]-4H-[1,2,4]triazol-3-yl}-6-isopropyl-benzene-1,3-diol (OH-a01)

Scheme (2-1B)

[Formula 29]

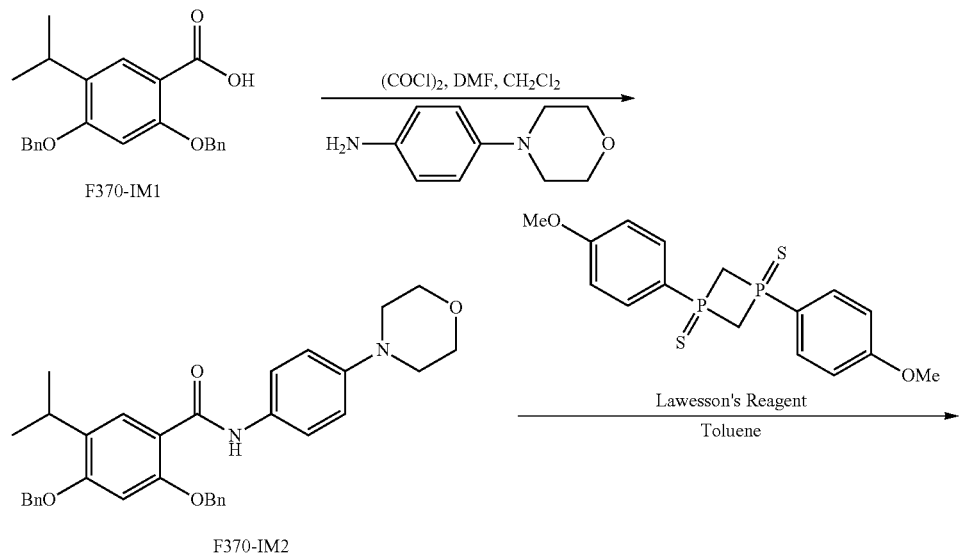

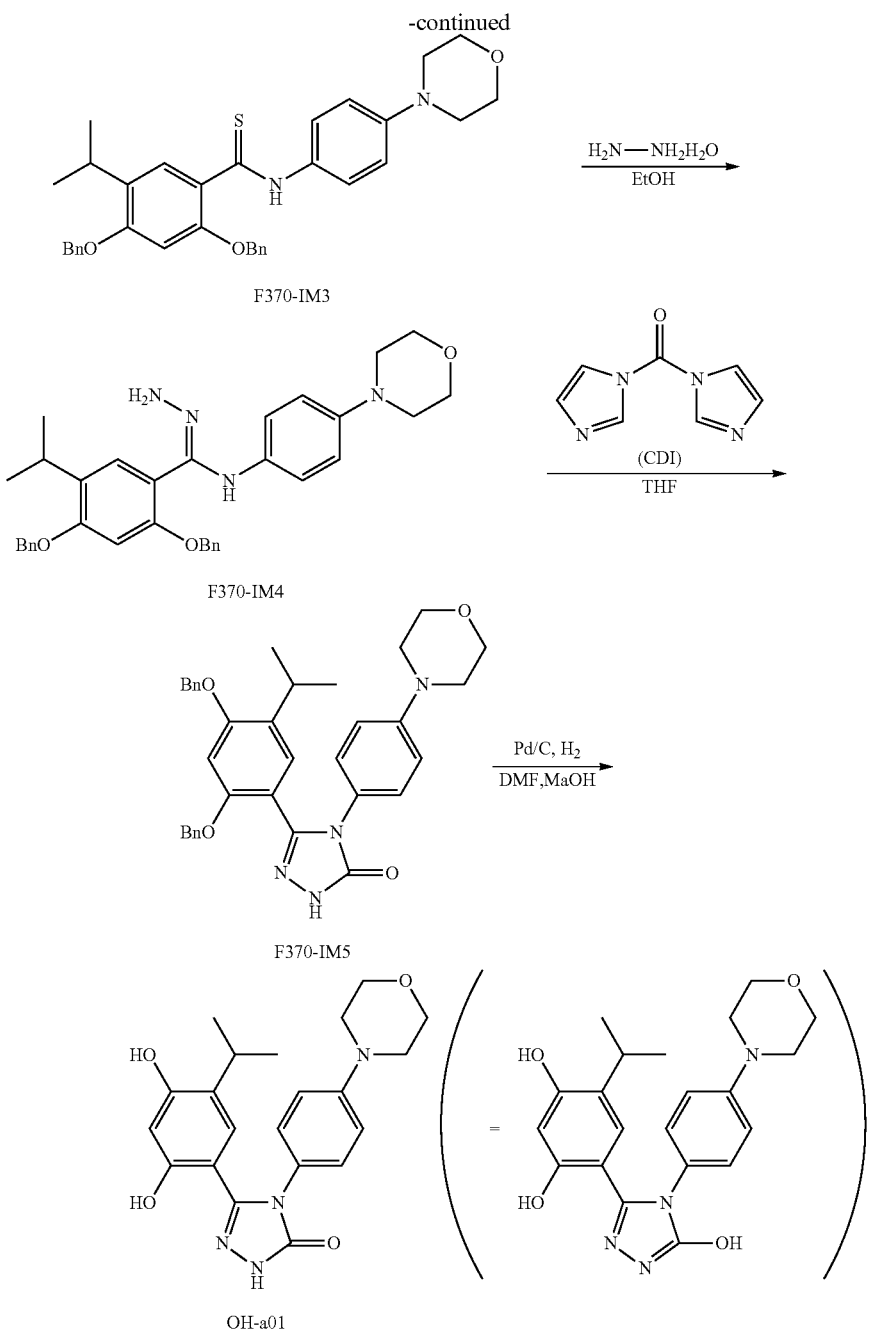

The First Step: Preparation of 2,4-bis-benzyloxy-5-isopropyl-N-[4-(morpholin-4-yl)-phenyl]benzamide (F370-IM2)

A dichloromethane (30 mL) solution of 2,4-bis-benzyloxy-5-isopropylbenzoic acid (F370-IM1, 2 g, 5.31 mmol) was mixed with dimethylformamide (0.053 mL, 0.05 mmol) and oxalylchloride (0.61 mL, 6.38 mmol) under ice cold conditions and the mixture was stirred at room temperature overnight. The reaction mixture was concentrated under reduced pressure, and the residue thus obtained was dissolved in tetrahydrofuran (30 mL) and pyridine (10 mL). To the solution was added 4-(4-morpholino)aniline (1.04 g, 5.84 mmol) under ice cold conditions. The reaction was carried out at room temperature for 1 hour. Dichloromethane (50 mL) and 5% aqueous sodium hydrogencarbonate (20 mL) were added to the reaction mixture. The aqueous layer was separated and extracted with dichloromethane, the combined organic layers thus obtained were washed with saturated aqueous sodium chloride solution (30 mL) and dried over anhydrous sodium sulfate. Sodium sulfate was removed by filtration, and the solvent was distilled off under reduced pressure. To the residue were added ethyl acetate (5 mL), toluene (5 mL) and hexane (20 mL), and the resulting suspension was stirred at room temperature for 1 hour. The precipitated solid was collected by filtration to obtain the title compound (F370-IM2: white crystals, 2.47 g, 87%).

LC/MS (Method 3): m/z (ESI, POS): 537 [M+H]$^+$; retention time: 8.61 minutes.

The Second Step: Preparation of 2,4-bis-benzyloxy-5-isopropyl-N-[4-(morpholin-4-yl)-phenyl]thiobenzamide (F370-IM3)

2,4-bis-benzyloxy-5-isopropyl-N-[4-(morpholin-4-yl)phenyl]benzamide (F370-IM2, 2.45 g, 4.60 mmol) was suspended in toluene (50 mL), mixed with Lawesson's reagent (2.05 g, 5.06 mmol) and the mixture was heated at 110° C. for 1 hour. As the reaction proceeded, the suspension changed to a yellow solution. The reaction mixture was cooled to room temperature, mixed with 5% aqueous sodium hydrogencarbonate (50 mL), and the organic layer was separated. The organic layer thus obtained was dried over anhydrous sodium sulfate. Sodium sulfate was removed by filtration, and the solvent was distilled off under reduced pressure. To the residue were added toluene (20 mL) and hexane (10 mL), and the resulting suspension was stirred at room temperature for 1 hour, crystals (F370-IM3) were collected by filtration. The mother liquor was concentrated and purified by silica gel column chromatography (ethyl acetate:hexane 2:1), to afford F370-IM3. The combined title compound (F370-IM3, about 4.1 g) was subjected to the next reaction.

LC/MS (Method 3): m/z (ESI, POS): 553 [M+H]$^+$; retention time: 8.72 minutes.

The Third Step: Preparation of 2,4-bis-benzyloxy-5-isopropyl-N-[4-(morpholin-4-yl)-phenyl]-benzene-carbohydrazonamide (F370-IM4)

2,4-bis-benzyloxy-5-isopropyl-N-[4-(morpholin-4-yl)-phenyl]thiobenzamide (F370-IM3; crude product, 4.2 g) was suspended in ethanol (30 mL), mixed with 80% aqueous hydrazine solution (15 mL) and heated under reflux for 4 hours. At this time, it was observed that the suspension was decolored and became a homogeneous solution. After cooling to room temperature, the reaction mixture was concentrated under reduced pressure and the residue thus obtained (crude F370-IM4) was used for the next reaction without purification.

LC/MS (Method 3): m/z(ESI, POS):551[M+H]$^+$; retention time: 4.67 minutes.

The Fourth Step: Preparation of 5-(2,4-bis-benzyloxy-5-isopropyl-phenyl)-4-(4-morpholin-4-yl-phenyl)-4H-[1,2,4]triazol-3-ol (F370-IM5)

2,4-bis-benzyloxy-5-isopropyl-N-[4-(morpholin-4-yl)-phenyl]-benzene-carbohydrazonamide (F370-IM4: crude product) was suspended in tetrahydrofuran (10 mL), mixed with 1,1'-carbonyldiimidazole (1.12 g, 6.9 mmol) and the mixture was stirred at room temperature for 2 hours. The reaction mixture was partitioned between ethyl acetate (50 mL) and 5% aqueous sodium hydrogencarbonate (50 mL), and the organic layer was separated. The organic layer obtained was dried over anhydrous sodium sulfate. Sodium sulfate was removed by filtration, and the solvent was distilled off under reduced pressure, and the residue thus obtained was purified by silica gel column chromatography (ethyl acetate 100%). The obtained product was purified by suspending in ethyl acetate to obtain the title compound (F370-IM5: white crystals, 1.2 g, 45% in 3 steps).

LC/MS (Method 3): m/z (ESI, POS): 576 [M+H]$^+$; retention time: 7.37 minutes.

The Fifth Step: Preparation of 4-{5-hydroxy-4-[4-(morpholin-4-yl)-phenyl]-4H-[1,2,4]triazol-3-yl}-6-isopropyl-benzene-1,3-diol (OH-a01)

5-(2,4-bis-benzyloxy-5-isopropyl-phenyl)-4-(4-morpholin-4-yl-phenyl)-4H-[1,2,4]triazol-3-ol (1.2 g, 2.07 mmol) was suspended in methanol (100 mL), acetic acid (50 mL) and dimethylformamide (50 mL), and mixed with palladium carbon (60 mg), and catalytic reduction was carried out under a hydrogen atmosphere at 80° C. for 1 hour and then at room temperature overnight. After completing the reaction, the catalyst was removed by filtration and the solvent was concentrated under reduced pressure. The residue was mixed with 5% aqueous sodium hydrogencarbonate to make it neutral and then extracted twice with chloroform. The organic layer thus obtained was dried over anhydrous sodium sulfate. Sodium sulfate was removed by filtration, and the solvent was distilled off under reduced pressure, and the residue thus obtained was purified by silica gel column chromatography (dichloromethane:methanol 15:1-10:1). The obtained product was purified by suspending in ethanol to obtain the title compound (OH-a01: white crystals, 489 mg, 59%). The analytical data of this compound were the same as that of the target compound obtained in Example 2-1A.

Example 2-2(A)

Preparation of 4-{5-hydroxy-4-[4-(morpholin-4-ylmethyl)-phenyl]-4H-[1,2,4]triazol-3-yl}-6-isopropyl-benzene-1,3-diol (OH-a02)

Scheme (2-2)

[Formula 30]

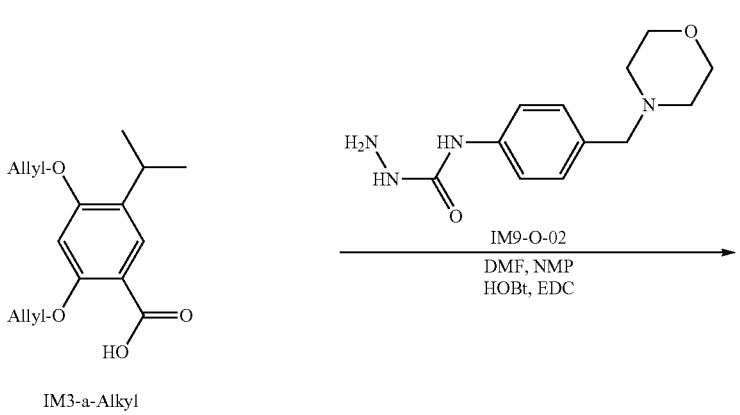

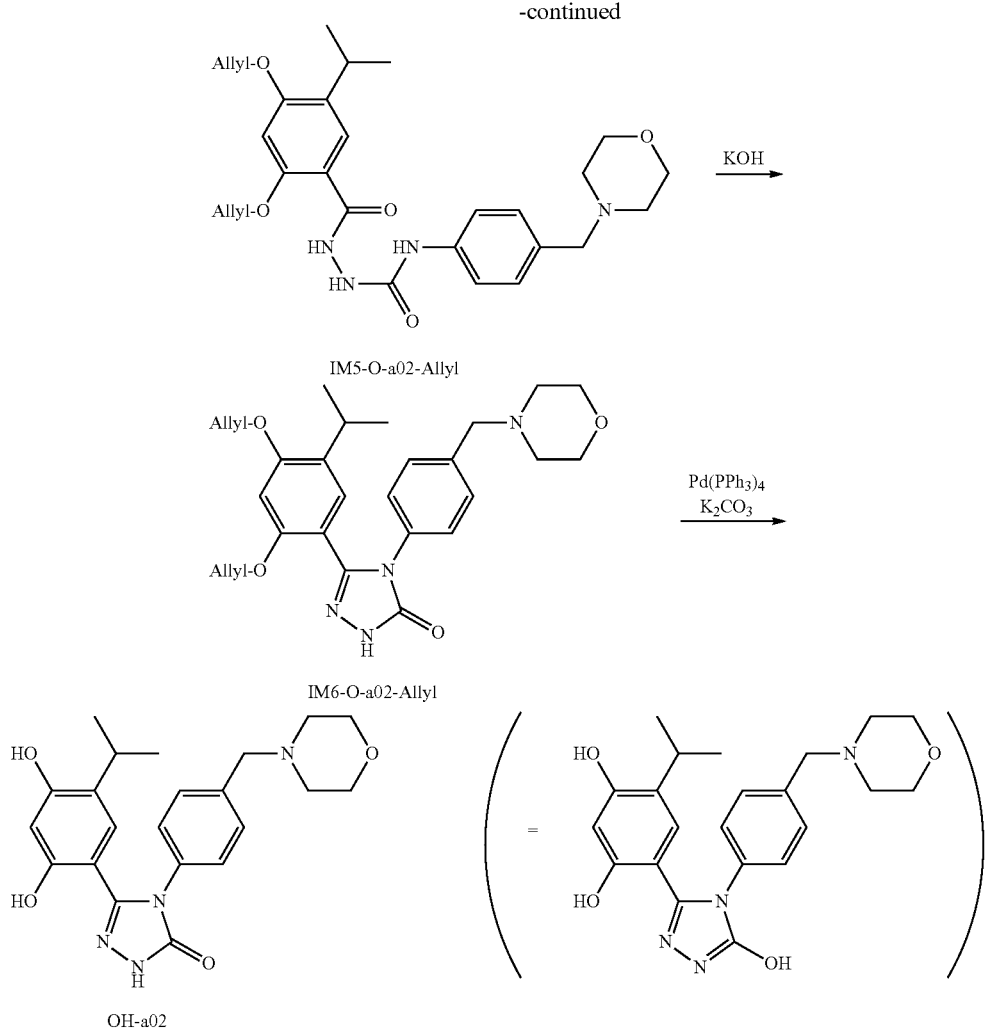

The First Step: Preparation of 4-[4-(morpholin-4-ylmethyl)-phenyl]-1-[2,4-bis-allyloxy-5-isopropyl-benzoyl]semicarbazide (IM5-O-a02-Allyl)

The title compound (IM5-O-a02-Allyl: white crystals, 232.5 mg, 90%) was obtained by a similar process to that of the first step of Example 2-1A, using 4-[4-(morpholin-4-ylmethyl)-phenyl]semicarbazide (IM9-O-02:125 mg, 0.5 mmol) in place of 4-[4-(morpholin-4-yl)-phenyl]semicarbazide and 2,4-bisallyloxy-5-isopropyl-benzoic acid (IM3-a-Allyl:156 mg, 0.5 mmol) in place of 5-isopropyl-2,4-bis-methoxy methoxy-benzoic acid.

The second Step: Preparation of 5-(5-isopropyl-2,4-bis-allyloxy-phenyl)-4-[4-(morpholin-4-ylmethyl)-phenyl]-4H-[1,2,4]triazol-3-ol (IM6-O-a02-Allyl)

The title compound (IM6-O-a02-Allyl: colorless syrup, 28.8 mg, 18%) was obtained by a similar process to that of the second step of Example 2-1A, using 4-[4-(morpholin-4-ylmethyl)-phenyl]-1-[2,4-bis-allyloxy-5-isopropyl-benzoyl]semicarbazide (IM5-O-a02-Allyl: 165.6 mg, 0.32 mmol) in place of 4-[4-(morpholin-4-yl)-phenyl]-1-[5-isopropyl-2,4-bis-methoxymethoxy-benzoyl]semicarbazide and potassium hydroxide in place of sodium hydroxide.

LC/MS (Method 3): m/z (ESI, POS): 485 [M+H]$^+$; retention time: 3.96 minutes.

The Third Step: Preparation of 4-[5-hydroxy-4-(4-morpholin-4-ylmethyl-phenyl)-4H-[1,2,4]triazol-3-yl]-6-isopropyl-benzene-1,3-diol (OH-a02)

A methanol solution of 5-(5-isopropyl-2,4-bis-allyloxy-phenyl)-4-[4-(morpholin-4-ylmethyl)-phenyl]-4H-[1,2,4]triazol-3-ol (37.9 mg, 0.077 mmol) was mixed with tetrakis (triphenylphosphine) palladium (7 mg, 0.007 mmol) and potassium carbonate (64 mg, 0.46 mmol) and reacted at 80° C. for 12 hours. The residue obtained after the concentration was purified by silica gel column chromatography (dichloromethane:methanol 15:1-10:1) to obtain the title compound (OH-a02: white solid, 4.5 mg, 14%).

LC/MS (Method 3): m/z (ESI, POS): 411 [M+H]$^+$; retention time: 1.19 minutes.

$^1$H-NMR (200 MHz, CDCl$_3$:CD$_3$OD=2:1, TMS) ppm: 0.79 (6H, d, J=6.8 Hz), 2.48-2.55 (4H, br), 2.99 (1H, sep, J=6.8 Hz), 3.58 (2H, s), 3.74 (4H, t, J=4.6 Hz), 6.37 (1H, s), 6.55 (1H, s), 7.29 (1H, d, J=8.4 Hz), 7.50 (1H, d, J=8.2 Hz).

55

Example 2-2(B)

Preparation of 5-(2,4-dihydroxy-5-isopropyl-phenyl)-4-(4-morpholin-4-ylmethyl-phenyl)-2,4-dihydro-[1,2,4]triazol-3-one (OH-a02) monohydrochloride

56

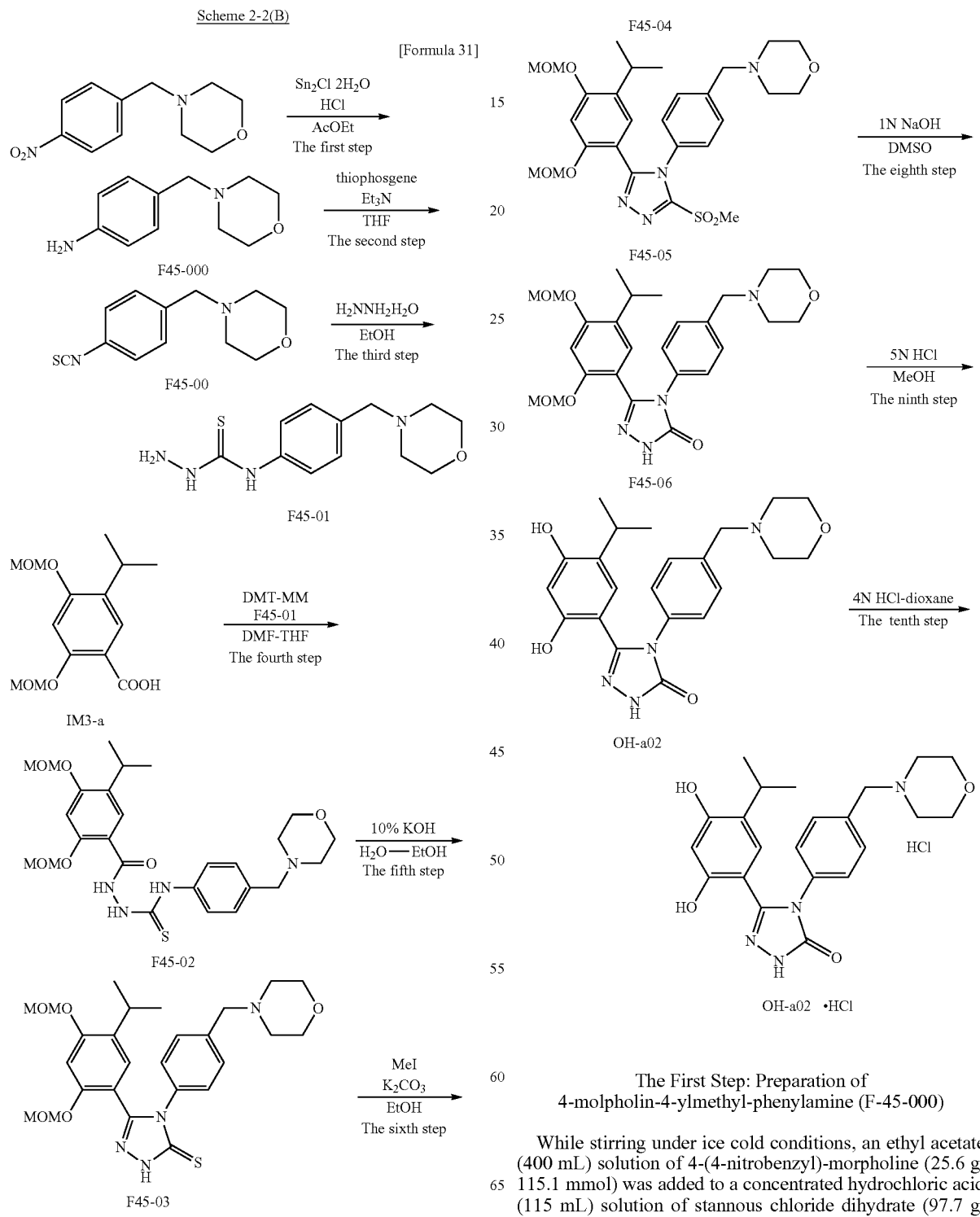

The First Step: Preparation of 4-molpholin-4-ylmethyl-phenylamine (F-45-000)

While stirring under ice cold conditions, an ethyl acetate (400 mL) solution of 4-(4-nitrobenzyl)-morpholine (25.6 g, 115.1 mmol) was added to a concentrated hydrochloric acid (115 mL) solution of stannous chloride dihydrate (97.7 g, 402.7 mmol) dropwise over 30 minutes. After stirring at room temperature overnight, sodium hydroxide was added to the reaction mixture until it became basic. The reaction mixture was extracted with ethyl acetate and washed with saturated aqueous sodium chloride solution. After drying the extract over anhydrous sodium sulfate, sodium sulfate was removed by filtration, and the solvent was distilled off under reduced pressure to obtain a yellow solid. After purification by being suspended in diethyl ether, the solid obtained was dried under reduced pressure. The filtrate, after concentrated, was purified by silica gel column chromatography (hexane, ethyl acetate). Combined yield of the title compound, 4-molpholin-4-ylmethyl-phenylamine (F45-000, white solid) was 16.2 g (73%).

LC/MS (Method 4): m/z (ESI, POS): 193 [M+H]$^+$; retention time: 1.10 minutes.

The Second Step: Preparation of 4-(4-isothiocyanatobenzyl)-morpholine (F45-00)

Triethylamine (4.5 mL, 65.4 mmol) was added to a tetrahydrofuran (500 mL) solution of 4-morpholin-4-ylmethyl-phenylamine (F45-000, 5.16 g, 26.8 mmol). After cooling in ice cold, thiophosgene (2.45 mL, 32.1 mmol) was added. After stirring at room temperature overnight, aqueous sodium hydroxide was added until the reaction mixture became basic. The reaction mixture was extracted with ethyl acetate, washed with water and then washed with saturated sodium chloride. The extract solution was dried over anhydrous sodium sulfate, and then sodium sulfate was removed by filtration and the solvent was distilled off under reduced pressure to obtain a red syrup like substance. The syrup like substance was purified by silica gel column chromatography (hexane, ethyl acetate) to obtain 4-(4-isothiocyanatobenzyl)-morpholine (F45-00, brown oil, 5.72 g, 91%).

LC/MS (Method 3): m/z (ESI, POS): 235 [M+H]$^+$; retention time: 1.84 minutes.

The Third Step: Preparation of F45-01

While stirring under ice cold conditions, an ethanol solution (5 mL) of 4-(4-isothiocyanatobenzyl)-morpholine (F45-00, 2.34 g, 10.0 mmol) was added to an ethanol solution (4 mL) of hydrazine monohydrate (1.0 g, 20.0 mmol) and stirred at room temperature for 40 minutes. The solids were collected from the suspension by filtration and washed with hexane. The solids thus obtained were dried under reduced pressure to obtain F45-01 (pale yellow solid, 2.34 g, 88%).

LC/MS (Method 3): m/z (ESI, POS): 267 [M+H]$^+$; retention time: 0.94 minutes.

The Fourth Step: Preparation of F45-02

At room temperature, 4-(4,6-dimethoxy-1,3,5-triadin-2-yl)-4-methyl morpholinium chloride n hydrate (DMT-MM, 2.55 g) was added to 5-isopropyl-2,4-bis-methoxymethoxy-benzoic acid (2.2 g, 7.74 mmol) and F45-01 (2.16 g, 8.11 mmol) in a mixed solvent of dimethylformamide (10 mL) and tetrahydrofuran (5 mL) and stirred for 5 hours. After terminating the reaction by adding water to the reaction mixture, the solution was neutralized by adding saturated aqueous sodium hydrogencarbonate. The reaction mixture was extracted with ethyl acetate, and the extract was washed with water and then saturated sodium chloride solution. After drying over anhydrous sodium sulfate, sodium sulfate was removed by filtration, and the solvent was distilled off under reduced pressure to obtain pale yellow solids. The solids thus obtained were suspension purified (hexane, ethyl acetate), collected by filtration and dried under reduced pressure to obtain F45-02 (white solid, 3.39 g, 82%).

LC/MS (Method 3): m/z (ESI, POS): 533 [M+H]$^+$; retention time: 3.80 minutes.

The Fifth Step: Preparation of 5-(5-isopropyl-2,4-bis-methoxymethoxyphenyl)-4-(4-morpholin-4-ylmethylphenyl)-2,4-dihydro-[1,2,4]triazol-3-thione (F45-03)

At room temperature, 10% aqueous potassium hydroxide (20 mL) and 5% ethanol solution of potassium hydroxide (12 mL) were added to F45-02 (3.39 g, 6.36 mmol) and then the reaction mixture was heated under reflux for 11 hours. After returning to room temperature, saturated sodium chloride solution was added and the mixture was stirred for a while. And then the reaction mixture was extracted with chloroform, and the extract was washed with saturated sodium chloride solution. After drying the extract over anhydrous sodium sulfate, sodium sulfate was removed by filtration and the solvent was distilled off under reduced pressure to obtain pale yellow solids. It was purified by silica gel column chromatography (NH silica, hexane, ethyl acetate, chloroform and methanol) to obtain 5-(5-isopropyl-2,4-bis-methoxymethoxyphenyl)-4-(4-morpholin-4-ylmethylphenyl)-2,4-dihydro-[1,2,4]triazol-3-thione (F45-03, white solid, 2.43 g, 74%).

LC/MS (Method 3): m/z (ESI, POS): 515 [M+H]$^+$; retention time: 3.56 minutes.

$^1$H-NMR (400 MHz, CDCl$_3$) δ 1.11 (d, J=7.0 Hz, 6H), 2.42 (t, J=4.6 Hz, 4H), 3.19 (sept., J=7.0 Hz, 1H), 3.26 (s, 3H), 3.46 (s, 3H), 3.47 (s, 2H), 3.70 (t, J=4.6 Hz, 4H), 4.74 (s, 2H), 5.16 (s, 2H), 6.81 (s, 1H), 7.09 (s, 1H), 7.23 (d, J=8.4 Hz, 2H), 7.35 (d, J=8.4 Hz, 2H).

The Sixth Step: Preparation of 3-(5-isopropyl-2,4-bis-methoxymethoxyphenyl)-4-(4-morpholin-4-ylmethylphenyl)-5-methylsulfanyl-4H-[1,2,4]triazole (F45-04)

5-(5-isopropyl-2,4-bis-methoxymethoxyphenyl)-4-(4-molpholin-4-ylmethylphenyl)-2,4-dihydro-[1,2,4]triazol-3-thione (F45-03, 2.43 g, 4.72 mmol) and potassium carbonate (653 mg, 4.72 mmol) were weighed and placed in a reaction vessel, and ethanol (30 mL) and then methyl iodide (0.29 mL, 4.72 mmol) were added. After heating at 80° C. stirring for an hour, the reaction mixture was returned to room temperature, and the solvent was distilled off under reduced pressure. The reaction system was mixed with water, extracted with ethyl acetate, and the extract was washed with saturated sodium chloride solution. After drying the extract over anhydrous sodium sulfate, sodium sulfate was removed by filtration and the solvent was distilled off under reduced pressure to obtain a pale yellow foam (2.18 g) containing 3-(5-isopropyl-2,4-bis-methoxymethoxyphenyl)-4-(4-molpholin-4-ylmethylphenyl)-5-methylsulfanyl-4H-[1,2,4]triazole (F45-04).

LC/MS (Method 3): m/z (ESI, POS): 529 [M+H]$^+$; retention time: 3.47 minutes.

$^1$H-NMR (400 MHz, CDCl$_3$) δ 1.13 (d, J=7.0 Hz, 6H), 2.42 (t, J=4.6 Hz, 4H), 2.73 (s, 3H), 3.19 (s, 3H), 3.21 (sept., J=7.0 Hz, 1H), 3.46 (s, 3H), 3.48 (s, 2H), 3.70 (t, J=4.6 Hz, 4H), 4.70 (s, 2H), 5.15 (s, 2H), 6.78 (s, 1H), 7.10 (d, J=8.4 Hz, 2H), 7.25 (s, 1H), 7.34 (d, J=8.4 Hz, 2H).

The Seventh Step: Preparation of 3-(5-isopropyl-2,4-bis-methoxymethoxyphenyl)-4-(4-morpholin-4-ylmethylphenyl)-5-methanesulfonyl-4H-[1,2,4]triazole (F45-05)

While stirring under ice cold conditions, 3-chloroperbenzoic acid (3.54 g, 20.5 mmol) was added to a methylene chloride solution (20 mL) of the crude product (2.15 g), obtained in the previous step, containing 3-(5-isopropyl-2,4-bis-methoxy methoxyphenyl)-4-(4-morpholin-4-ylmethylphenyl)-5-methylsulfanyl-4H-[1,2,4]triazole (F45-04). After stirring at room temperature for 3.5 hours, additional 3-chloroperbenzoic acid (701 mg, 4.06 mmol) was added to the reaction mixture and further stirred for 1.5 hours. After cooling to ice cold temperature, saturated aqueous sodium thiosulfate and then 10% aqueous potassium hydrogen sulfite were added, and the mixture was stirred for some time. Further, saturated aqueous sodium hydrogencarbonate was added, and the mixture was stirred and then extracted with ethyl acetate. The extract was washed with saturated sodium chloride solution and dried over anhydrous sodium sulfate. Sodium sulfate was removed by filtration and the solvent was distilled off under reduced pressure to obtain a red brown foam (2.49 g) containing 3-(5-isopropyl-2,4-bis-methoxymethoxyphenyl)-4-(4-molpholin-4-ylmethylphenyl)-5-methanesulfonyl-4H-[1,2,4]triazole (F45-05).

LC/MS (Method 3): m/z (ESI, POS): 561 [M+H]$^+$; retention time: 3.63 minutes.

$^1$H-NMR (400 MHz, CDCl$_3$) δ 1.11 (d, J=7.0 Hz, 6H), 2.41 (t, J=4.6 Hz, 4H), 3.20 (sept., J=7.0 Hz, 1H), 3.25 (s, 3H), 3.46 (s, 3H), 3.48 (s, 2H), 3.54 (s, 3H), 3.69 (t, J=4.6 Hz, 4H), 4.78 (s, 2H), 5.17 (s, 2H), 6.82 (s, 1H), 7.18 (s, 1H), 7.26 (d, J=8.4 Hz, 2H), 7.36 (d, J=8.4 Hz, 2H).

The Eighth Step: Preparation of 5-(5-isopropyl-2,4-bis-methoxymethoxyphenyl)-4-(4-morpholin-4-ylmethylphenyl)-2,4-dihydro-[1,2,4]triazole-3-one (F45-06)

At room temperature aqueous sodium hydroxide (1.0 M aqueous solution, 7 mL) was added to a dimethylsulfoxide solution (7 mL) of the crude product (1.01 g), which was obtained in the previous step, containing 3-(5-isopropyl-2,4-bis-methoxymethoxyphenyl)-4-(4-molpholin-4-ylmethylphenyl)-5-methanesulfonyl-4H-[1,2,4]triazole (F45-05). The reaction mixture was heated at 90° C. for 5.5 hours while stirring, cooled to room temperature, extracted with ethyl acetate, and the extract was washed twice with water and then saturated sodium chloride solution. The extract was dried over anhydrous sodium sulfate, and then sodium sulfate was removed by filtration. The solvent was distilled off under reduced pressure to obtain a pale yellow foam. Reprecipitation purification was carried out (chloroform, diethyl ether), and the solids were washed with diethyl ether and dried under reduced pressure to obtain 5-(5-isopropyl-2,4-bis-methoxymethoxyphenyl)-4-(4-morpholin-4-ylmethylphenyl)-2,4-dihydro-[1,2,4]triazole-3-one (F45-06, pale yellow solid, 469 mg, 53%).

LC/MS (Method 3): m/z (ESI, POS): 499 [M+H]$^+$; retention time: 3.41 minutes.

The Ninth Step: Preparation of 5-(2,4-dihydroxy-5-isopropylphenyl)-4-(4-molpholin-4-ylmethylphenyl)-2,4-dihydro-[1,2,4]triazole-3-one (OH-a02)

5 N hydrochloric acid (2 mL) was added to a methanol solution (5 mL) of 5-(5-isopropyl-2,4-bis-methoxymethoxyphenyl)-4-(4-morpholin-4-ylmethylphenyl)-2,4-dihydro-[1,2,4]triazole-3-one (F45-06, 469 mg, 0.94 mmol) and the mixture was stirred at room temperature for 3 hours. An additional 5 N hydrochloric acid (2 mL) was added and the stirring was continued overnight. The reaction mixture was cooled to ice cold conditions and neutralized by adding saturated aqueous sodium hydrogencarbonate. The solution was extracted with a mixed solvent of chloroform-methanol, and the extract was washed with water and saturated sodium chloride solution. After drying the extract over anhydrous sodium sulfate, sodium sulfate was removed by filtration and the solvent was distilled off under reduced pressure to obtain white solids. The solids thus obtained were dissolved in methanol (20 mL) and methylene chloride (100 mL) and insoluble components were removed by filtration. The mother liquor after the filtration was concentrated under reduced pressure, and the solids obtained were purified by silica gel column chromatography (methanol:methylene chloride=1:9) to obtain the title compound (537.7 mg).

LC/MS (Method 3): m/z (ESI, POS): 411 [M+H]$^+$; retention time: 1.69 minutes.

$^1$H-NMR (400 MHz, DMSO-d$_6$) δ 0.94 (d, J=7.0 Hz, 6H), 2.33 (s, 4H), 2.96 (sept., J=7.0 Hz, 1H), 3.44 (s, 2H), 3.56 (t, J=4.6 Hz, 4H), 6.32 (s, 1H), 6.76 (s, 1H), 7.13 (d, J=8.4 Hz, 2H), 7.30 (d, J=8.4 Hz, 2H), 9.45 (bs, 1H), 9.70 (bs, 1H), 11.93 (bs, 1H).

The Tenth Step: Preparation of 5-(2,4-dihydroxy-5-isopropylphenyl)-4-(4-morpholin-4-ylmethylphenyl)-2,4-dihydro-[1,2,4]triazol-3-one (OH-a02) monohydrochloride 5-(2,4-dihydroxy-5-isopropylphenyl)-4-(4-molpholin-4-ylmethylphenyl)-2,4-dihydro-[1,2,4]triazole-3-on (OH-a02, 532 mg, 1.3 mmol) and 1,4-dioxane (50 mL) were placed in a 200 mL eggplant shaped flask, and 4 N hydrochloric acid/1,4-dioxane solution (0.33 mL, 1.3 mmol) was added at room temperature while stirring. The stirring was continued at room temperature for further 2 hours. After completing the reaction, most of the 1,4-dioxane was removed under reduced pressure, and the reaction mixture was purified by being suspended in diethyl ether. The solids were collected by filtration and dried under reduced pressure to obtain the title compound (OH-02a monohydrochloride, 542.1 mg).

LC/MS (Method 4): m/z (ESI, POS): 411 [M–HCl+H]$^+$; retention time: 3.81 minutes.

$^1$H-NMR (400 MHz, DMSO-d$_6$) δ 1.01 (d, J=6.8 Hz, 6H), 3.01 (sept., J=6.8 Hz, 1H), 3.08 (m, 2H), 3.19 (m, 2H), 3.72 (m, 2H), 3.94 (m, 2H), 4.32 (m, 2H), 6.27 (s, 1H), 6.89 (s, 1H), 7.25 (d, J=7.7 Hz, 2H), 7.56 (d, J=7.7 Hz, 2H), 9.36 (s, 1H), 9.64 (s, 1H), 10.85 (bs, 1H), 11.97 (s, 1H).

Example 2-3A and Example 2-3B

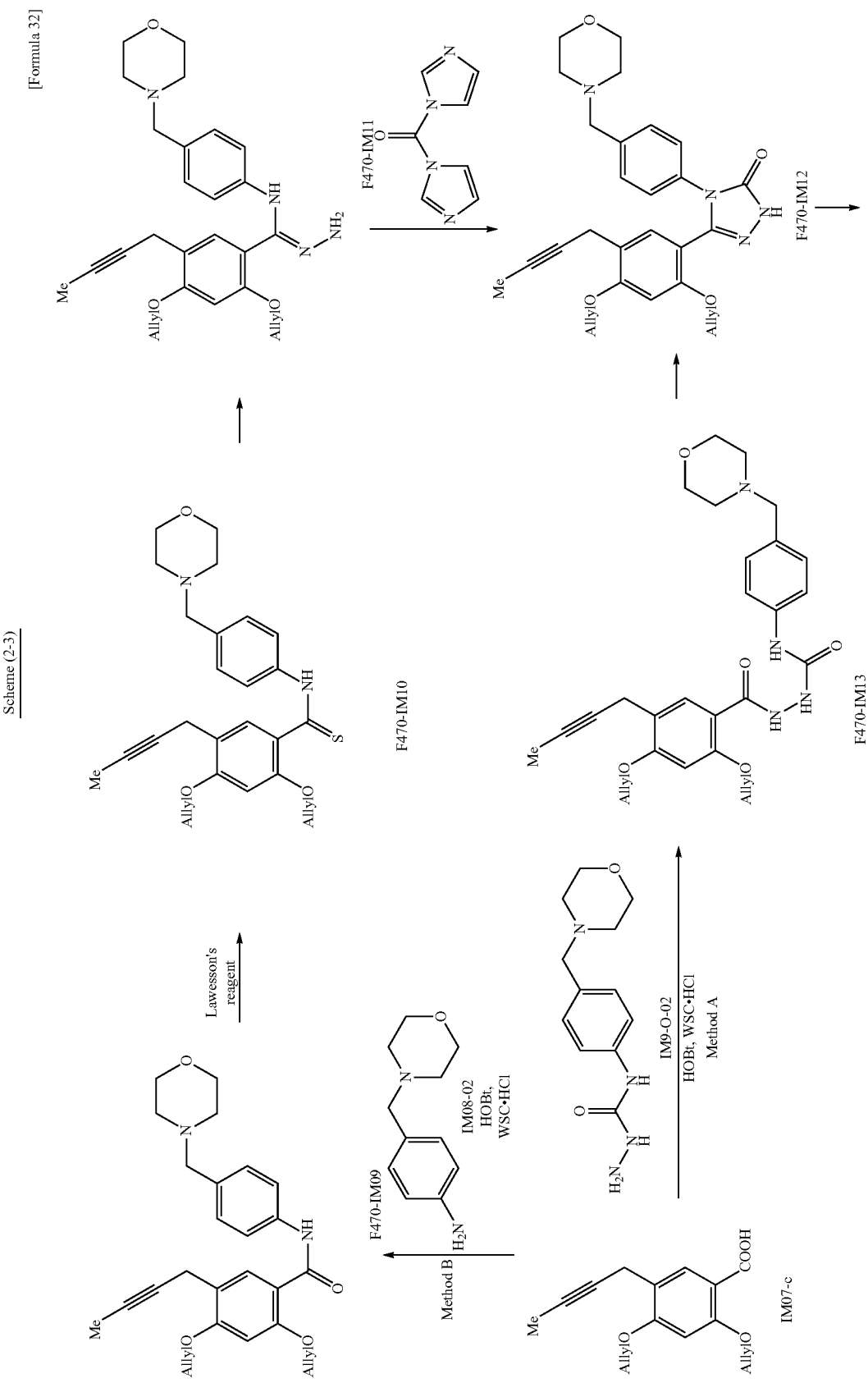

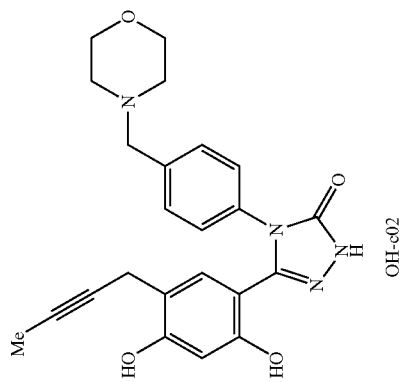
OH-c02
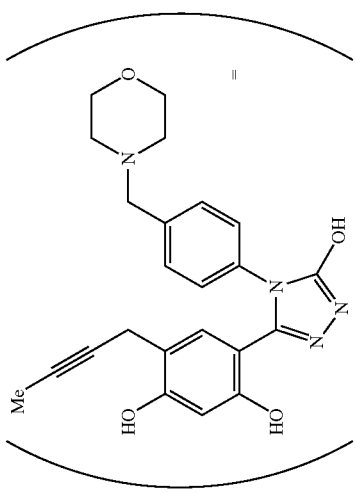

Example 2-3A

Production (Method A) of 5-[5-(but-2-ynyl)-2,4-dihydroxy-phenyl]-4-[4-(morpholin-4-ylmethyl)-phenyl]-2,4-dihydro-[1,2,4]triazol-3-one (OH-c02)

The title compound (OH-c02) was prepared from 2,4-bis-allyloxy-5 (but-2-ynyl)-benzoic acid (IM07-c) via F470-IM13 in a similar manner to Example 2-2. The MS, and NMR spectral data of the title compound (OH-a02) are described in Example 2-3B.

Example 2-3B

Preparation (Method B) of 5-[5 (but-2-ynyl)-2,4-dihydroxy-phenyl]-4-[4-(morpholin-4-ylmethyl)-phenyl]-2,4-dihydro-[1, 2-4]triazol-3-one (OH-c02)

The First Step: Preparation of 2,4-bis-allyloxy-5-(but-2-ynyl)-N-[4-(morpholin-4-ylmethyl)-phenyl]-benzamide (F470-IM09)

2,4-bis-allyloxy-5 (but-2-ynyl)-benzoic acid (Example 1-4, IM07-c: 287 mg, 1 mmol) and 4-(morpholin-4-ylmethyl)-phenylamine (IM08-02: 193 mg, 1 mmol) were dissolved in dimethylformamide (4 mL) and mixed with 1-hydroxybenzotriazole monohydrate (176 mg, 1.3 mmol) and 1-ethyl-3-(3-dimethylaminopropyl)carbodiimide hydrochloride (249 mg, 1.3 mmol) at 0° C., and the resulting mixture was stirred for 4 hours under ice cold conditions. The reaction mixture was mixed with water (40 mL) and extracted twice with ethyl acetate (50 mL). The combined organic layers were washed with saturated aqueous sodium chloride solution, dried over sodium sulfate and then were concentrated. The residue was purified by silica gel column chromatography (hexane-ethylacetate=1:2-1:5) to obtain the title compound (F470-IM09: 0.40 g, yield 82%).

LC/MS: m/z(ESI, POS): 461[M+H]$^+$ $^1$H-NMR (400 MHz, CDCl$_3$, TMS)ppm:9.90 (1H, s), 8.39 (1H, s), 7.63 (2H, d, J=8.4 Hz), 7.36 (2H, d, J=8.4 Hz), 6.46 (1H, s), 6.18 (2H, m), 6.05 (2H, m), 5.57-5.31 (4H, m), 4.70 (2H, m), 4.61 (2H, m), 3.80 (4H, brs), 3.65 (2H, m), 2.62 (4H, brs), 4.61 (2H, m), 3.46 (2H, m), 1.85 (3H, t, J=2.6 Hz).

The Second Step: Preparation of 2,4-bis-allyloxy-5-(but-2-ynyl)-N-[4-(morpholin-4-ylmethyl)-phenyl]-thiobenzamide (F470-IM10)

2,4-bis-allyloxy-5 (but-2-ynyl)-N-[4-(morpholin-4-ylmethyl)-phenyl]-benzamide (F470-IM09: 400 mg, 0.86 mmol) and Lawesson's reagent (352 mg, 0.86 mmol) were dissolved in toluene (20 mL), and the mixture was heated under reflux for 3 hours. The reaction mixture was mixed with saturated aqueous sodium carbonate (30 mL) and extracted twice with ethyl acetate (40 mL). The combined organic layers were washed with saturated aqueous sodium chloride solution, dried over anhydrous sodium sulfate and then concentrated. The residue was purified by silica gel column chromatography (ethyl acetate) to obtain the crude title compound (F470-IM10:240 mg).

LC/MS: m/z(ESI, POS): 477[M+H]$^+$

The Third Step: Preparation of 2,4-bis-allyloxy-5-(but-2-ynyl)-N-[4-(morpholin-4-yl)-phenyl]-benzene-carbohydrazonamide (F470-IM11)

Crude 2,4-bis-allyloxy 5-(but-2-ynyl)-N-[4-(morpholin-4-ylmethyl)-phenyl]-thiobenzamide (F470-IM10: 240 mg, 0.86 mmol) and hydrazine monohydrate (700 mg, 14 mmol) were dissolved in ethanol (6 mL) and the mixture was heated under reflux for 1 hour and then concentrated to obtain the crude title compound (F470-IM11: 243 mg).

LC/MS (Method 4): m/z(ESI, POS): 475[M+H]$^+$; retention time: 3.88 minutes.

The Fourth Step: Preparation of 5-[2,4-bis-allyloxy 5-(but-2-ynyl)-phenyl]-4-[4-(morpholin-4-ylmethyl)-phenyl]-2,4-dihydro-[1,2,4]triazol-3-one (F470-IM12)

Crude 2,4-bis-allyloxy-5 (but-2-ynyl)-N-[4-(morpholin-4-yl)-phenyl]-benzene-carbohydrazonamide (F470-IM11: 243 mg) was dissolved in anhydrous tetrahydrofuran (5 mL) and mixed with 1,1'-carbonyldiimidazole (121 mg, 0.75 mmol), and the mixture was stirred for 1.5 hours. The reaction mixture was mixed with saturated sodium carbonate solution (15 mL) and extracted twice with ethyl acetate (30 mL). The organic layer was washed with saturated sodium chloride solution, dried over anhydrous sodium sulfate and then concentrated to obtain the crude title compound (F470-IM12: 208 mg).

LC/MS (Method 4): m/z(ESI, POS): 501[M+H]$^+$; retention time: 4.90 minutes.

The Fifth Step: Preparation of 5-[5-(but-2-ynyl)-2,4-dihydroxy-phenyl]-4-[4-(morpholin-4-ylmethyl)-phenyl]-2,4-dihydro-[1,2,4]triazol-3-one (OH-c02)

Under a nitrogen atmosphere crude 5-[2,4-bis-allyloxy-5-(but-2-ynyl)-phenyl]-4-[4-(morpholin-4-ylmethyl)-phenyl]-2,4-dihydro-[1,2,4]triazol-3-one(F470-IM12: 208 mg) was dissolved in methanol (10 mL) and mixed with potassium carbonate (348 mg, 2.52 mmol) and tetrakis (triphenylphosphine) palladium (20 mg, 0.016 mmol), and the mixture was heated for 3 hours under reflux. After adding water (5 mL), the reaction mixture was adjusted to pH 6.5 with 2M hydrochloric acid. Silica gel (2.0 g) was added to this mixture and the mixture was concentrated. The residue was purified by silica gel column chromatography (chloroform-methanol=30:1-10:1) to obtain the title compound (OH-c02: 38 mg, yield 10.4%, in 4 steps).

LC/MS (Method 3): m/z(ESI, POS): 421[M+H]$^+$; retention time: 1.15 minutes.

$^1$H-NMR (400 MHz, CDCl$_3$:CD$_3$OD=4:1, TMS)ppm:7.46 (2H, d, J=8.1), 7.26 (2H, d, J=8.1), 6.83 (1H, s), 6.35 (1H, s), 3.75 (4H, brs), 3.40 (2H, s), 3.16 (2H, m), 2.58 (4H, brs), 1.74 (3H, t, J=2.6 Hz).

Example 2-4
Preparation of 5-[2,4-dihydroxy-5-(prop-2-ynyl)-phenyl]-4-[4-(morpholin-4-ylmethyl)-phenyl]-2,4-dihydro-[1,2,4]triazol-3-one (OH-e02)
[Formula 33]
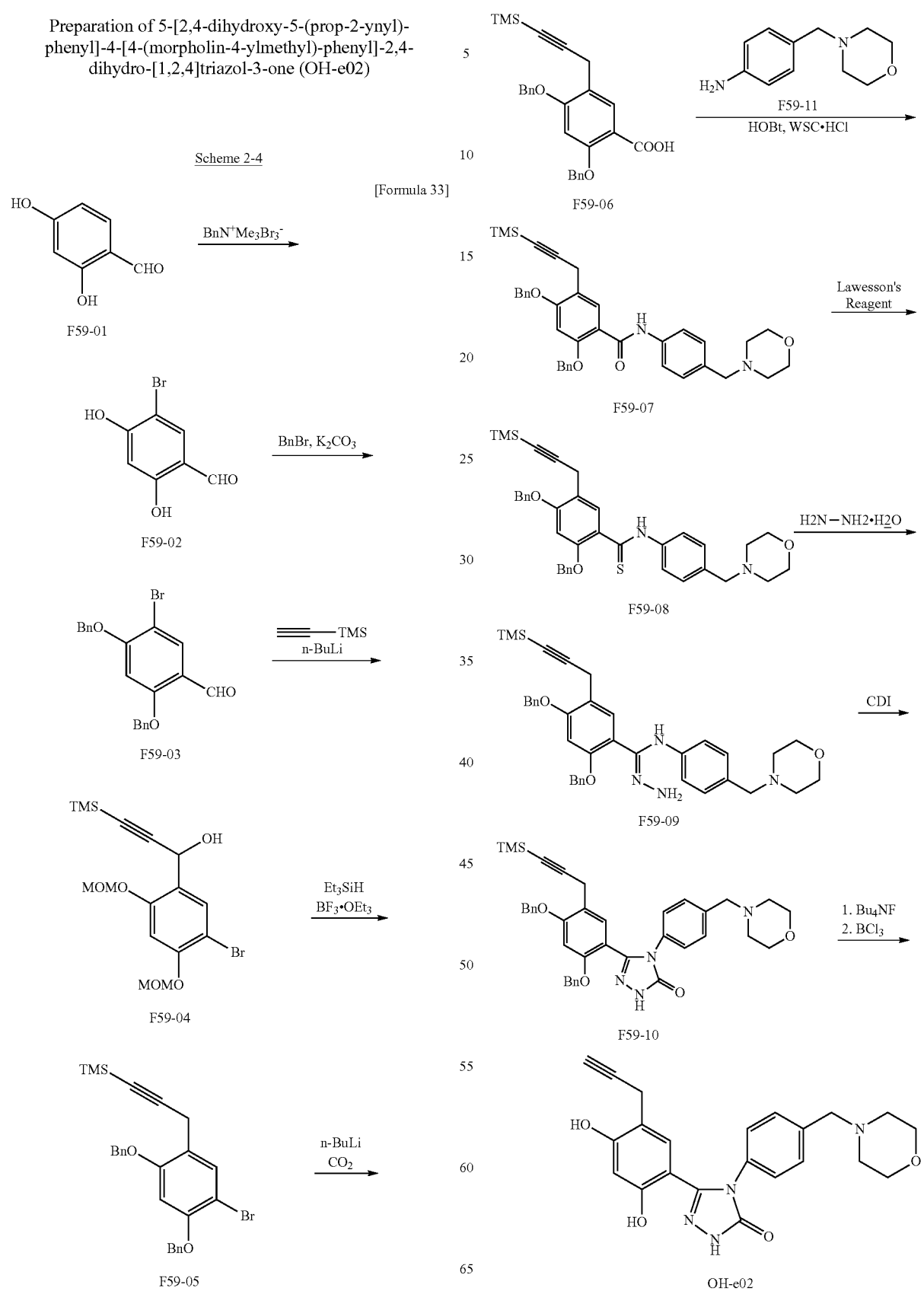

The First Step: Preparation of F59-02

Under a nitrogen atmosphere, 2,4-dihydroxybenzaldehyde (F59-01, 3.0 g, 21.72 mmol) was suspended in anhydrous dichloromethane (300 mL) in a 1 L flask. Benzyltrimethylammonium tribromide (10.0 g, 25.64 mmol) was added to this mixture and the mixture was stirred at room temperature for 2.5 hours. The reaction mixture was mixed with water (200 mL) and chloroform (100 mL). The organic layer was separated and washed with saturated aqueous sodium chloride solution, dried with sodium sulfate and, after filtration, concentrated under reduced pressure to obtain the crude title compound (F59-02: 5250 mg).

The Second Step: Preparation of F59-03

Crude F59-02 (5250 mg) was dissolved in anhydrous dimethylformamide (50 mL) and under ice cold conditions mixed with potassium carbonate (7.56 g, 54.68 mmol) and benzylbromide (5.42 mL, 45.57 mmol), and the mixture was stirred overnight. The reaction mixture was mixed with water (500 mL) and extracted twice with ethyl acetate (300 mL). The combined organic layers were washed with saturated aqueous sodium chloride solution, then dried with sodium sulfate and concentrated. The residue was purified by silica gel column chromatography (hexane:ethyl acetate=:4:1) to obtain the title compound (F59-03: 6.2 g, yield 72.0% in 2 steps).

LC/MS (Method 3): m/z (ESI, POS): 399 [M+H]$^+$; retention time: 7.62 minutes.

$^1$H-NMR (400 MHz, CDCl$_3$, ppm): 10.30 (1H, s), 8.04 (1H, s), 7.41-7.37 (12H, m), 6.53 (1H, s), 5.16 (2H, s), 5.11 (2H, s)

The Third Step: Preparation of F59-04

Trimethylsilylacetylene (1.04 mL, 7.5 mmol) and anhydrous tetrahydrofuran (15 mL) were placed in a 100 mL three-neck flask under a atmosphere of nitrogen. n-Butyllithium (4.72 mL, 1.59M/hexane) were added to this mixture dropwise over 30 minutes at −78° C. A solution of F59-03 (1987 mg, 5 mmol) in tetrahydrofuran (30 mL) was added to this mixture dropwise over 20 minutes at −78° C. After being stirred for 3 hours under ice cold conditions, the reaction mixture was mixed with saturated aqueous ammonium chloride (30 mL) and water, and extracted twice with ethyl acetate (100 mL). The combined organic layers were washed with saturated sodium hydrogencarbonate and saturated aqueous sodium chloride solution, and then dried with sodium sulfate. The mixture was filtered and the filtrate was concentrated under reduced pressure to obtain the crude title compound (F59-04, 2770 mg).

LC/MS (Method 7): m/z (ESI, POS): 477 [M−H$_2$O]$^+$; retention time: 7.36 minutes.

The Fourth Step: Preparation of F59-05

Under a nitrogen atmosphere, crude F59-04 (2770 mg) dissolved in anhydrous acetonitrile (4 mL) was placed in a 200 mL two-neck flask. To the solution were added triethylsilane (0.878 mL, 5.5 mmol) and borontrifluoride diethylether (0.697 mL, 5.5 mmol) and this mixture was stirred for 1 hour under ice cold conditions. The reaction mixture was mixed with potassium carbonate (2000 mg) and water (150 mL) and extracted twice with ethyl acetate (150 mL). The organic layer was washed with saturated aqueous sodium chloride solution, dried with sodium sulfate and concentrated under reduced pressure. The residue was purified by silica gel column chromatography (hexane:ethyl acetate=5:1) to obtain the title compound (F59-05: 2135 mg, yield 89% in 2 steps).

The Fifth Step: Preparation of F59-06

Under a nitrogen atmosphere, F59-05 (2135 mg, 4.45 mmol) dissolved in anhydrous tetrahydrofuran (20 mL) was placed in a 100 mL two-neck flask. n-Butyl lithium (3.08 mL, 1.59M/hexane, 4.90 mmol) was added to this mixture dropwise over 10 minutes at −78° C. And then the mixture was stirred for 15 minutes. A large excess of solid carbon dioxide was quickly added to the reaction mixture and the mixture was stirred at room temperature for 1 hour. The reaction mixture was mixed with 10% aqueous potassium hydrogen sulfate (50 mL), extracted twice with ethyl acetate (100 mL). After washing with saturated sodium chloride solution, the organic layer was dried with sodium sulfate, filtered and concentrated under reduced pressure. The residue was purified by silica gel column chromatography (hexane:ethyl acetate=4:1-2:1) to obtain the title compound (F59-06: 370 mg, yield 18.7%).

LC/MS (Method 3): m/z(ESI, POS): 445[M+H]$^+$; retention time: 8.26 minutes.

$^1$H-NMR (400 MHz, CDCl$_3$, ppm):10.52 (1H, brs), 8.28 (1H, s), 7.40 (10H, s), 6.56 (1H, s), 5.19 (2H, s), 5.12 (2H, s), 3.58 (2H, s), 0.19 (9H, s)

The Sixth Step: Preparation of F59-07

A solution of F59-06 (370 mg, 0.83 mmol) and F59-11 (192 mg, 1.0 mmol) in dimethylformamide (5 mL) was placed in a 100 mL flask. 1-Hydroxybenzotriazole monohydrate (146 mg, 1.08 mmol) and 1-ethyl-3-(3'-dimethylaminopropyl)carbodiimide hydrochloride (207 mg, 1.08 mmol) were added to the solution under ice cold conditions and the mixture was stirred for 20 hours. The reaction mixture was mixed with water (30 mL) and saturated aqueous sodium hydrogencarbonate (20 mL) and extracted twice with ethyl acetate (50 mL). The organic layer was washed with saturated aqueous sodium chloride solution, dried with sodium sulfate and concentrated under reduced pressure. The residue was purified by silica gel column chromatography (chloroform:methanol=30:1) to obtain the title compound (F59-07: 447 mg, yield 87.0%).

LC/MS (Method 5): m/z (ESI, POS): 619 [M+H]$^+$; retention time: 8.26 minutes.

The Seventh Step: Preparation of F59-08

A solution of F-59-07 (477 mg, 0.72 mmol) and Lawesson's reagent (381 mg, 0.94 mmol) in toluene (15 mL) was placed in a 100 mL flask, and the mixture was heated for 8 hours under reflux. The reaction mixture was mixed with saturated aqueous sodium hydrogencarbonate solution (30 mL) and extracted twice with ethyl acetate (30 mL). The organic layer was washed with saturated sodium chloride solution, dried with sodium sulfate and then concentrated. The residue was purified by silica gel column chromatography (chloroform:methanol=40:1) to obtain the title compound (F59-08: 339 mg, yield 74.1%).

LC/MS (Method 5): m/z (ESI, POS): 635 [M+H]$^+$; retention time: 4.52 minutes.

The Eighth Step: Preparation of F59-09

F59-08 (339 mg, 0.53 mmol) and hydrazine-monohydrate (0.7 mL) were dissolved in ethanol (6 mL) and heated for 1 hour under reflux, and then the mixture was concentrated to obtain the crude title compound (F59-09, 345 mg).

LC/MS (Method 3): m/z (ESI, POS): 633 [M+H]$^+$; retention time: 3.79 minutes.

The Ninth Step: Preparation of F59-10

Crude F59-09 (345 mg) was dissolved in anhydrous tetrahydrofuran (6 mL), mixed with 1-1' carbonyldiimidazole (130 mg, 0.8 mmol) and stirred for 5 hours. The reaction mixture was mixed with saturated aqueous sodium carbonate solution (30 mL) and extracted twice with ethyl acetate (30 mL). The organic layer was washed with saturated aqueous sodium chloride solution, dried with sodium sulfate and then concentrated. The residue was purified by silica gel column chromatography (ethyl acetate:acetone=:8:1) to obtain the title compound (F59-10: 101 mg, yield 21.3% in 3 steps).

LC/MS (Method 3): m/z (ESI, POS): 659 [M+H]$^+$; retention time: 4.99 minutes.

$^1$H-NMR (400 MHz, CDCl$_3$, ppm): 10.33 (1H, s), 7.44 (1H, s), 7.30-7.08 (10H, m), 6.93 (2H, d, J=8.24 Hz), 6.84 (2H, m), 6.13 (1H, s), 4.80 (2H, s), 4.47 (2H, s), 3.59 (4H, s), 3.49 (2H, s), 3.37 (2H, s), 2.37 (4H, s), 0.06 (9H, s)

The Tenth Step: Preparation of 5-[2,4-dihydroxy-5-(prop-2-ynyl)-phenyl]-4-[4-(molpholin-4-ylmethyl)-phenyl]-2,4-dihydro-[1,2,4]triazol-3-one (OH-e02)

F59-10 (101 mg, 0.15 mmol) was dissolved in anhydrous tetrahydrofuran (5 mL) in a 50 mL flask, mixed with tetrabutylammonium fluoride (0.16 mL, 1.0M/tetrahydrofuran) and stirred for 1 hour. The reaction mixture was mixed with saturated aqueous sodium hydrogencarbonate (20 mL) and extracted twice with ethyl acetate (20 mL). The organic layer was washed with saturated aqueous sodium chloride solution, dried with sodium sulfate, filtered and then concentrated. The residue was dissolved in anhydrous dichloromethane (3 mL), mixed with boron trichloride (3 mL, 1.0M/dichloromethane) at −200 C and then stirred for 2 hours under ice cold conditions. After adding methanol (5 mL) to the reaction mixture, solid sodium hydrogencarbonate was added so that the pH of the solution was adjusted to 7.0 by pH-test paper. The reaction mixture was filtered and the filter cake was washing sufficiently with chloroform:methanol (3:1). The filtrate and washing were combined and concentrated. The residue was purified by silica gel column chromatography (chloroform:methanol=10:1–5:1) to obtain the title compound (OH-e02: 21.5 mg, yield 35.2%).

LC/MS (Method 4): m/z(ESI, POS): 407[M+H]$^+$; retention time: 3.58 minutes.

$^1$H-NMR (400 MHz, CDCl$_3$:CD$_3$OD=3:1, ppm):7.47 (2H, d, J=8.06 Hz), 7.27 (2H, d, J=8.06 Hz), 6.88 (1H, s), 6.38 (1H, s), 3.75 (4H, brs), 3.59 (2H, s), 3.22 (2H, m), 2.54 (4H, brs), 1.94 (1H, s)

Example 2-5

Preparation of 5-(2,4-dihydroxy-5-isopropylphenyl)-4-[4-(4-methylpiperazin-1-ylmethyl)phenyl]-2,4-dihydro-[1,2,4]triazol-3-one (OH-a13) dihydrochloride

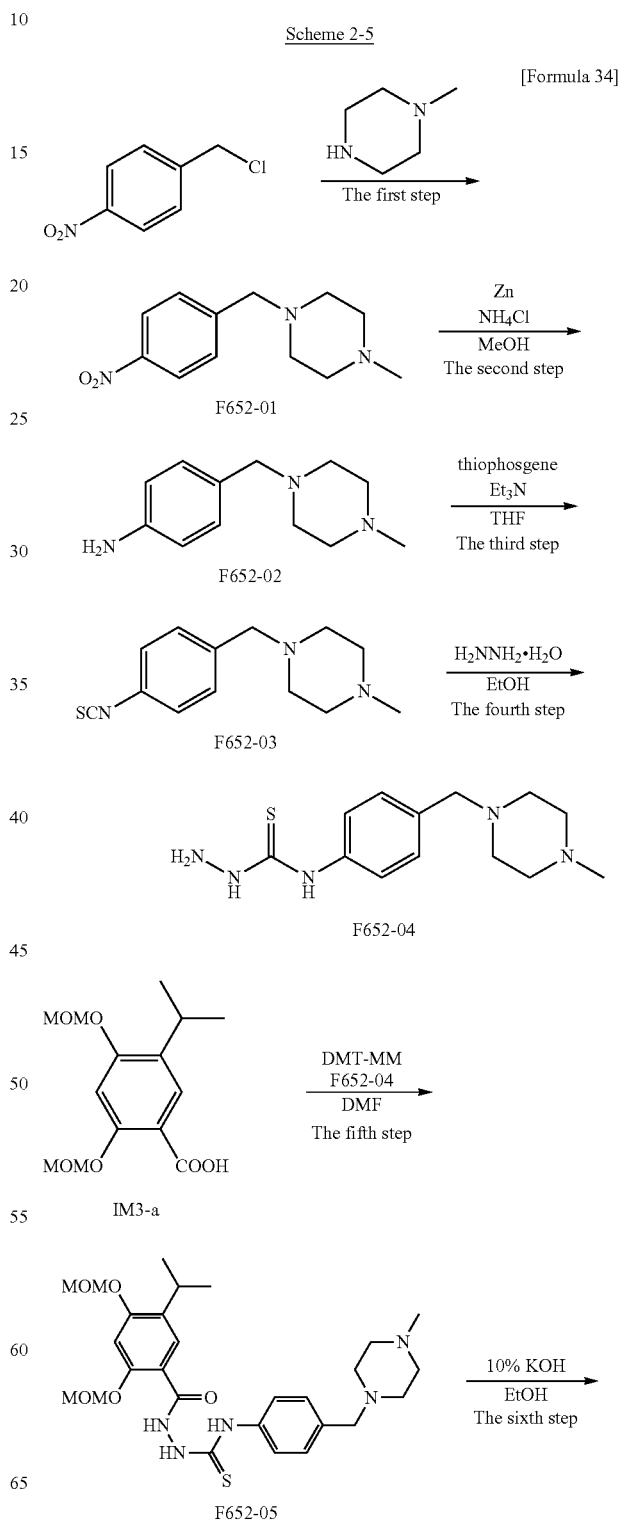

Scheme 2-5

[Formula 34]

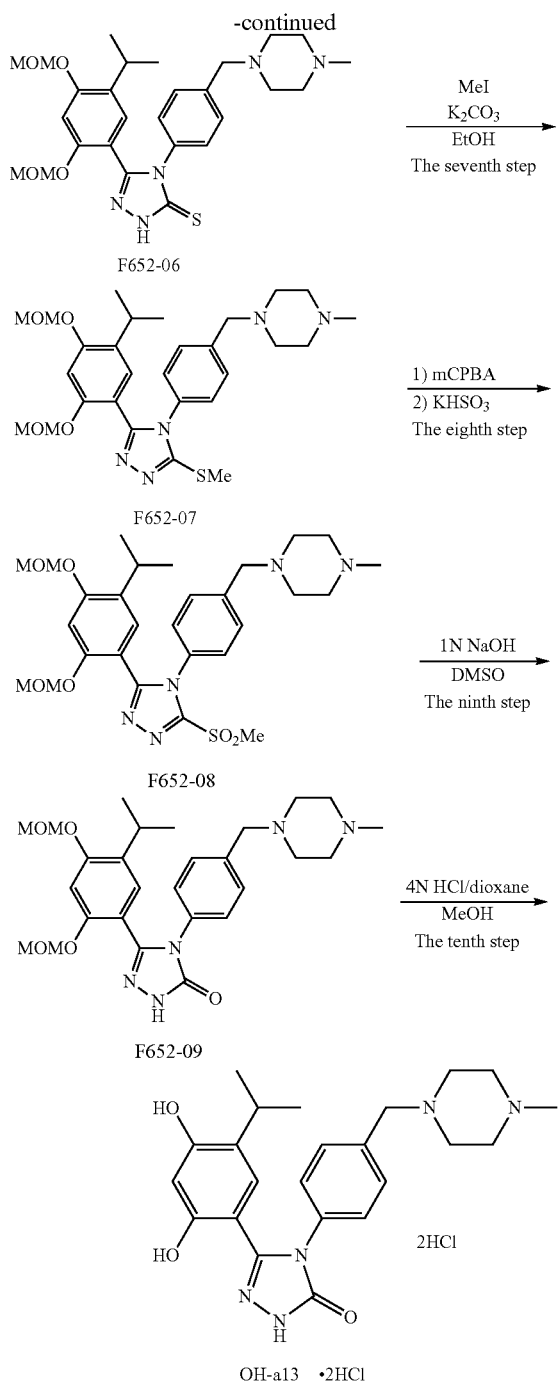

F652-06

F652-07

F652-08

F652-09

OH-a13 · 2HCl

The First Step: Preparation of 1-methyl-4-(4-nitrobenzyl)-piperazine (F652-01)

Monomethylpiperazine (15 mL) and tetrahydrofuran (60 mL) were placed in a 200 mL eggplant shaped flask, and a solution of 4-nitrobenzylchloride (8.58 g, 50 mmol) in tetrahydrofuran was added dropwise to the mixture at room temperature while stirring. After finishing the instillation, the mixture was stirred at room temperature for 24 hours. The reaction mixture was mixed with distilled water, and the precipitated solids were collected by filtration and dried under reduced pressure to obtain the title compound (5.9 g, 50%).

LC/MS (Method 3): m/z (ESI, POS): 236 [M+H]$^+$; retention time: 1.28 minutes.

The Second Step: Preparation of 4-(4-methylpiperazin-1-ylmethyl)phenylamine (F652-02)

1-methyl-4-(4-nitrobenzyl)-piperazine (F652-01, 4.67 g, 19.9 mmol), methanol (100 mL), zinc powder (6.5 g, 99.3 mmol) and ammonium chloride (4.3 g, 79.5 mmol) were placed in a reaction vessel and heated for 2 hours under reflux. After returning to room temperature, the reaction mixture was filtered through Celite. The solvent of the filtrate was distilled off under reduced pressure to obtain a solid. Diethyl ether was added to the solid, and insoluble components were removed by filtration. 4-(4-methylpiperazin-1-ylmethyl)phenylamine (F652-02, white solid, 3.16 g, 77%) was obtained by removing the solvent of the filtrate by distillation.

LC/MS (Method 6): m/z (ESI, POS): 206 [M+H]$^+$; retention time: 1.15 minutes.

$^1$H-NMR (400 MHz, DMSO-d$_6$) δ 2.12 (s, 3H), 2.29 (bs, 8H), 3.23 (s, 2H), 4.93 (s, 2H), 6.49 (d, J=8.4 Hz, 2H), 6.89 (d, J=8.4 Hz, 2H).

The Third Step: Preparation of 1-(4-isothiocyanatobenzyl)-4-methylpiperazine (F652-03)

Triethylamine (5.1 mL, 36.6 mmol) was added to a solution of 4-(4-methylpiperazin-1-ylmethyl)phenylamine (F652-02, 3.14 g, 15.3 mmol) in tetrahydrofuran (250 mL), and after cooling by ice, thiophosgene (1.11 mL, 14.6 mmol) was added. After stirring at room temperature overnight, aqueous sodium hydrogencarbonate was added to the mixture. The reaction mixture was extracted with ethyl acetate, and the extract was washed with saturated sodium chloride solution, dried over anhydrous sodium sulfate, filtered to remove sodium sulfate, and the solvent was distilled off under reduced pressure to obtain brown oil. The brown oil was purified by silica gel column chromatography (chloroform, methanol) to obtain 1-(4-isothiocyanatobenzyl)-4-methylpiperazine (F652-03, brownish oil, 2.64 g, 70%).

LC/MS (Method 3): m/z(ESI, POS): 248[M+H]$^+$; retention time: 2.87 minutes.

$^1$H-NMR (400 MHz, CDCl$_3$) δ 2.29 (s, 3H), 2.45 (bs, 8H), 3.48 (s, 2H), 7.17 (d, J=8.4 Hz, 2H), 7.31 (d, J=8.4 Hz, 2H).

The Fourth Step: Preparation of F652-04

An ethanol solution (2 mL) of hydrazine monohydrate (1.07 g, 21.3 mmol) was added to an ethanol solution (15 mL) of 1-(4-isothiocyanatobenzyl)-4-methylpiperazine (F652-03, 2.64 g, 10.7 mmol) while stirring under ice cold conditions, and the mixture was stirred at room temperature for 1 hour. The precipitated solids were collected by filtration and washed with ethanol and hexane. The solids thus obtained were dried under reduced pressure to obtain F652-04 (pale yellow solid, 2.69 g, 90%).

LC/MS (Method 4): m/z (ESI, POS): 280 [M+H]$^+$; retention time: 1.32 minutes.

The Fifth Step: Preparation of F652-05

4-(4,6-dimethoxy-1,3,5-triazin-2-yl)-4-methylmorpholinium chloride n hydrate (DMT-MM, 3.22 g) was added at room temperature to a dimethylformamide (25 mL) solution of 5-isopropyl-2,4-bis-methoxymethoxybenzoic acid (2.54 g, 8.92 mmol) and F652-04 (2.62 g, 9.37 mmol) obtained in the fourth step, and the mixture was stirred for 4 hours. After stopping the reaction by adding water, the resulting mixture was neutralized by adding saturated aqueous sodium hydrogencarbonate. The resulting mixture was extracted with ethyl acetate, and the extract was washed with water and then with saturated sodium chloride solution. After drying over anhydrous sodium, the extract was filtered to remove sodium sulfate, and then the solvent was distilled off under reduced pressure to obtain pale yellow solids. To the solids thus obtained was added diethylether, and the resulting suspension was stirred at room temperature. The precipitated solid was collected by filtration, and dried under reduced pressure to obtain F652-05 (pale yellow solid, 4.02 g, 83%).

LC/MS (Method 3): m/z(ESI, POS): 546[M+H]$^+$; retention time: 3.70 minutes.

$^1$H-NMR (400 MHz, CDCl$_3$) δ 1.06 (d, J=6.8 Hz, 6H), 2.32 (s, 3H), 2.49 (bs, 8H), 3.16 (sept., J=6.8 Hz, 1H), 3.48 (s, 2H), 3.50 (s, 3H), 3.59 (s, 3H), 5.26 (s, 2H), 5.47 (s, 2H), 6.99 (s, 1H), 7.33 (d, J=8.3 Hz, 2H), 7.40 (d, J=8.4 Hz, 2H), 7.87 (s, 1H).

The Sixth Step: Preparation of 5-(5-isopropyl-2,4-bis-methoxymethoxyphenyl)-4-[4-(4-methylpiperazin-1-ylmethyl)phenyl]-2,4-dihydro-[1,2,4]triazol-3-thione (F652-06)

10% aqueous potassium hydroxide (15 mL) and 5% potassium hydroxide-ethanol solution (5 mL) were added to F652-05 (4.02 g, 7.38 mmol) obtained in the fifth step at room temperature. After heating the mixture for 3 hours under reflux, the solvent was distilled off under reduced pressure. Saturated aqueous sodium chloride solution was added and stirring was continued for a while, and then the reaction mixture was extracted with chloroform. The combined chloroform extracts were washed with saturated sodium chloride solution and dried over anhydrous sodium sulfate. Filtration and evaporation gave yellow solid, which was purified by silica gel column chromatography (chloroform, methanol) to obtain 5-(5-isopropyl-2,4-bis-methoxymethoxyphenyl)-4-[4-(4-methylpiperazin-1-ylmethyl)phenyl]-2,4-dihydro-[1,2,4]triazol-3-thione (F652-06, a pale yellow solid, 3.19 g, 82%).

LC/MS (Method 3): m/z (ESI, POS): 528 [M+H]$^+$; retention time: 3.54 minutes.

$^1$H-NMR (400 MHz, CDCl$_3$) δ 1.11 (d, J=7.0 Hz, 6H), 2.33 (s, 3H), 2.50 (bs, 8H), 3.20 (sept., J=7.0 Hz, 1H), 3.26 (s, 3H), 3.46 (s, 3H), 3.49 (s, 2H), 4.73 (s, 2H), 5.16 (s, 2H), 6.80 (s, 1H), 7.09 (s, 1H), 7.23 (d, J=8.4 Hz, 2H), 7.34 (d, J=8.4 Hz, 2H).

The Seventh Step: 3-(5-isopropyl-2,4-bis-methoxymethoxyphenyl)-4-[4-(4-methylpiperazin-1-ylmethyl)phenyl]-5-methylsulfanyl-[1,2,4]triazole (F652-07)

5-(5-isopropyl-2,4-bis-methoxymethoxyphenyl)-4-[4-(4-methylpiperazin-1-ylmethyl)phenyl]-2,4-dihydro-[1,2,4]triazol-3-thione (F652-06, 3.17 g, 6.01 mmol) and potassium carbonate (829 mg, 6.00 mmol) were weighed and placed in a reaction vessel. After adding ethanol (30 mL), methyl iodide (0.374 mL, 6.01 mmol) was added to the mixture. After heating for 1 hour under reflux, the temperature was returned to room temperature, and the solvent was distilled off under reduced pressure. To the reaction mixture was added water, and the mixture was extracted with ethyl acetate. The extract was washed with saturated sodium chloride solution, dried over anhydrous sodium sulfate and then filtered to remove sodium sulfate, and the solvent was distilled off under reduced pressure to obtain pale yellow foam. Diethyl ether was added to the foam and the insoluble material was removed by filtration. After washing with water, the filtrate was washed with saturated sodium chloride solution. The extract was dried with sodium sulfate, and sodium sulfate was removed by filtration. The solvent was distilled off under reduced pressure to obtain 3-(5-isopropyl-2,4-bis-methoxymethoxyphenyl)-4-[4-(4-methylpiperazin-1-ylmethyl)phenyl]-5-methylsulfanyl-[1,2,4]triazole (F652-07, pale yellow foam, 2.05 g, 63%).

LC/MS (Method 3): m/z (ESI, POS): 542 [M+H]$^+$; retention time: 3.68 minutes.

$^1$H-NMR (400 MHz, CDCl$_3$) δ 1.14 (d, J=7.0 Hz, 6H), 2.29 (s, 3H), 2.45 (bs, 8H), 2.73 (s, 3H), 3.19 (s, 3H), 3.21 (sept., J=7.0 Hz, 1H), 3.46 (s, 3H), 3.49 (s, 2H), 4.69 (s, 2H), 5.15 (s, 2H), 6.78 (s, 1H), 7.09 (d, J=8.3 Hz, 2H), 7.26 (s, 1H), 7.33 (d, J=8.3 Hz, 2H).

The Eighth Step: 3-(5-isopropyl-2,4-bis-methoxymethoxyphenyl)-4-[4-(4-methylpiperazin-1-ylmethyl)phenyl]-5-methanesulfonyl-[1,2,4]triazole (F652-08)

3-chloroperbenzoic acid (3.91 g, 22.7 mmol) was added to a methylene chloride (9 mL) solution of 3-(5-isopropyl-2,4-bis-methoxymethoxyphenyl)-4-[4-(4-methylpiperazin-1-ylmethyl)phenyl]-5-methylsulfanyl-[1,2,4]triazole (F652-07, 2.05 g, 3.78 mmol). After stirring at room temperature for 9.5 hours, additional 3-chloroperbenzoic acid (717 mg, 4.15 mmol) was added and stirring was continued overnight. After cooling to ice cold, saturated aqueous sodium thiosulfate and then 10% aqueous potassium bisulfite were added, and stirring was continued for a while. Further, saturated aqueous sodium hydrogencarbonate was added and the mixture was stirred, and then extracted with chloroform. The extract was washed sequentially with saturated aqueous sodium hydrogencarbonate, water and saturated sodium chloride solution, and dried over anhydrous sodium sulfate. Filtration and evaporation gave pale brown foam. After adding diethyl ether, the insoluble solids were removed by filtration, and the solvent in the filtrate was distilled off under reduced pressure. The solids thus obtained were purified by silica gel column chromatography (chloroform, methanol) to obtain 3-(5-isopropyl-2,4-bis-methoxymethoxyphenyl)-4-[4-(4-methylpiperazin-1-ylmethyl)phenyl]-5-methanesulfonyl-[1,2,4]triazole (F652-08, pale yellow foam, 1.08 g, 50%).

LC/MS (Method 3): m/z (ESI, POS): 574 [M+H]$^+$; retention time: 3.69 minutes.

$^1$H-NMR (400 MHz, CDCl$_3$) δ 1.12 (d, J=6.8 Hz, 6H), 2.29 (s, 3H), 2.44 (bs, 8H), 3.20 (sept., J=6.8 Hz, 1H), 3.25 (s, 3H), 3.47 (s, 3H), 3.48 (s, 2H), 3.54 (s, 3H), 4.77 (s, 2H), 5.17 (s, 2H), 6.82 (s, 1H), 7.18 (s, 1H), 7.25 (d, J=8.5 Hz, 2H), 7.35 (d, J=8.5 Hz, 2H).

The Ninth Step: 5-(5-isopropyl-2,4-bis-methoxymethoxyphenyl)-4-[4-(4-methylpiperazin-1-ylmethyl)phenyl]-2,4-dihydro-[1,2,4]triazol-3-one (F652-09)

At room temperature, aqueous sodium hydroxide (1.0 M aqueous solution, 5 mL) was added to a dimethylsulfoxide (5 mL) solution of 3-(5-isopropyl-2,4-bis-methoxymethoxyphenyl)-4-[4-(4-methylpiperazin-1-ylmethyl)phenyl]-5-methanesulfonyl-[1,2,4]triazole (F652-08, 1.07 g, 1.86 mmol), and the mixture was heated for 3 hours under reflux. An additional aqueous sodium hydroxide (1.0 M aqueous solution, 5 mL) was added, and the mixture was heated under flux for further 1 hour. After returned to room temperature, the reaction mixture was extracted with ethyl acetate and chloroform. The combined extracts were washed twice with water and then with saturated sodium chloride solution, and dried over anhydrous sodium sulfate, and sodium sulfate was filtered off, and the solvent was distilled off under reduced pressure. The residue was purified by silica gel column chromatography (NH silica, chloroform, methanol) to obtain 5-(5-isopropyl-2,4-bis-methoxymethoxyphenyl)-4-[4-(4-methylpiperazin-1-ylmethyl)phenyl]-2,4-dihydro-[1,2,4]triazol-3-one (F652-09, pale yellow foam, 900 mg, 95%)

LC/MS (Method 3): m/z(ESI, POS): 512[M+H]$^+$; retention time: 3.47 minutes.

$^1$H-NMR (400 MHz, CDCl$_3$) δ 1.16 (d, J=6.9 Hz, 6H), 2.28 (s, 3H), 2.45 (br, 8H), 3.17 (s, 3H), 3.23 (sept., J=6.9 Hz, 1H), 3.44 (s, 2H), 3.48 (s, 3H), 4.63 (s, 2H), 5.17 (s, 2H), 6.81 (s, 1H), 7.13 (d, J=8.4 Hz, 2H), 7.21 (s, 1H), 7.29 (d, J=8.4 Hz, 2H), 9.92 (bs, 1H).

The Tenth Step: 5-(2,4-dihydroxy-5-isopropylphenyl)-4-[4-(4-methylpiperazin-1-ylmethyl)phenyl]-2,4-dihydro-[1,2,4]triazol-3-one dihydrochloride (F652-10)

At room temperature, 4 N hydrochloric acid/1,4-dioxane solution (5 mL) was added to a methanol (5 mL) solution of 5-(5-isopropyl-2,4-bis-methoxymethoxyphenyl)-4-[4-(4-methyl piperazin-1-ylmethyl)phenyl]-2,4-dihydro-[1,2,4]triazol-3-one (F652-09, 644 mg, 1.26 mmol). After stirring at 40° C. for 1 hour, the solvent was distilled off under reduced pressure. Methanol was added to the crude product thus obtained, and the resulting suspension was stirred at room temperature. The precipitated solid was collected by filtration to obtain 5-(2,4-dihydroxy-5-isopropylphenyl)-4-[4-(4-methylpiperazin-1-ylmethyl)phenyl]-2,4-dihydro-[1,2,4]triazol-3-one (OH-a13) dihydrochloride (white solids).

LC/MS (Method 4): m/z(ESI, POS): 424[M-2HCl+H]$^+$: retention time: 3.81 minutes.

FAB-MS: m/z(POS): 424[M-2HCl+H]$^+$: melting point: 276-277° (dec.)

$^1$H-NMR (400 MHz, DMSO-d$_6$) δ 1.02 (d, J=7.0 Hz, 6H), 2.80 (bs, 3H), 3.01 (sept., J=7.0 Hz, 1H), 3.38 (br, 4H), 3.81 (br, 4H), 4.24 (br, 2H), 6.30 (s, 1H), 6.90 (s, 1H), 7.22 (d, J=8.4 Hz, 2H), 7.57 (bs, 2H), 9.34 (bs, 1H), 9.65 (bs, 1H), 11.97 (s, 1H).

Example 2-6

Preparation of 5-(2,4-dihydroxy-5-isopropylphenyl)-4-[4-(4-(morpholin-4-carbonyl)-phenyl]-2,4-dihydro-[1,2,4]triazol-3-one (OH-a14)

Scheme 2-6

[Formula 35]

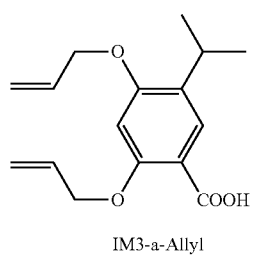

IM3-a-Allyl

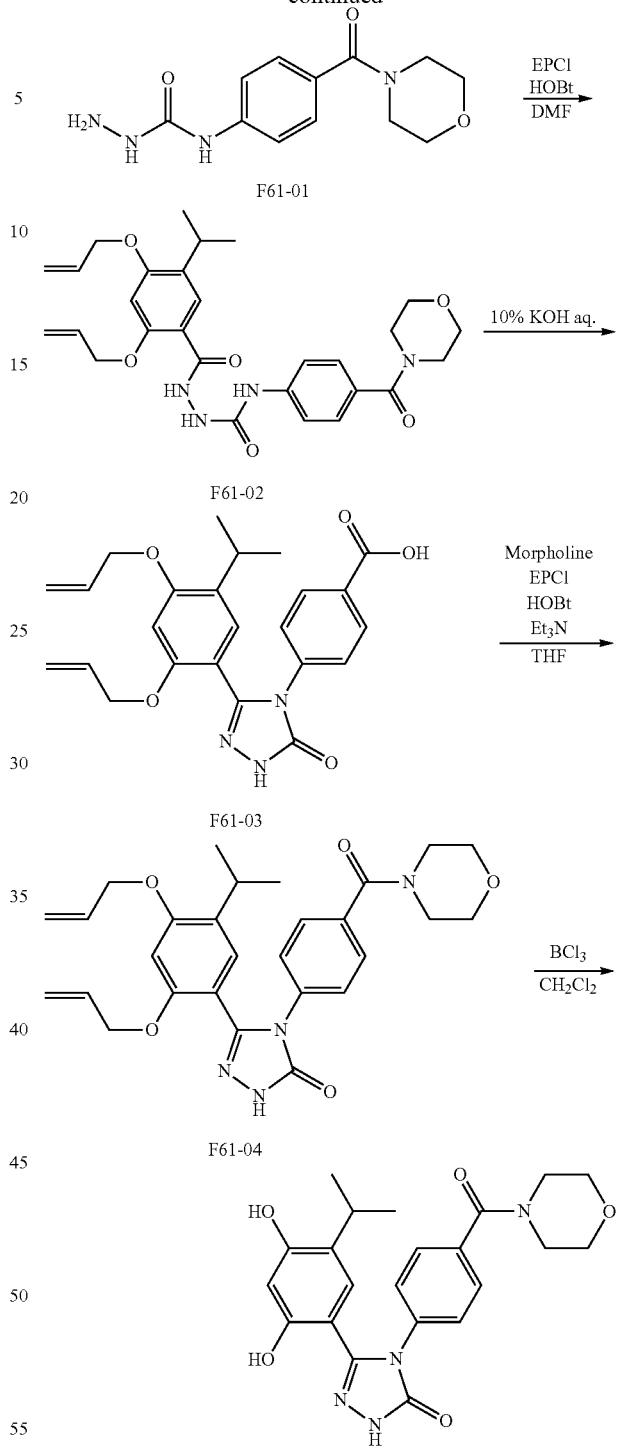

The First Step: Preparation of F61-02

At room temperature, 1-hydroxybenzotriazole n hydrate (HOBt, 496 mg) and 1-[3-(dimethylamino)propyl]-3-ethyl-carbodiimide hydrochloride (EPCI, 938 mg, 4.89 mmol) were added sequentially to a dimethylformamide (5 mL) solution of 2,4-bisallyloxy-5-isopropylbenzoic acid (676 mg, 2.45 mmol) and F61-01 (646 mg, 2.45 mmol), and the mixture was stirred for 3.5 hours. After adding water, the reaction mixture was extracted with ethyl acetate. The extract as washed with saturated aqueous ammonium chloride solution, saturated aqueous sodium hydrogencarbonate and then saturated sodium chloride solution. The extract was dried over anhydrous sodium sulfate, and then sodium sulfate was removed by filtration and the solvent was distilled off under reduced pressure to obtain a pale yellow syrup, which was purified by silica gel column chromatography (hexane, ethyl acetate, chloroform, methanol) to obtain F61-02 (pale yellow foam, 1.14 g, 89%).

LC/MS (Method 3): m/z (ESI, POS): 527 [M+H]$^+$; retention time: 6.13 minutes.

The Second Step: Preparation of 4-[3-(2,4-bis-allyloxy-5-isopropylphenyl)-5-oxo-1,5-dihydro-[1,2,4]triazol-4-yl]-benzoic acid (F61-03)

Potassium hydroxide (999 mg, 17.8 mmol) was added to an aqueous solution (10 mL) of F61-02 (1.14 g, 2.17 mmol) that was obtained in the first step, and the mixture was heated for 14 hours under reflux. After cooling to room temperature, 1 N hydrochloric acid was added until the solution became acidic (pH4-5). The reaction mixture was extracted with ethyl acetate, and the extract was washed with saturated sodium chloride solution. The extract was dried over anhydrous sodium sulfate, and then sodium sulfate was removed by filtration and the solvent was distilled off under reduced pressure. The residue was purified by silica gel column chromatography (hexane, ethyl acetate, chloroform, methanol) and the solids thus obtained were washed with diethyl ether to obtain 4-[3-(2,4-bis-allyloxy-5-isopropylphenyl)-5-oxo-1,5-dihydro-[1,2,4]triazol-4-yl]-benzoic acid (F61-03, white solids, 67.9 mg, 7%).

LC/MS (Method 3): m/z (ESI, POS): 436 [M+H]$^+$; retention time: 5.95 minutes.

$^1$H-NMR (400 MHz, CDCl$_3$) δ 1.21 (d, J=7.0 Hz, 6H), 3.27 (sept., J=7.0 Hz, 1H), 4.01 (d, J=5.3 Hz, 2H), 4.49 (d, J=4.9 Hz, 2H), 5.05 (dd, J=1.3, 17.3 Hz, 1H), 5.11 (dd, J=1.3, 10.6 Hz, 1H), 5.29 (dd, J=1.5, 10.6 Hz, 1H), 5.40 (dd, J=1.5, 17.3 Hz, 1H), 5.50-5.62 (m, 1H), 5.98-6.09 (m, 1H), 6.22 (s, 1H), 7.23 (d, J=8.7 Hz, 2H), 7.31 (s, 1H), 8.00 (d, J=8.7 Hz, 2H).

The Third Step: Preparation of 5-(2,4-bis-allyloxy-5-isopropylphenyl)-4-[4-(molpholin-4-carbonyl)phenyl]-2,4-dihydro-[1,2,4]triazol-3-one (F61-04)

At room temperature, 4-[3-(2,4-bis-allyloxy-5-isopropylphenyl)-5-oxo-1,5-dihydro-[1,2,4]triazol-4-yl]-benzoic acid (F61-03, 30 mg, 68.9 μmol), 1-[3-(dimethylamino)propyl]-3-ethylcarbodiimide hydrochloride (EPCI, 14.6 mg, 76.2 μmol) and 1-hydroxybenzotriazole n hydrate (HOBt, 10.3 mg) were weighed and placed in a reaction vessel, and morpholine (6.4 μL, 73.5 μmol) and tetrahydrofuran (0.5 mL) were added. Triethylamine (10.6 μL, 76.1 μmol) was added and the mixture was stirred for 2.5 hours. After adding water to the reaction mixture, the solvent was distilled off under reduced pressure. The solution was extracted with ethyl acetate, and the extract was washed with saturated aqueous ammonium chloride, saturated aqueous sodium hydrogencarbonate and then saturated sodium chloride solution. After drying over anhydrous sodium, the extract was filtered to remove sodium sulfate, and the solvent was distilled off under reduced pressure to obtain a brown oil, which was purified by silica gel column chromatography (chloroform, methanol) to obtain a crude product (34.2 mg) containing 5-(2,4-bis-allyloxy-5-isopropylphenyl)-4-[4-(molpholin-4-carbonyl)phenyl]-2,4-dihydro-[1,2,4]triazol-3-one (F61-04).

LC/MS (Method 3): m/z (ESI, POS): 505 [M+H]$^+$; retention time: 5.89 minutes.

The Fourth Step: Preparation of 5-(2,4-dihydroxy-5-isopropyl-phenyl)-4-[4-(molpholin-4-carbonyl)phenyl]-2,4-dihydro-[1,2,4]triazol-3-one (OH-a14)

Under argon atmosphere while stirring at −20° C., trichloroborane (1.0M methylene chloride solution, 0.2 mL) was added to a methylene chloride (0.2 mL) solution of the crude product (10.2 mg) containing 5-(2,4-bis-allyloxy-5-isopropylphenyl)-4-[4-(morpholin-4-carbonyl)phenyl]-2,4-dihydro-[1,2,4]triazol-3-one (F61-04) obtained in the previous step, and the stirring was continued for 2 hours. After this, the mixture was stirred at room temperature overnight. After adding methanol, the reaction mixture was neutralized by adding saturated aqueous sodium hydrogencarbonate. The solution was extracted with chloroform and then the extract was washed with saturated sodium chloride solution. After drying over anhydrous sodium, the extract was filtered to remove sodium sulfate, and the solvent was distilled off under reduced pressure. The residue was purified crudely by thin layer chromatography (chloroform, methanol) and then purified by HPLC fractionation to obtain 5-(2,4-dihydroxy-5-isopropyl-phenyl)-4-[4-(molpholin-4-carbonyl)phenyl]-2,4-dihydro-[1,2,4]triazol-3-one (OH-a14, 0.9 mg, 10%).

LC/MS (Method 3): m/z (ESI, POS): 425 [M+H]$^+$; retention time: 4.11 minutes.

$^1$H-NMR [400 MHz, CDCl$_3$-CD$_3$OD (four drops)] δ 0.83 (d, J=6.8 Hz, 6H), 3.00 (sept., J=6.8 Hz, 1H), 3.50 (br, 2H), 3.64 (br, 2H), 3.79 (br, 4H), 6.53 (s, 1H), 6.56 (s, 1H), 7.38 (d, J=8.4 Hz, 2H), 7.53 (d, J=8.4 Hz, 2H).

Example 2-7

Preparation of 5-(2,4-dihydroxy-5-isopropyl-phenyl)-4-(4-methoxy-phenyl)-2,4-dihydro-[1,2,4]triazol-3-one (OH-a08)

Scheme 2-7

[Formula 36]

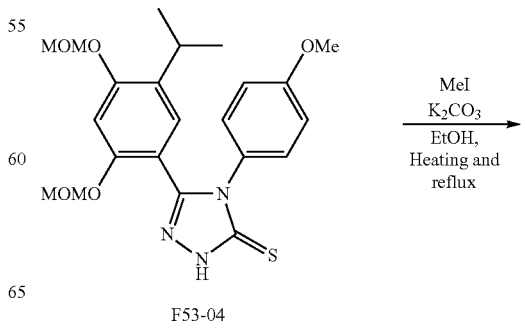

F53-04

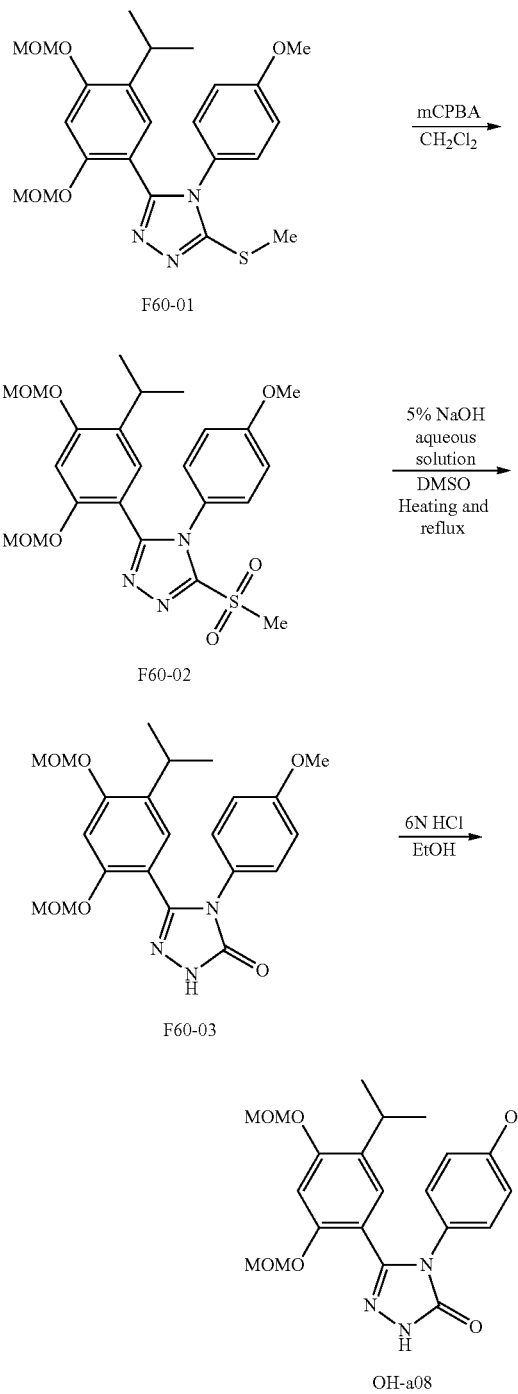

ing in the similar manner to the first step of Example 3-1. LC/MS (Method 3): m/z (ESI, POS): 460 [M+H]$^+$; retention time: 6.54 minutes.

The Second Step: Preparation of 3-(5-isopropyl-2,4-bis-methoxymethoxy-phenyl)-5-methanesulfonyl-4-(4-methoxy-phenyl)-4H-[1,2,4]triazole (F60-02)

3-(5-isopropyl-2,4-bis-methoxymethoxy-phenyl)-4-(4-methoxy-phenyl)-5-methylsulfanyl-4H-[1,2,4]triazole (F60-01: 2.87 g, 6.3 mmol) and methylene chloride (60 mL) were placed in a 200 mL eggplant shaped flask, cooled to 0° C., and methylene chloride solution of metachloroperbenzoic acid (3.77 g, 21.9 mmol) was gradually added in 4 portions, and the mixture was stirred for 9.5 hours. After completing the reaction, 10% aqueous potassium sulfite (100 mL) was added and stirring was continued for 10 minutes. After that, the organic layer was extracted, washed twice with 1 N sodium hydroxide (50 mL), dried with sodium sulfate and concentrated under reduced pressure. The residue was purified by silica gel column chromatography (hexane/ethyl acetate) to obtain the title compound (F60-02: 2.67 g, 87%)

$^1$H-NMR (400 MHz, CDCl$_3$, TMS) ppm: 7.22 (2H, d, J=9.0 Hz), 7.20 (1H, s), 6.86 (2H, d, J=9.0 Hz), 6.83 (1H, s), 5.17 (2H, s), 4.81 (2H, s), 3.80 (3H, s), 3.53 (3H, s), 3.47 (3H, s), 3.27 (3H, s), 3.22 (1H, sept, J=7.0 Hz), 1.15 (6H, d, J=7.0 Hz)

LC/MS (Method 3): m/z (ESI, POS): 492 [M+H]$^+$; retention time: 6.36 minutes.

The Third Step: Preparation of 5-(5-isopropyl-2,4-bis-methoxy methoxy-phenyl)-4-[4-(molpholin-4-ylmethyl)-phenyl]-2,4-dihydro-[1,2,4]triazol-3-one (F60-03)

3-(5-isopropyl-2,4-bis-methoxymethoxy-phenyl)-5-methanesulfonyl-4-(4-methoxy-phenyl)-4H-[1,2,4]triazole (F60-02: 2.5 g, 5.1 mmol), dimethylsulfoxide (50 mL) and 5% aqueous sodium hydroxide (10 mL) were placed in a 200 mL eggplant shaped flask and stirred at 120° C. for 2 hours. After completing the reaction, the reaction mixture was cooled to 0° C., neutralized with saturated aqueous ammonium chloride, and deposited solids were collected by filtration. The solids thus obtained were suspension purified by hexane to obtain the title compound (F60-03: 2.0 g, 93%).

LC/MS (Method 3): m/z (ESI, POS): 430 [M+H]$^+$; retention time: 5.89 minutes.

$^1$H-NMR (400 MHz, DMSO-d$_6$, TMS) ppm: 12.0 (1H, brs), 7.18 (1H, s), 7.07 (2H, d, J=9.0 Hz), 6.90 (2H, d, J=9.0 Hz), 6.75 (2H, s) 5.20 (2H, s), 4.84 (3H, s), 3.34 (3H, s), 3.15 (1H, sept, J=6.8 Hz), 3.14 (3H, s), 1.11 (6H, d, J=6.8 Hz)

The Fourth Step: Preparation of 5-(2,4-dihydroxy-5-isopropyl-phenyl)-4-(4-methoxy-phenyl)-2,4-dihydro-[1,2,4]triazol-3-one (OH-a08)

The First Step: Preparation of 3-(5-isopropyl-2,4-bis-methoxymethoxy-phenyl)-4-(4-methoxy-phenyl)-5-methylsulfanyl-4H-[1,2,4]triazole (F60-01)

The title compound (F60-01: 2.87 g, 85.3%) was obtained by using 5-(5-isopropyl-2,4-bis-methoxymethoxy-phenyl)-4-[4-methoxy-phenyl]-2,4-dihydro-[1,2,4]triazol-3-thione (F53-04: 3.26 g, 7.3 mmol) in place of 5-(5-isopropyl-2,4-bis-methoxy methoxy-phenyl)-4-[4-(molpholin-4-ylmethyl-phenyl]-2,4-dihydro-[1,2,4]triazol-3-thione, and by process- 5-(5-isopropyl-2,4-bis-methoxymethoxy-phenyl)-4-[4-(molpholin-4-ylmethyl-phenyl]-2,4-dihydro-[1,2,4]triazol-3-one (F60-03: 1.96 g, 4.6 mmol), ethanol (75 mL) and 6 N hydrochloric acid (75 mL) were placed in a 200 mL eggplant shaped flask and stirred at room temperature for 6 hours. After completing the reaction, distilled water (400 mL) was added, and deposited solids were dried under reduced pressure to obtain the title compound (OH-a08: 1.4 g, 91%).

LC/MS (Method 3): m/z (ESI, POS): 342 [M+H]+; retention time: 4.94 minutes.

1H-NMR (400 MHz, CD3OD, TMS) ppm: 7.19 (2H, d, J=9.1 Hz), 7.00 (2H, d, J=9.1 Hz), 6.70 (1H, s), 6.27 (1H, s), 3.02 (1H, sept, J=6.8 Hz), 0.91 (6H, d, J=6.8 Hz)

IR (KBr): 1708, 1627, 1514, 1394, 1302, 1253, 1174, 604.

Melting point: 272° C. (decomposition)

Example 2-8

Preparation of 5-(2,4-dihydroxy-5-isopropyl-phenyl)-4-(3-methoxy-phenyl)-2,4-dihydro-[1,2,4]triazol-3-one (OH-a09)

5-(5-isopropyl-2,4-bis-methoxymethoxy-phenyl)-4-[3-methoxy-phenyl]-2,4-dihydro-[1,2,4]triazol-3-thione was obtained using 3-methoxy-phenyl isothiocyanate in place of F53-01 of Example 1-6 by the similar process to that of Example 1-6 in 3 steps. This compound was led to the title compound (OH-a09) by the similar process to that of Example 2-7 in 4 steps.

LC/MS (Method 1): m/z (ESI, POS): 342 [M+H]+; retention time: 5.39 minutes.

Example 2-9

Preparation of 5-(2,4-dihydroxy-5-isopropyl-phenyl)-4-(3,4-dimethoxy-phenyl)-2,4-dihydro-[1,2,4]triazol-3-one (OH-a10)

5-(5-isopropyl-2,4-bis-methoxymethoxy-phenyl)-4-(3,4-dimethoxy-phenyl)-2,4-dihydro-[1,2,4]triazol-3-thione was obtained using 3,4-dimethoxy-phenyl isothiocyanate in place of F53-01 of Example 1-6 by the similar process to that of Example 1-6 in 3 steps. This compound was led to the title compound (OH-a10) by the similar process to that of Example 2-7 in 4 steps.

LC/MS (Method 1): m/z (ESI, POS): 373 [M+H]+; retention time: 4.98 minutes.

Example 2-10

Preparation of 5-(2,4-dihydroxy-5-isopropylphenyl)-4-(4-hydroxyphenyl)-4H-[1,2,4]triazol-3-one (OH-a11)

Crystals (3.30 g, 7.68 mmol) of 5-(2,4-bis(methoxymethoxy)-5-isopropyl phenyl)-4-(4-methoxyphenyl)-4H-[1,2,4]triazol-3-one (F60-03: an intermediate of Example 2-7) was added to a suspension of tribromoborane dimethylsulfide complex (11.65 g, 37.26 mol) and 1,2-dichloroethane (250 mL) in 300 mL eggplant shaped flask and stirred at room temperature for 2 hours and further at an external temperature of 80° C. for 24 hours. After completing the reaction, the reaction mixture was returned to room temperature and mixed with n-hexane (250 mL). The precipitates were collected by filtration, washed with diethyl ether and then purified by DIAION HP-20 column chromatography (water-methanol gradient elution), followed by CHP-20 column chromatography (water-methanol gradient elution) to obtain the title compound (OH-a11: 370 mg, 14.8%). The fractions which were not sufficiently separated and purified were purified by HPLC fractionation to obtain the title compound (OH-a11: 300 mg, total 670 mg, 26.8%).

LC/MS (Method 3): m/z (ESI, POS): 328 [M+H]+; retention time: 4.13 minutes.

1H-NMR (400 MHz, DMSO-d6, TMS) ppm: 11.84 (1H, brs), 9.65 (1H, brs), 9.59 (1H, brs), 9.44 (1H, brs), 6.98 (2H, d, J=8.8 Hz), 6.77 (1H, s), 6.73 (2H, d, J=8.8 Hz), 6.26 (1H, s), 2.97 (1H, m), 0.96 (6H, d, J=7.0 Hz).

Example 2-11

Preparation of 4-[3-(2,4-dihydroxy-5-isopropylphenyl)-5-oxo-1,5-dihydro-[1,2,4]triazol-4-yl]-benzoic acid (OH-a12)

Scheme 2-11

[Formula 37]

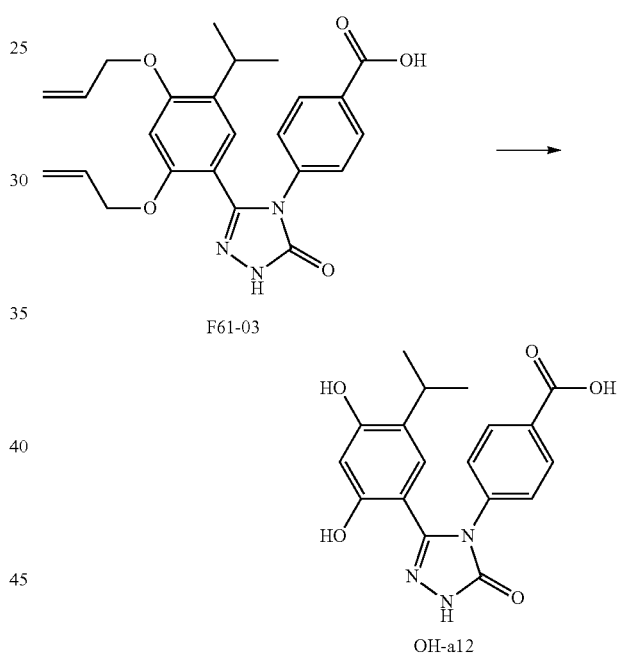

25% hydrogen bromide-acetic acid (3.5 mL) was added to an intermediate of Example 2-6, 4-[3-(2,4-bis-allyloxy-5-isopropylphenyl)-5-oxo-1,5-dihydro-[1,2,4]triazol-4-yl]-benzoic acid (F61-03, 25 mg, 57 μmol) and stirred at room temperature for 1.5 hours and then at 45° C. overnight. The solvent was distilled off to some extent under reduced pressure, and azeotropic distillation was carried out after adding toluene and acetonitrile. The crude product thus obtained was purified by silica gel column chromatography (chloroform, methanol) to obtain 4-[3-(2,4-dihydroxy-5-isopropylphenyl)-5-oxo-1,5-dihydro-[1,2,4]triazol-4-yl]-benzoate (OH-a12: 11.8 mg, 58%).

LC/MS (Method 3): m/z (ESI, POS): 356 [M+H]+; retention time: 4.09 minutes.

1H-NMR (400 MHz, CDCl3:CD3OD=3:1) δ 0.86 (d, J=6.8 Hz, 6H), 3.02 (sept., J=6.8 Hz, 1H), 6.33 (s, 1H), 6.61 (s, 1H), 7.39 (d, J=8.6 Hz, 2H), 8.14 (d, J=8.6 Hz, 2H).

Example 2-12
Preparation of 5-(2,4-dihydroxy-5-isopropyl-phenyl)-4-[2-(molpholin-4-yl)-pyrimidin-5-yl]-2,4-dihydro-[1,2,4]triazol-3-one (OH-a17)
Scheme 2-12
[Formula 38]
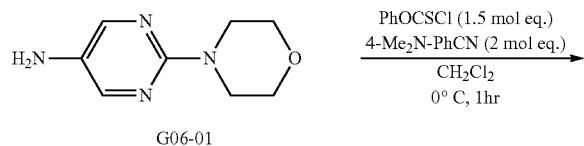
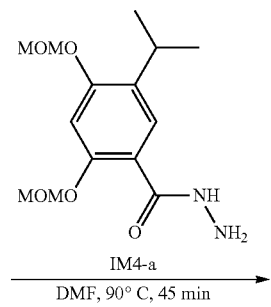
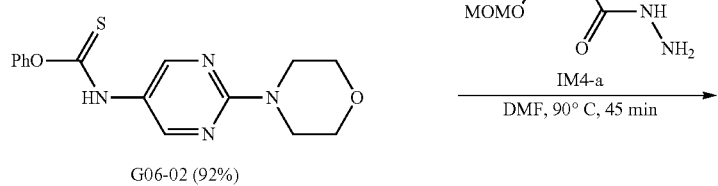
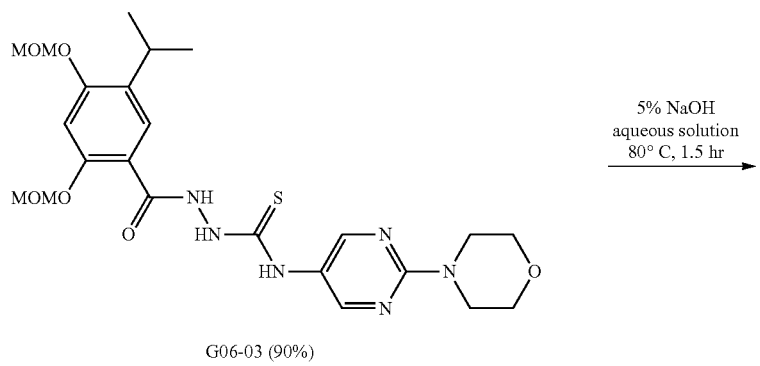
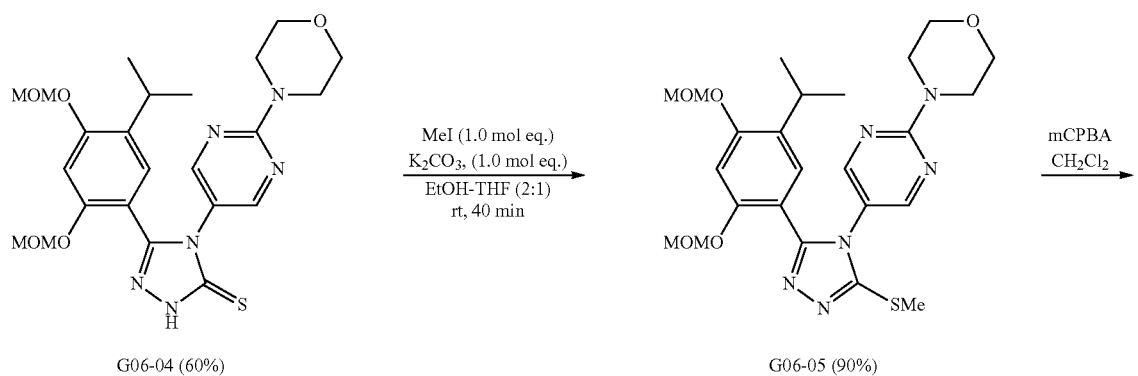

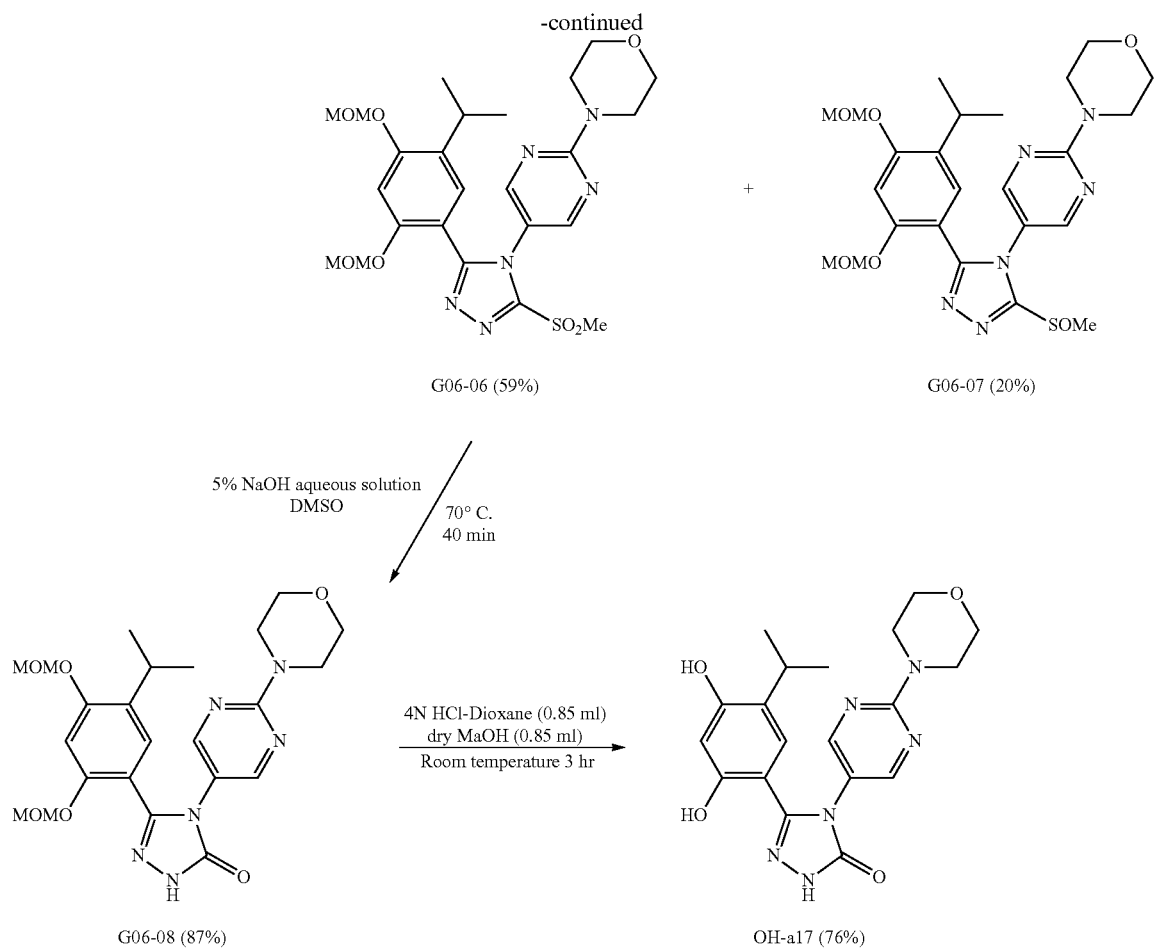

G06-06 (59%)

G06-07 (20%)

G06-08 (87%)

OH-a17 (76%)

The First Step: Preparation of G06-02

Under argon atmosphere, while stirring in an ice bath, phenyl chlorothiono-formate (0.180 mL, 231 mg, 1.34 mmol) was added to a dichloromethane (5 mL) solution of G06-01 [Heterocycles Vol. 6 (No. 12), 1999-2004 (1977).; 161 mg, 0.893 mmol] and 4-(dimethyl-amino)-benzonitrile (261 mg, 1.79 mmol) and the mixture was stirred for 1 hour under ice cold conditions. The reaction mixture was mixed with saturated sodium chloride solution (5 mL) and 5% aqueous sodium hydrogencarbonate solution (5 mL) and extracted with ethyl acetate. The ethyl acetate extracts were combined, washed with saturated sodium chloride solution and dried over anhydrous sodium sulfate. Sodium sulfate was removed by filtration, and the solvent was distilled off under reduced pressure. Brown solids thus obtained were purified by column chromatography (silica gel, dichloromethane-methanol) to obtain the title compound (G06-02: yellow solids, 261 mg, 92%).

LC/MS (Method 3): m/z (ESI, POS): 317 [M+H]$^+$; retention time: 5.82 minutes.

The Second Step: Preparation of G06-03

Under argon atmosphere, while stirring at room temperature, IM4-a (271 mg, 0.908 mmol) was added to a dimethylformamide (3 mL) solution of G06-02 [261 mg, 0.825 mmol] and the mixture was stirred for 45 minutes while heating at a temperature of 90° C. The reaction mixture was mixed with saturated sodium chloride solution and extracted with ethyl acetate. The ethyl acetate extracts were combined, washed with saturated sodium chloride solution and dried over anhydrous sodium sulfate. Sodium sulfate was removed by filtration, and the solvent was distilled off under reduced pressure. Yellow solids thus obtained were washed with ether-hexane to obtain the title compound (G06-03: white solids, 388 mg, 90%).

LC/MS (Method 3): m/z (ESI, POS): 521 [M+H]$^+$, 543 [M+Na]$^+$; retention time: 5.97 minutes.

NMR [400 MHz, CDCl$_3$, TMS] ppm: 1.000 (6H, d, J=7.0 Hz), 3.134 (1H, sept., J=7.0 Hz), 3.492 (3H, s), 3.580 (3H, s), 3.74-3.82 (8H, m), 5.252 (2H, s), 5.468 (2H, s), 7.004 (1H, s), 7.743 (1H, s), 8.365 (2H, s), 9.153 (1H, bs), 11.26 (1H, b), 12.06 (1H, b).

The Third Step: Preparation of G06-04

A mixture of G06-03 (380 mg, 0.73 mmol) and 1.25M aqueous sodium hydroxide (10 mL, 12.5 mmol) was stirred while heating at 80° C. for 1.5 hours. Under ice cold conditions, the reaction mixture was mixed with 1M aqueous potassium bisulfite and aqueous sodium hydrogencarbonate for neutralization, and extracted with ethyl acetate. The ethyl acetate extracts were combined, washed with saturated sodium chloride solution and dried over anhydrous sodium sulfate. Sodium sulfate was removed by filtration, and the solvent was distilled off under reduced pressure. Yellow solids thus obtained were purified by column chromatography (silica gel, hexane-ethyl acetate) to obtain the title compound (G06-04: colorless foamy compound, 220 mg, 60%).

LC/MS (Method 3): m/z (ESI, POS): 503 [M+H]$^+$, 525 [M+Na]$^+$; retention time: 6.15 minutes.

$^1$H-NMR [400 MHz, CDCl$_3$, TMS] ppm: 1.181 (6H, d, J=7.0 Hz), 3.232 (1H, sept., J=7.0 Hz), 3.271 (3H, s), 3.487 (3H, s), 3.73-3.83 (8H, m), 4.906 (2H, s), 5.196 (2H, s), 6.861 (1H, s), 7.217 (1H, s), 8.227 (2H, s), 11.745 (1H, s).

The Fourth Step: Preparation of G06-05

Under argon atmosphere, while stirring at room temperature, methyl iodide (0.026 mL, 59 mg, 0.414 mmol) was added to a mixture of G06-04 (208 mg, 0.414 mmol), solid potassium carbonate (57 mg, 0.414 mmol), ethanol (3 mL) and tetrahydrofuran (1.5 mL), and stirring was continued at room temperature for 40 minutes. Under ice cold conditions, the reaction mixture was mixed with aqueous ammonium chloride and extracted with ethyl acetate. The ethyl acetate extracts were combined, washed with saturated sodium chloride solution and dried over anhydrous sodium sulfate. Sodium sulfate was removed by filtration, and the solvent was distilled off under reduced pressure. The colorless syrup thus obtained was purified by column chromatography (silica gel, 1. hexane-ethyl acetate; 2. ethyl acetate-methanol) to obtain the title compound (G06-05: colorless foam, 193 mg, 90%).

LC/MS (Method 3): m/z (ESI, POS): 517 [M+H]$^+$, 539 [M+Na]$^+$; retention time: 6.29 minutes.

$^1$H-NMR [400 MHz, CDCl$_3$, TMS] ppm: 1.185 (6H, d, J=7.0 Hz), 2.745 (3H, s), 3.228 (1H, sept., J=7.0 Hz), 3.247 (3H, s), 3.480 (3H, s), 3.73-3.83 (8H, m), 4.896 (2H, s), 5.179 (2H, s), 6.823 (1H, s), 7.326 (1H, s), 8.117 (2H, s).

The Fifth Step: Preparation of G06-06 (sulfone) and G-06-07 (sulfoxide)

Under argon atmosphere, while stirring under ice cold conditions, 3-chloroperbenzoic acid (65 mg, 0.38 mmol) was added to a dichloromethane (3 mL) solution of G06-05 (191 mg, 0.37 mmol) and the mixture was stirred under ice cold conditions for 50 minutes. Next, while stirring under ice cold conditions, additional 3-chloroperbenzoic acid (27 mg, 0.15 mmol) was added and the mixture was stirred for 70 minutes under ice cold conditions. Further, an additional 3-chloroperbenzoic acid (36 mg, 0.21 mmol) was added and the mixture was stirred for 1 hour and 40 minutes under ice cold conditions, and 3 hours at room temperature. Under ice cold conditions, an aqueous solution (5 mL) of sodium sulfite (126 mg, 1 mmol) was added to the ice-cold reaction mixture and the mixture was stirred for 10 minutes. Finally, the reaction mixture was made alkaline by adding sodium hydrogencarbonate and extracted with dichloromethane. The dichloromethane extracts were combined, dried over anhydrous sodium sulfate. Sodium sulfate was filtered off and the solvents of the filtrate were distilled off under reduced pressure and a colorless syrup was obtained, which was purified by column chromatography (silica gel, 1. hexane-ethyl acetate; 2. ethyl acetate-methanol) to obtain the title sulfone (G06-06: colorless foam, 119 mg, 59%) and the title sulfoxide (G06-07: colorless foam, 39 mg, 20%). G06-06 (sulfone)

LC/MS (Method 3): m/z (ESI, POS): 549 [M+H]$^+$, 571 [M+Na]$^+$; retention time: 6.20 minutes.

$^1$H-NMR [400 MHz, CDCl$_3$, TMS] ppm: 1.189 (6H, d, J=7.0 Hz), 3.238 (1H, sept., J=7.0 Hz), 3.279 (3H, s), 3.488 (3H, s), 3.565 (3H, s), 3.742 (4H, t, J=4.6 Hz), 3.814 (4H, t, J=4.6 Hz), 4.937 (2H, s), 5.199 (2H, s), 6.867 (1H, s), 7.296 (1H, s), 8.226 (2H, s). G06-07 (sulfoxide)

LC/MS (Method 3): m/z (ESI, POS): 533 [M+H]$^+$; retention time: 5.62 minutes.

$^1$H-NMR [400 MHz, CDCl$_3$, TMS] ppm: 1.191 (6H, d, J=7.0 Hz), 3.241 (1H, sept., J=7.0 Hz), 3.260 (3H, s), 3.320 (3H, s), 3.489 (3H, s), 3.73-3.77 (4H, m), 3.80-3.85 (4H, m), 4.917 (2H, s), 5.198 (2H, s), 6.865 (1H, s), 7.318 (1H, s), 8.237 (2H, s).

The Sixth Step: Preparation of G06-08

While stirring at room temperature, 1.25M aqueous sodium hydroxide (0.84 mL, 1.05 mmol) was added to a dimethylsulfoxide (0.84 mL) solution of G06-06 (sulfone, 115 mg, 0.21 mmol) and the mixture was heated at 70° C. for 40 minutes while stirring. After completing the reaction, an aqueous solution of ammonium chloride was added to the reaction mixture under ice cold conditions, and the reaction mixture was extracted with ethyl acetate. The ethyl acetate extracts were combined, washed with sodium chloride solution and then dried over anhydrous sodium sulfate. Sodium sulfate was removed by filtration, and the solvent was distilled off under reduced pressure, and a colorless syrup was obtained, which was purified by column chromatography (silica gel, hexane-ethyl acetate) to obtain the title compound (G06-08, colorless foam, 89 mg, 87%).

LC/MS (Method 3): m/z (ESI, POS): 487 [M+H]$^+$; retention time: 5.605 minutes.

$^1$H-NMR [400 MHz, CDCl$_3$, TMS] ppm: 1.194 (6H, d, J=7.0 Hz), 3.240 (1H, sept., J=7.0 Hz), 3.245 (3H, s), 3.486 (3H, s), 3.710-3.755 (4H, m), 3.755-3.800 (4H, m), 4.884 (2H, s), 5.190 (2H, s), 6.850 (1H, s), 7.254 (1H, s), 8.163 (2H, s), 9.521 (1H, s).

The Seventh Step: Preparation of 5-(2,4-dihydroxy-5-isopropyl-phenyl)-4-[2-(morpholin 4-yl)-pyrimidin-5-yl]-2,4-dihydro-[1,2,4]triazol-3-one (OH-a17)

Under argon atmosphere, while stirring in ice cold conditions, a 1,4-dioxane solution of hydrochloric acid (4 N, 0.85 mL, 3.4 mmol) was added to a methanol (0.85 mL) solution of G06-08 (85 mg, 0.175 mmol) and stirred at room temperature for 3 hours. After completing the reaction, the reaction mixture was poured into a cold 5% aqueous sodium hydrogencarbonate (10 mL)-saturated sodium chloride solution, and the mixture was extracted with ethyl acetate. The ethyl acetate extracts were combined, washed with sodium chloride solution and dried over anhydrous sodium sulfate. Sodium sulfate was removed by filtration, the solvent was distilled off under reduced pressure, and thus obtained white solids were washed with ether-hexane to obtain the title compound (OH-a17: white solids, 53 mg, 76%).

LC/MS (Method 3): m/z (ESI, POS): 399 [M+H]$^+$, 421 [M+Na]$^+$; retention time: 4.400 minutes.

$^1$H-NMR [400 MHz, DMSO-d$_6$, TMS] ppm: 1.071 (6H, d, J=7.0 Hz), 3.022 (1H, sept., J=7.0 Hz), 3.60-3.68 (8H, m), 6.248 (1H, s), 6.984 (1H, s), 8.150 (2H, s), 9.40-9.70 (2H, b), 11.94 (1H, b).

Example 2-13

Synthesis of 5-(2,4-dihydroxy-5-isopropyl-phenyl)-4-isopropyl-2,4-dihydro-[1,2,4]triazol-3-one (OH-a21)

Scheme 2-13

[Formula 39]

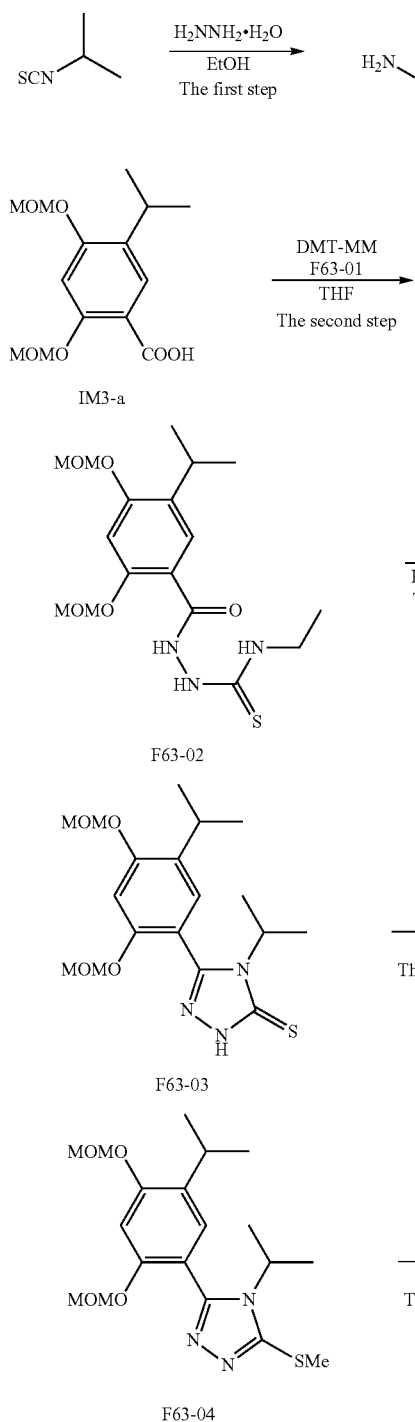

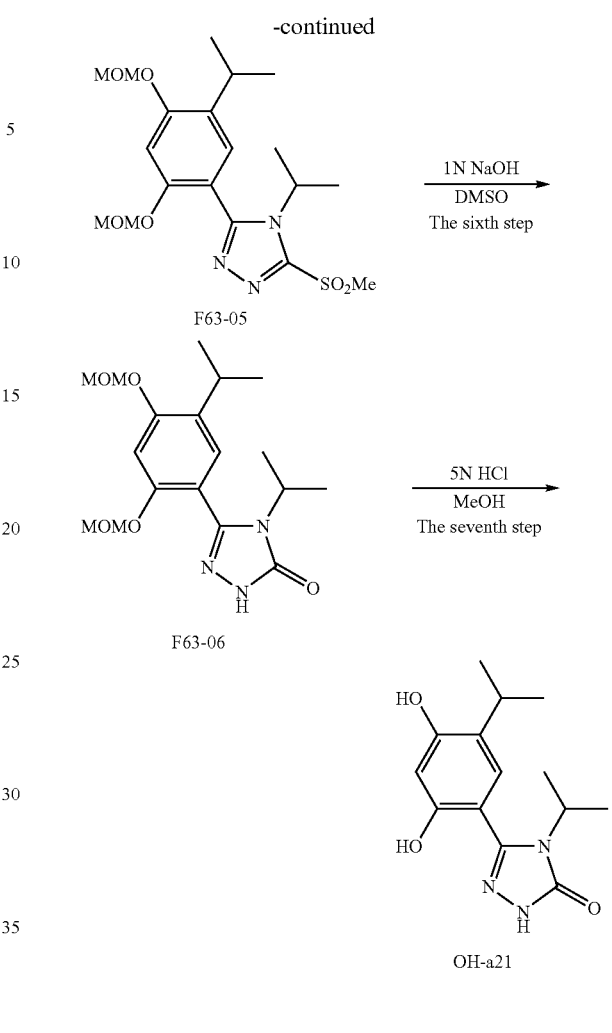

The First Step: Synthesis of F63-01

While stirring in ice cold conditions, isopropylisocyanate (2-isothiocyanato-propane) (3.0 mL, 28.2 mmol) was added to an ethanol (10 mL) solution of hydrazine monohydrate (2.88 g, 56.4 mmol). After stirring at room temperature for 30 minutes, the solvent was distilled off under reduced pressure. The residue was extracted with chloroform, and the extract was washed twice with water and then with saturated sodium chloride solution. After drying over anhydrous sodium, sodium sulfate was removed by filtration and the solvent was distilled off under reduced pressure. Solids thus obtained were dried under reduced pressure to obtain F-63-01 (white solids, 3.59 g, 95.8%).

LC/MS (Method 3): m/z (ESI, POS): 134 [M+H]$^+$; retention time: 2.19 minutes.

$^1$H-NMR (400 MHz, CDCl$_3$) δ 1.26 (d, J=6.6 Hz, 6H), 3.71 (s, 2H), 4.49-4.58 (m, 1H), 7.14 (bs, 1H), 7.25 (br, 1H).

The Second Step: Synthesis of F63-02

At room temperature, 4-(4,6-dimethoxy-1,3,5-triazin-2-yl)-4-methyl morpholinium chloride n hydrate (DMT-MM, 2.34 g) was added to a dimethylformamide (10 mL) solution of 5-isopropyl-2,4-bis-methoxymethoxy-benzoic acid (2.00 g, 7.05 mmol) and F63-01 (984.0 mg, 7.39 mmol) obtained in the first step and stirred. After 3 hours, DMT-MM (250.4 mg) was further added and stirred for 1 hour, and then the reaction was stopped by adding water. The reaction mixture was neutralized by adding an aqueous solution of saturated sodium hydrogencarbonate and extracted with ethyl acetate. The extract was washed with water and then saturated sodium chloride solution. After drying the extract over anhydrous sodium, sodium sulfate was removed by filtration, and the solvent was distilled off under reduced pressure. The solids thus obtained were dried under reduced pressure to obtain F63-02 (white solids, 2.82 g, 100%).

LC/MS (Method 3): m/z (ESI, POS): 400 [M+H]$^+$; retention time: 6.32 minutes.

$^1$H-NMR (400 MHz, CDCl$_3$) δ 1.23 (d, J=7.0 Hz, 6H), 3.26 (sept., J=7.0 Hz, 1H), 3.51 (s, 3H), 3.58 (s, 3H), 4.40-4.49 (m, 1H), 5.27 (s, 2H), 5.43 (s, 2H), 6.99 (s, 1H), 7.97 (s, 1H).

The Third Step: 4-isopropyl-5-(5-isopropyl-2,4-bis-methoxymethoxy-phenyl)-2,4-dihydro-[1,2,4]triazol-3-thione (F63-03)

At room temperature, 10% aqueous potassium hydroxide (20 mL) and 5% potassium hydroxide-ethanol solution (5 mL) were added to F63-02 (2.81 g, 7.04 mmol) obtained in the second step, and the mixture was stirred at 90° C. for 13 hours. After returned to room temperature, chloroform and saturated sodium chloride solution were added and stirred for a while. After this the reaction mixture was extracted with chloroform, and the extract was washed with saturated sodium chloride solution. After drying over anhydrous sodium, sodium sulfate was removed by filtration, and the solvent was distilled off under reduced pressure to obtain an orange colored foam. After suspension purification in hexane-ethyl acetate (2:1), the solids were collected by filtration and dried under reduced pressure. After evaporating the solvent from the filtrate under reduced pressure, the residue was purified by silica gel column chromatography (hexane, ethyl acetate). Together, 4-isopropyl-5-(5-isopropyl-2,4-bis-methoxymethoxyphenyl)-2,4-dihydro-[1,2,4]triazol-3-thione (F63-03, white solids, 1.96 g, 73%) was obtained.

LC/MS (Method 3): m/z (ESI, POS): 382 [M+H]$^+$; retention time: 6.59 minutes.

$^1$H-NMR (400 MHz, CDCl$_3$) δ 1.20 (d, J=7.0 Hz, 6H), 1.50 (d, J=7.0 Hz, 6H), 3.29 (sept., J=7.0 Hz, 1H), 3.41 (s, 3H), 3.52 (s, 3H), 4.62 (sept., J=7.0 Hz, 1H), 5.12 (s, 2H), 5.26 (s, 2H), 7.00 (s, 1H), 7.10 (s, 1H), 10.53 (s, 1H).

The Fourth Step: 4-isopropyl-3-(5-isopropyl-2,4-bis-methoxymethoxyphenyl)-5-methylsulfanyl-4H-[1,2,4]triazole (F63-04)

4-isopropyl-5-(5-isopropyl-2,4-bis-methoxymethoxyphenyl)-2,4-dihydro-[1,2,4]triazol-3-thione (F63-03, 1.96 g, 5.14 mmol) and potassium carbonate (710.4 mg, 5.14 mmol) were weighed and placed in a reaction vessel, and ethanol (30 mL) was added and then methyl iodide (0.32 mL, 5.14 mmol) was added. After heating at 80° C. for 1 hour while stirring, the mixture was returned to room temperature, and the solvent was distilled off under reduced pressure. After adding water, the reaction system was extracted with ethyl acetate, and the extract was washed with saturated sodium chloride solution. After drying the extract over anhydrous sodium, sodium sulfate was removed by filtration and the solvent was distilled off under reduced pressure to obtain yellow syrup. After purification by silica gel column chromatography (chloroform, methanol), 4-isopropyl-3-(5-isopropyl-2,4-bis-methoxy methoxyphenyl)-5-methylsulfanyl-4H-[1,2,4]triazole (F63-04, pale yellow syrup, 1.93 g, 95%) was obtained.

LC/MS (Method 3): m/z (ESI, POS): 396 [M+H]$^+$; retention time: 6.49 minutes.

The Fifth Step: 4-isopropyl-3-(5-isopropyl-2,4-bis-methoxymethoxyphenyl)-5-methylsulfonyl-4H-[1,2,4]triazole (F63-05)

While stirring in ice cold conditions, 3-chloroperbenzoic acid (4.20 g, 24.4 mmol) was added to a methylene chloride (10 mL) solution of 4-isopropyl-3-(5-isopropyl-2,4-bis-methoxymethoxyphenyl)-5-methylsulfanyl-4H-[1,2,4]triazole (F63-04, 1.93 g, 4.87 mmol). After stirring at room temperature for 2 hours, the mixture was bring back to ice cold conditions again, and saturated aqueous sodium thiosulfate and then saturated sodium hydrogencarbonate were added. After stirring for a while, the reaction mixture was extracted with ethyl acetate, and the extract was washed with saturated sodium chloride solution. After drying the extract over anhydrous sodium, sodium sulfate was removed by filtration and the solvent was distilled off under reduced pressure to obtain a pale yellow foam. After purification by silica gel column chromatography (hexane, ethyl acetate), 4-isopropyl-3-(5-isopropyl-2,4-bis-methoxymethoxyphenyl)-5-methylsulfonyl-4H-[1,2,4]triazole (F63-05, colorless foam, 1.65 g, 79%) was obtained.

LC/MS (Method 3): m/z (ESI, POS): 428 [M+H]$^+$; retention time: 6.56 minutes.

$^1$H-NMR (400 MHz, CDCl$_3$) δ 1.20 (d, J=7.0 Hz, 6H), 1.51 (d, J=7.0 Hz, 6H), 3.30 (sept., J=7.0 Hz, 1H), 3.39 (s, 3H), 3.53 (s, 3H), 3.63 (s, 3H), 4.69 (sept., J=7.0 Hz, 1H), 5.11 (s, 2H), 5.27 (s, 2H), 7.02 (s, 1H), 7.16 (s, 1H).

The Sixth Step: 4-isopropyl-5-(5-isopropyl-2,4-bis-methoxymethoxyphenyl)-2,4-dihydro-[1,2,4]triazol-3-one (F63-06)

At room temperature, aqueous sodium hydroxide (1.0 M aqueous solution, 9 mL) was added to a dimethylsulfoxide (11 mL) solution of 4-isopropyl-3-(5-isopropyl-2,4-bis-methoxymethoxyphenyl)-5-methyl sulfonyl-4H-[1,2,4]triazole (F63-05, 1.63 g, 3.82 mmol). The mixture was heated at 90-100° C. for 12 hours while stirring. After returning to room temperature, water was added. The reaction mixture was extracted with ethyl acetate, and the extract was washed twice with water and then with saturated sodium chloride solution. After drying the extract over anhydrous sodium, sodium sulfate was removed by filtration and the solvent was distilled off under reduced pressure to obtain white solids. After suspension purification by diethyl ether, the solids obtained by filtration were dried under reduced pressure to obtain 4-isopropyl-5-(5-isopropyl-2,4-bis-methoxymethoxyphenyl)-2,4-dihydro-[1,2,4]triazol-3-one (F63-06, white solids, 1.09 g, 78%).

LC/MS (Method 3): m/z (ESI, POS): 366 [M+H]$^+$; retention time: 5.88 minutes.

$^1$H-NMR (400 MHz, CDCl$_3$) δ 1.21 (d, J=7.0 Hz, 6H), 1.46 (d, J=7.0 Hz, 6H), 3.28 (sept., J=7.0 Hz, 1H), 3.43 (s, 3H), 3.52 (s, 3H), 3.93 (sept., J=7.0 Hz, 1H), 5.14 (s, 2H), 5.25 (s, 2H), 6.99 (s, 1H), 7.16 (s, 1H), 8.93 (s, 1H).

The Seventh Step: 5-(2,4-dihydroxy-5-isopropylphenyl)-4-isopropyl-2,4-dihydro-[1,2,4]triazol-3-one (OH-a21)

5 N hydrochloric acid (7 mL) was added to a methanol (13 mL) solution of 4-isopropyl-5-(5-isopropyl-2,4-bis-methoxymethoxyphenyl)-2,4-dihydro-[1,2,4]triazol-3-one (F63-

06, 1.03 g, 2.82 mmol) and the mixture was stirred overnight. After cooling to ice cold conditions, the reaction mixture was neutralized by adding saturated aqueous sodium hydrogencarbonate. The solution was extracted with ethyl acetate, and the extract was washed with water and then with saturated sodium chloride solution. After drying the extract over anhydrous sodium, sodium sulfate was removed by filtration and the solvent was distilled off under reduced pressure to obtain white solids. After crude purification by silica gel column chromatography (chloroform, methanol), the solids were further purified by silica gel column chromatography (NHsilica, diethyl ether, methanol) to obtain 5-(2,4-dihydroxy-5-isopropylphenyl)-4-isopropyl-2,4-dihydro-[1,2,4]triazol-3-one (OH-a21, white solids, 581 mg, 74%).

LC/MS (Method 3): m/z(ESI, POS): 278[M+H]$^+$; retention time: 4.38 minutes.

FAB-MS: m/z(POS): 278[M+H]$^+$; melting point: 261-262° C. (dec.).

$^1$H-NMR (400 MHz, DMSO-d$_6$) δ 1.11 (d, J=7.0 Hz, 6H), 1.31 (d, J=6.8 Hz, 6H), 3.08 (sept., J=7.0 Hz, 1H), 3.80 (sept., J=6.8 Hz, 1H), 6.45 (s, 1H), 6.88 (s, 1H), 9.69 (bs, 2H), 11.47 (bs, 1H).

Example 2-14

Preparation of 5-(2,4-dihydroxy-5-isopropyl-phenyl)-4-piperidin-1-yl-2,4-dihydro-[1,2,4]triazol-3-one (OH-a24) trifluoroacetate Scheme 2-14

[Formula 40]

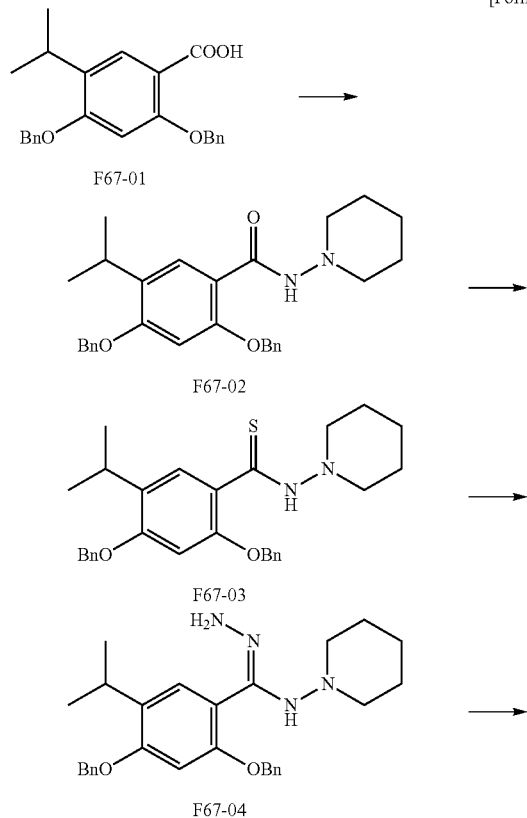

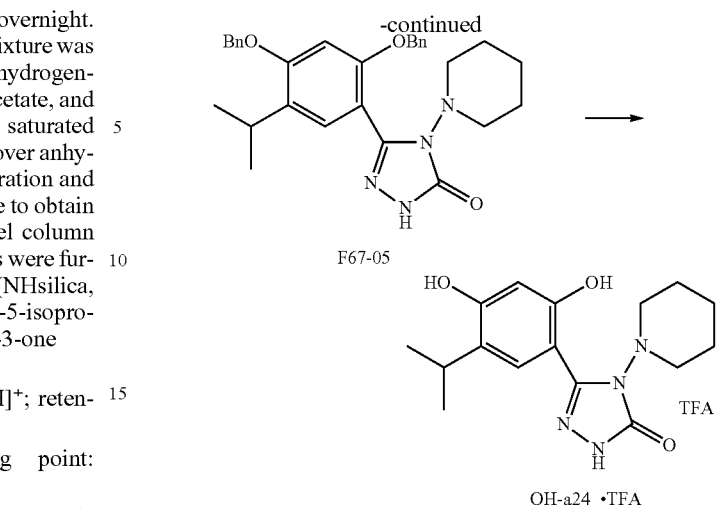

The First Step: Preparation of 2,4-bis-benzyloxy-5-isopropyl-N-piperidin-1-yl-benzamide (F67-02)

2,4-bis-benzyloxy-5-isopropylbenzoic acid (F67-01: 188 mg, 0.5 mmol), dimethylformamide (2 mL) and 1-hydroxy-1,2,3-benzotriazole (72 mg, 0.55 mmol) were placed in a test tube and then 1-amino-piperidine (0.059 mL, 0.55 mmol) was added. A mixed solution of dimethylformamide (1 mL), 1-ethyl-3-(3'-dimethylaminopropyl)carbodiimide hydrochloride (105 mg, 0.55 mmol) and triethylamine (0.15 mL, 1.1 mmol) was slowly added to the reaction mixture at 0° C. while stirring. Further, the reaction mixture was allowed to come to room temperature and stirred for 24 hours. After completing the reaction, the reaction mixture was extracted with ethyl acetate, and the extract was washed 4 times with saturated sodium chloride, dried with sodium sulfate and then concentrated under reduced pressure. The residue was purified by silica gel column chromatography (methylene chloride/methanol) followed by silica gel column chromatography (hexane/ethyl acetate) to obtain the title compound (F67-02: 198 mg, 86.4%).

LC/MS (Method 5): m/z (ESI, POS): 459 [M+H]$^+$; retention time: 7.44 minutes.

The Second Step: Preparation of 2,4-bis-benzyloxy-5-isopropyl-N-piperidin-1-yl-thiobenzamide (F67-03)

2,4-bis-benzyloxy-5-isopropyl-N-piperidin-1-yl-benzamide (F67-02: 198 mg, 0.43 mmol), toluene (5 mL) and Lawesson's reagent (157 mg, added in two portions) were placed in a test tube and heated for 2.5 hours under reflux. After the reaction was completed, the reaction mixture was concentrated under reduced pressure. The foam thus obtained was subjected to the next reaction without further purification.

LC/MS (Method 5): m/z (ESI, POS): 475 [M+H]$^+$; retention time: 7.86 minutes.

The Third Step: Preparation of 2,4-bis-benzyloxy-5-isopropyl-N-piperidin-1-yl-benzene-carbohydrazonamide (F67-04)

2,4-bis-benzyloxy-5-isopropyl-N-piperidin-1-yl-thiobenzamide (unpurified product of the previous step: F67-03), ethanol (5 mL), hydrazine monohydrate (0.5 mL) was placed in a test tube and heated for 1.5 hours under reflux. After completing the reaction, the reaction mixture was concentrated under reduced pressure while adding toluene several times. The residue thus obtained was subjected to the next step without purification.

LC/MS (Method 5): m/z (ESI, POS): 473 [M+H]$^+$; retention time: 3.51 minutes.

The Fourth Step: Preparation of 5-(2,4-bis-benzyloxy-5-isopropyl-phenyl)-4-piperidin-1-yl-2,4-dihydro-[1,2,4]triazol-3-thione (F67-05)

2,4-bis-benzyloxy-5-isopropyl-N-piperidin-1-yl-benzene-carbohydrazonamide (unpurified product of the previous step: F67-04), tetrahydrofuran (3 mL) and triphosgene (42 mg) were placed in a test tube and stirred at room temperature. After completing the reaction, methanol and sodium hydrogencarbonate were added and the mixture was stirred for a while, and then solids were separated by filtration. The mother liquor thus obtained was concentrated under reduced pressure, and the residue was purified by silica gel column chromatography (hexane/ethyl acetate) to obtain the title compound (F67-05: 92 mg, 36.7%).

LC/MS (Method 5): m/z (ESI, POS): 499 [M+H]$^+$; retention time: 7.44 minutes.

The Fifth Step: Preparation of 5-(2,4-dihydroxy-5-isopropyl-phenyl)-4-piperidin-1-yl-2,4-dihydro-[1,2,4]triazol-3-one (OH-a24) trifluoroacetate 5-(2,4-bis-benzyloxy-5-isopropyl-phenyl)-4-piperidin-1-yl-2,4-dihydro-[1,2,4]triazol-3-thione (F67-05: 92 mg, 0.18 mmol), methylene chloride (2 mL) and a methylene chloride solution of boron trichloride (1 mol/L, 1 mL) were placed in a test tube and stirred at room temperature for 1 hour. After completing the reaction, methanol and sodium hydrogencarbonate were added to the reaction mixture and solids were separated by filtration. The mother liquor thus obtained was concentrated under reduced pressure and the residue was purified by HPLC fractionation to obtain the title compound (OH-a24 trifluoroacetate, 9.5 mg, 16.6%).

LC/MS (Method 3): m/z (ESI, POS): 319 [M+H]$^+$; retention time: 5.74 minutes.

$^1$H-NMR (400 MHz, DMSO-d$_6$, TMS) ppm: 11.8 (1H, s), 9.94 (1H, s), 9.75 (1H, s), 7.74 (1H, s), 6.38 (1H, s), 3.70-3.45 (2H, brs), 3.12 (1H, sept, J=6.6 Hz), 3.20-2.90 (2H, brs), 1.80-1.40 (6H, brs), 1.15 (6H, d, J=6.6 Hz)

Example 2-15

Preparation of 5-(2,4-dihydroxy-5-isopropyl-phenyl)-4-(2-morpholin-4-yl-ethyl)-2,4-dihydro-[1,2,4]triazol-3-one (OH-a26) monohydrochloride The title compound (OH-a26monohydrochloride) was synthesized in the similar manner to that of Example 2-16 using (2-morpholin-4-yl-ethyl)-thiocarbamic acid O-phenyl ester in place of F93-06 of Example 2-16.

LC/MS (Method 6): m/z (ESI, POS): 349 [M–HCl+H]$^+$; retention time: 3.86 minutes.

$^1$H-NMR (400 MHz, DMSO-d$_6$) δ 1.13 (d, J=7.0 Hz, 6H), 2.96-3.14 (m, 3H), 3.59-3.74 (m, 2H), 4.10 (t, J=6.1 Hz, 2H), 3.94 (bd, J=12.3 Hz, 2H), 6.56 (s, 1H), 7.00 (s, 1H), 9.86 (s, 1H), 10.03 (s, 1H), 10.32 (br, 1H), 11.92 (s, 1H).

Example 2-16

Preparation of 5-(2,4-dihydroxy-5-isopropyl-phenyl)-4-[3-(molpholin-4-yl)-propyl]-2,4-dihydro-[1,2,4]triazol-3-one (OH-a27)

Scheme 2-16

[Formula 41]

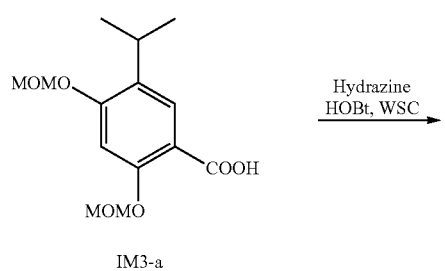

IM3-a

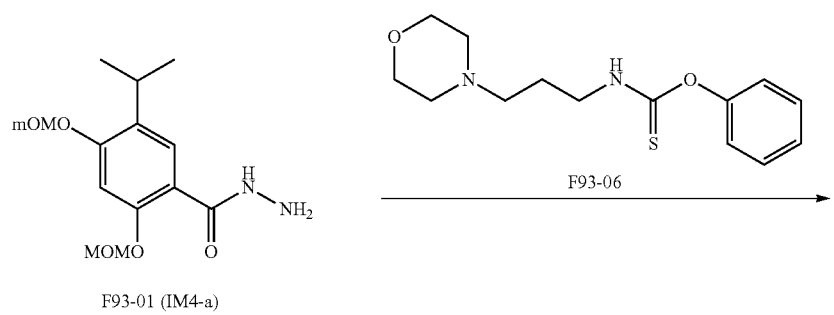

F93-01 (IM4-a)

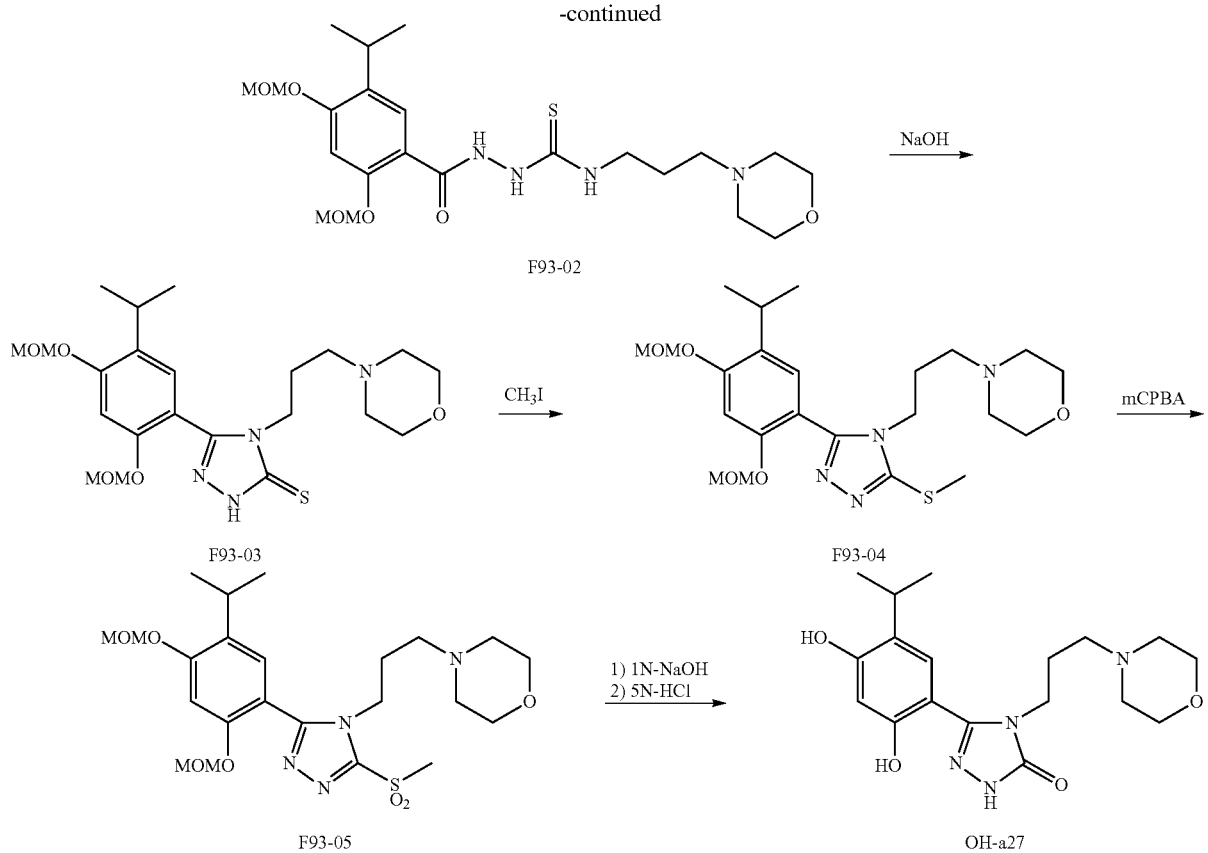

The First Step: Preparation of F93-01 (IM4-a)

IM3-a (1137 mg, 4 mmol), hydrazine-monohydrate (240 mg, 4.8 mmol) and dimethylformamide (15 mL) were placed in a 100 mL flask, and to this 1-hydroxy benztriazolemonohydrate (656 mg, 4.8 mmol) and 1-ethyl-3-(3'-dimethylaminopropyl)carbodiimidehydrochloride (932 mg, 4.86 mmol) were added under ice cold conditions, and the mixture was stirred for 20 hours. After adding water (100 mL) and saturated aqueous sodium hydrogencarbonate (15 mL), the reaction mixture was extracted twice with ethyl acetate (100 mL). The organic layer was washed with saturated sodium chloride solution, dried with sodium sulfate and then concentrated under reduced pressure to obtain the title crude compound (F93-01: 1302 mg).

LC/MS (Method 3): m/z (ESI, POS): 299 [M+H]$^+$; retention time: 4.69 minutes.

The Second Step: Preparation of F93-02

Crude F93-01 (298 mg, 1.0 mmol), F93-06 (280 mg, 1.5 mmol) and ethanol (15 mL) were placed in a 50 mL flask and heated for 2 hours under reflux, and then the reaction mixture was concentrated under reduced pressure to obtain the crude title compound (F93-02).

LC/MS (Method 3): m/z (ESI, POS): 485 [M+H]$^+$; retention time: 3.36 minutes.

Preparation of F93-06

3-morpholinopropylamine (288.4 mg, 2 mmol) and anhydrous dichloromethane (10 mL) were placed in a 100 mL flask, and to this a mixture of O-phenyl chlorothionoformate (332 µL, 2.4 mmol) and pyridine (232 µL, 2.88 mmol) under ice cold conditions and stirred for 2 hours. The reaction mixture was mixed with water (10 mL) and saturated aqueous sodium hydrogencarbonate (5 mL), and extracted twice with chloroform (15 mL). After washing with saturated sodium chloride solution, the organic layer was dried with sodium sulfate and concentrated under reduced pressure. The residue was purified by silica gel column chromatography (chloroform:methanol=10:1) to obtain the title compound (F93-06: 425 mg, yield 75.7%).

LC/MS (Method 3): m/z (ESI, POS): 281 [M+H]$^+$; retention time: 1.08 minutes.

The Third Step: Preparation of F93-03

The crude product produced in the second step (F93-02, 465 mg) was dissolved in 10% aqueous potassium hydroxide (12 mL) and 5% ethanol solution of potassium hydroxide (6 mL) and heated for 1.5 hours under reflux. After concentrating the reaction mixture, the residue was mixed with water (30 mL) and extracted twice with ethyl acetate (30 mL). After concentrating the extract under reduced pressure, the residue was purified by silica gel column chromatography (chloroform:methanol=20:1) to obtain the title compound (F93-03: 247 mg, yield 52.0%, in total 3 steps)

LC/MS (Method 3): m/z (ESI, POS): 467 [M+H]$^+$; retention time: 3.30 minutes.

The Fourth Step: Preparation of F93-04

F93-03 (247 mg, 0.52 mmol) dissolved in ethanol (8 mL) was mixed with potassium carbonate (72 mg, 0.52 mmol) and methyl iodide (33 μL, 0.52 mmol) and heated for 1 hour under reflux. After concentrating, the reaction mixture was mixed with water (10 mL) and extracted twice with ethyl acetate (15 mL). The organic layer was concentrated under reduced pressure to obtain the title crude compound (F93-04, 234 mg).

LC/MS (Method 3): m/z (ESI, POS): 481 [M+H]$^+$; retention time: 3.11 minutes.

The Fifth Step: Preparation of F93-05

After dissolving the crude F93-04 (234 mg) in dichloromethane (10 mL), m-chloroperbenzoate (345 mg, 2 mmol) was added to it and the mixture was stirred for 20 hours. The reaction mixture was mixed with chloroform (20 mL) and 10% potassium bisulfite solution (30 mL), stirred for 10 minutes, and then the organic layer was separated. The organic layer was washed with saturated sodium chloride solution, dried with sodium sulfate and concentrated under reduced pressure. The residue was purified by silica gel column chromatography (chloroform:methanol=20:1) to obtain the title compound (F93-05: 147 mg, yield 55.1%, in total 2 steps).

LC/MS (Method 3): m/z (ESI, POS): 513 [M+H]$^+$; retention time: 3.40 minutes.

The Sixth Step: Preparation of 5-(2,4-dihydroxy-5-isopropyl-phenyl)-4-[3-(molpholin-4-yl)-propyl]-2,4-dihydro-[1,2,4]triazol-3-one (OH-a27)

After dissolving F93-05 (91 mg, 0.177 mmol) in dimethylsulfoxide (0.5 mL), 3 N aqueous sodium hydroxide (0.5 mL) was added to it and stirred at 90° C. for 1.5 hours. After adding water (15 mL), the reaction mixture was extracted twice with ethyl acetate (15 mL). The organic layer was washed with saturated sodium chloride solution, dried with sodium sulfate and then concentrated under reduced pressure. The residue was dissolved in methanol (2 mL) and mixed with 5 N hydrochloric acid (1.5 mL), and the mixture was stirred at 55° C. for 1 hour. After concentrating, the residue was dissolved in methanol (6 mL) and mixed with silica gel (350 mg) and concentrated under reduced pressure. The residue was purified by silica gel column chromatography (chloroform:methanol=10:1-3:1) to obtain the title compound (OH-a27: 53 mg, yield 82.6%).

LC/MS (Method 4): m/z (ESI, POS): 363 [M+H]$^+$; retention time: 6.42 minutes.

$^1$H-NMR (400 MHz, CD$_3$OD, ppm): 7.06 (1H, s), 6.43 (1H, s), 4.61 (2H, brs), 3.78 (2H, brs), 3.75 (4H, brs), 3.18 (1H, m), 2.86 (4H, brs), 1.98 (2H, m), 1.19 (6H, d, J=6.95)

Example 2-17

Preparation of 5-(2,4-dihydroxy-5-isopropyl-phenyl)-4-[3-(2-oxo-pyrrolidin-1-yl)propyl]-2,4-dihydro-[1,2,4]triazol-3-one (OH-a30)

N-(3-isothiocyanatopropyl)-2-pyrrolidinone was obtained by the similar process to that of Example 2-2(B) in 1 step using N-(3-aminopropyl)-2-pyrrolidinone in place of 4-molpholin-4-ylmethyl-phenylamine (F45-000) in Example 2-2 (B). The title compound (OH-a30) was obtained using this compound in the similar process to that of Example 2-13 in 7 steps.

LC/MS (Method 1): m/z (ESI, POS): 361 [M+H]$^+$; retention time: 4.10 minutes.

$^1$H-NMR [400 MHz, CDCl$_3$+CD$_3$OD (three drops)] δ 1.20 (d, J=7.0 Hz, 6H), 1.82-2.00 (m, 4H), 2.34 (t, J=7.9 Hz, 2H), 3.14-3.28 (m, 5H), 3.62-3.70 (m, 2H), 6.40 (s, 1H), 7.30 (s, 1H).

Example 2-18

Preparation of 5-(2,4-dihydroxy-5-isopropyl-phenyl)-4-(2-methoxy-ethyl)-2,4-dihydro-[1,2,4]triazol-3-one (OH-a32)

The bis(methoxymethyl) protected compound of the title compound (OH-a32) was obtained from the compound of Example 3-14 (SFN-a32) protected by a bis(methoxymethyl) group by the similar manner to that of the sixth step of Example 2-12. This compound was deprotected in the similar manner to that in the seventh step of Example 1-1 to obtain the title compound (OH-a32).

LC/MS (Method 3): m/z (ESI, POS): 294 [M+H]$^+$; retention time: 3.99 minutes.

$^1$H-NMR (400 MHz, CDCl$_3$:CD$_3$OD=3:1, ppm): 7.25 (1H, s), 6.39 (1H, s), 3.91 (2H, t, J=5.86 Hz), 3.57 (2H, t, J=5.86 Hz), 3.24 (3H, s), 3.23 (1H, m), 1.20 (6H, d, J=6.96 Hz)

Example 2-19

Preparation of 5-(2,4-dihydroxy-5-isopropyl-phenyl)-4-(2-hydroxy-1-hydroxymethyl-ethyl)-2,4-dihydro-[1,2,4]triazol-3-one (OH-a33)

Scheme 2-19

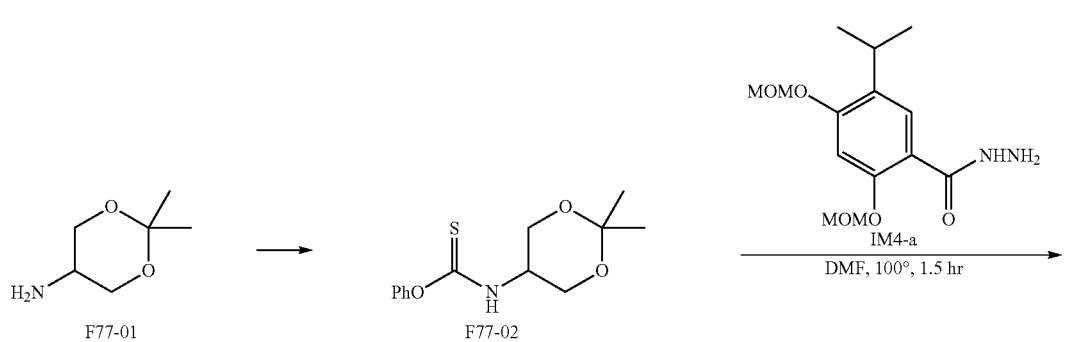

[Formula 42]

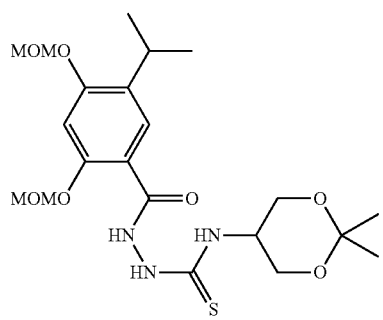

F77-03 (68%)

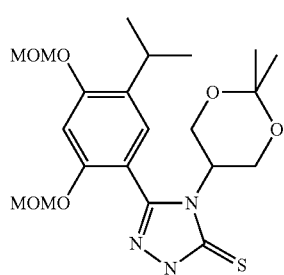

F77-04

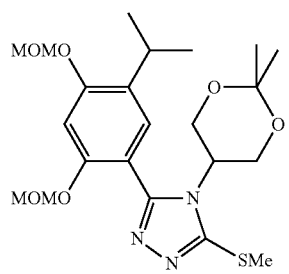

F77-05 (91%)

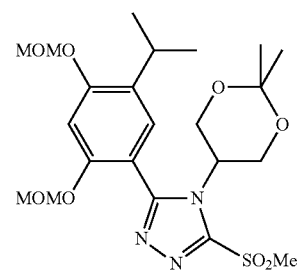

F77-06 (75%)

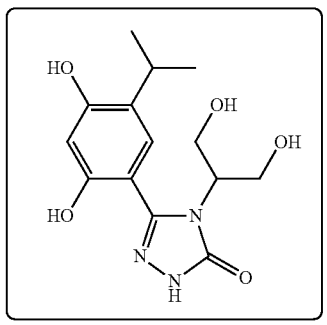

OH-a33 (80%)

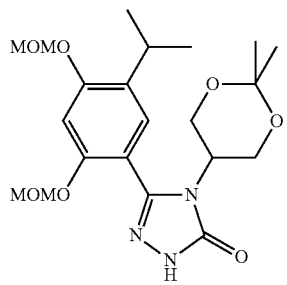

F77-07 (60 mg, 92%)

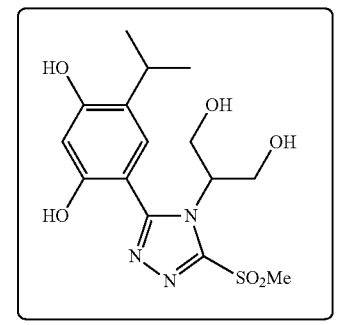

SFN-a33 (82%)

The First Step: Preparation of F77-02

The title compound was synthesized from 5-amino-2,2-dimethyl-1,3-dioxane (F77-01) that is known in the literature (Chem. Pharm. Bull. Vol. 44, No. 12, 2205-2212, 1996) by the similar manner to that of the first step of Example 2-12.

LC/MS (Method 3): m/z (ESI, POS): 268 [M+H]⁺, 210.; retention time: 6.007 minutes.

¹H-NMR [400 MHz, CDCl₃, TMS] ppm: 1.464 (3H, s), 1.532 (3H, s), 3.875-4.050 (2H, m), 4.150-4.270 (3H, m), 7.07-7.13 (2H, m), 7.21-7.36 (1H, m), 7.38-7.47 (2H, m), 7.595 (1H, d, J=7.7 Hz).

The Second Step; Preparation of F77-03

Under argon atmosphere, a dimethylformamide (2 mL) solution of IM4-a (180 mg, 0.603 mmol) and F77-02 [161 mg, 0.603 mmol] was heated at 100° C. for 1.5 hours on an oil bath while stirring. The reaction mixture was mixed with sodium chloride solution and extracted with ethyl acetate. The ethyl acetate extracts were combined, washed with sodium chloride solution and dried over anhydrous sodium sulfate. Sodium sulfate was removed by filtration, the solvent was distilled off under reduced pressure and the yellow syrup thus obtained was purified by column chromatography (silica gel, hexane-ethyl acetate) to obtain the title compound (F77-03: colorless foam, 194 mg, 68%).

LC/MS (Method 3): m/z (ESI, POS): 472 [M+H]⁺, 494 [M+Na]⁺, 414.; retention time: 6.31 minutes.

¹H-NMR [400 MHz, CDCl₃, TMS] ppm: 1.220 (6H, d, J=6.9 Hz), 1.446 (3H, s), 1.641 (3H, s), 3.243 (1H, sept., J=6.9 Hz), 3.499 (3H, s), 3.564 (3H, s), 3.856 (2H, m), 4.143 (2H, m), 4.399 (1H, dt, Jd=8.3 Hz, Jt=2.5 Hz), 5.256 (2H, s), 5.408 (2H, s), 6.967 (1H, s), 7.496 (1H, d, J=8.3 Hz), 8.011 (1H, s), 8.00-11.5 (2H, b).

The Third Step: Preparation of F77-04

A mixture of F77-03 (165 mg, 0.35 mmol) and 1.25M aqueous sodium hydroxide (5 mL, 6.25 mmol) was heated for 3 hours under reflux. Under ice cold conditions, the reaction mixture was mixed with 1M aqueous potassium bisulfate (6.25 mL) and extracted with ethyl acetate. The ethyl acetate extracts were combined, washed with saturated sodium chloride solution, dried over anhydrous sodium sulfate. Sodium sulfate was removed by filtration, the solvent was distilled off under reduced pressure, and the colorless syrup thus obtained was purified by column chromatography (silica gel, hexane-ethyl acetate) to obtain the title compound (F77-04: colorless foam, 113 mg, 71%).

LC/MS (Method 3): m/z (ESI, POS): 454 [M+H]$^+$, 396.; retention time: 6.75 minutes.

$^1$H-NMR [400 MHz, CDCl$_3$, TMS] ppm: 1.206 (6H, d, J=7.0 Hz), 1.370 (3H, s), 1.684 (3H, s), 3.276 (1H, sept., J=7.0 Hz), 3.435 (3H, s), 3.533 (3H, s), 3.75 (2H, m), 4.311 (1H, m), 5.159 (2H, s), 5.281 (2H, s), 5.40 (2H, m), 7.051 (1H, s), 7.133 (1H, s).

The Fourth Step: Preparation of F77-05

Under argon atmosphere, while stirring at room temperature, methyl iodide (0.0182 mL, 42 mg, 0.293 mmol) was added to an ethanol (2 mL) suspension of F-77-04 (133 mg, 0.293 mmol) and solid potassium carbonate, and the mixture was stirred at room temperature for 2 hours. Under ice cold conditions, the reaction mixture was mixed with aqueous ammonium chloride and extracted with ethyl acetate. The ethyl acetate extracts were combined, washed with saturated sodium chloride solution, dried over anhydrous sodium sulfate. Sodium sulfate was removed by filtration and the solvent was distilled off under reduced pressure to obtain the title compound (F77-05: yellow foam, 125 mg, 91%).

$^1$H-NMR [400 MHz, CDCl$_3$, TMS] ppm: 1.206 (6H, d, J=7.0 Hz), 1.369 (3H, s), 1.573 (3H, s), 2.837 (3H, s), 3.275 (1H, sept., J=7.0 Hz), 3.394 (3H, s), 3.526 (3H, s), 3.80 (2H, m), 4.340 (1H, tt, J=11.0, 5.5 Hz), 4.510 (2H, t, J=11.0 Hz), 5.104 (2H, s), 5.267 (2H, s), 7.017 (1H, s), 7.232 (1H, s).

The Fifth Step: Preparation of F77-06

Under argon atmosphere, while stirring under ice cold conditions, 3-chloroperbenzoic acid (95 mg, 0.55 mmol) was added to a dichloromethane (2 mL) solution of F77-05 (123 mg, 0.263 mmol) and the mixture was stirred at room temperature for 3.5 hours. The reaction mixture was diluted by adding dichloromethane, and washed with aqueous sodium sulfite followed by sodium chloride solution, and then dried over anhydrous sodium sulfate. Sodium sulfate was removed by filtration and the solvent was distilled off under reduced pressure, and the colorless foam thus obtained was purified by column chromatography (silica gel, hexane-ethyl acetate) to obtain the title compound (F77-06: colorless foam, 98 mg, 75%) G06-06 (sulfone)

LC/MS (Method 3): m/z (ESI, POS): 500 [M+H]$^+$, 522 [M+Na]$^+$.; retention time: 6.74 minutes.

$^1$H-NMR [400 MHz, CDCl$_3$, TMS] ppm: 1.217 (6H, d, J=7.0 Hz), 1.353 (3H, s), 1.501 (3H, s), 3.296 (1H, sept., J=7.0 Hz), 3.412 (3H, s), 3.533 (3H, s), 3.660 (3H, s), 3.84 (2H, m), 4.57-4.70 (3H, m), 5.138 (2H, s), 5.289 (2H, s), 7.071 (1H, s), 7.208 (1H, s).

The Sixth Step: Preparation of F77-07

While stirring at room temperature, 1.25M aqueous sodium hydroxide (0.6 mL, 0.75 mmol) was added to a dimethylsulfoxide (0.6 mL) solution of F77-06 (75 mg, 0.15 mmol) and the mixture was heated at 90° C. for 1 hour and 15 minutes while stirring. After completing the reaction, the reaction mixture was mixed with aqueous ammonium chloride under ice cold conditions and extracted with ethyl acetate. The ethyl acetate extracts were combined, washed with sodium chloride solution and then dried over anhydrous sodium sulfate. Sodium sulfate was removed by filtration, and the solvent was distilled off under reduced pressure, and the colorless syrup was purified by column chromatography (silica gel, hexane-ethyl acetate) to obtain the title compound (F77-07: colorless foam, 60 mg, 92%).

LC/MS (Method 3): m/z (ESI, POS): 438 [M+H]$^+$, 460 [M+Na]$^+$, 380.; retention time: 6.054 minutes.

$^1$H-NMR [400 MHz, CDCl$_3$, TMS] ppm: 1.210 (6H, d, J=6.9 Hz), 1.360 (3H, s), 1.635 (3H, s), 3.271 (1H, sept., J=6.9 Hz), 3.453 (3H, s), 3.531 (3H, s), 3.69-3.80 (2H, m), 3.959 (1H, tt, J=11.2, 5.5 Hz), 4.816 (2H, t, J=11.2 Hz), 5.169 (2H, s), 5.269 (2H, s), 7.022 (1H, s), 7.161 (1H, s), 9.442 (1H, s).

The Seventh Step: Preparation of 5-(2,4-dihydroxy-5-isopropyl-phenyl)-4-(2-hydroxy-1-hydroxymethyl-ethyl)-2,4-dihydro-[1,2,4]triazol-3-one (OH-a33)

While stirring under ice cold conditions, 6 N aqueous hydrochloric acid (0.5 mL, 3.0 mmol) was added to a methanol (1.0 mL) solution of F77-07 (58 mg, 0.133 mmol), and the mixture was stirred at room temperature for 17.5 hours. While stirring under ice cold conditions, 5% aqueous sodium hydrogencarbonate (5 mL) and saturated sodium chloride were added to the reaction mixture, and the mixture was extracted with ethyl acetate. The ethyl acetate extracts were combined, washed with sodium chloride solution and then dried over anhydrous sodium sulfate. Sodium sulfate was removed by filtration, and the solvent was distilled off under reduced pressure, and the white solids thus obtained were washed with ether to obtain the title compound (OH-a33: white solids, 33 mg, 80%).

LC/MS (Method 1): m/z (ESI, POS): 310 [M+H]$^+$, 332 [M+Na]$^+$.; retention time: 2.54 minutes.

$^1$H-NMR [400 MHz, DMSO-d$_6$, TMS] ppm: 1.108 (6H, d, J=6.8 Hz), 3.067 (1H, sept., J=6.8 Hz), 3.60-3.80 (5H, m), 4.81 (2H, bs), 6.424 (1H, s), 6.963 (1H, s), 9.50-9.70 (1H, b), 9.612 (1H, s), 11.624 (1H, s).

Example 3-1

Preparation of 4-isopropyl-6-{5-methylsulfanyl-4-[4-(morpholin-4-ylmethyl)-phenyl]-4H-[1,2,4]triazol-3-yl}-benzene-1,3-diol trifluoroacetate (SMe-a02-TF)

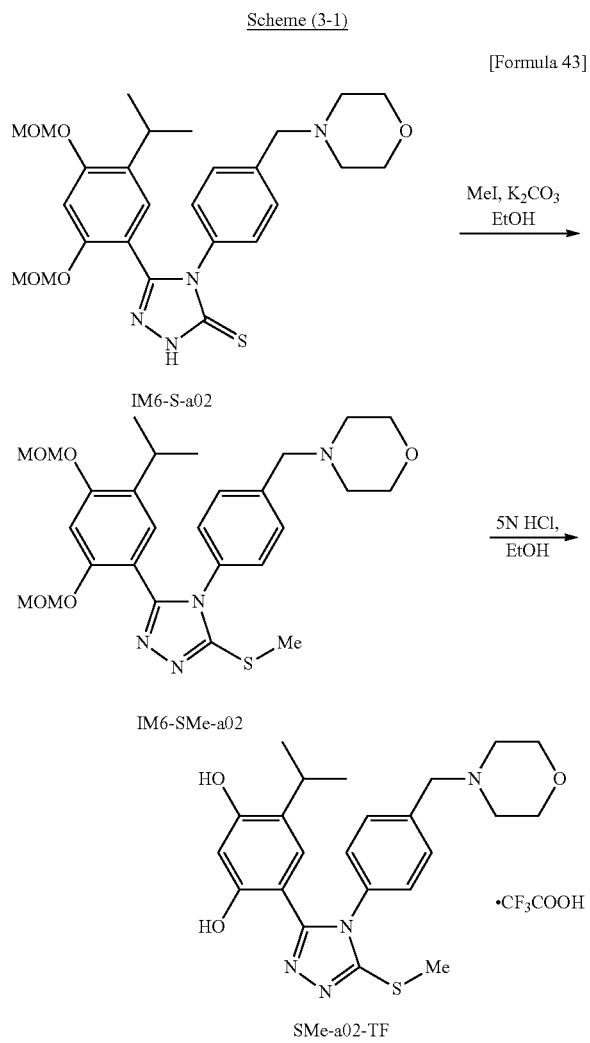

Scheme (3-1)

[Formula 43]

The First Step: Preparation of 4-{4-[3-(5-isopropyl-2,4-bis-methoxymethoxy-phenyl)-5-methylsulfanyl-[1,2,4]traizol-4-yl]-benzyl}-morpholine (IM6-SMe-a02)

5-(5-isopropyl-2,4-bis-methoxymethoxy-phenyl)-4-[4-(morpholin-4-ylmethyl)-phenyl]-2,4-dihydro-[1,2,4]triazol-3-thione (IM6-S-a02: 292 mg, 0.57 mmol), potassium carbonate (78.6 mg, 0.57 mmol) and ethanol (5 mL) were placed in a 50 mL eggplant shaped flask, and then methyl iodide (0.035 mL, 0.57 mL) was added, and the mixture was heated for 2 hours under reflux. The reaction mixture was filtered, and the mother liquor was concentrated under reduced pressure, and the residue thus obtained was purified by silica gel column chromatography to obtain the title compound (IM6-SMe-a02: 206 mg, 39.1%).

LC/MS (Method 3): m/z (ESI, POS): 529 [M+H]$^+$; retention time: 3.34 minutes.

The Second Step: Preparation of 4-isopropyl-6-{5-methylsulfanyl-4-[4-(morpholin-4-ylmethyl)-phenyl]-4H-[1,2,4]triazol-3-yl}-benzene-1,3-diol (SMe-a02-TF)

4-{4-[3-(5-isopropyl-2,4-bis-methoxymethoxy-phenyl)-5-methylsulfanyl-[1,2,4]traizol-4-yl]-benzyl}-morpholine (IM6-SMe-a02: 150 mg, 0.284 mmol), ethanol (1.5 mL) and then 5 N hydrochloric acid (1.5 mL) were placed in a 50 mL eggplant shaped flask, and the mixture was stirred at room temperature for 24 hours. After completing the reaction, the reaction mixture was neutralized with 10 N aqueous sodium hydroxide and then extracted with ethyl acetate. The collected organic layer was dried with sodium sulfate and then concentrated under reduced pressure. The residue thus obtained was purified by HPLC fractionation to obtain the title compound (SMe-a02-TF: 32.6 mg, 20%).

LC/MS (Method 6): m/z (ESI, POS): 441 [M+H]$^+$; retention time: 4.25 minutes.

$^1$H-NMR (400 MHz, CD$_3$OD, TMS) ppm: 7.77 (2H, d, J=8.4 Hz), 7.61 (2H, d, J=8.4 Hz), 6.80 (1H, s), 6.36 (1H, s), 4.48 (2H, s), 4.10-3.90 (2H, br), 3.90-3.60 (2H, br), 2.72 (1H, sept, J=6.4 Hz).

Example 3-2

Preparation of 4-isopropyl-6-{5-methylsulfinyl-4-[4-(morpholin-4-oxid-4-ylmethyl)-phenyl]-4H-[1,2,4]triazol-3-yl}-benzene-1,3-diol trifluoroacetate (SFX-a07-TF) and 4-isopropyl-6-{5-methanesulfonyl-4-[4-(morpholin-4-oxid-4-ylmethyl)-phenyl]-4H-[1,2,4]triazol-3-yl}benzene-1,3-diol (SFN-a07)

Scheme (3-2)

[Formula 44]

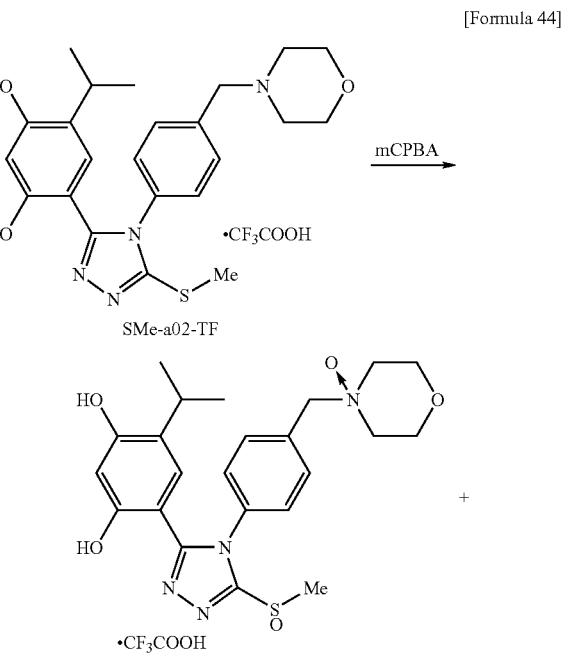

109

-continued

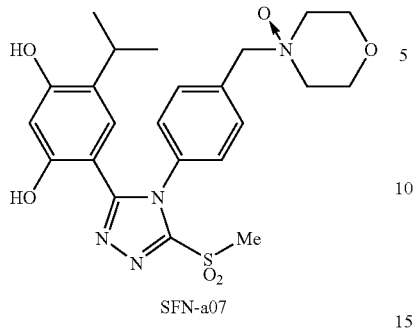

SFN-a07

4-isopropyl-6-{5-methylsulfanyl-4-[4-(morpholin-4-ylmethyl)-phenyl]-4H-[1,2,4]triazol-3-yl}-benzene-1,3-diol trifluoroacetate (SMe-a02-TF: 41.4 mg, 0.093 mmol) and methylene chloride (2 mL) were placed in a test tube, and then metachloroperbenzoic acid (38 mg, 0.372 mmol) was added and the mixture was stirred at room temperature for 24 hours. After competing the reaction, the reaction mixture was concentrated under reduced pressure, and the residue thus obtained was purified by HPLC fractionation to obtain the title compound (SFX-a07-TF: 20.6 mg, 37.8%) and the title compound (SFN-a07: 15.9 mg, 35%) SFX-a07-TF LC/MS (Method 6): m/z (ESI, POS): 473 [M+H]$^+$; retention time: 3.99 minutes.

MS (FAB, POS) m/z: 473 [M+H]$^+$, 371 [M-morpholine N-oxide+H]$^+$.

SFN-a07

LC/MS (Method 6): m/z (ESI, POS): 489 [M+H]$^+$; retention time: 4.16 minutes.

Example 3-3

Preparation of 4-bromo-6-{5-methylsulfanyl-4-[4-(morpholin-4-yl)-phenyl]-4H-[1,2,4]triazol-3-yl}-benzene-1,3-diol trifluoroacetate (SMe-d01-TF)

Scheme (3-3)

[Formula 45]

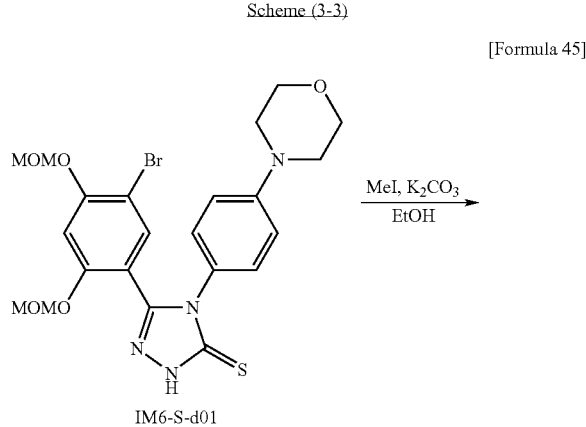

110

-continued

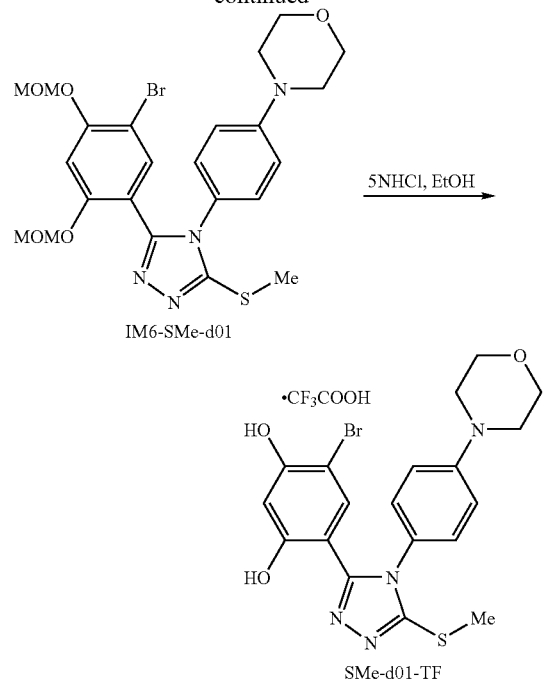

The First Step: Preparation of 4-{4-[3-(5-bromo-2,4-bis-methoxymethoxy-phenyl)-5-methylsulfanyl-[1,2,4]triazol-4-yl]-phenyl}-morpholine (IM6-SMe-d01)

5-(5-bromo-2,4-bis-methoxymethoxy-phenyl)-4-[4-(morpholin-4-yl)-phenyl]-2,4-dihydro-[1,2,4]triazol-3-thione (Example 1-5, IM6-S-d01: 54 mg, 0.1 mmol), potassium carbonate (13.8 mg, 0.17 mmol) and ethanol (5 mL) were placed in a test tube, and then methyl iodide (14.2 mg, 0.1 mmol) was added, and the mixture was heated for 2 hours under reflux. After completing the reaction, potassium carbonate was removed by filtration, and the mother liquor was concentrated. The crude product (IM6-SMe-d01) thus obtained was subjected to the next reaction without further purification in particular.

LC/MS (Method 3): m/z (ESI, POS): 551 [M+H]$^+$; retention time: 5.86 minutes.

The Second Step: Preparation of 4-bromo-6-{5-methylsulfanyl-4-[4-(morpholin-4-yl)-phenyl]-4H-[1,2,4]triazol-3-yl}-benzene-1,3-diol trifluoroacetate (SMe-d01-TF)

The crude product of 4-{4-[3-(5-bromo-2,4-bis-methoxymethoxy-phenyl)-5-methylsulfanyl-[1,2,4]triazol-4-yl]-phenyl}-morpholine (IM6-SMe-d01), ethanol (1 mL) and then 5 N hydrochloric acid (1 mL) were placed in a test tube, and the mixture was stirred for 24 hours. After completing the reaction, the reaction mixture was neutralized with 10 N aqueous sodium hydroxide and then extracted with ethyl acetate. The collected organic layer was dried with sodium sulfate and then concentrated under reduced pressure. The residue thus obtained was purified by HPLC fractionation to obtain the title compound (SMe-d01-TF: 18.5 mg, 32%).

LC/MS (Method 3): m/z (ESI, POS): 461 [M+H]$^+$; retention time: 5.48 minutes.

¹H-NMR (400 MHz, CD₃OD, TMS) ppm: 7.23 (2H, d, J=9.2), 7.09 (2H, d, J=9.2), 6.94 (1H, s), 6.81 (1H, s), 4.00-3.95 (4H, br), 3.40-3.30 (4H, br), 2.70 (3H, s).

Example 3-4 (A)

Preparation of 4-isopropyl-6-{5-methanesulfonyl-4-[4-(morpholin-4-ylmethyl)-phenyl]-4H-[1,2,4]triazol-3-yl}-benzene-1,3-diol (SFN-a02)

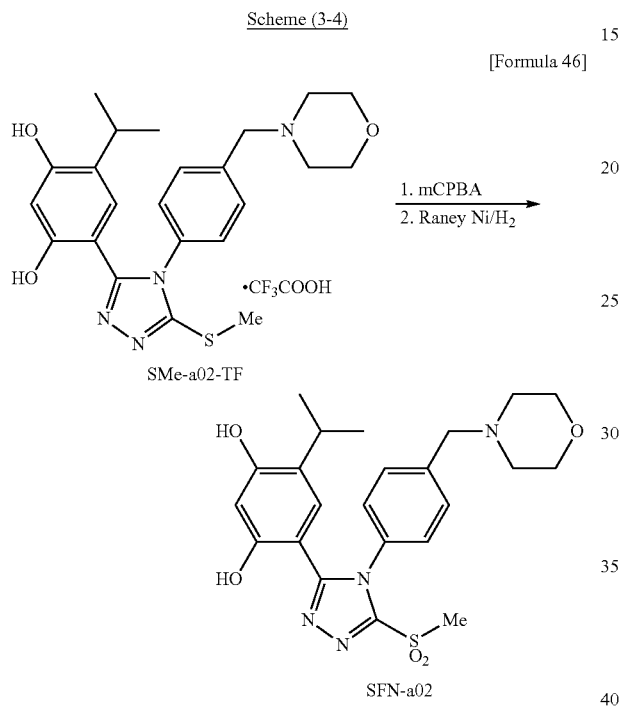

Scheme (3-4)

[Formula 46]

4-isopropyl-6-{5-methylsulfanyl-4-[4-(morpholin-4-ylmethyl)-phenyl]-4H-[1,2,4]triazol-3-yl}-benzene-1,3-diol trifluoroacetate (SMe-a02-TF: 56.8 mg, 0.129 mmol), methylene chloride (3 mL) and then metachloroperbenzoic acid (112 mg, 0.645 mmol) were placed in a test tube, and the mixture was stirred at room temperature for 24 hours. After completing the reaction, the reaction mixture was concentrated under reduced pressure. To the residue were added ethanol (3 ml) and a suspension of Raney nickel in ethanol (0.3 ml) successively, and the mixture was stirred at room temperature for 5.5 hours in a hydrogen atmosphere.

After completing the reaction, the reaction mixture was filtered through Celite, and the filtrate was concentrated under reduced pressure. The residue thus obtained was purified by preparative HPLC to obtain the title compound (SFN-a02: 3.7 mg, 6.1%).

LC/MS (Method 1): m/z(ESI, POS): 473[M+H]⁺; retention time: 1.07 minutes.

¹H-NMR (400 MHz, CDCL₃, TMS) ppm: 7.61 (2H, d, J=8.0), 7.46 (2H, d, J=8.0), 7.26 (1H, s), 6.53 (1H, s), 3.80-3.72 (4H, m), 3.64 (2H, s), 3.50 (3H, s), 2.90 (1H, sept, J=6.8), 2.60-2.50 (4H, br), 0.75 (3H, s), 0.73 (3H, s).

MS (FAB,POS)m/z: 473[M+H]⁺,387[M-morpholine+H]⁺.

Example 3-4 (B)

Preparation of 4-isopropyl-6-{5-methanesulfonyl-4-[4-(molpholin-4-ylmethyl)-phenyl]-4H-[1,2,4]triazol-3-yl}-benzene-1,3-diol (SFN-a02)

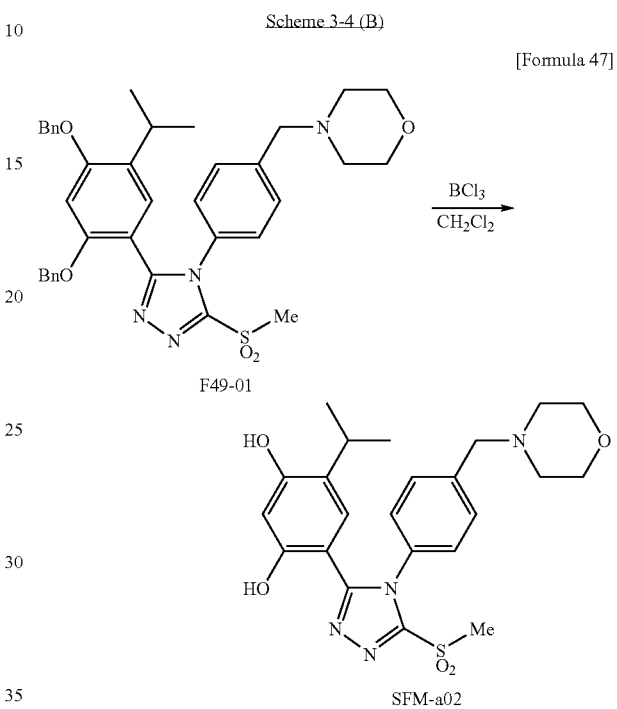

Scheme 3-4 (B)

[Formula 47]

A methylene chloride (8 mL) solution of 1,3-bis-benzyloxy-4-isopropyl-6-{5-methanesulfonyl-4-[4-(molpholin-4-ylmethyl)-phenyl]-4H-[1,2,4]triazol-3-yl}-benzene (1.05 g, 1.61 mmol: synthesized in the similar manner to that of the intermediate F45-05 of Example 2-2(B) was cooled to −20° C., mixed with 1 N methylene chloride solution of boron trichloride (8 mL, 8.00 mmol) and warmed to room temperature in the course of 2 hours, and then the reaction was continued overnight. The reaction mixture was cooled again to −20° C., mixed with 1 N methylene chloride solution of boron trichloride (1 mL, 1.00 mmol) and warmed to room temperature in the course of 2 hours for the reaction to proceed. After completing the reaction, the reaction mixture was cooled to 0° C., and solid sodium hydrogencarbonate was added until the pH was adjusted to about 7. The reaction mixture was filtered to remove insoluble substances and washed with a mixture (30 mL) of methylene chloride/methanol (10/1). After concentrating under reduced pressure, the residue thus obtained was purified by silica gel column chromatography (methylene chloride/methanol=10/1-2/1) to obtain the title compound (SFN-a02: 672 mg, 88.1%) as white solids.

LC/MS (Method 1): m/z (ESI, POS): 473 [M+H]⁺; retention time: 2.19 minutes.

¹H-NMR (400 MHz, CDCL₃, TMS) ppm: 7.61 (2H, d, J=8.4 Hz), 7.45 (2H, d, J=8.4 Hz), 6.53 (1H, s), 6.46 (1H, s), 3.74 (4H, brt, J=4.6 Hz), 3.61 (2H, s), 3.50 (3H, s), 2.89 (1H, sept, J=6.8 Hz), 2.51 (4H, brt, J=4.6 Hz), 0.74 (6H, t, J=7.0 Hz).

Example 3-5

Preparation of 4-isopropyl-6-[5-methylsulfinyl-4-(4-methoxy-phenyl)-4H-[1,2,4]triazol-3-yl]-benzene-1,3-diol (SFX-a08) and 4-isopropyl-6-[5-methanesulfonyl-4-(4-methoxy-phenyl)-4H-[1,2,4]triazol-3-yl]-benzene-1,3-diol (SFN-a08)

Scheme (3-5)

[Formula 48]

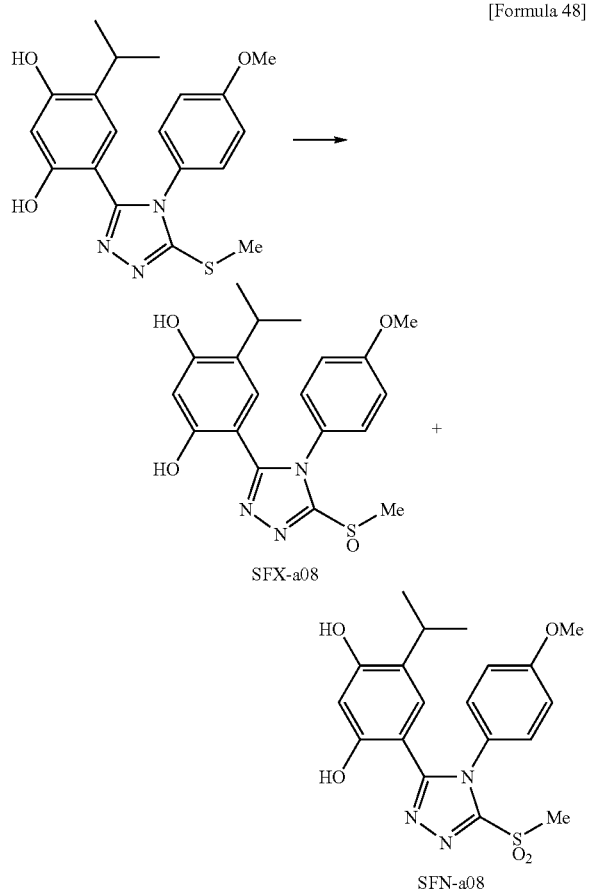

4-isopropyl-6-[4-(4-methoxy-phenyl)-5-methylsulfanyl-4H-[1,2,4]triazol-3-yl]-benzene-1,3-diol was produced according to Example 1-2 and Example 3-1 from 5-isopropyl-2,4-bis-methoxymethoxybenzoic acid hydrazide [IM4-a (Example 1-2)] in 4 steps.

4-isopropyl-6-[4-(4-methoxy-phenyl)-5-methylsulfanyl-4H-[1,2,4]triazol-3-yl]-benzene-1,3-diol (21.2 mg, 0.057 mmol) and methylene chloride (3 mL) were placed in a test tube and metachloroperbenzoic acid (29.5 mg, 0.171 mmol) was added, and the mixture was stirred at room temperature for 5 hours. The reaction mixture was extracted with chloroform, and the organic layer was washed with saturated sodium chloride solution and concentrated under reduced pressure. The residue thus obtained was purified by HPLC fractionation to obtain the title compound (SFX-a08: 2.0 mg, 9.1%) and the title compound (SFN-a08: 4.6 mg, 20.0%).
SFX-a08
LC/MS (Method 1): m/z (ESI, POS): 388 [M+H]$^+$; retention time: 5.16 minutes.
SFN-a08
LC/MS (Method 1): m/z (ESI, POS): 404 [M+H]$^+$; retention time: 5.77 minutes.

Example 3-7

Preparation of 4-isopropyl-6-[4-(4-methoxy-phenyl)-5-methylsulfanyl-4H-[1,2,4]triazol-3-yl]-benzene-1,3-diol (SMe-a08)

Scheme 3-7

[Formula 49]

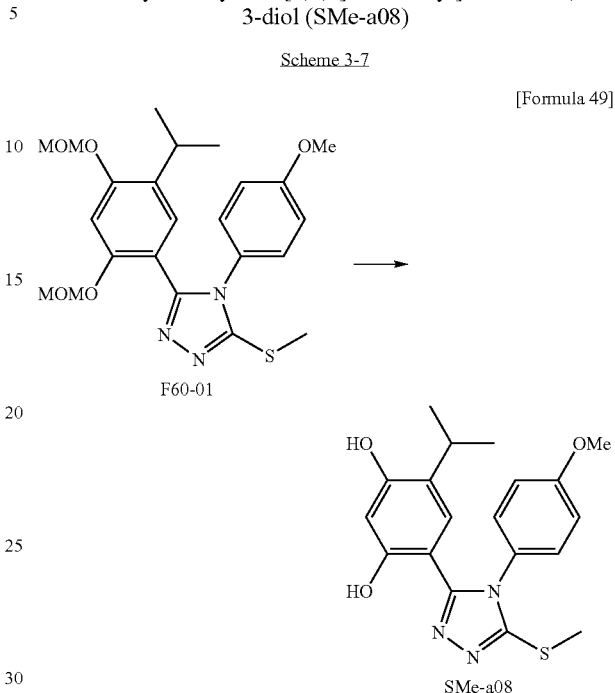

The title compound (SMe-a08: 23.7 mg, 39.4%) was obtained by a similar process to that of Example 3-9 using 3-(5-isopropyl-2,4-bis-methoxymethoxy-phenyl)-4-(4-methoxy-phenyl)-5-methylsulfanyl-4H-[1,2,4]triazole (Intermediate of Example 2-7, F60-01: 74.5 mg, 0.162 mmol) in place of 5-(5-isopropyl-2,4-bis-methoxymethoxy-phenyl)-4-[4-(molpholin-4-ylmethyl)-phenyl]-2,4-dihydro-[1,2,4]triazol-3-one.
LC/MS (Method 3): m/z (ESI, NEG): 370 [M+H]$^+$; retention time: 6.19 minutes.
$^1$H-NMR (400 MHz, CD3CN, TMS) ppm: 7.19 (2H, d, J=9.0 Hz), 6.99 (2H, d, J=9.0 Hz), 6.73 (1H, s), 6.26 (1H, s), 3.82 (3H, s), 2.91 (1H, sept, J=7.0 Hz), 2.63 (3H, s), 0.94 (6H, d, J=7.0 Hz)

Example 3-8

Preparation of 4-[5-(3-dimethylamino-ethylsulfanyl)-4-(4-methoxy-phenyl)-4H-[1,2,4]triazol-3-yl]-6-isopropyl-benzene-1,3-diol (SR2-a08)

Scheme 3-8

[Formula 50]

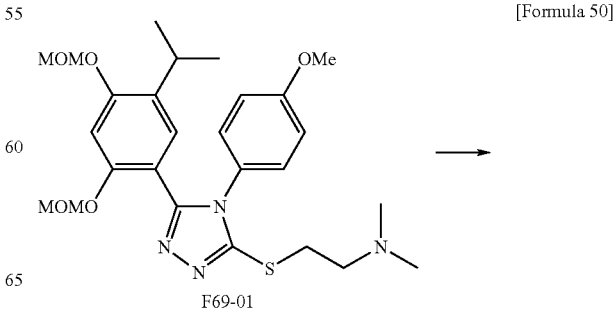

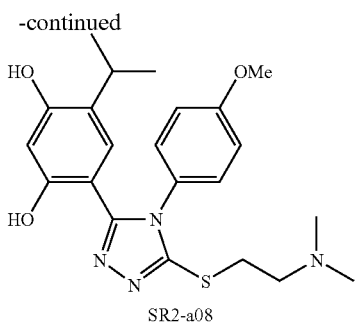

SR2-a08

Preparation of {2-[5-(5-isopropyl-2,4-bis-methoxymethoxy-phenyl)-4-(4-methoxy-phenyl)-4H-[1,2,4]triazol-3-sulfanyl]-ethyl}-dimethyl-amine (F69-01): F69-01 was synthesized by a similar process to that of the first step of Example 3-16 using 2-dimethylamino-ethyl chloride hydrochloride in place of 3-dimethylamino-propyl chloride hydrochloride of Example 3-16.

Preparation of 4-[5-(3-dimethylamino-ethylsulfanyl)-4-(4-methoxy-phenyl)-4H-[1,2,4]triazol-3-yl]-6-isopropyl-benzene-1,3-diol (SR2-a08)

The title compound (SR2-a08: 9.3 mg, 15.5%) was obtained by a similar process to that of Example 3-9 using F69-01 (72.3 mg, 0.054 mmol).
LC/MS (Method 3): m/z (ESI, POS): 429 [M+H]$^+$; retention time: 3.66 minutes.

Example 3-9

Preparation of 4-isopropyl-6-(4-isopropyl-5-methanesulfonyl-4H-[1,2,4]triazol-3-yl)-benzene-1,3-diol (SFN-a21)

Scheme 3-9

[Formula 51]

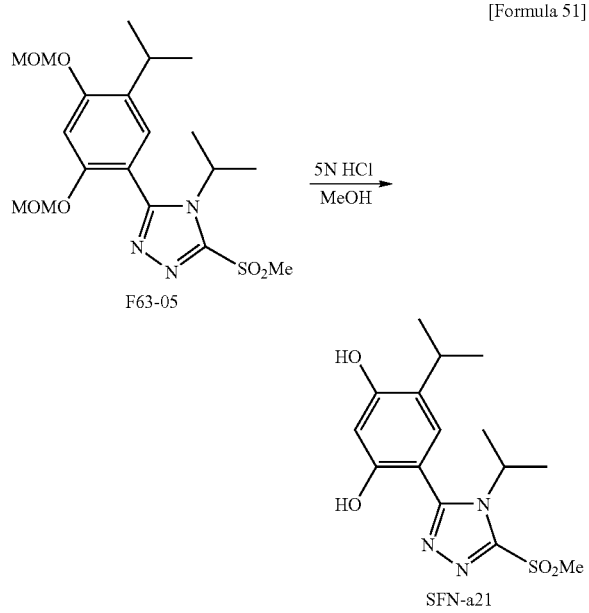

5 N hydrochloric acid (0.5 mL) was added to a methanol solution (0.5 mL) of 4-isopropyl-3-(5-isopropyl-2,4-bis-methoxymethoxyphenyl)-5-methylsulfonyl-4H-[1,2,4]triazole (an intermediate of Example 2-13 F63-05: 35 mg, 82 μmol) and the mixture was stirred for 8 hours. After cooling to ice cold conditions, it was neutralized by adding saturated aqueous sodium hydrogencarbonate. The solution was extracted with ethyl acetate, and the extract was washed with saturated sodium chloride solution, dried over anhydrous sodium sulfate, and then sodium sulfate was removed by filtration and the solvent was distilled off under reduced pressure. The solids thus obtained were dried under reduced pressure to obtain 4-isopropyl-6-(4-isopropyl-5-methanesulfonyl-4H-[1,2,4]triazol-3-yl)-benzene-1,3-diol (SFN-a21, white solids, 20.8 mg, 75%).
LC/MS (Method 3): m/z (ESI, POS): 340 [M+H]$^+$; retention time: 5.12 minutes.
$^1$H-NMR [400 MHz, CDCl$_3$+CD$_3$OD (nine drops)] δ 1.19 (d, J=6.8 Hz, 6H), 1.55 (d, J=7.0 Hz, 6H), 3.22 (sept., J=6.8 Hz, 1H), 3.60 (s, 3H), 4.80 (sept., J=7.0 Hz, 1H), 6.38 (s, 1H), 7.04 (s, 1H).

Example 3-10

Preparation of 4-isopropyl-6-[5-methanesulfonyl-4-(2-molpholin-4-ylethyl)-4H-[1,2,4]triazol-3-yl]-benzene-1,3-diol (SFN-a26)

The bis(methoxymethyl) protected title compound (SFN-a26) was obtained in 6 steps by a similar process to that of Example 2-2(B) using 4-(2-aminoethyl)-morpholine in place of 4-molpholin-4-ylmethyl-phenylamine (F45-000) of Example 2-2(B). This compound was deprotected by a similar operation to that of Example 3-9 to obtain the title compound (SFN-a26).
LC/MS (Method 3): m/z (ESI, POS): 428 [M+H]$^+$; retention time: 6.56 minutes.
$^1$H-NMR (400 MHz, CDCl$_3$) δ 1.25 (d, J=6.8 Hz, 6H), 2.40 (t, J=4.6 Hz, 4H), 2.86 (t, J=6.6 Hz, 2H), 3.20 (sept., J=6.8 Hz, 1H), 3.58 (t, J=4.6 Hz, 4H), 3.60 (s, 3H), 4.59 (t, J=6.6 Hz, 2H), 6.51 (s, 1H), 7.29 (s, 1H).

Example 3-11

Preparation of 4-isopropyl-6-[5-methanesulfonyl-4-[3-(molpholin-4-yl)-propyl]-4H-[1,2,4]triazol-3-yl]-benzene-1,3-diol (SFN-a27)

The intermediate, F93-05, of Example 2-16 was deprotected according to Example 3-9 to obtain the title compound (SFN-a27).
LC/MS (Method 4): m/z (ESI, POS): 425 [M+H]$^+$; retention time: 3.80 minutes.
$^1$H-NMR (400 MHz, CD$_3$OD, ppm): 7.09 (1H, s), 6.47 (1H, s), 4.37 (2H, m), 3.54 (3H, s), 3.52 (4H, m), 3.20 (1H, m), 2.24 (2H, m), 2.16 (4H, brs), 1.84 (2H, m), 1.19 (6H, d, J=6.96 Hz)

Example 3-12

5-(2,4-dihydroxy-5-isopropylphenyl)-4-[2-(1-oxopyridin-3-yl)ethyl]-3-methanesulfonyl-4H-[1,2,4]triazole (SFN-a29)

The bis(methoxymethyl) protected compound of the title compound (SFN-a29) was obtained in 6 steps by a similar process to that of Example 2-2(B) using 3-(2-aminoethyl)

pyridine in place of 4-molpholin-4-ylmethyl-phenylamine (F45-000) of Example 2-2(B). This compound was deprotected by a similar operation to that of Example 3-9 to obtain the title compound (SFN-a29).

LC/MS (Method 1): m/z (ESI, POS): 419 [M+H]$^+$; retention time: 4.00 minutes.

$^1$H-NMR [400 MHz, CDCl$_3$-CD$_3$OD (three drops)] δ 1.19 (d, J=6.8 Hz, 6H), 3.15-3.25 (m, 3H), 3.61 (s, 3H), 4.43-4.50 (m, 2H), 6.44 (s, 1H), 7.09 (s, 1H), 7.25-7.27 (m, 2H), 7.94 (s, 1H), 8.06-8.10 (m, 1H).

Example 3-13

Preparation of 1-{3-[3-(2,4-dihydroxy-5-isopropylphenyl)-5-methanesulfonyl[1,2,4]triazol-4-yl]-propyl}-pyrrolidine (SFN-a30)

N-(3-isothiocyanatopropyl)-2-pyrrolidinone was obtained by a similar process to that of Example 2-2(B) in 1 step using N-(3-aminopropyl)-2-pyrrolidinone in place of 4-molpholin-4-ylmethyl-phenylamine (F45-000) of Example 2-2(B). Using this compound, a bis(methoxymethyl) protected title compound (SFN-a30) was obtained in 5 steps by a similar process to that of Example 2-13. This compound was deprotected by a similar operation to that of Example 3-9 to obtain the title compound (SFN-a30).

LC/MS (Method 1): m/z (ESI, POS): 423 [M+H]$^+$; retention time: 4.73 minutes.

$^1$H-NMR (400 MHz, CDCl$_3$:CD$_3$OD=5:1) δ 1.20 (d, J=6.8 Hz, 6H), 1.90-2.00 (m, 4H), 2.33 (t, J=8.1 Hz, 2H), 3.16-3.27 (m, 5H), 3.55 (s, 3H), 4.19-4.26 (m, 2H), 6.42 (s, 1H), 7.12 (s, 1H).

Example 3-14

Preparation of 4-isopropyl-6-[5-methanesulfonyl-4-(2-methoxy-ethyl)-4H-[1,2,4]triazol-3-yl]-benzene-1,3-diol (SFN-a32)

A bis(methoxymethyl) protected title compound (SFN-a32) was obtained by a similar process to that of the fourth and fifth step of Example 2-12 from the bis(methoxymethyl) protected compound (SH-a32) of Example 1-15. This compound was deprotected by a similar operation to that of Example 3-9 to obtain the title compound (SFN-a32).

LC/MS (Method 3): m/z (ESI, POS): 356 [M+H]$^+$; retention time: 4.69 minutes.

$^1$H-NMR (400 MHz, CDCl$_3$:CD$_3$OD=3:1, ppm): 7.27 (1H, s), 6.44 (1s), 4.59 (2H, t, J=5.49 Hz), 3.63 (2H, t, J=5.49 Hz), 3.54 (3H, s) 3.23 (1H, m), 3.20 (3H, s), 1.20 (6H, d, J=6.77 Hz)

Example 3-15

Preparation of 4-[4-(2-hydroxy-1-hydroxymethyl-ethyl)-5-methanesulfonyl-4H-[1,2,4]triazol-3-yl]-6-isopropyl-benzene-1,3-diol (SFN-a33)

The title compound (SFN-a33: white solids, yield 82%) was obtained by deprotecting the intermediate F77-06 of Example 2-19 by a similar process to that of the seventh step of Example 2-19.

LC/MS (Method 1): m/z (ESI, POS): 372 [M+H]$^+$, 394 [M+Na]$^+$.; retention time: 3.45 minutes.

$^1$H-NMR [400 MHz, DMSO-d$_6$, TMS] ppm: 1.115 (6H, d, J=7.0 Hz), 3.101 (1H, sept., J=7.0 Hz), 3.598 (3H, s), 3.674 (4H, bs), 4.58 (1H, b), 5.007 (2H, bs), 6.480 (1H, s), 7.019 (1H, s), 9.705 (1H, s), 9.747 (1H, s).

Example 3-16

Preparation of 4-[5-(3-dimethylamino-propane-1-sulfonyl)-4-(4-methoxy-phenyl)-4H-[1,2,4]triazol-3-yl]-6-isopropyl-benzene-1,3-diol (SFN2-a08) hydrochloride Scheme 3-16

[Formula 52]

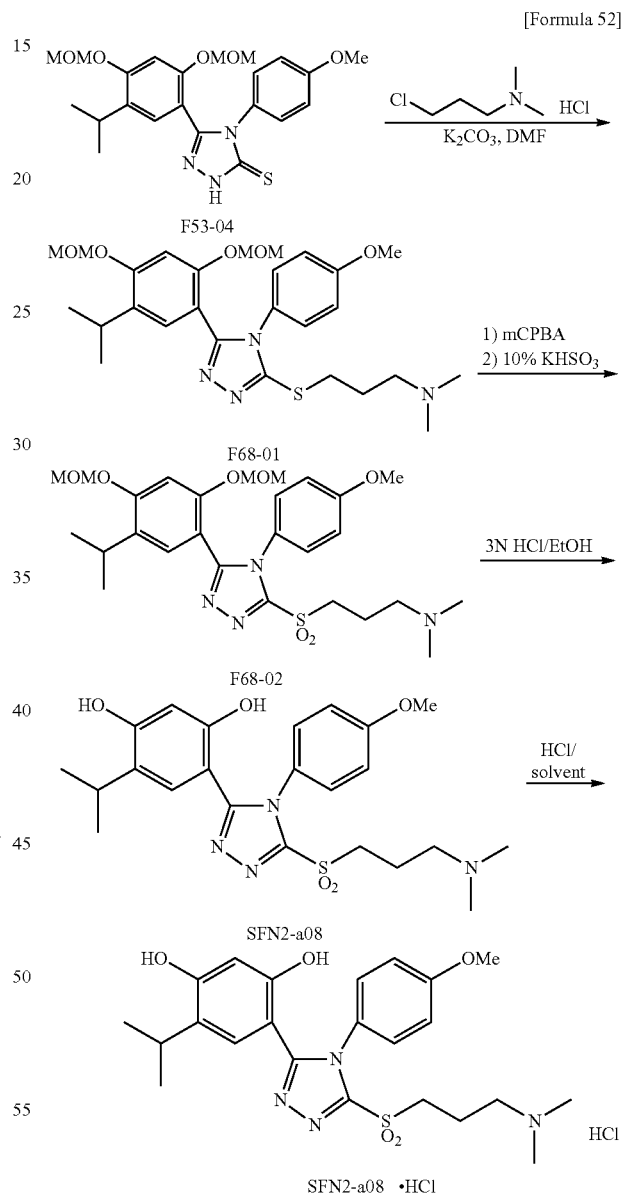

The First Step: Preparation of {3-[5-(5-isopropyl-2,4-bis-methoxymethoxy-phenyl)-4-(4-methoxy-phenyl)-4H-[1,2,4]triazol-3-ylsulfanyl]-propyl}-dimethylamine (F68-01)

5-(5-isopropyl-2,4-bis-methoxymethoxy-phenyl)-4-(4-methoxy-phenyl)-2,4-dihydro-[1,2,4]triazol-3-thione (F53-

04: 3.5 g, 7.9 mmol), potassium carbonate (2.6 g, 18.9 mmol) and dimethylformamide (150 mL) were placed in a 500 mL eggplant shaped flask, and then 3-dimethylaminopropyl chloride hydrochloride (1.49 g, 9.4 mmol) was added, and the mixture was stirred at 100° C. for 2 hours. A similar operation was carried out using the same amount of materials, and after the reaction was completed, the mixture was cooled, mixed with saturated sodium chloride solution (700 mL) and extracted twice with ethyl acetate. The organic layers were combined, washed 4 times with saturated sodium chloride solution (500 mL), dried with sodium sulfate and concentrated under reduced pressure. The residue was purified by silica gel column chromatography (methylene chloride/methanol) to obtain the title compound (F68-01: 5.1 g, 61%).

LC/MS (Method 3): m/z (ESI, POS): 531 [M+H]$^+$; retention time: 4.07 minutes.

$^1$H-NMR (400 MHz, CDCl$_3$, TMS) ppm: 7.27 (1H, s), 7.06 (2H, d, J=8.8 Hz), 6.86 (2H, d, J=8.8 Hz), 6.79 (1H, s), 5.15 (2H, s), 4.74 (2H, s), 3.79 (3H, s), 3.46 (3H, s), 3.28 (2H, d, J=7.1 Hz), 3.22 (3H, s), 3.20 (1H, sept, J=7.0 Hz), 2.39 (2H, d, J=7.1 Hz), 2.22 (6H, s), 1.96 (2H, m), 1.16 (6H, d, J=7.0 Hz)

The Second Step: Preparation of {3-[5-(5-isopropyl-2,4-bis-methoxymethoxy-phenyl)-4-(4-methoxy-phenyl)-4H-[1,2,4]triazole-3-sulfanyl]-propyl}-dimethylamine (F68-02)

{3-[5-(5-isopropyl-2,4-bis-methoxymethoxy-phenyl)-4-(4-methoxy-phenyl)-4H-[1,2,4]triazol-3-ylsulfanyl]-propyl}-dimethylamine (F68-01: 4.7 g, 8.9 mmol) and methylene chloride (350 mL) were placed in a 1000 mL eggplant shaped flask and cooled to 0° C., and a solution of metachloroperbenzoic acid (15.3 g, 88.7 mmol) in methylene chloride was instilled in 3 portions. After the reaction was completed, 10% aqueous potassium bisulfite (100 mL) was added and the mixture was stirred for 15 minutes. The organic layer was collected, washed twice with 1 N sodium hydroxide (50 mL), dried with sodium sulfate and concentrated under reduced pressure to obtain yellow solids. The solids thus obtained were subjected to the next reaction without purification.

LC/MS (Method 3): m/z (ESI, POS): 563 [M+H]$^+$; retention time: 4.03 minutes.

The Third Step: Preparation of 4-[5-(3-dimethylamino-propane-1-sulfonyl)-4-(4-methoxy-phenyl)-4H-[1,2,4]triazol-3-yl]-6-isopropyl-benzene-1,3-diol (SFN2-a08)

{3-[5-(5-isopropyl-2,4-bis-methoxymethoxy-phenyl)-4-(4-methoxy-phenyl)-4H-[1,2,4]triazole-3-sulfonyl]-propyl}-dimethylamine (6.8 g, crude F68-02 in the previous step), ethanol (50 mL) and 3 N hydrochloric acid (50 mL) were placed in a 200 mL eggplant shaped flask and the mixture was stirred at 50° C. for 5 hours. After completing the reaction, the reaction mixture was neutralized with saturated sodium hydrogencarbonate, extracted twice with ethyl acetate. The organic layer was washed 4 times with saturated sodium chloride, dried with sodium sulfate and then concentrated under reduced pressure. The residue was purified by silica gel column chromatography (methylene chloride/methanol), followed by basic silica gel column chromatography (methylene chloride/methanol) to obtain the title compound (F68-03: 1.5 g, 35.7% in 2 steps)

LC/MS (Method 3): m/z (ESI, POS): 475 [M+H]$^+$; retention time: 3.60 minutes.

$^1$H-NMR (400 MHz, DMSO-d$_6$, TMS) ppm: 7.37 (2H, d, J=9.0 Hz), 7.00 (2H, d, J=9.0 Hz), 6.80 (1H, s), 6.30 (1H, s), 3.78 (3H, s), 3.45 (2H, d, J=7.7 Hz), 2.96 (1H, sept, J=6.8 Hz), 2.27 (2H, d, J=7.5 Hz), 2.08 (6H, s), 1.83 (2H, m), 0.94 (6H, d, J=6.8 Hz)

The Fourth Step: Preparation of 4-[5-(3-dimethylamino-propane-1-sulfonyl)-4-(4-methoxy-phenyl)-4H-[1,2,4]triazol-3-yl]-6-isopropyl-benzene-1,3-diol (SFN2-a08) hydrochloride 4-[5-(3-dimethylamino-propane-1-sulfonyl)-4-(4-methoxy-phenyl)-4H-[1,2,4]triazol-3-yl]-6-isopropyl-benzene-1,3-diol (700 mg, 1.5 mmol) and 1.4 dioxane (160 mL) were placed in a 300 mL eggplant shaped flask and the mixture was stirred at room temperature, and then 4 N hydrochloric acid/dioxane solution was slowly added and stirred for 20 minutes. After completing the reaction, deposited crystals were collected by filtration, washed with hexane a few times and dried under reduced pressure to obtain the title compound (SFN2-a08 hydrochloride, 735 mg, 97.5%).

LC/MS (Method 3): m/z (ESI, POS): 475 [free M+H]$^+$; retention time: 3.60 minutes.

$^1$H-NMR (400 MHz, DMSO-d$_6$, TMS) ppm: 10.31 (1H, brs), 10.01 (1H, s), 9.83 (1H, s), 6.80 (2H, d, J=9.0 Hz), 7.01 (2H, d, J=9.0 Hz), 6.80 (1H, s), 6.35 (1H, s), 3.78 (3H, s), 3.69 (2H, d, J=7.5 Hz), 3.15 (2H, d, J=7.5 Hz), 2.96 (1H, sept, J=6.8 Hz), 2.75 (6H, s), 2.16 (2H, m), 0.93 (6H, d, J=6.8 Hz), IR (KBr): 2961, 1628, 1514, 1254, 1175, 1144, 623, 556.

Melting point: 233° C. (decomposition)

Example 3-17

Preparation of 4-[5-(3-dimethylamino-propylsulfonyl)-4-(4-hydroxy-phenyl)-4H-[1,2,4]triazol-3-yl]-6-isopropyl-benzene-1,3-diol (SFN2-a11) trifluoroacetate

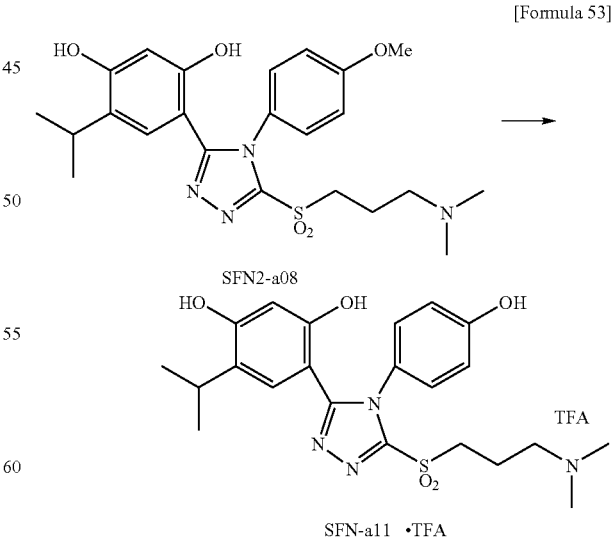

4-[5-(3-dimethylamino-propane-1-sulfonyl)-4-(4-methoxy-phenyl)-4H-[1,2,4]triazol-3-yl]-6-isopropyl-benzene-1,3-diol (SNF2-a08 of Example 3-16: 47.5 mg, 0.1 mmol) and methylene chloride (5 mL) were placed in a 10 mL eggplant-shaped flask, cooled to −78° C., and then boron trichloride (0.4 mL) was added. The reaction mixture was warmed slowly to room temperature in the course of 7 hours. After completing the reaction, methanol and sodium hydrogencarbonate were added, and inorganic substances were removed by filtration. The mother liquor was concentrated, and the residue thus obtained was purified by HPLC fractionation to obtain the title compound (SFN-all-trifluoroacetate: 46.9 mg, 99%).

LC/MS (Method 3): m/z (ESI, POS): 461 [M+H]$^+$; retention time: 3.02 minutes.

Example 3-18

Preparation of 4-isopropyl-6-[4-(4-methoxy-phenyl)-5-(3-piperidin-1-yl-propane-1-sulfonyl)-4H-[1,2,4]triazol-3-yl]-benzene-1,3-diol (SFN3-a08) hydrochloride The title compound (SFN3-a08 hydrochloride) can be obtained by a similar process to that of Example 3-16. That is, the title compound (SFN3-a08 hydrochloride) was obtained in 4 steps from F53-04, by reacting 1-(3-chloropropyl)piperidine hydrochloride, in place of 3-dimethylaminopropyl chloride hydrochloride, to F53-04, and by carrying out the reactions sequentially as in Example 3-16.

LC/MS (Method 3): m/z (ESI, POS): 515 [M+H]$^+$; retention time: 3.86 minutes.

$^1$H-NMR (400 MHz, CDCl$_3$:CD$_3$OD=2:1, ppm): 7.34 (2H, d, J=8.97 Hz), 7.09 (2H, d, J=8.98 Hz), 6.00 (1H, s), 6.40 (1H, s), 3.89 (3H, s), 3.68 (2H, d, J=7.14 Hz), 3.55 (2H, d, J=12.27 Hz), 3.28 (2H, m), 3.01 (1H, m), 2.90 (2H, m), 2.41 (2H, m), 1.93 (5H, m), 1.51 (1H, m), 0.84 (6H, d, J=6.96 Hz)

Example 3-19

Preparation of 4-(4-hydroxy-phenyl)-6-[4-isopropyl-5-(3-piperidin-1-yl-propane-1-sulfonyl)-4H-1,2,4-triazol-3-yl]-benzene-1,3-diol (SFN3-all) trifluoroacetate The title compound (SFN-all trifluoroacetate) was obtained by carrying out a similar reaction to that of Example 3-17 using 4-isopropyl-6-[4-(4-methoxy-phenyl)-5-(3-piperidin-1-yl-propane-1-sulfonyl)-4H-[1,2,4]triazol-3-yl]-benzene-1,3-diol (SFN3-a08) in place of 4-[5-(3-dimethylamino-propane-1-sulfonyl)-4-(4-methoxy-phenyl)-4H-[1,2,4]triazol-3-yl]-6-isopropyl-benzene-1,3-diol (SFN2-a08).

LC/MS (Method 3): m/z (ESI, POS): 501 [M+H]$^+$; retention time: 3.33 minutes.

Example 3-20

Preparation of 4-isopropyl-6-[4-(4-methoxy-phenyl)-5-(pyridin-3-ylmethanesulfonyl)-4H-[1,2,4]triazol-3-yl]-benzene-1,3-diol (SFN4-a08)

The title compound (SFN4-a08) can be obtained by a similar process to that of Example 3-23. That is, the bis(methoxymethyl) protected title compound (SFN4-a08) and the bis(methoxymethyl) protected compound of Example 3-21 (SFN5-a08) were obtained from F53-04 in 2 steps by reacting 3-(bromomethyl)pyridine hydrobromide, in place of 2-(bromomethyl)tetrahydro-2H-pyran, to F53-04, and carrying out sequentially the reactions similar to those of Example 3-23. After separating both compounds, the bis(methoxymethyl) protected title compound (SFN4-a08) was deprotected by the similar operation to that of Example 3-9 to obtain the title compound (SFN4-a08).

LC/MS (Method 3): m/z (ESI, POS): 481 [M+H]$^+$; retention time: 4.39 minutes.

$^1$H-NMR (400 MHz, CD$_3$OD, ppm): 8.68 (1H, d), 8.60 (1H, d, J=6.60Hz), 7.97 (1H, d, J=7.77 Hz), 7.77 (1H, m), 7.47 (2H, d, J=8.97 Hz), 7.16 (2H, d, J=8.97 Hz), 6.76 (1H, s), 6.44 (1H, s), 4.98 (2H, m), 3.88 (3H, s), 3.00 (1H, m), 0.87 (3H, d, J=6.96 Hz), 0.86 (3H, d, J=6.96)

Example 3-21

Preparation of 4-isopropyl-6-[4-(4-methoxy-phenyl)-5-(1-oxy-pyridin-3-ylmethane sulfonyl)-4H-[1,2,4]triazol-3-yl]-benzene-1,3-diol (SFN5-a08)

The title compound (SFN5-a08) can be obtained by a similar process to that of Example 3-23. That is, the bis(methoxymethyl) protected compound of Example 3-21 (SFN4-a08) and the bis(methoxymethyl) protected title compound (SFN5-a08) were obtained from F53-04 in 2 steps by reacting 3-(bromomethyl)pyridine hydrobromide, in place of 2-(bromomethyl)tetrahydro-2H-pyran, to F53-04, and carrying out sequentially the reactions similar to those of Example 3-23. After separating both compounds, the bis(methoxymethyl) protected title compound (SFN5-a08) was deprotected by the similar operation to that of Example 3-9 to obtain the title compound (SFN5-a08).

LC/MS (Method 4): m/z (ESI, POS): 497 [M+H]$^+$; retention time: 5.55 minutes.

$^1$H-NMR (400 MHz, CD$_3$OD, ppm): 8.62 (1H, brs), 8.54 (1H, brs), 7.88 (1H, brs), 7.7 (1H, brs), 7.32 (2H, d, J=8.24 Hz), 7.05 (2H, d, J=8.24 Hz), 6.71 (1H, s), 6.35 (1H, s), 5.13 (2H, m), 3.85 (3H, s), 3.00 (1H, m), 0.88 (6H, d, J=6.77 Hz)

Example 3-22

Preparation of 2-[5-(2,4-dihydroxy-5-isopropyl-phenyl)-4-(4-methoxy-phenyl)-4H-[1,2,4]triazol-3-sulfonyl]-N,N-dimethyl-acetamide (SFN6-a08)

Scheme 3-22

[Formula 54]

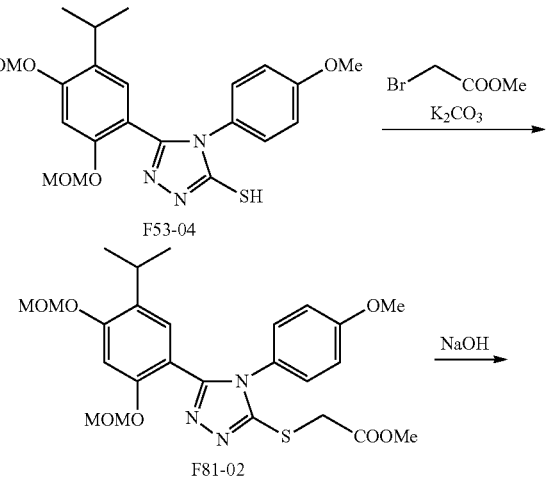

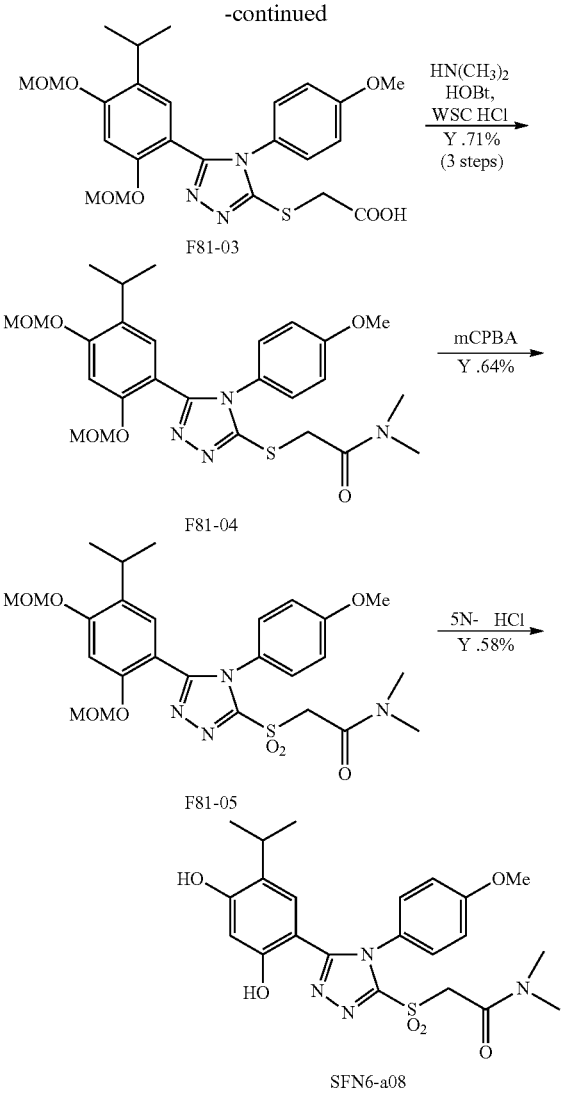

The First Step: Preparation of F81-02

Under an atmosphere of nitrogen, F53-04 (89 mg, 0.2 mmol), potassium carbonate (84 mg, 0.6 mmol), methyl bromoacetate (59 μL, 0.6 mmol) and methanol (5 mL) were placed in a 50 mL flask, and the mixture was heated for 2 hours under reflux. The reaction mixture was mixed with water (30 mL) and extracted twice with ethyl acetate (30 mL). The organic layer was washed with saturated sodium chloride solution, dried with sodium sulfate and concentrated under reduced pressure to obtain the crude title compound (F81-02: 101 mg).

LC/MS (Method 3): m/z (ESI, POS): 518 [M+H]$^+$; retention time: 6.78 minutes.

The Second Step: Preparation of F81-03

The crude preparation of F81-02 (101 mg), methanol (5 mL) and 1 N aqueous sodium hydroxide (0.25 mL) were placed in a 30 mL flask, and the mixture was stirred at room temperature for 2 hours. Ethyl acetate (20 mL) and 10% aqueous citric acid were added to the reaction mixture, and the organic layer was separated. After washing with saturated sodium chloride solution, the organic layer was dried with sodium sulfate and concentrated under reduced pressure to obtain the crude title compound (F81-03, 100 mg).

LC/MS (Method 3): m/z (ESI, POS): 504 [M+H]$^+$; retention time: 6.07 minutes.

The Third Step: Preparation of F81-04

The crude preparation of F81-03 (100 mg) and dimethylformamide (3 mL) were placed in a 30 mL flask, and under ice cold conditions 50% aqueous dimethylamine (20 μL, 0.22 mmol), 1-hydroxybenzotriazole monohydrate (33 mg, 0.24 mmol), and 1-ethyl-3-(3'-dimethylaminopropyl)carbodiimide-hydrochloride (46 mg, 0.24 mmol) were sequentially added. After stirring overnight, the reaction mixture was mixed with water (30 mL) and extracted twice with ethyl acetate (30 mL). The organic layer was washed sequentially with 10% aqueous citric acid, saturated aqueous sodium hydrogencarbonate and saturated sodium chloride, and then dried with sodium sulfate and concentrated under reduced pressure. The residue was purified by silica gel column chromatography (chloroform:methanol=20:1) to obtain the title compound (F81-04: 76 mg, yield 71.6%, in total 3 steps).

LC/MS (Method 3): m/z (ESI, POS): 531 [M+H]$^+$; retention time: 6.06 minutes.

The Fourth Step: Preparation of F81-05

F81-04 (76 mg, 0.14 mmol) and dichloromethane (3 mL) were placed in a 30 mL flask, and under ice cold conditions m-chloroperbenzoic acid (97 mg, 0.56 mmol) was added, and the mixture was stirred for 20 hours. Chloroform (20 mL) and 10% aqueous potassium bisulfite (10 mL) were added to the reaction mixture, and after stirring the mixture for 10 minutes, the organic layer was separated. The organic layer was washed with saturated sodium chloride solution, dried with sodium sulfate and then concentrated under reduced pressure. The residue was purified by silica gel column chromatography (chloroform:methanol=20:1) to obtain the title compound (F81-05: 51 mg, yield 64.2%).

LC/MS (Method 3): m/z (ESI, POS): 563 [M+H]$^+$; retention time: 6.11 minutes.

The Fifth Step: Preparation of 2-[5-(2,4-dihydroxy-5-isopropyl-phenyl)-4-(4-methoxy-phenyl)-4H-[1,2,4]triazol-3-sulfonyl]-N,N-dimethyl-acetamide (SFN6-a08)

F81-05 (51 mg, 0.09 mmol) and methanol (3 mL) were placed in a 30 Ml Flask, and then 5 N Hydrochloric acid (2 mL) was added, and the mixture was stirred at 41° C. for 3 hours. The reaction mixture was concentrated and dissolved in methanol (3 mL), then mixed with silica gel (200 mg) concentrated under reduced pressure. The residue was purified by silica gel column chromatography (chloroform:methanol=20:1-10:1) to obtain the title compound (SFN6-a08: 25 mg, yield 58.5%).

LC/MS (Method 3): m/z (ESI, POS): 475 [M+H]$^+$; retention time: 5.51 minutes.

$^1$H-NMR (400 MHz, DMSO-d$_6$, ppm): 10.07 (1H, s), 9.79 (1H, s), 7.36 (2H, d, J=6.96 Hz), 7.01 (2H, d, J=6.96 Hz), 6.71

(1H, s), 6.32 (1H, s), 4.05 (2H, s), 3.78 (3H, s), 2.96 (3H, s), 2.94 (1H, m), 2.81 (3H, s), 0.92 (6H, d, J=7.2 Hz)

Example 3-23

Preparation of 4-isopropyl-6-[4-(4-methoxy-phenyl)-5-(tetrahydro-pyran-2-ylmethane sulfonyl)-4H-[1,2,4]triazol-3-yl]-benzene-1,3-diol (SFN7-a08)

Scheme 3-23

[Formula 55]

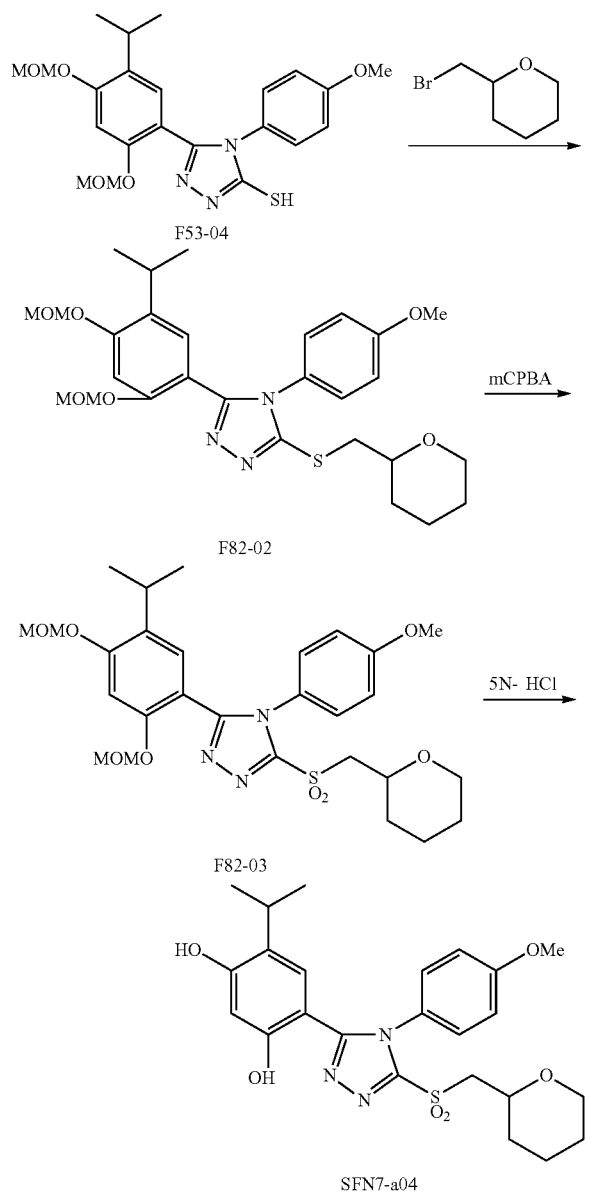

The First Step

Preparation of F82-02

F53-04 (67 mg, 0.15 mmol) and ethanol (4 mL) were placed in a 50 mL flask, and potassium carbonate (124 mg, 0.9 mmol) and 2-(bromomethyl)tetrahydro-2H-pyran (58 μL, 0.45 mmol) were sequentially added, and the mixture was heated for 4 hours under reflux. The reaction mixture was mixed with water (30 mL) and extracted twice with ethyl acetate (30 mL). After washing with saturated sodium chloride, the organic layer was dried with sodium sulfate and concentrated under reduced pressure to obtain the crude title compound (F82-02: 128 mg).

LC/MS (Method 3): m/z (ESI, POS): 544 [M+H]$^+$; retention time: 7.14 minutes.

The Second Step: Preparation of F82-03

After dissolving the crude F82-02 (128 mg) obtained in the first step in dichloromethane (3 mL), m-chloroperbenzoic acid (104 mg, 0.60 mmol) was added, and the mixture was stirred for 20 hours. The reaction mixture was mixed with chloroform (15 mL) and 10% aqueous potassium bisulfite (10 mL), and stirred for 10 minutes, and then the organic layer was separated. The organic layer was washed with saturated sodium chloride solution, dried with sodium sulfate and then concentrated under reduced pressure. The residue was purified by silica gel column chromatography (chloroform:methanol=20:1) to obtain the title compound (F82-03: 72 mg, yield 83.3% in total 2 steps).

LC/MS (Method 3): m/z (ESI, POS): 576 [M+H]$^+$; retention time: 6.90 minutes.

The Third Step: Preparation of 4-isopropyl-6-[4-(4-methoxy-phenyl)-5-(tetrahydro-pyran-2-ylmethane sulfonyl)-4H-[1,2,4]triazol-3-yl]-benzene-1,3-diol (SFN7-a08)

F82-03 (72 mg, 0.12 mmol) obtained in the second step was dissolved in methanol (3 mL) and mixed with 5 N hydrochloric acid (2 mL), and the mixture was stirred at 41° C. for 3 hours. After concentrating, the reaction mixture was dissolved in methanol (3 mL), mixed with silica gel (250 mg) and concentrated under reduced pressure. The residue was purified by silica gel column chromatography (hexane:ethyl acetate=1:1) to obtain the title compound (SFN-a08: 38 mg, yield 64.9%).

LC/MS (Method 3): m/z (ESI, POS): 488 [M+H]$^+$; retention time: 6.42 minutes.

$^1$H-NMR (400 MHz, CDCl$_3$:CD$_3$OD=3:1, ppm): 7.41 (2H, d, J=8.98), 7.11 (2H, d, J=8.98), 6.47 (1H, s), 6.44 (1H, s), 6.71 (1H, s), 4.05 (4H, m), 3.91 (3H, s), 3.71 (1H, m), 2.98 (1H, m), 1.86-1.42 (6H, m), 0.92 (6H, d, J=7.2 Hz)

Example 3-24

Preparation of 4-isopropyl-6-{5-[2-(2-methoxy-ethoxy)-ethanesulfonyl]-4-(4-methoxy-phenyl)-4H-[1,2,4]triazol-3-yl}-benzene-1,3-diol (SFN8-a08)

The title compound (SFN8-a08) can be obtained by a similar process to that of Example 3-23. That is, the title compound (SFN8-a08) was obtained from F53-04 in 3 steps by reacting 1-bromo-2-(2-methoxyethoxy)ethane, in place of 2-(bromomethyl)tetrahydro-2H-pyran, to F53-04 and by carrying out sequentially the similar reactions as in Example 3-23.

LC/MS (Method 3): m/z (ESI, POS): 492 [M+H]$^+$; retention time: 6.20 minutes.

$^1$H-NMR (400 MHz, CDCl$_3$, ppm): 7.48 (2H, d, J=8.79 Hz), 7.18 (2H, d, J=8.79 Hz), 6.49 (1H, s), 6.47 (1H, s), 5.48

(1H, brs), 3.95 (2H, t, J=5.31 Hz), 3.89 (3H, s), 3.50 (4H, m), 3.26 (2H, m), 3.10 (3H, s), 2.91 (1H, m), 0.79 (6H, d, J=6.8 Hz)

Example 3-25

Preparation of 4-[5-(3-dimethylamino-propane-1-sulfonyl)-4-isopropyl-4H-[1,2,4]triazol-3-yl]-benzene-1,3-diol (SFN2-a21) trifluoroacetate Scheme 3-25

[Formula 56]

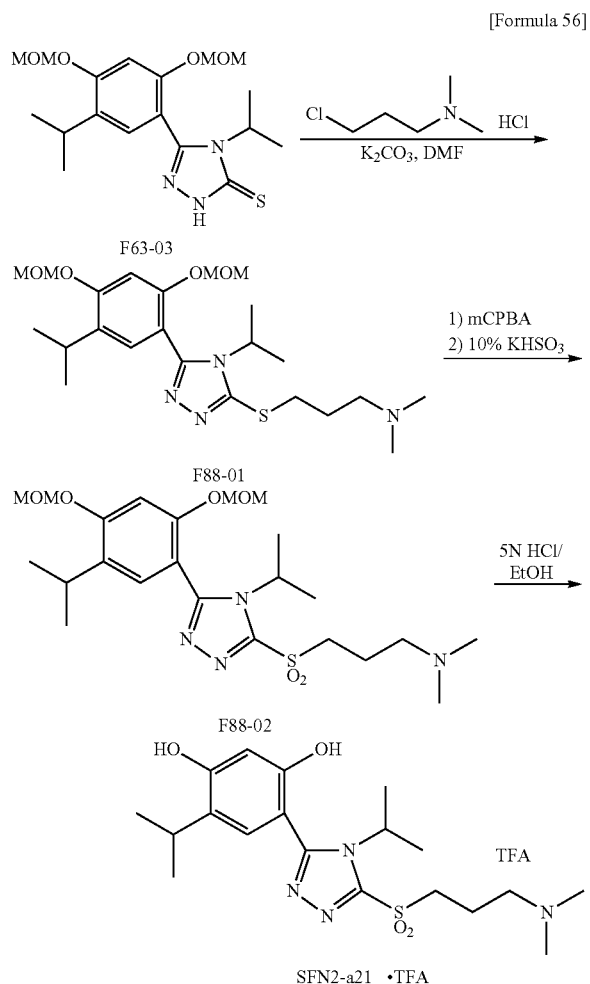

The First Step: Preparation of {3-[5-(5-isopropyl-2,4-bis-methoxymethoxy-phenyl)-4-isopropyl-4H-[1,2,4]triazol-3-ylsulfanyl]-propyl}-dimethylamine (F88-01)

5-(5-isopropyl-2,4-bis-methoxymethoxy-phenyl)-4-isopropyl-2,4-dihydro-[1,2,4]triazol-3-thione (F63-03: 114 mg, 0.3 mmol), potassium carbonate (249 mg, 1.8 mmol) and ethanol (10 mL) were placed in a test tube, and next 3-dimethylaminopropyl chloride hydrochloride (1.49 g, 9.4 mmol) was added. The mixture was stirred at 100° C. for 1 hour. After completing the reaction, the reaction mixture was cooled naturally, mixed with saturated sodium chloride solution and extracted twice with ethyl acetate. The organic layers were combined, washed 4 times with saturated sodium chloride solution, then dried with sodium sulfate and concentrated under reduced pressure.

The residue thus obtained was subjected to the next reaction without purification.

LC/MS (Method 3): m/z (ESI, POS): 467 [M+H]$^+$; retention time: 4.09 minutes.

The Second Step: Preparation of {3-[5-(5-isopropyl-2,4-bis-methoxymethoxy-phenyl)-4-isopropyl-4H-[1,2,4]triazol-3-sulfanyl]-propyl}-dimethylamine (F88-02)

{3-[5-(5-isopropyl-2,4-bis-methoxymethoxy-phenyl)-4-isopropyl-4H-[1,2,4]triazol-3-ylsulfanyl]-propyl}-dimethylamine (the crude product of the previous step (F88-01)) and methylene chloride (10 mL) were placed in a test tube, cooled to 0° C., and a solution of metachloroperbenzoic acid (0.62 g, 1.8 mmol) in methylene chloride was instilled in 3 portions. After completing the reaction, 10% aqueous potassium bisulfite was added, and the mixture was stirred for 30 minutes. After this, the organic layer was collected, washed twice with 1 N sodium hydroxide, dried with sodium sulfate and concentrated under reduced pressure to obtain a liquid. The liquid thus obtained was subjected to the next reaction without purification.

LC/MS (Method 6): m/z (ESI, POS): 499 [M+H]$^+$; retention time: 6.86 minutes.

The Third Step: Preparation of 4-[5-(3-dimethylamino-propane-1-sulfonyl)-4-isopropyl-4H-1,2,4-triazol-3-yl]-6-isopropyl-benzene-1,3-diol (SFN2-a21) trifluoroacetate {3-[5-(5-isopropyl-2,4-bis-methoxymethoxy-phenyl)-4-isopropyl-4H-1,2,4-triazol-3-sulfonyl]-propyl}-dimethylamine (6.8 g, unpurified in the previous step), ethanol (3 mL) and 5 N hydrochloric acid (3 mL) were placed in a 200 mL eggplant shaped flask and the mixture was stirred at room temperature for 10 hours. After completing the reaction, the reaction mixture was neutralized with saturated sodium hydrogencarbonate and extracted twice with ethyl acetate. The organic layer was washed 4 times with saturated sodium chloride solution, dried with sodium sulfate and concentrated under reduced pressure. The residue was purified by HPLC fractionation to obtain the title compound (SFN2-a21-trifluoroacetate: 29 mg, 18.4%: in 3 steps).

LC/MS (Method 4): m/z (ESI, POS): 411 [M+H]$^+$; retention time: 4.22 minutes.

$^1$H-NMR (400 MHz, DMSO-d$_6$, TMS) ppm: 9.85 (1H, brs), 9.55 (1H, brs), 6.97 (1H, s), 6.52 (1H, s), 3.97 (2H, d, J=7.7 Hz), 3.32-3.22 (2H, m), 4.61 (1H, sept, J=6.8 Hz), 3.12 (1H, sept, J=6.8 Hz), 2.29-2.20 (2H, m), 1.41 (6H, d, J=6.8 Hz), 1.12 (6H, d, J=6.8 Hz)

Example 3-26

Preparation of 4-isopropyl-6-[4-isopropyl-5-(3-piperidine-1-yl-propane-1-sulfonyl)-4H-[1,2,4]triazol-3-yl]-benzene-1,3-diol (SFN3-a21) trifluoroacetate The title compound (SFN3-a21 trifluoroacetate) was obtained in 3 steps by a similar process to that of Example 3-25 using 1-(3-chloro-propyl)-piperazine hydrochloride in place of 3-dimethylaminopropyl chloride hydrochloride.

LC/MS (Method 4): m/z (ESI, POS): 451 [M+H]$^+$; retention time: 4.37 minutes.

$^1$H-NMR (400 MHz, DMSO-d$_6$, TMS) ppm: 9.95 (1H, brs), 9.15 (1H, brs), 6.95 (1H, s), 6.52 (1H, s), 4.61 (1H, sept, J=7.0 Hz), 3.97 (2H, d, J=7.9 Hz), 3.52-3.43 (2H, m), 3.29-3.21 (2H, m), 3.21 (1H, sept, J=7.0 Hz), 2.97-2.85 (2H, m), 2.36-2.24 (2H, m), 1.88-21.77 (2H, m), 1.68-1.55 (3H, m), 1.50-1.34 (2H, m), 1.41 (6H, d, J=7.0 Hz), 1.12 (6H, d, J=7.0 Hz)

Example 3-27

Preparation of N-[5-(2,4-dihydroxy-5-isopropyl-phenyl)-4-(4-methoxy-phenyl)-4H-[1,2,4]triazol-3-yl]-methanesulfonamide (N-1-a08)

Scheme 3-27

[Formula 57]

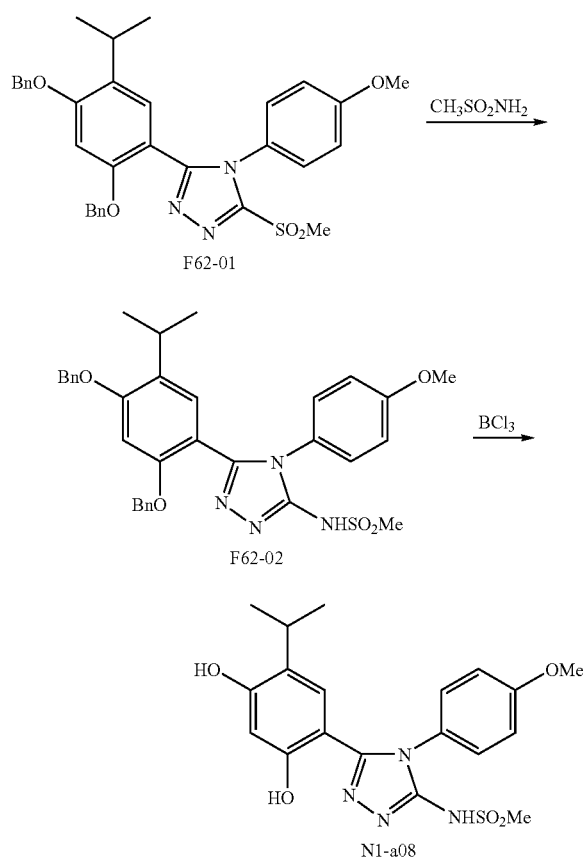

The First Step: Preparation of F62-02

F62-01 (synthesized in a similar manner to the intermediate F63-05 of Example 2-3: 362 mg, 0.62 mmol), methane sulfonamide (117 mg, 1.86 mmol), potassium carbonate (514 mg, 3.72 mmol) and dimethylsulfoxide (3.5 mL) were placed in a 30 mL flask and the mixture was stirred at 90° C. for 120 hours. The reaction mixture was mixed with water (50 mL), and after adjusting the pH to 7.5 with 2 N hydrochloric acid, the mixture was extracted twice with ethyl acetate (100 mL). The organic layer was washed with saturated sodium chloride solution, dried with sodium sulfate and then concentrated under reduced pressure. The residue was purified by silica gel column chromatography (hexane:ethyl acetate=1:1-1:2) to obtain the title compound (F62-02: 108 mg, yield 29.0%).

LC/MS (Method 5): m/z (ESI, POS): 599 [M+H]$^+$; retention time: 6.84 minutes.

The Second Step: Preparation of N-[5-(2,4-dihydroxy-5-isopropyl-phenyl)-4-(4-methoxy-phenyl)-4H-[1,2,4]triazol-3-yl]-methanesulfonamide (N-1-a08)

After dissolving F62-02 (99 mg, 0.165 mmol) in anhydrous dichloromethane (3 mL), the solution was cooled to −20° C. and mixed with 1 mol trichloroborane solution (3 mL). After warming to 0° C., the mixture was stirred for 2 hours. The reaction mixture was mixed with methanol (3 mL) and then with solid sodium hydrogencarbonate until pH became about 7.0 with pH paper. The reaction mixture was filtered and the insoluble fraction was washed sufficiently with chloroform:methanol (3:1). The filtrate and the wash were combined and concentrated, and the residue was purified by silica gel column chromatography (chloroform: methanol=15:1-10:1) to obtain the title compound (N1-a08: 44.2 mg, yield 63.9%).

LC/MS (Method 3): m/z (ESI, POS): 419 [M+H]$^+$; retention time: 4.93 minutes.

$^1$H-NMR (400 MHz, DMSO-d$_6$, ppm): 13.04 (1H, brs), 9.44 (1H, brs), 7.15 (2H, d, J=8.98 Hz), 6.92 (2H, d, J=8.98), 6.89 (1H, s), 6.24 (1H, s), 4.04 (H, s), 3.73 (3H, s), 2.98 (1H, m), 2.87 (3H, s), 1.00 (3H, d, J=6.96)

Test Example 1

To confirm the binding of the compound of the present invention to HSP90, an HSP90 binding assay system was constructed using BIACORE (a device for measuring biomolecular binding activity which measures the binding of biomolecules in real time by reproducing the biomolecular binding on a sensor chip applying Surface Plasmon Resonance (SPR))(refer to Adamczyk, M., Moore, J. A., Yu, Z. (2000) Methods, 20, p. 319-328).

The HSP90 binding assay system is a system for detecting the change of mass as SPR signal caused by the binding between herbimycin A fixed on a sensor chip and rHSP90 by BIACORE-X, in which 17-(6-amino hexylamino)herbimycin A is fixed through a carboxyl group on the surface of the sensor chip (CM5, BIACORE) on which carboxymethyldextran has been introduced. The method was according to the protocol of BIACORE. In addition, 17-(6-aminohexylamino) herbimycin A was synthesizes as described below.

Reagent Synthesis Example 1

Preparation of 17-(6-aminohexylamino)herbimycin A 17-(6-aminohexylamino)herbimycin A (17(A)) was synthesized according to the following scheme (4).

Next, using following formula (1), the inhibitory activity (binding inhibition rate (%)) of the compound of the present invention to the binding between rHSP90 and fixed herbimycin A was obtained.

binding inhibition rate (%)=((b−s)/b)×100     Formula (1):

wherein b is the SPR signal when the compound of the present invention is not added to the sample: s is the SPR signal when the compound of the present invention is added to the sample.

From the concentration of the triazole derivative of the present invention and its inhibitory activity, the concentration, at which the binding between HSP90 protein and fixed herbimycin A was inhibited by 50%, was calculated and termed an IC50 value.

The triazole derivatives of the present invention reduced the SPR signal, concentration dependently, indicating that the compounds of the present invention inhibited the binding between HSP90 and fixed herbimycin A. Table 4-1-Table 6-4 show IC50 values of the binding inhibition.

Comparative Example 1

As comparative examples, the inhibitory activity (binding inhibition rate (%)) against the binding between rHSP90 and fixed herbimycin A of SH-b04, SH-b05 and SH-b06 (all from Scientific Exchange Co.), which are shown below, were measured in a similar manner to the triazole derivatives of the present invention. Table 7 shows IC 50 values of the binding inhibition.

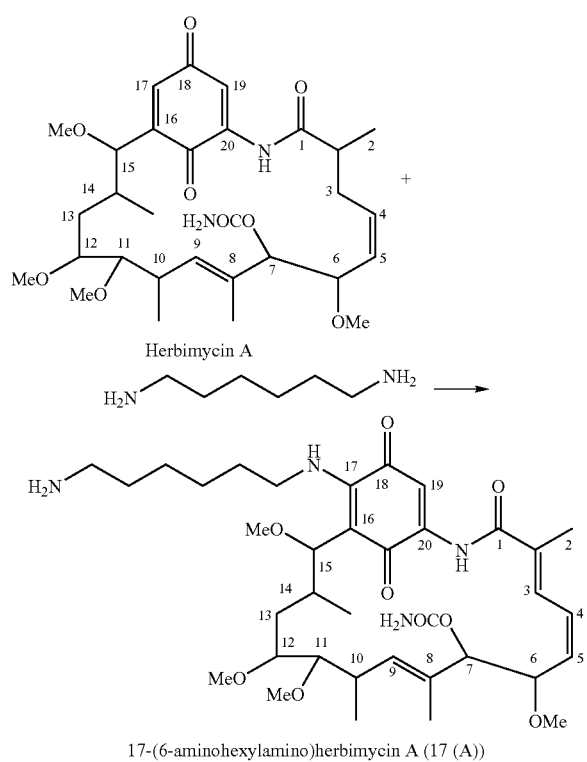

Scheme (4)

Herbimycin A 17-(6-aminohexylamino)herbimycin A (17 (A))

Herbimycin A (472 mg, 0.82 mmol) was dissolved in chloroform (42 mL), mixed with hexamethylenediamine (691 mg, 11.9 mmol) and the mixture was stirred at room temperature for 18 hours. Water (50 mL) and chloroform (50 mL) were added to the reaction mixture, and the chloroform layer was separated. The chloroform layer was washed with saturated sodium chloride solution, dried with sodium sulfate, and the solvent was distilled off. The residue was subjected to silica gel column chromatography (150 mL, chloroform: methanol: acetic acid=30:6:1) to obtain the crude compound (80 mg). Further, NH-silica gel column chromatography (40 mL, chloroform, Fuji Sylisia Chemical Ltd.) was performed to obtain 17-(6-aminohexylamino)herbimycin A (17(A)) (48 mg, yield 8.5%).

LC/MS: m/z (ESI, POS): 689 [M+H]$^+$ $^1$H-NMR (200 MHz, CDCl$_3$) ppm: 9.52 (1H, br), 7.70 (1H, br), 7.00 (1H, s, H-19), 7.00 (1H, d, J=11.3 Hz), 6.51 (1H, t, J=10.9 Hz, H-4), 5.84 (1H, dd, J=10.9 and 7.3 Hz, H-5), 5.4-5.6 (2H, br, H-7 and H9), 4.75 (2H, br, CONH$_2$), 4.71 (1H, s, H-15), 4.48 (1H, d, J=7.3 Hz, H-6), 3.68 (2H, m), 3.52 (3H, OMe), 3.35 (3H, OMe), 3.33 (3H, OMe), 3.32 (3H, OMe), 2.00 (3H, s), 1.95-1.22 (11H, m), 1.68 (3H, s, Me), 1.07 (3H, d, J=6.8 Hz), 0.96 (3H, d, J=6.5 Hz)

rHSP90 (Stressgen Biotchnologies Corp., Victoria, BC Canada) at 50 µg/mL was exposed for 10 seconds to the surface of the sensor chip on which herbimycin A was fixed and the SPR signal (numerical value of interaction) was detected. As the result, the increase of the SPR signal was observed, confirming the binding of rHSP90 and herbimycin A fixed on the sensor chip.

After mixing rHSP90 protein (5×10$^{-7}$M (50 µg/mL)) with the triazole derivative of the present invention, the mixture was exposed for 10 seconds to the surface of the sensor chip on which herbimycin A was fixed, and the SPR signal was measured by BIACORE-X.

[Formula 59]

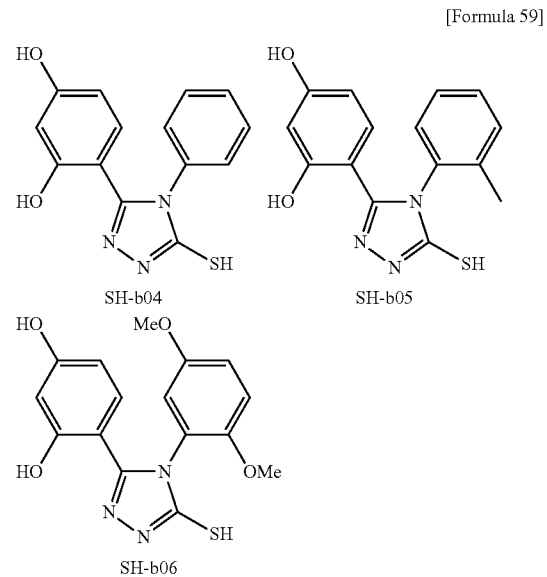

Test Example 2

Measurement Test for Amount of HSP90 Client Protein

MCF7 cells (American Type Culture Collection, Rockville, Md.) were treated with the compounds of the present invention at various concentrations for 16 hours to confirm that the HSP90 inhibitors of the present invention induce a depression of intracellular concentration of the client protein or target polypeptide that bind to HSP90. The amount of the HSP90 client protein Her2 and $ER_\alpha$ was evaluated by the Western blotting method.

One million cells were seeded in a 6 cm dish, and 24 hours later the compounds of the present invention (Example 1-2, Example 2-1, Example 2-13, Example 2-2, Example 3-4, Example 2-5, Example 3-16, Example 3-6, Example 2-7, Example 3-27, Example 2-10 and Example 3-18) were added. Cells treated with the compounds were washed, mixed with 150 μl of lysis buffer (RIPA, 150 mM NaCl, 1% NP40, 0.1% deoxycholate (sodium salt), 0.1% SDS, 1 mM EDTA, 10 mM Tris-HCl (pH 8.0)) and incubated at 4° C. for 30 minutes. The cell lysates were centrifuged (15,000 rpm, 20 minutes) and protein (20 μg) of the supernatant was subjected to SDS polyacrylamide gel electrophoresis (SDS-PAGE). After finishing the electrophoresis, proteins in the gel were transferred to a PVDF membrane. The membrane after the transfer was treated with a primary antibody against the HSP90 client protein (anti Her2 or anti ERα antibody, both from Santa Cruz Biotechnology, Santa Cruz, Calif.), then treated with secondary antibodies (anti-rabbit Ig, horse radish peroxidase conjugated F(ab')2 fragment (derived from donkey): Amersham Biosciences, UK Limited, Buckinghamshire, UK.) and then the amount of the client protein was detected as the intensity of chemiluminescence signal with a chemiluminescence reagent (ECL: Amersham Biosciences UK Limited, Buckinghamshire, UK). FIG. 1-FIG. 7 shows the results of electrophoresis.

Test Example 3

Human breast cancer cells (MCF7) were treated with samples of various concentrations of known HSP90 inhibitors (that is, geldanamycin, herbimycin, radicicol and PU3) and the compounds of the present invention for 72 hours to confirm the effect of the triazole derivatives of the present invention on the cell growth. The cell ratio after the drug treatment was evaluated by measuring 660 nm absorbance by a microplate reader (BioRad) after staining the cells with the methylene blue method.

Cells were distributed to wells of 96 well plates at 2000 cells per well and treated with drugs 24 hours later. Further, the medium was removed 72 hours later and the cells were fixed by adding 50 μL of methanol and standing at room temperature for 2 minutes. After removing methanol, 100 μL of a staining solution was added and stained for 30 minutes. After washing 3 times with 200 μL of distilled water, 3% HCl solution was added, and the 660 nm absorbance of methylene blue was measured by a microplate reader (BioRad).

Next, the antiproliferative activity rate (%) was obtained by the formula (2) below.

Antiproliferative activity rate $(\%) = ((B-A)/B) \times 100$    Formula (2)

wherein B is 660 nm absorbance of the sample when the compound of the present invention is not added, and A is 660 nm absorbance of the sample when the compound of the present invention is added.

From the concentration of the triazole derivative of the present invention and the antiproliferative activity rate, the concentration was obtained using the above formula, at which the cell growth was suppressed by 50% by comparing with the control, and termed an IC50 value.

The IC50 value of the HSP90 inhibitors, geldanamycin, herbimycin, radicicol and PU3 was 0.012 μM, 0.16 μM, 0.019 μM and 91 μM, respectively. The IC 50 values for antiproliferative activity of the triazole derivatives of the present invention are shown in Tables 4-1-6-4.

Comparative Example 2

The antiproliferative activity rate (%) was obtained for SH-b04, SH-b05 and SH-b06 described above by a similar manner to that of the triazole derivatives of the present invention. Table 7 shows IC 50 values of antiproliferative activity.

The above results have made it clear that the triazole derivatives of the present invention have a antiproliferative activity on MCF7 cells and that their antiproliferative effect is superior compared to that of other compounds known to have the HSP90 inhibitory activity.

The above results have made it clear that the triazole derivatives of the present invention have the HSP90 inhibitory activity as well as the antiproliferative activity against cancer cells, and are useful as therapeutic drugs for cancer.

Test Example 4

Antitumor Effect on Nude Mice Transplanted with Human Lung Cancer

Human lung cancer H460 tumor fragment, which had been passaged subcutaneously in nude mice, was made into about 3 mm fragment and transplanted subcutaneously to the back of nude mice using a trocar. When the tumor volume grew to about 50 mm³ or above, the compound of the present invention was administered to the tail vein once a day for 5 or 7 days every day. The compound of the present invention was dissolved in DMSO, mixed with TWEEN 80, and then diluted with a 5% glucose injection solution and used. The vehicle of the compound was administered to the control group of OH-a01. The control groups in other experiments were not treated. The tumor volume was measured on the first administration day and on the evaluation day (7 or 8 days after the start of the administration), and the relative tumor volume of the evaluation day was obtained from the tumor volume on the first administration day. Further, the tumor volume was calculated by measuring the major axis (Lmm) and minor axis (Wmm) of the tumor and by the formula $(L \times W^2)/2$. The results are shown in Tables 8, 9 and 10.

Table 8 shows the anti-tumor effect (7 days continuous intravenous administration) of OH-a01 (Example 2-1) on human lung cancer H460. Relative tumor volume represents the average relative tumor volume on day 7 after the start of the administration, assuming the tumor volume of the starting day is 1.0.

Table 9 shows the anti-tumor effect (5 days continuous intravenous administration) of OH-a02 (Example 2-2) and OH-a08 (Example 2-7) on human lung cancer H460. Relative tumor volume represents the average relative tumor volume on day 8 after the start of the administration, assuming the tumor volume of the starting day is 1.0.

Table 10 shows the anti-tumor effect (5 days continuous intravenous administration) of OH-a13 (Example 2-5) and SFN3-a08 (Examples 3-18) on human lung cancer H460. Relative tumor volume represents the average relative tumor volume on day 8 after the start of the administration, assuming the tumor volume of the starting day is 1.0.

INDUSTRIAL APPLICABILITY

It was made it clear that the compounds of the present invention concentration dependently inhibited the tumor growth of human lung cancer H460 transplanted on nude mice and that they are useful as anti-cancer agent.

TABLE 1
Table 1. Compounds represented by General formula (1) or General formula (4)
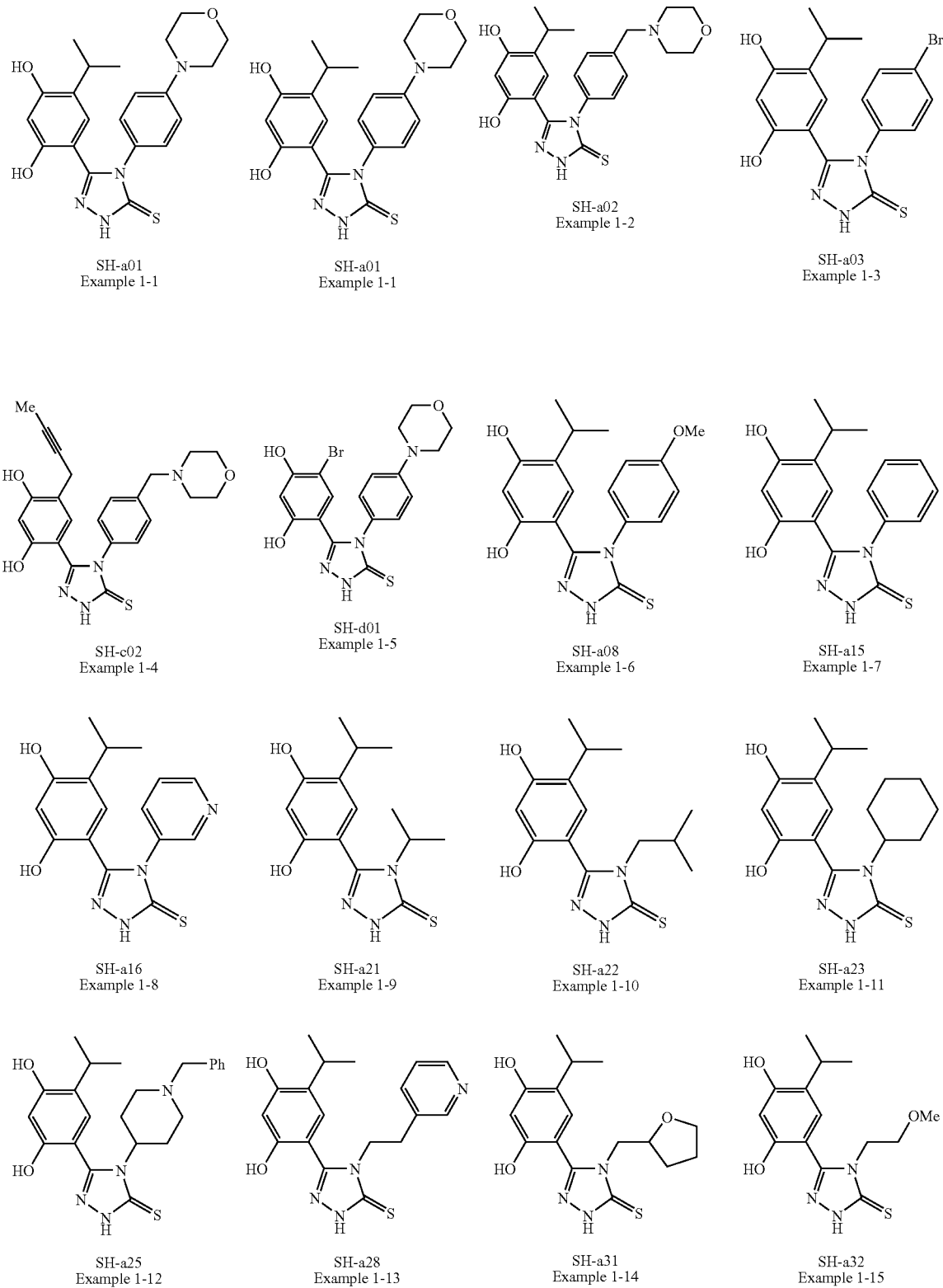

TABLE 1-continued
Table 1. Compounds represented by General formula (1) or General formula (4)
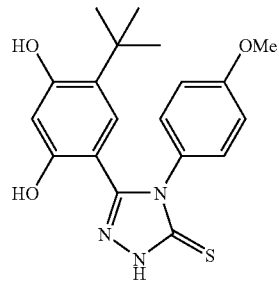
SH-f08
Example 1-16
TABLE 2
Table 2. Compounds represented by General formula (1) or General formula (4)
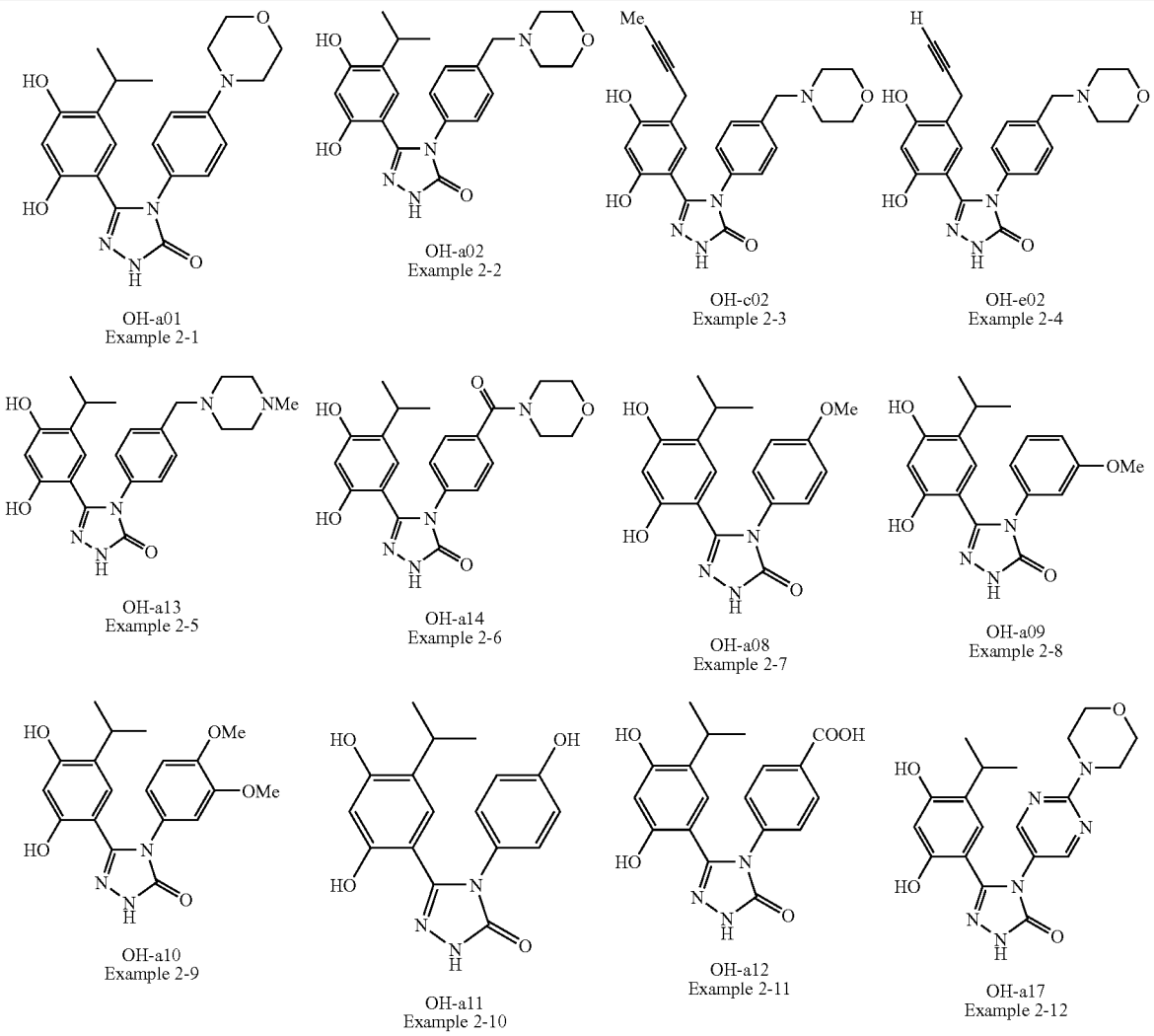

TABLE 2-continued
Table 2. Compounds represented by General formula (1) or General formula (4)
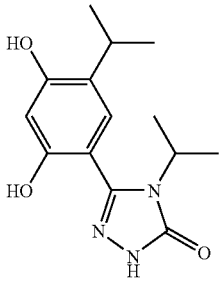
OH-a21
Example 2-13
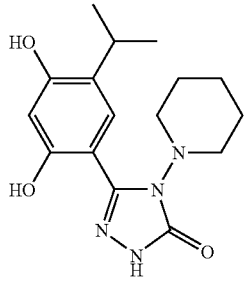
OH-a24
Example 2-14
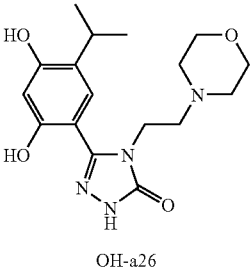
OH-a26
Example 2-15
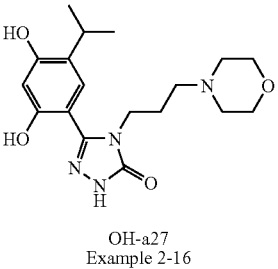 [SMILES: CC(C)c1cc(-c2n[nH]c(=O)n2CCCN2CCOCC2)c(O)cc1O]
OH-a27
Example 2-16
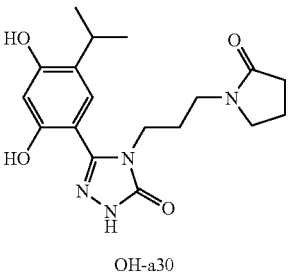
OH-a30
Example 2-17
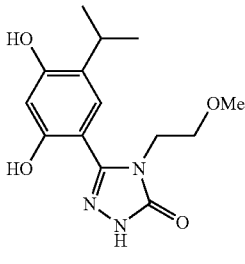
OH-a32
Example 2-18
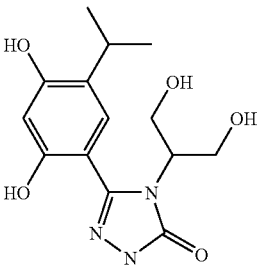
OH-a33
Example 2-19
TABLE 3-1
Table 3-1. Compounds represented by General formula (1) or General formula (4)
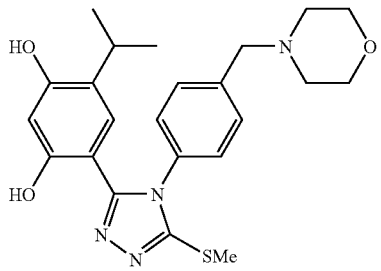
SMe-a02
Example 3-1
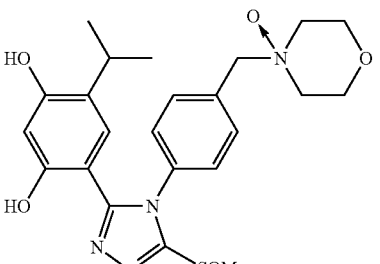
SFX-a07
Example 3-2
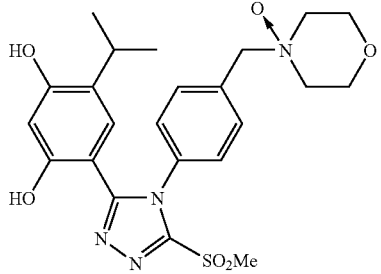
SFN-a07
Example 3-2
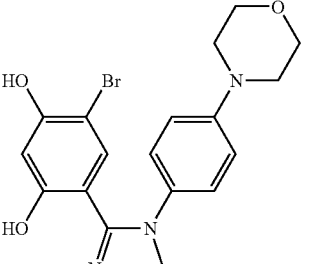
SMe-d01
Example 3-3

TABLE 3-1-continued
Table 3-1. Compounds represented by General formula (1) or General formula (4)
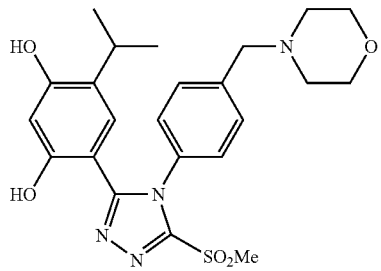
SFN-a02
Example 3-4
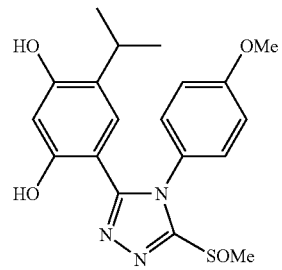
SFX-a08
Example 3-5
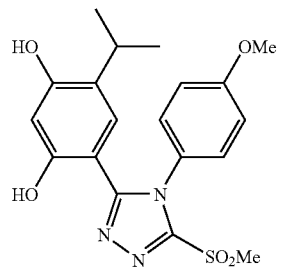
SFN-a08
Example 3-6
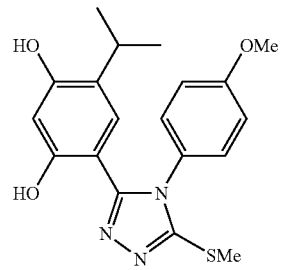
SMe-a08
Example 3-7
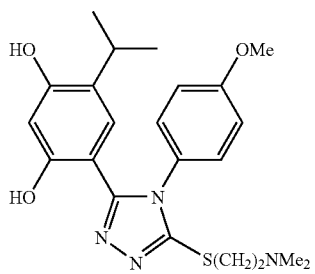
SR2-a08
Example 3-8
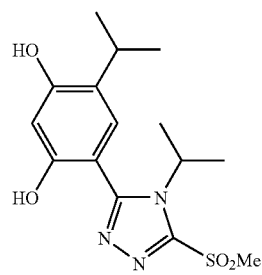
SFN-a21
Example 3-9
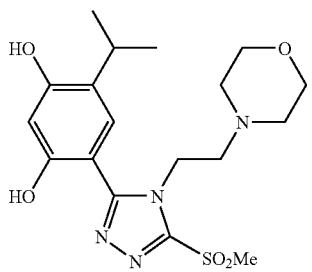
SFN-a26
Example 3-10
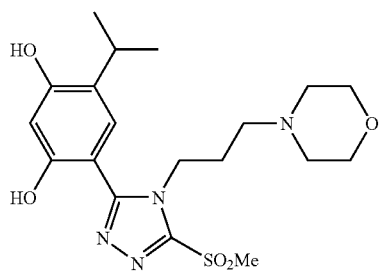
SFN-a27
Example 3-11

TABLE 3-1-continued
Table 3-1. Compounds represented by General formula (1) or General formula (4)
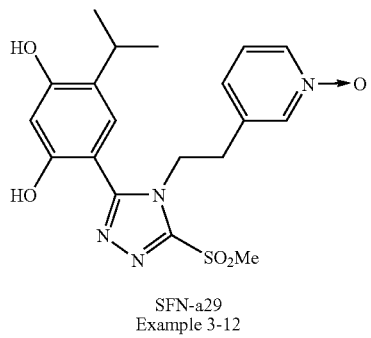
SFN-a29
Example 3-12
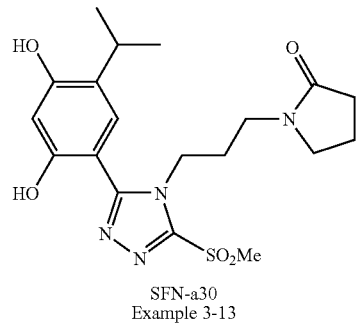 [SMILES: CC(C)c1cc(-c2nnc(S(C)(=O)=O)n2CCCN2CCCC2=O)c(O)cc1O]
SFN-a30
Example 3-13
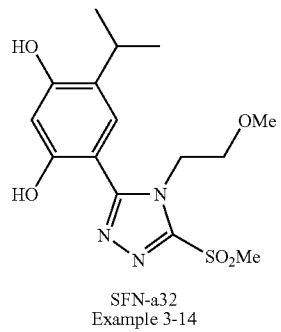 [SMILES: COCCn1c(-c2cc(C(C)C)c(O)cc2O)nnc1S(C)(=O)=O]
SFN-a32
Example 3-14
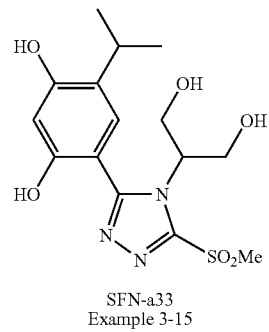 [SMILES: CC(C)c1cc(-c2nnc(S(C)(=O)=O)n2C(CO)CO)c(O)cc1O]
SFN-a33
Example 3-15
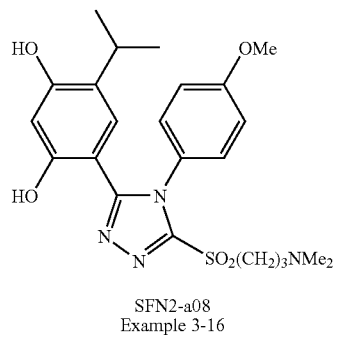
SFN2-a08
Example 3-16
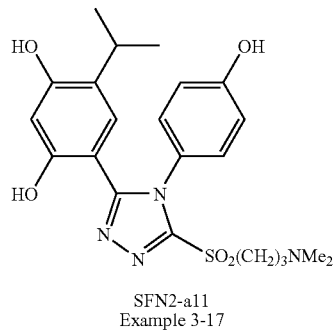
SFN2-a11
Example 3-17
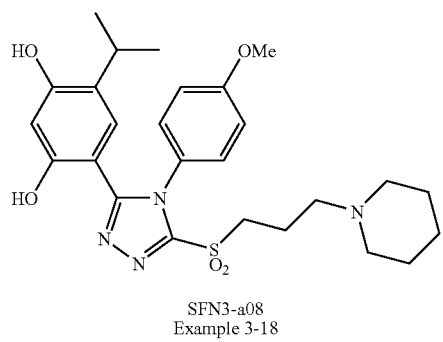 [SMILES: COc1ccc(-n2c(-c3cc(C(C)C)c(O)cc3O)nnc2S(=O)(=O)CCCN2CCCCC2)cc1]
SFN3-a08
Example 3-18
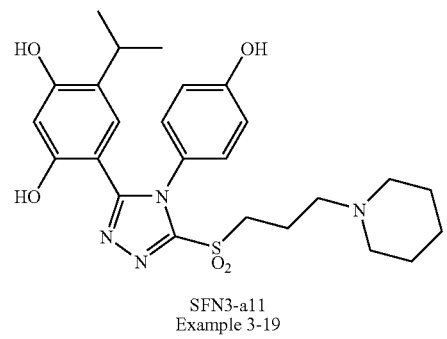 [SMILES: CC(C)c1cc(-c2nnc(S(=O)(=O)CCCN3CCCCC3)n2-c2ccc(O)cc2)c(O)cc1O]
SFN3-a11
Example 3-19

TABLE 3-2
Table 3-2. Compounds represented by General formula (1) or General formula (4)
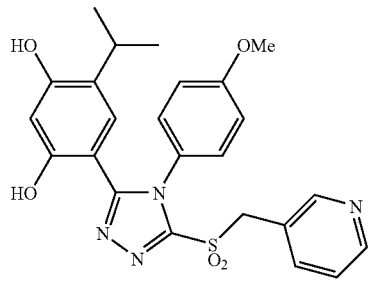
SFN4-a08
Example 3-20
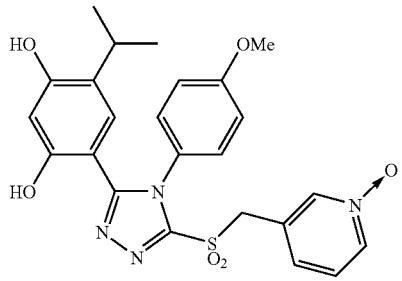
SFN5-a08
Example 3-21
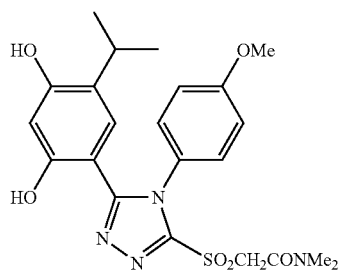
SFN6-a08
Example 3-22
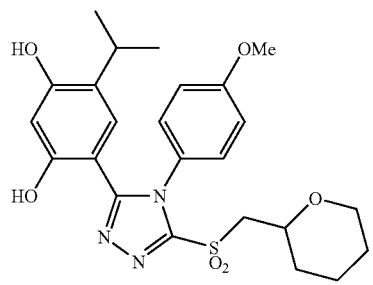
SFN7-a08
Example 3-23
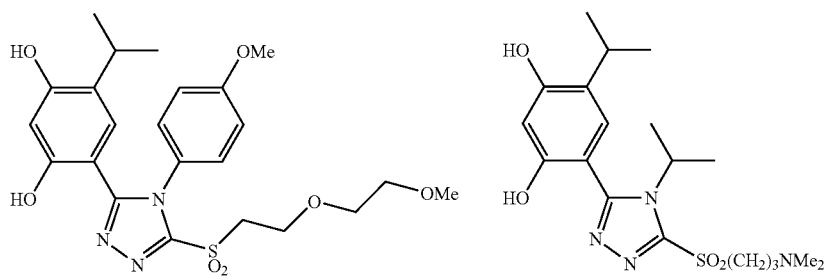
SFN8-a08
Example 3-24
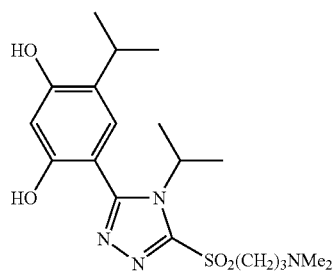
SFN2-a21
Example 3-25
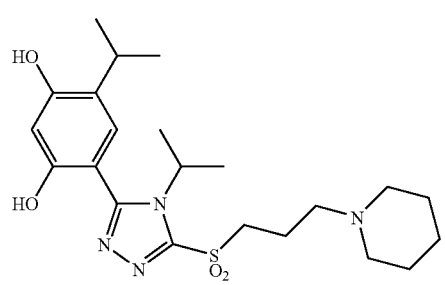
SFN3-a21
Example 3-26
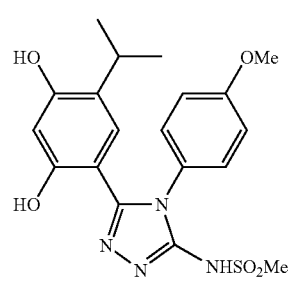
N1-a08
Example 3-27

TABLE 4-1

Table 4-1. HSP90 inhibitory activity and antiproliferative activity (1)

| No. | Structure | Test Example 1 HSP90 inhibitory activity IC50 (μM) | Test Example 2 Antiproliferative activity IC50 (μM) |
| --- | --- | --- | --- |
| SH-a01-TF Example 1-1 | | 0.19 | 0.020 |
| SH-a01 Example 1-1 | | 0.14 | 0.014 |
| SH-a02 Example 1-2 | | 0.24 | 0.036 |
| SH-a03 Example 1-3 | | 0.15 | 0.15 |

TABLE 4-1-continued
Table 4-1. HSP90 inhibitory activity and antiproliferative activity (1)
| No. | Structure | IC50 (μM) Test Example 1 HSP90 inhibitory activity | Test Example 2 Antiproliferative activity |
|---|---|---|---|
| SH-c02-TF Example 1-4 | 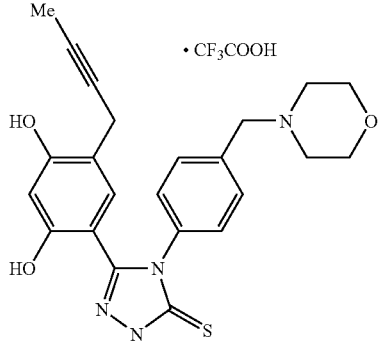 | 0.25 | 0.48 |
| SH-d01 Example 1-5 | 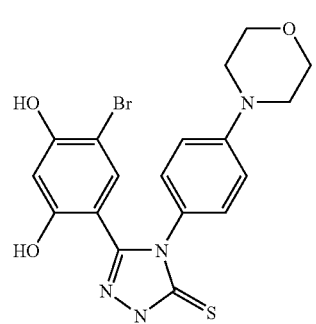 | 0.15 | 0.58 |
| SH-a08 Example 1-6 | 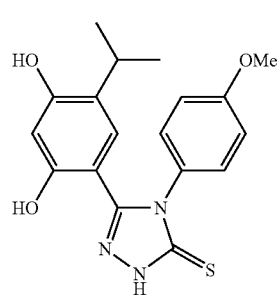 [SMILES: COc1ccc(-n2c(-c3cc(C(C)C)c(O)cc3O)n[nH]c2=S)cc1] | 0.085 | 0.057 |
| SH-a15 Example 1-7 | 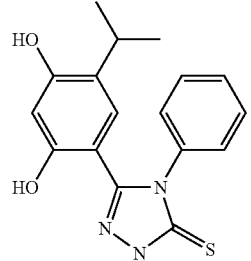 | 0.25 | 0.040 |

TABLE 4-2

Table 4-2. HSP90 inhibitory activity and antiproliferative activity (1)

| No. | Structure | IC50 (μM) Test Example 1 HSP90 inhibitory activity | Test Example 2 Antiproliferative activity |
|---|---|---|---|
| SH-a16 Example 1-8 | 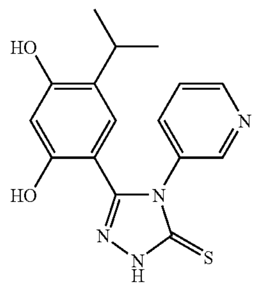 [SMILES: CC(C)c1cc(-c2n[nH]c(=S)n2-c2cccnc2)c(O)cc1O] | 0.14 | 0.24 |
| SH-a21 Example 1-9 | 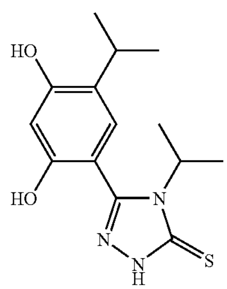 [SMILES: CC(C)c1cc(-c2n[nH]c(=S)n2C(C)C)c(O)cc1O] | 0.22 | 0.40 |
| SH-a22 Example 1-10 | 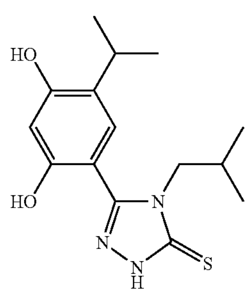 [SMILES: CC(C)Cn1c(-c2cc(C(C)C)c(O)cc2O)n[nH]c1=S] | 0.27 | 0.45 |
| SH-a23 Example 1-11 | 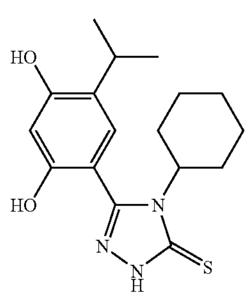 [SMILES: CC(C)c1cc(-c2n[nH]c(=S)n2C2CCCCC2)c(O)cc1O] | 0.42 | 0.33 |

TABLE 4-2-continued
Table 4-2. HSP90 inhibitory activity and antiproliferative activity (1)
| No. | Structure | IC50 (µM) | |
|---|---|---|---|
| | | Test Example 1 HSP90 inhibitory activity | Test Example 2 Antiproliferative activity |
| SH-a25•TFA Example 1-12 | 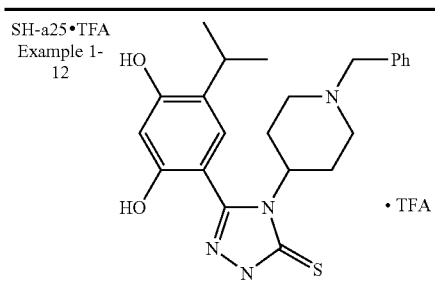 | 1.0 | 0.89 |
| SH-a28 Example 1-13 | 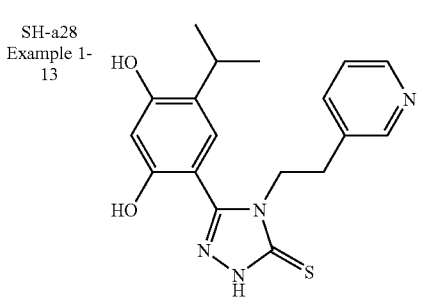 | 0.43 | 7.2 |
| SH-a31 Example 1-14 | 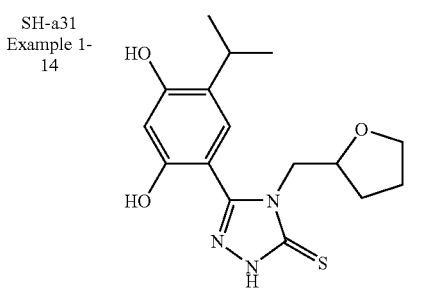 | 0.31 | 0.55 |
| SH-a32 Example 1-15 | 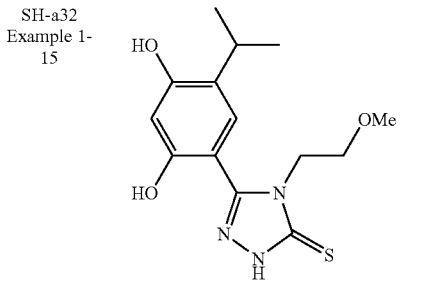 | 0.24 | 0.55 |

TABLE 4-3

Table 4-3. HSP90 inhibitory activity and antiproliferative activity (1)

| No. | Structure | Test Example 1 HSP90 inhibitory activity IC50 (μM) | Test Example 2 Antiproliferative activity IC50 (μM) |
|---|---|---|---|
| SH-f08 Example 1-16 | 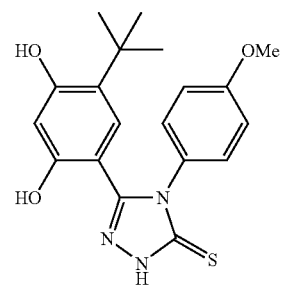 [SMILES: COc1ccc(-n2c(-c3cc(C(C)(C)C)c(O)cc3O)n[nH]c2=S)cc1] | 0.56 | 3.0 |

TABLE 5-1

Table 5-1. HSP90 inhibitory activity and antiproliferative activity (2)

| No. | Structure | Test Example 1 HSP90 inhibitory activity IC50 (μM) | Test Example 2 Antiproliferative activity IC50 (μM) |
|---|---|---|---|
| OH-a01 Example 2-1 | 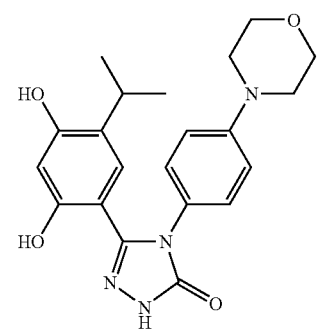 [SMILES: CC(C)c1cc(-c2n[nH]c(=O)n2-c2ccc(N3CCOCC3)cc2)c(O)cc1O] | 0.14 | 0.0049 |
| OH-a02 Example 2-2 | 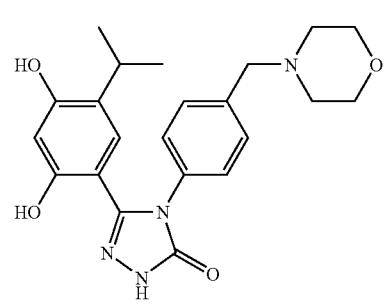 [SMILES: CC(C)c1cc(-c2n[nH]c(=O)n2-c2ccc(CN3CCOCC3)cc2)c(O)cc1O] | 0.18 | 0.016 |

TABLE 5-1-continued

Table 5-1. HSP90 inhibitory activity and antiproliferative activity (2)

| No. | Structure | IC50 (μM) Test Example 1 HSP90 inhibitory activity | Test Example 2 Antiproliferative activity |
|---|---|---|---|
| OH-c02 Example 2-3 | (structure) | 0.22 | 0.14 |
| OH-a02 Example 2-4 | (structure) | 0.15 | 0.24 |
| OH-a13·TFA Example 2-5 | (structure) | 0.25 | 0.071 |
| OH-a14 Example 2-6 | (structure) | 0.19 | 0.72 |

TABLE 5-1-continued

Table 5-1. HSP90 inhibitory activity and antiproliferative activity (2)

| No. | Structure | Test Example 1 HSP90 inhibitory activity IC50 (µM) | Test Example 2 Antiproliferative activity IC50 (µM) |
|---|---|---|---|
| OH-a08 Example 2-7 | (structure) | 0.12 | 0.011 |

TABLE 5-2

Table 5-2. HSP90 inhibitory activity and antiproliferative activity (2)

| No. | Structure | Test Example 1 HSP90 inhibitory activity IC50 (µM) | Test Example 2 Antiproliferative activity IC50 (µM) |
|---|---|---|---|
| OH-a09 Example 2-8 | (structure) | 0.16 | 0.0067 |
| OH-a10 Example 2-9 | (structure) | 0.21 | 0.014 |

TABLE 5-2-continued

Table 5-2. HSP90 inhibitory activity and antiproliferative activity (2)

| No. | Structure | IC50 (µM) | |
|---|---|---|---|
| | | Test Example 1 HSP90 inhibitory activity | Test Example 2 Antiproliferative activity |
| OH-a11 Example 2-10 | | 0.22 | 0.077 |
| OH-a12 Example 2-11 | | 0.19 | >20 |
| OH-a17 Example 2-12 | | 0.22 | 0.026 |
| OH-a21 Example 2-13 | | 0.13 | 0.038 |

TABLE 5-2-continued

Table 5-2. HSP90 inhibitory activity and antiproliferative activity (2)

| No. | Structure | Test Example 1 HSP90 inhibitory activity IC50 (µM) | Test Example 2 Antiproliferative activity IC50 (µM) |
|---|---|---|---|
| OH-a24•TFA Example 2-14 | 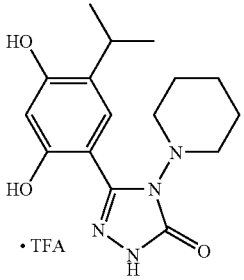 [SMILES: CC(C)c1cc(-c2n[nH]c(=O)n2N2CCCCC2)c(O)cc1O] | 1.1 | 0.79 |
| OH-a26•HCl Example 2-15 | 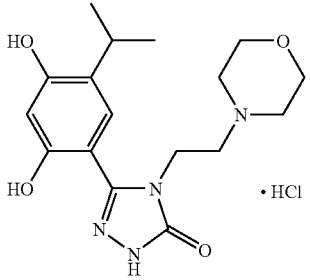 [SMILES: CC(C)c1cc(-c2n[nH]c(=O)n2CCN2CCOCC2)c(O)cc1O ; "· HCl"] | 0.18 | 0.60 |

TABLE 5-3

Table 5-3. HSP90 inhibitory activity and antiproliferative activity (2)

| No. | Structure | Test Example 1 HSP90 inhibitory activity IC50 (µM) | Test Example 2 Antiproliferative activity IC50 (µM) |
|---|---|---|---|
| OH-a27 Example 2-16 | 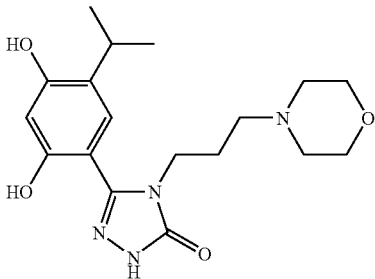 [SMILES: CC(C)c1cc(-c2n[nH]c(=O)n2CCCN2CCOCC2)c(O)cc1O] | 0.24 | 0.22 |

TABLE 5-3-continued
Table 5-3. HSP90 inhibitory activity and antiproliferative activity (2)
| No. | Structure | Test Example 1 HSP90 inhibitory activity | Test Example 2 Antiproliferative activity |
|---|---|---|---|
| | | IC50 (μM) | |
| OH-a30 Example 2-17 | 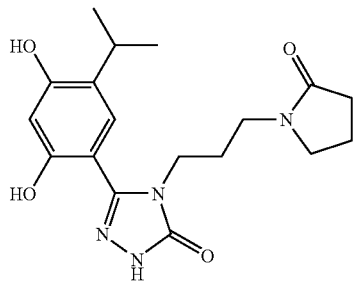 [SMILES: CC(C)c1cc(-c2n[nH]c(=O)n2CCCN2CCCC2=O)c(O)cc1O] | 0.14 | 1.1 |
| OH-a32 Example 2-18 | 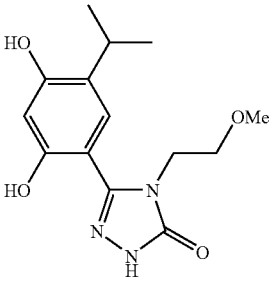 [SMILES: COCCn1c(-c2cc(C(C)C)c(O)cc2O)n[nH]c1=O] | 0.35 | 0.39 |
| OH-a33 Example 2-19 | 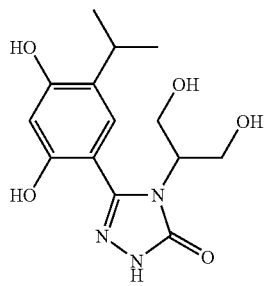 [SMILES: CC(C)c1cc(-c2n[nH]c(=O)n2C(CO)CO)c(O)cc1O] | 0.37 | 3.3 |

TABLE 6-1

Table 6-1. HSP90 inhibitory activity and antiproliferative activity (3)

| No. | Structure | IC50 (μM) | |
|---|---|---|---|
| | | Test Example 1 HSP90 inhibitory activity | Test Example 2 Antiproliferative activity |
| SMe-a02-TF Example 3-1 | *structure* · CF$_3$COOH | 0.47 | 0.53 |
| SFX-a07-TF Example 3-2 | *structure* · CF$_3$COOH | 0.064 | 12 |
| SFN-a07 Example 3-2 | *structure* | 0.32 | 24 |
| SMe-d01-TF Example 3-3 | *structure* · CF$_3$COOH | 0.60 | 5.5 |

TABLE 6-1-continued

Table 6-1. HSP90 inhibitory activity and antiproliferative activity (3)

| No. | Structure | IC50 (μM) | |
| --- | --- | --- | --- |
| | | Test Example 1 HSP90 inhibitory activity | Test Example 2 Antiproliferative activity |
| SFN-a02 Example 3-4 | (structure) | 0.12 | 0.15 |
| SFX-a08 Example 3-5 | (structure) | 0.12 | 0.36 |
| SFN-a08 Example 3-5 | (structure) | 0.094 | 0.27 |

TABLE 6-2

Table 6-2. HSP90 inhibitory activity and antiproliferative activity (3)

| No. | Structure | IC50 (μM) | |
| --- | --- | --- | --- |
| | | Test Example 1 HSP90 inhibitory activity | Test Example 2 Antiproliferative activity |
| SMe-a08 Example 3-7 | (structure) | 0.59 | 3.1 |

TABLE 6-2-continued

Table 6-2. HSP90 inhibitory activity and antiproliferative activity (3)

| No. | Structure | IC50 (μM) | |
|---|---|---|---|
| | | Test Example 1 HSP90 inhibitory activity | Test Example 2 Antiproliferative activity |
| SR2-a08 Example 3-8 | 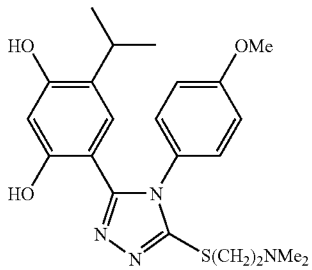 | 0.74 | 1.8 |
| SFN-a21 Example 3-9 | 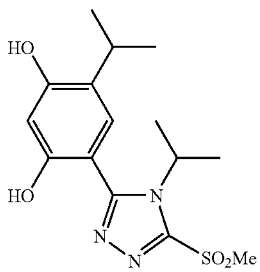 [SMILES: CC(C)c1cc(-c2nnc(S(C)(=O)=O)n2C(C)C)c(O)cc1O] | 0.23 | 16 |
| SFN-a26 Example 3-10 | 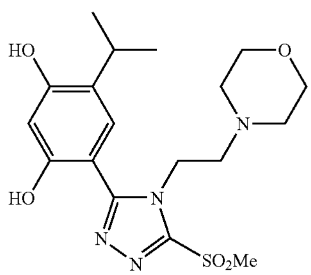 [SMILES: CC(C)c1cc(-c2nnc(S(C)(=O)=O)n2CCN2CCOCC2)c(O)cc1O] | 3.4 | >20 |
| SFN-a27 Example 3-11 | 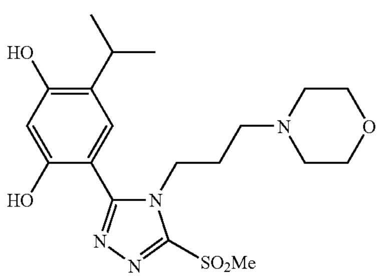 [SMILES: CC(C)c1cc(-c2nnc(S(C)(=O)=O)n2CCCN2CCOCC2)c(O)cc1O] | 1.6 | >20 |
| SFN-a29 Example 3-12 | 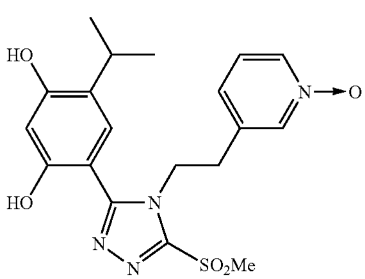 [SMILES: CC(C)c1cc(-c2nnc(S(C)(=O)=O)n2CCc2ccc[n+]([O-])c2)c(O)cc1O] | 3.6 | >20 |

TABLE 6-2-continued

Table 6-2. HSP90 inhibitory activity and antiproliferative activity (3)

| No. | Structure | IC50 (μM) Test Example 1 HSP90 inhibitory activity | Test Example 2 Antiproliferative activity |
|---|---|---|---|
| SFN-a30 Example 3-13 | 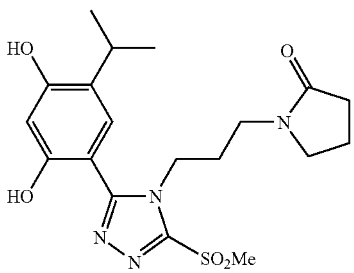 [SMILES: CC(C)c1cc(-c2nnc(S(C)(=O)=O)n2CCCN2CCCC2=O)c(O)cc1O] | 2.4 | >20 |

TABLE 6-3

Table 6-3. HSP90 inhibitory activity and antiproliferative activity (3)

| No. | Structure | IC50 (μM) Test Example 1 HSP90 inhibitory activity | Test Example 2 Antiproliferative activity |
|---|---|---|---|
| SFN-a32 Example 3-14 | 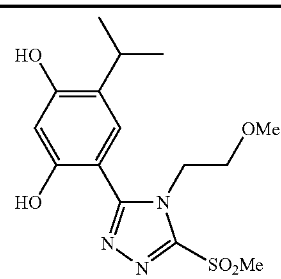 | 1.9 | >20 |
| SFN-a33 Example 3-15 | 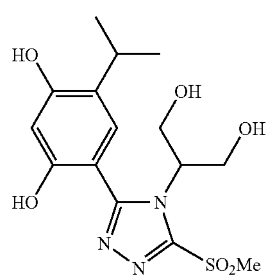 [SMILES: CC(C)c1cc(-c2nnc(S(C)(=O)=O)n2C(CO)CO)c(O)cc1O] | 1.3 | 15 |
| SFN2-a08•TFA Example 3-16 | 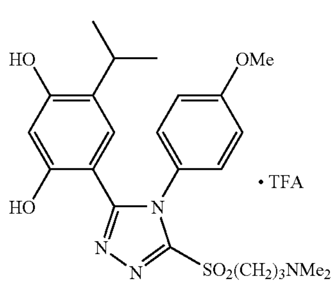 | 0.70 | 0.069 |

TABLE 6-3-continued

Table 6-3. HSP90 inhibitory activity and antiproliferative activity (3)

| No. | Structure | Test Example 1 HSP90 inhibitory activity IC50 (μM) | Test Example 2 Antiproliferative activity IC50 (μM) |
|---|---|---|---|
| SFN2-a11•TFA Example 3-17 | | 0.43 | 0.098 |
| SFN3-a08 Example 3-18 | | 0.59 | 0.044 |
| SFN3-a11•TFA Example 3-19 | | 0.73 | 0.044 |
| SFN4-a08 Example 3-20 | | 0.23 | 9.9 |

TABLE 6-4

Table 6-4. HSP90 inhibitory activity and antiproliferative activity (3)

| No. | Structure | IC50 (μM) | |
|---|---|---|---|
| | | Test Example 1 HSP90 inhibitory activity | Test Example 2 Antiproliferative activity |
| SFN5-a08 Example 3-21 | | 0.43 | 3.9 |
| SFN6-a08 Example 3-22 | | 0.58 | 0.55 |
| SFN7-a08 Example 3-23 | | 0.72 | 0.72 |
| SFN8-a08 Example 3-24 | | 0.60 | 2.4 |
| SFN2-a21•TFA Example 3-25 | | 1.0 | 5.2 |

TABLE 6-4-continued

Table 6-4. HSP90 inhibitory activity and antiproliferative activity (3)

| No. | Structure | IC50 (µM) | |
|---|---|---|---|
| | | Test Example 1 HSP90 inhibitory activity | Test Example 2 Antiproliferative activity |
| SFN3-a21•TFA Example 3-26 | (structure) | 1.4 | 4.1 |
| N1-a08 Example 3-27 | (structure) | 0.29 | 0.18 |

TABLE 7

Table 7. HSP90 inhibitory activity and antiproliferative activity (4)

| No. | Structure | IC50 (µM) | |
|---|---|---|---|
| | | Test Example 1 HSP90 inhibitory activity | Test Example 2 Antiproliferative activity |
| SH-b04 Comparative Example (1) | (structure) | 0.17 | 5.7 |
| SH-b05 Comparative Example (2) | (structure) | 0.20 | 9.0 |

TABLE 7-continued

Table 7. HSP90 inhibitory activity and antiproliferative activity (4)

| No. | Structure | IC50 (μM) Test Example 1 HSP90 inhibitory activity | Test Example 2 Antiproliferative activity |
|---|---|---|---|
| SH-b06 Comparative Example (3) | (structure) | 0.69 | 77 |

TABLE 8

Table 8

| Compound | Administration dose (mg/kg/day) | Relative tumor volume (Average ± SD) |
|---|---|---|
| Control group | 0 | 7.3 ± 1.7 |
| Example 2-1 | 7.5 | 1.7 ± 0.5 |
|  | 3.8 | 3.3 ± 0.7 |

TABLE 9

Table 9

| Compound | Administration dose (mg/kg/day) | Relative tumor volume (Average ± SD) |
|---|---|---|
| Control group | 0 | 4.6 ± 3.1 |
| Example 2-2 | 150 | 2.1 ± 0.1 |
|  | 75 | 3.5 ± 2.3 |
| Example 2-7 | 200 | 1.1 ± 0.3 |
|  | 100 | 1.9 ± 1.0 |

TABLE 10

Table 10

| Compound | Administration dose (mg/kg/day) | Relative tumor volume (Average ± SD) |
|---|---|---|
| Control group | 0 | 6.5 ± 2.0 |
| Example 2-5 | 100 | 1.1 ± 0.3 |
|  | 50 | 1.4 ± 0.5 |
| Example 3-18 | 150 | 2.9 ± 0.6 |
|  | 100 | 5.4 ± 1.3 |

Figure 1:
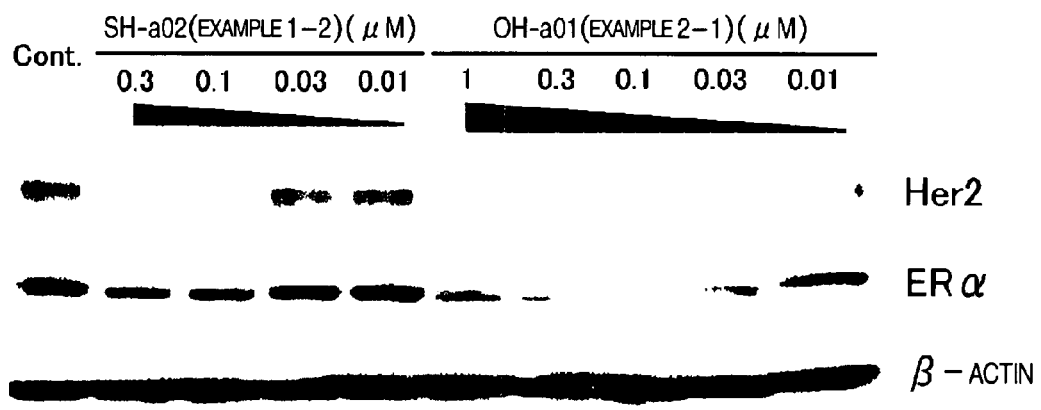
FIG. 1 shows a depression of the amount of HSP90 client protein Her2 and $ER_\alpha$ by the HSP90 inhibitor of the present invention (Example 1-2 and Example 2-1) in the protein assay for the HSP90 client protein in Test example 2. After treating MCF7 cells with 4 or 5 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.
Figure 2:
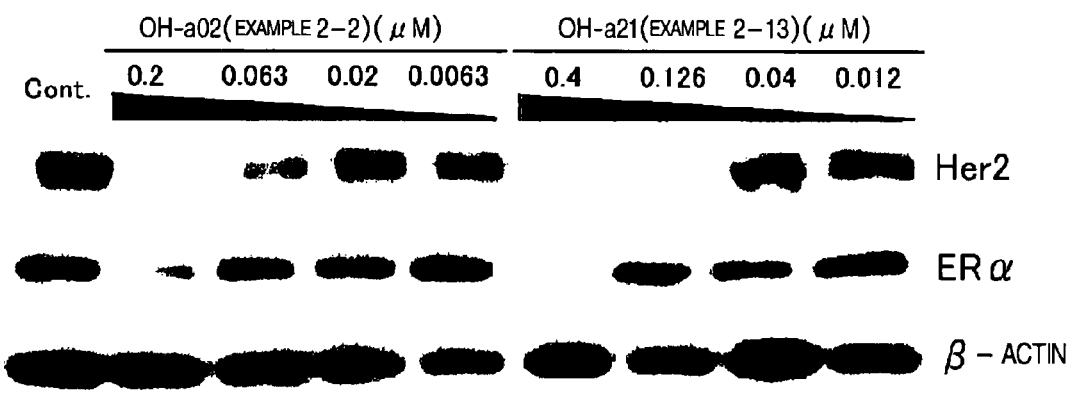
FIG. 2 shows a depression of the amount of HSP90 client protein Her2 and $ER_\alpha$ by the HSP90 inhibitor of the present invention (Example 2-2 and Example 2-13) in the protein assay for the HSP90 client protein in Test example 2. After treating MCF7 cells with 4 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.
Figure 3:
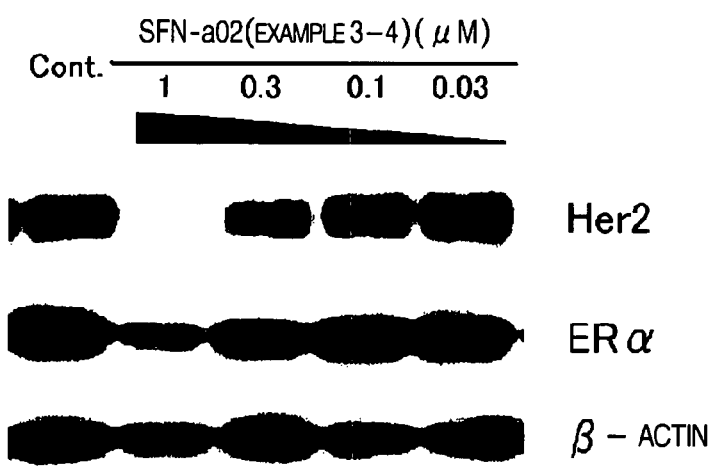
FIG. 3 shows a depression of the amount of HSP90 client protein Her2 and $ER_\alpha$ by the HSP90 inhibitor of the present invention (Example 3-4) in the protein assay for the HSP90 client protein in Test example 2. After treating MCF7 cells with 4 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.
Figure 4:
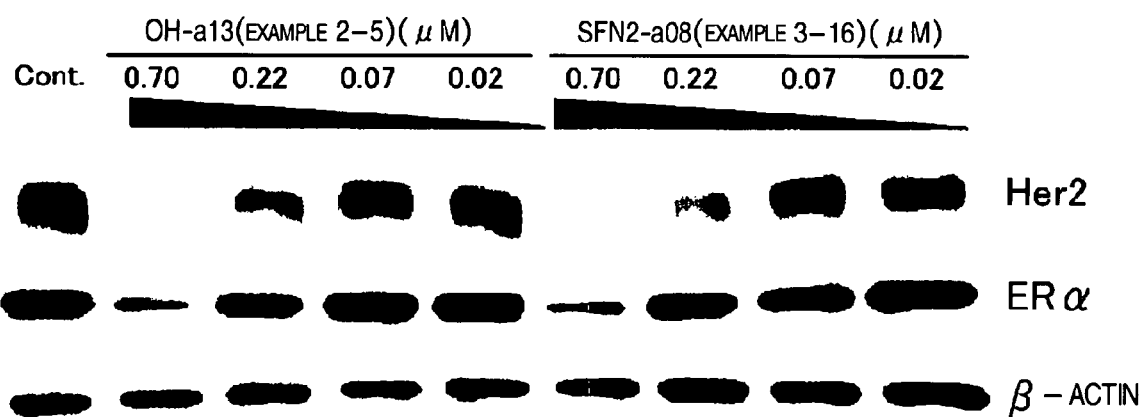
FIG. 4 shows a depression of the amount of HSP90 client protein Her2 and $ER_\alpha$ by the HSP90 inhibitor of the present invention (Example 2-5 and Example 3-16) in the protein assay for the HSP90 client protein in Test example 2. After treating MCF7 cells with 4 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.
Figure 5:
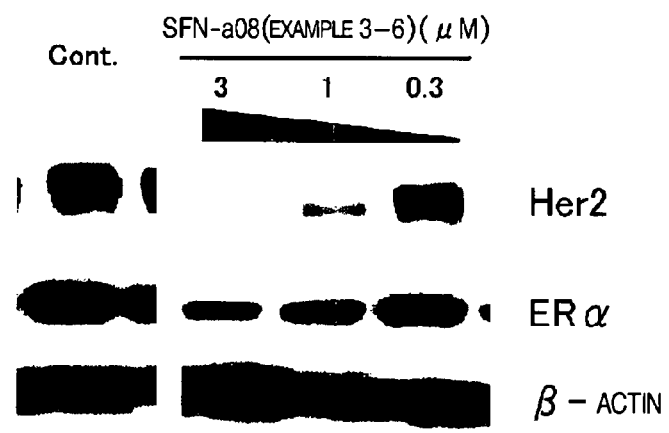
FIG. 5 shows a depression of the amount of HSP90 client protein Her2 and $ER_\alpha$ by the HSP90 inhibitor of the present invention (Example 3-6) in the protein assay for the HSP90 client protein in Test example 2. After treating MCF7 cells with 3 concentrations of each HSP90 inhibitor for 16 hours, the amount of each Her2 and $ER_a$ protein in the lysate obtained from the cells was evaluated by Western blotting method. β-actin is the intra-cellular standard substance. Cont. represents a control.
Figure 6:
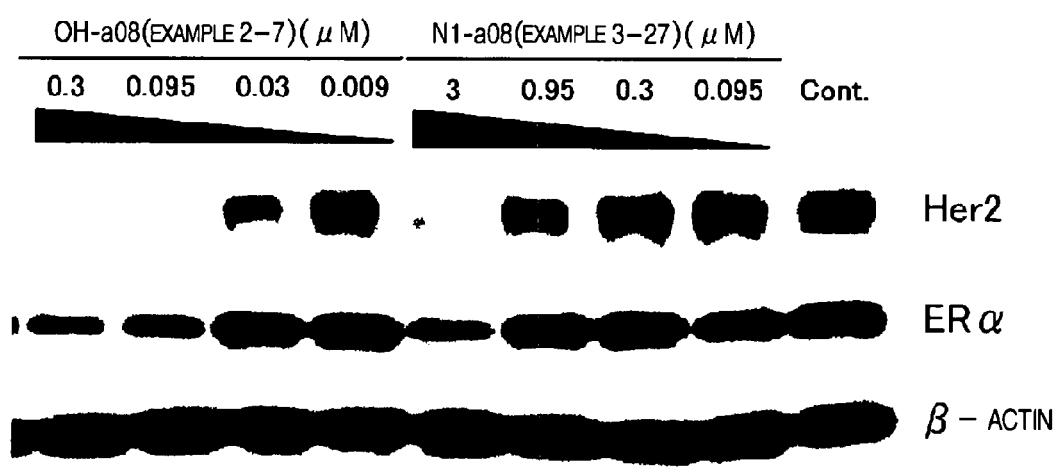
FIG. 6 shows a depression of the amount of HSP90 client protein Her2 and $ER_\alpha$ by the HSP90 inhibitor of the present invention (Example 2-7 and Example 3-27) in the protein assay for the HSP90 client protein in Test example 2. After treating MCF7 cells with 4 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.
Figure 7:
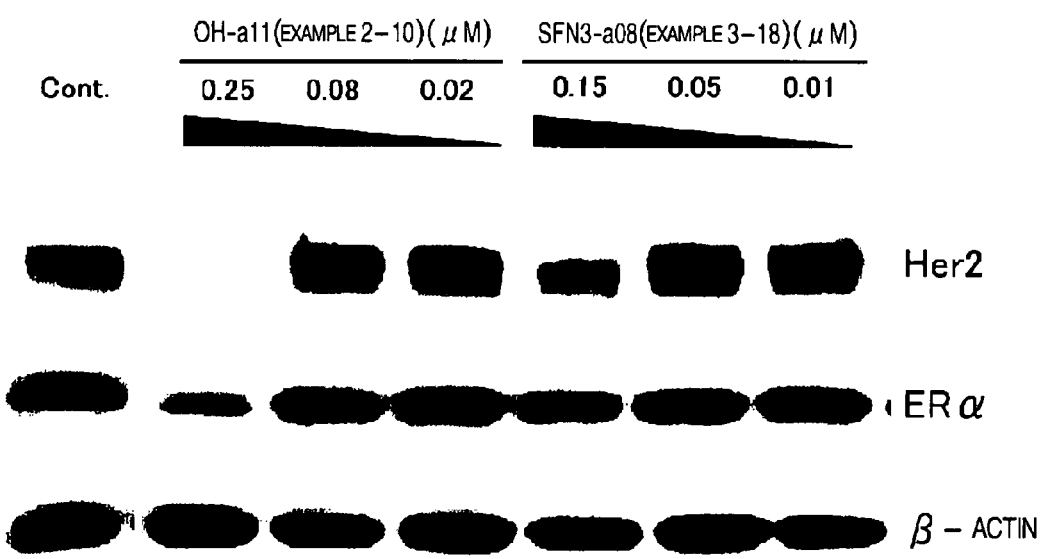
FIG. 7 shows a depression of the amount of HSP90 client protein Her2 and $ER_\alpha$ by the HSP90 inhibitor of the present invention (Example 2-10 and Example 3-18) in the protein assay for the HSP90 client protein in Test example 2. After treating MCF7 cells with 3 concentrations of each HSP90 inhibitor for 16 hours, the amount of each Her2 and $ER_\alpha$ protein in the lysate obtained from the cells was evaluated by Western blotting method. β-actin is the intra-cellular standard substance. Cont. represents a control.

The invention claimed is:

1. A triazole derivative represented by the following general formula (1) or a pharmaceutically acceptable salt thereof,

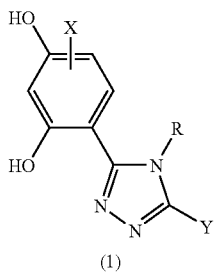

[Formula 1]

(1)

wherein N represents a nitrogen atom; X represents a mercapto group, hydroxy group, halogen atom, nitro group, cyano group, an optionally substituted alkyl group, an optionally substituted alkenyl group, an optionally substituted alkynyl group, an optionally substituted carbocyclic or heterocyclic aryl group, an optionally substituted alkylthio group, an optionally substituted arylthio group, an optionally substituted alkylsulfinyl group, an optionally substituted arylsulfinyl group, an optionally substituted alkylsulfonyl group, an optionally substituted arylsulfonyl group, an optionally substituted sulfamoyl group, an optionally substituted alkoxyl group, an optionally substituted aryloxy group, an optionally substituted acyloxy group, an optionally substituted alkoxycarbonyloxy group, an optionally substituted carbamoyloxy group, an optionally substituted amino group, an optionally substituted acylamino group, an optionally substituted alkoxycarbonylamino group, an optionally substituted ureido group, an optionally substituted sulfonylamino group, an optionally substituted sulfamoylamino group, a formyl group, an optionally substituted acyl group, carboxyl group, an optionally substituted alkoxycarbonyl group, an optionally substituted carbamoyl group, or an optionally substituted silyl group; Y represents a mercapto group, hydroxy group, halogen atom, cyano group, a sulfonyl group, an alkylthio group, an arylthio group, an alkylsulfinyl group, an arylsulfinyl group, a sulfamoyl group, an alkoxyl group, an aryloxy group, an acyloxy group, an alkoxycarbonyloxy group, a carbamoyloxy group, an optionally substituted amino group, an acylamino group, an alkoxycarbonylamino group, an ureido group, a sulfonylamino group, a sulfamoylamino group, a formyl group, an acyl group or a silyl group; R is represented by the following general formula (2),

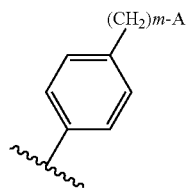

(2)

wherein m is an integer from 0 to 5, A represents an optionally substituted cyclic or non-cyclic amino group, an acylamino group or a sulfonylamino group, in said general formula (1), or a pharmaceutically acceptable salt thereof.

2. The triazole derivative according to claim 1, wherein X is located at the 5 position of 2,4-dihydroxyphenyl group which binds to the triazole ring at 1 position in said general formula (1), or a pharmaceutically acceptable salt thereof.

3. The triazole derivative according to claim 1 or 2, wherein X is an optionally substituted alkyl group, an optionally substituted alkenyl group or an optionally substituted alkynyl group, or a halogen atom in said general formula (1), or a pharmaceutically acceptable salt thereof.

4. The triazole derivative according to claim 1, wherein the compound represented by the general formula (1) is an acetylene derivative represented by the following general formula (1-1),

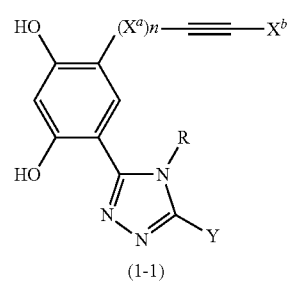

[Formula 2]

(1-1)

wherein R and Y represent the same meaning as in R and Y of said general formula (1), $X^a$ represents an optionally substituted methylene group, n is an integer from 0 to 3, $X^b$ represents a hydrogen atom, an optionally substituted alkyl group, an optionally substituted alkenyl group or an optionally substituted alkynyl group, an optionally substituted carbocyclic or heterocyclic aryl group, halogen atom, sulfamoyl group, formyl group, acyl group, carboxyl group, carbamoyl group or silyl group, or a pharmaceutically acceptable salt thereof.

5. The triazole derivative according to claim 4, wherein n is 1 in said general formula (1-1), or a pharmaceutically acceptable salt thereof.

6. The triazole derivative according to claim 1, wherein Y is any of a mercapto group, hydroxy group, an optionally substituted sulfonyl group or alkylthio group in said general formula (1) or said general formula (1-1), or a pharmaceutically acceptable salt thereof.

7. The triazole derivative according to claim 1, wherein Y is an alkylsulfonyl group optionally substituted on the alkyl group thereof, or an arylsulfonyl group optionally substituted on the aryl group thereof in said general formula (1) or said general formula (1-1), or a pharmaceutically acceptable salt thereof.

8. The triazole derivative according to claim 1, wherein Y is a mercapto group in said general formula (1) or said general formula (1-1), or a pharmaceutically acceptable salt thereof.

9. The triazole derivative according to claim 1, wherein Y is a hydroxy group in said general formula (1), or a pharmaceutically acceptable salt thereof.

10. The triazole derivative according to claim 1, wherein m is 0 or 1, and A is a cyclic amino group in the general formula (2), or a pharmaceutically acceptable salt thereof.

11. The triazole derivative according to claim 1, wherein the compound represented by the general formula (1) is represented by the following general formula (4),

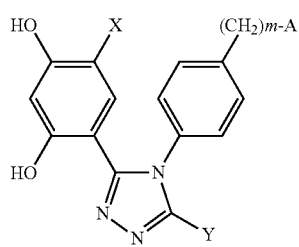

(4)

wherein X represents a chlorine atom, ethyl group, isopropyl group, tert-butyl group, 2,2-dimethylpropyl group, 2-propynyl group or 2-butynyl group; Y represents a mercapto group, an optionally substituted alkylsulfonyl group or hydroxy group; m is 0 or 1; and A represents a cyclic amino group, or a pharmaceutically acceptable salt thereof.

12. The triazole derivative according to claim 1, which is selected from the group consisting of:
4-isopropyl-6-{5-mercapto-4-[4-(morpholin-4-yl)-phenyl]-4H-[1,2,4]triazol-3-yl}-benzene-1,3-diol (SH-a01),
4-isopropyl-6-{5-mercapto-4-[4-(morpholin-4-ylmethyl)-phenyl]-4H-[1,2,4]triazol-3-yl}-benzene-1,3-diol (SH-a02),
4-{5-hydroxy-4-[4-(morpholin-4-yl)-phenyl]-4H-[1,2,4]triazol-3-yl}-6-isopropyl-benzene-1,3-diol (OH-a01),
4-{5-hydroxy-4-[4-(morpholin-4-ylmethyl)-phenyl]-4H-[1,2,4]triazol-3-yl}-6-isopropyl-benzene-1,3-diol (OH-a02),
5-[5-(but-2-ynyl)-2,4-dihydroxy-phenyl]-4-[4-(morpholin-4-ylmethyl)-phenyl]-2,4-dihydro-[1,2,4]triazol-3-one (OH-c02),
4-(but-2-ynyl)-6-{5-mercapto-4-[4-(morpholin-4-ylmethyl)-phenyl]-4H-[1,2,4]triazol-3-yl}-benzene-1,3-diol (SH-c02),
4-bromo-6-{5-mercapto-4-[4-(morpholin-4-yl)-phenyl]-4H-[1,2,4]triazol-3-yl}-benzene-1,3-diol (SH-d01),
4-isopropyl-6-{5-methanesulfonyl-4-[4-(morpholin-4-ylmethyl)-phenyl]-4H-[1,2,4]triazol-3-yl}-benzene-1,3-diol (SFN-a02),
5-[2,4-dihydroxy-5-(prop-2-ynyl)-phenyl]-4-[4-(morpholin-4-ylmethyl)-phenyl]-2,4-dihydro-[1,2,4]triazol-3-one (OH-e02), and
5-(2,4-dihydroxy-5-isopropyl-phenyl)-4-[4-(4-methyl-piperazin-1-ylmethyl)-phenyl]-2,4-dihydro-[1,2,4]triazol-3-one (OH-a13),
or a pharmaceutically acceptable salt thereof.

13. An HSP90 inhibitor comprising as an active ingredient the triazole derivative according to claim 1, or a pharmaceutically acceptable salt thereof.

14. An anticancer agent comprising as an active ingredient the triazole derivative according to claim 1, or a pharmaceutically acceptable salt thereof.

* * * * *